US010935917B2

(12) United States Patent
Sehgal et al.

(10) Patent No.: US 10,935,917 B2

(45) Date of Patent: Mar. 2, 2021

(54) SERPINA1 SIRNAS: COMPOSITIONS OF MATTER AND METHODS OF TREATMENT

(71) Applicant: ALNYLAM PHARMACEUTICALS, INC., Cambridge, MA (US)

(72) Inventors: Alfica Sehgal, Cambridge, MA (US); David Bumcrot, Cambridge, MA (US); Brian Bettencourt, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/513,903

(22) Filed: Jul. 17, 2019

(65) Prior Publication Data

US 2019/0354055 A1 Nov. 21, 2019

Related U.S. Application Data

(63) Continuation of application No. 15/843,656, filed on Dec. 15, 2017, now abandoned, which is a (Continued)

(51) Int. Cl.

| | |
|---|---|
| ***A61K 48/00*** | (2006.01) |
| ***C12N 15/11*** | (2006.01) |

(Continued)

(52) U.S. Cl.

CPC ......... *G03G 15/556* (2013.01); *C12N 15/113* (2013.01); *G03G 15/086* (2013.01); *G03G 15/0853* (2013.01); *C12N 2310/14* (2013.01); *C12N 2310/321* (2013.01); *C12N 2310/3515* (2013.01); *C12N 2310/3521* (2013.01); *G03G 2215/0888* (2013.01)

(58) Field of Classification Search

CPC .............. C12N 15/113; C12N 2310/14; C12N 2310/321; C12N 2310/3515; C12N 2310/3521

See application file for complete search history.

(56) References Cited

U.S. PATENT DOCUMENTS 7,691,997 B2 4/2010 Khvorova et al.

10,450,565 B2 * 10/2019 Li ..................... G01N 33/6893

(Continued)

FOREIGN PATENT DOCUMENTS

JP 2006507841 A 3/2006

WO 1997044348 A1 11/1997

(Continued)

OTHER PUBLICATIONS

An et al., "Quantitative isolation of alphaIAT mutant Z protein polymers from human and mouse livers and the effect of heat", Hepatology, 41(1):160-167 (2005).

(Continued)

*Primary Examiner* — Terra C Gibbs

(74) *Attorney, Agent, or Firm* — Nixon Peabody LLP; Mark J. FitzGerald; Nicole D. Kling

(57) ABSTRACT

The technology described herein relates to double-stranded ribonucleic acid (dsRNA) compositions targeting the Serpina 1 gene, and methods of using such dsRNA compositions to inhibit expression of Serpina 1.

29 Claims, 20 Drawing Sheets

Specification includes a Sequence Listing.

Related U.S. Application Data continuation of application No. 14/974,650, filed on Dec. 18, 2015, now Pat. No. 9,879,261, which is a continuation of application No. 14/127,782, filed as application No. PCT/US2012/043782 on Jun. 22, 2012, now abandoned.

(60) Provisional application No. 61/500,387, filed on Jun. 23, 2011, provisional application No. 61/509,974, filed on Jul. 20, 2011, provisional application No. 61/608,698, filed on Mar. 9, 2012.

(51) Int. Cl.

| | |
|---|---|
| ***G03G 15/00*** | (2006.01) |
| ***C12N 15/113*** | (2010.01) |
| ***G03G 15/08*** | (2006.01) |

(56) References Cited

U.S. PATENT DOCUMENTS

| | | | |
|---|---|---|---|
| 2005/0137153 A1 | 6/2005 | McSwiggen et al. | |
| 2006/0234247 A1 | 10/2006 | Puttaraju et al. | |
| 2007/0253936 A1 | 11/2007 | Kay et al. | |
| 2009/0247608 A1 | 10/2009 | Manoharan et al. | |

FOREIGN PATENT DOCUMENTS

| | | | |
|---|---|---|---|
| WO | WO-2004044136 A2 * | 5/2004 | ............ C07H 21/00 |
| WO | 2004045543 A2 | 6/2004 | |
| WO | 2005070948 A1 | 8/2004 | |
| WO | 2008086524 A2 | 7/2008 | |
| WO | 2009142822 A2 | 11/2009 | |

OTHER PUBLICATIONS

Burrows et al., "Chemical chaperones mediate increased secretion of mutant alpha 1-antitrypsin (alpha 1-AT) Z: A potential pharmacological strategy for prevention of liver injury and emphysema in alpha 1-AT deficiency", Proc Natl Acad Sci. USA, 97(4):1796-801 (2000).

Cruz et al., "In vivo post-transcriptional gene siencing of alpha-1 antitrypsin by adeno-associated virus vectors expressing siRNA", Laboratory Investigation, 87(9):893-902 (2007).

Cruz et al., "Post-Transcriptional Gene Silencing of Alpha-1 Antitrypsin by Small Interfering RNAs (siRNA)", Molecular Therapy, 13(1): S45-S46 (2006).

Flotte et al., "Gene Therapy for Alpha-1 Antitrypsin Deficiency", Human Molecular Genetics, 20:R87-R92 (2011).

Hidvegi et al., "An autophagy-enhancing drug promotes degradation of mutant alpha1-antitrypsin Z and reduces hepatic fibrosis", Science 329(5988):229-32 (2010).

Knoell et al., "Clinical implications of gene therapy for alpha 1-antitrypsin deficiency", Chest. 107(2):535-45 (1995).

Li et al., "Combination Therapy Utilizing shRNA and Optimize Alpha-1 Antitrypsin (AAT) Expression Cassette for Treatment and Correction of ATT Liver Deficiency", Molecular Therapy, 17(1): S12 (2009).

Lomas et al., "The mechanism of Z alpha 1-antitrypsin accumulation in the liver", Nature, 357(6379):605-7 (1992).

Mueller et al., "Development of Simultaneous Gene Augmentation and Reduction of Mutant Gene Expression with a Single Recombinant AAV for Alpha One Antitrypsin Disease", Molecular Therapy, 17(1): S391 (2009).

Mueller et al., "In Vivo Allele Specific Knockdown of Mutant Alpha One Antitrypsin Using Recombinant AAV Delivered shRNA", Molecular Therapy, 17(1): S313 (2009).

Smart et al., "The localisation of intracellular immunoglobulin and alpha-1-antitrypsin by immunoelectron staining of post-osmicated, resin-embedded tissue", J Immunol Methods, 56(1):97-107 (1983).

Teckman et al., "Mitochondrial autophagy and injury in the liver in alpha 1-antitrypsin deficiency", Am J Physiol Gastrointest Liver Physiol., 286(5):G851-62 (2004).

XP-002733137, http://ibis/exam/dbfetch.jsp?id=EM_PAT:FZ808787 found on Nov. 28, 2014.

XP-002733138, http://ibis/exam/dbfetch.jsp?id=EM_PAT:FZ808825 found on Nov. 28, 2014.

XP-002733139, http://ibis/exam/dbfetch.jsp?id=EM_PAT:FZ808748 found on Nov. 28, 2014.

Sequence alignment #1 for SEQ ID No. 106 of the present invention. Downloaded on Dec. 20, 2018.

Sequence alignment #2 for SEQ ID No. 62 of the present invention. Downloaded on Dec. 20, 2018.

Grimm et al. "Fatality in mice due to oversaturation of cellular microRNA/short hairpin RNA pathways." Nature 441(7092): 537-541 (2006).

Grimm et al. "Fatality in mice due to oversaturation of cellular microRNA/short hairpin RNA pathways." Nature 441(7092): 537-541 (2006) [Supplementary Information].

Rao et al. "Comparative assessment of siRNA and shRNA off target effects: what is slowing clinical development." Cancer Gene Therapy 16(11): 807-809 (2009).

* cited by examiner

6A

6B

7A

7B

9A

9B

11A
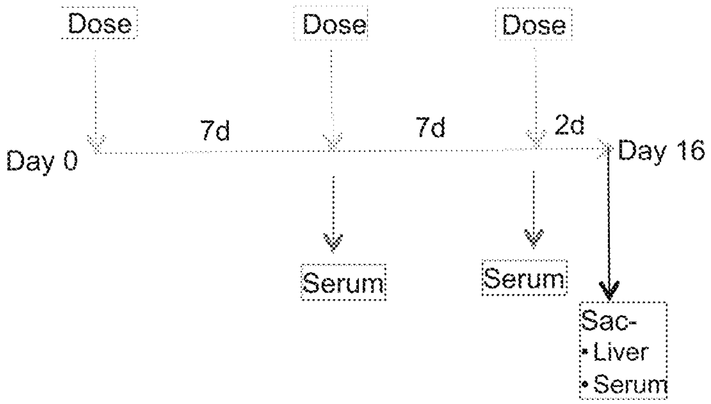
11B
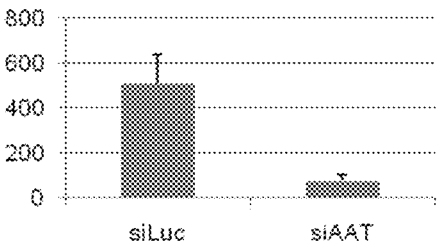
11C
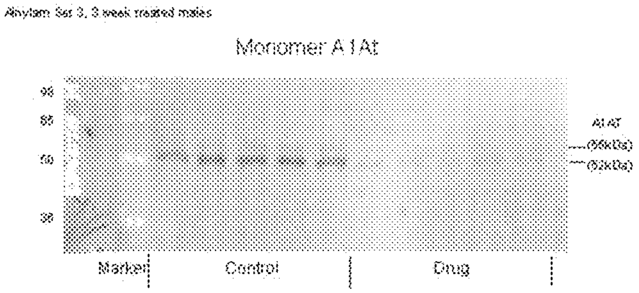
Figures 11A-11E

11D
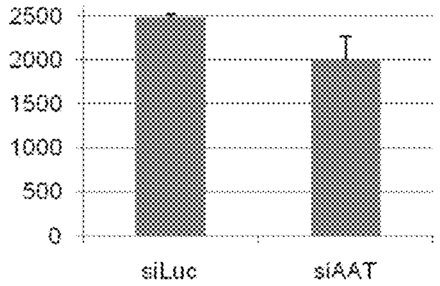
11E
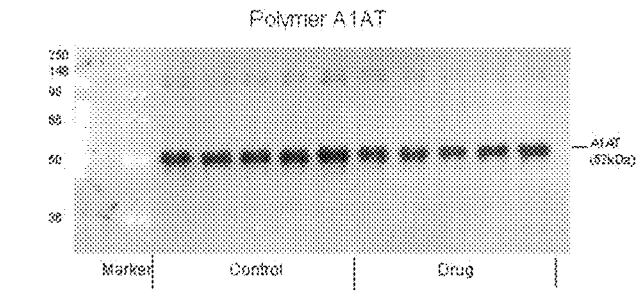
Figures 11A-11E, cont.

12A
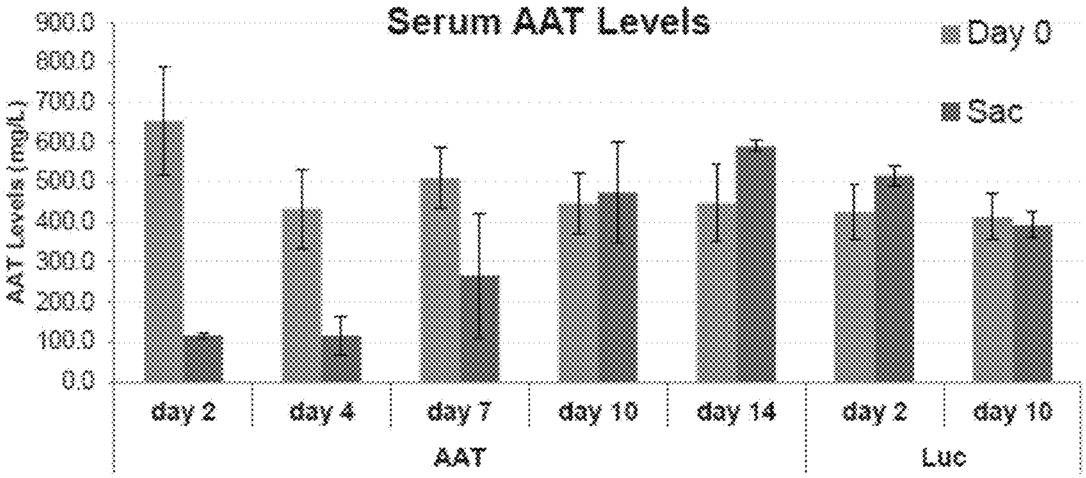
12B
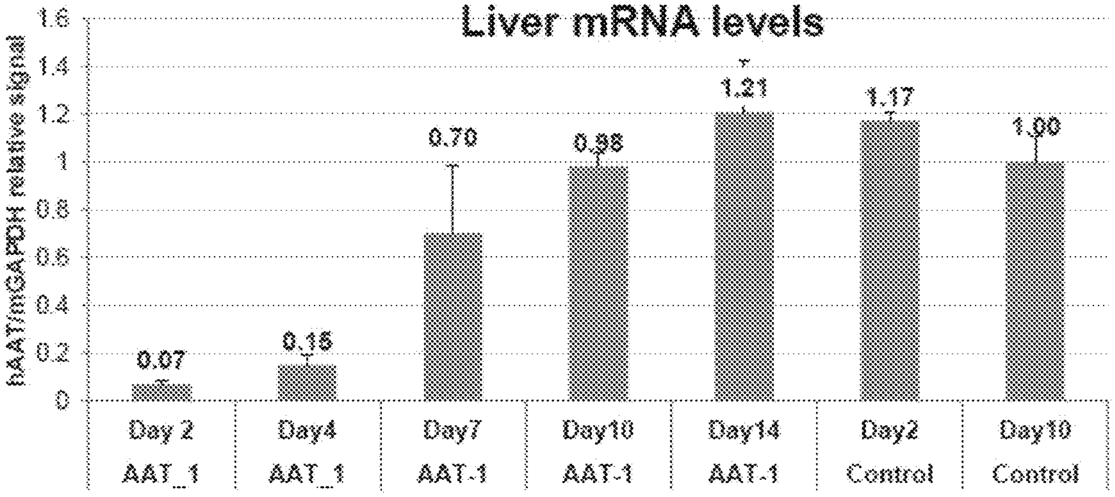
Figures 12A-12C

12C
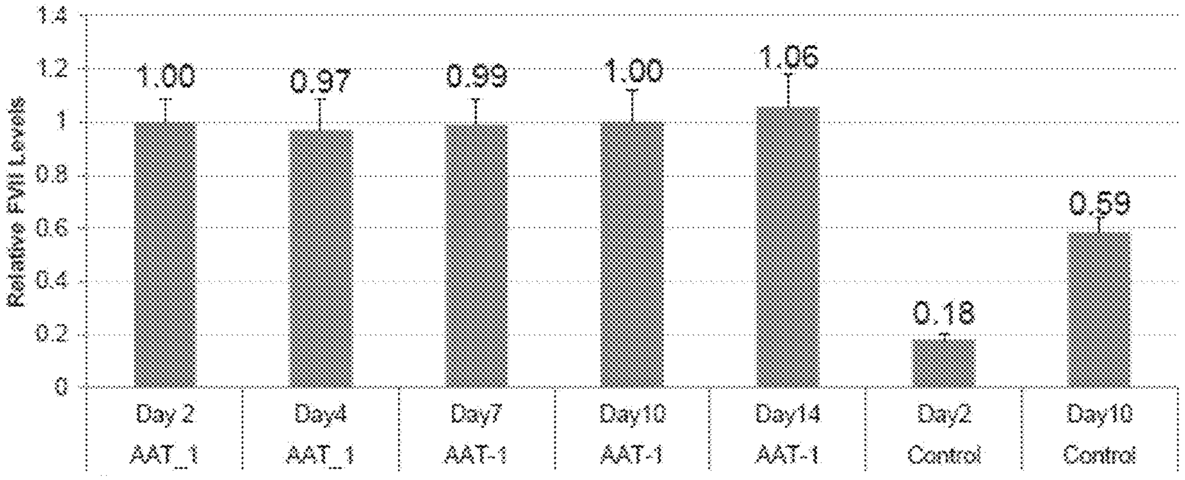
Figures 12A-12C, cont.

14A

14B
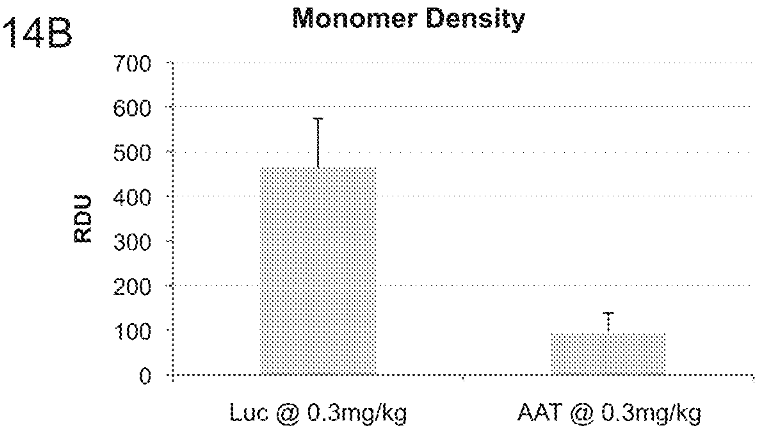
14C
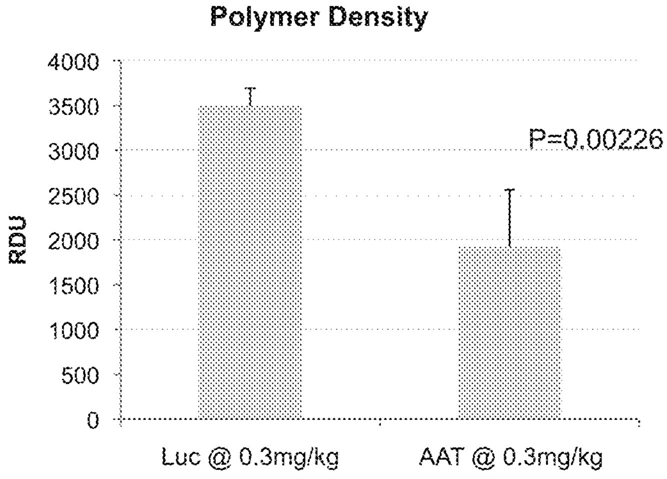
Figures 14A-14C, cont.

SERPINA1 SIRNAS: COMPOSITIONS OF MATTER AND METHODS OF TREATMENT

CROSS-REFERENCE TO RELATED APPLICATIONS

This application is a continuation of U.S. application Ser. No. 15/843,656 filed Dec. 15, 2017 now abandoned, which is a continuation of U.S. application Ser. No. 14/974,650 filed Dec. 18, 2015 which issued as U.S. Pat. No. 9,879,261 on Jan. 30, 2018 and which is a continuation of Ser. No. 14/127,782, filed Dec. 19, 2013 now abandoned, which is a 35 U.S.C. § 371 National Phase Entry Application of International Application No. PCT/US2012/043782 filed Jun. 22, 2012, which designates the U.S., and which claims benefit under 35 U.S.C. § 119(e) of U.S. Provisional Application Nos. 61/500,387 filed Jun. 23, 2011, 61/509,974 filed Jul. 20, 2011 and 61/608,698 filed Mar. 9, 2012, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Dec. 19, 2013, is named 05105807.txt and is 146,610 bytes in size.

TECHNICAL FIELD

The technology described herein relates to the specific inhibition of gene expression.

BACKGROUND

Serpina 1 (α-1 antitrypsin or AAT) is an inhibitor of neutrophil elastase produced by hepatocytes, mononuclear monocytes, alveolar macrophages, enterocytes, and myeloid cells. Individuals with mutations in one or both copies of the Serpina 1 gene can suffer from alpha-1 anti-trypsin deficiency, which presents as a risk of developing pulmonary emphysema or chronic liver disease due to greater than normal elastase activity in the lungs and liver.

In affected individuals, the deficiency in alpha-1 antitrypsin is a deficiency of wildtype, functional alpha-1 antitrypsin. In some cases, the individual is producing significant quantities of alpha-1 antitrypsin, but a proportion of the alpha-1 antitrypsin protein being produced is misfolded or contains mutations that compromise the functioning of the protein. In some cases, the individual is producing misfolded proteins which cannot be properly transported from the site of synthesis to the site of action within the body. Liver disease resulting from alpha-1 antitrypsin deficiency can be caused by such misfolded proteins. Mutant forms of alpha-1 antitypsin are produced in liver cells and in the misfolded configuration they are not readily transported out of the cells. This leads to a buildup of misfolded protein in the liver cells and can cause one or more diseases or disorders of the liver including, but not limited to, chronic liver disease, liver inflammation, cirrhosis, liver fibrosis, and/or hepatocellular carcinoma.

There are currently very limited options for the treatment of patients with liver disease arising from alpha-1 antitrypsin deficiency, including hepatitis vaccination, supportive care, avoidance of injurious agents (e.g. alcohol and NSAIDs). Replacement of alpha-1 antitrypsin has no impact liver disease in these patients but liver transplantation can be effective. Provided herein are methods for treating or preventing chronic liver disease due to Serpina 1 deficiency using inhibitory RNAs (iRNAs).

Double-stranded RNA molecules (dsRNA) have been shown to block gene expression in a highly conserved regulatory mechanism known as RNA interference (RNAi). WO 99/32619 (Fire et al.) disclosed the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus of a new class of pharmaceutical agents for treating disorders that are caused by the aberrant or unwanted regulation of a gene.

SUMMARY

Described herein are compositions and methods that effect the RNA-induced silencing complex (RISC)-mediated cleavage of RNA transcripts of the Serpina 1 gene, such as in a cell or mammal. Also described are compositions and methods for treating alpha-1 anti-trypsin related liver disease and related pathological conditions caused by the expression of a Serpina 1 gene, (e.g. chronic liver disease, inflammation, fibrosis and/or cirrhosis).

As used herein, the term "iRNA" refers to an agent that contains RNA as that term is defined herein, and which mediates the targeted cleavage of an RNA transcript via an RNA-induced silencing complex (RISC) pathway. In one embodiment, the iRNA inhibits the expression of Serpina 1 in a cell or mammal. Alternatively, in another embodiment, the iRNA up-regulates the expression of Serpina 1 in a cell or mammal.

The iRNAs included in the compositions featured herein encompass a dsRNA having an RNA strand (the antisense strand) having a region that is 30 nucleotides or less, generally 19-24 nucleotides in length, that is substantially complementary to at least part of an mRNA transcript of a Serpina 1 gene. In one embodiment, the dsRNA comprises a region of at least 15 contiguous nucleotides.

In one embodiment, an iRNA for inhibiting expression of a Serpina 1 gene includes at least two sequences that are complementary to each other. The iRNA includes a sense strand having a first sequence and an antisense strand having a second sequence. The antisense strand includes a nucleotide sequence that is substantially complementary to at least part of an mRNA encoding Serpina 1, and the region of complementarity is 30 nucleotides or less, and at least 15 nucleotides in length. Generally, the iRNA is 19 to 24, e.g., 19 to 21 nucleotides in length. In some embodiments the iRNA is from about 15 to about 25 nucleotides in length, and in other embodiments the iRNA is from about 25 to about 30 nucleotides in length. The iRNA, upon contacting with a cell expressing Serpina 1, inhibits the expression of a Serpina 1 gene by at least 10%, at least 20%, at least 25%, at least 30%, at least 35% or at least 40% or more, such as when assayed by a method as described herein. In one embodiment, the Serpina 1 iRNA is formulated in a stable nucleic acid lipid particle (SNALP).

In one embodiment, an iRNA featured herein includes a first sequence of a dsRNA that is selected from the group consisting of the sense sequences of Tables 3 and/or 4, and a second sequence that is selected from the group consisting of the corresponding antisense sequences of Tables 3 and/or 4. The iRNA molecules featured herein can include naturally occurring nucleotides or can include at least one modified nucleotide, including, but not limited to a 2'-O-methyl modified nucleotide, a nucleotide having a 5'-phosphorothioate group, and a terminal nucleotide linked to a cholesteryl derivative. Alternatively, the modified nucleotide can be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such a modified sequence will be based on a first sequence of said iRNA selected from the group consisting of the sense sequences of Tables 3 and 4 and a second sequence selected from the group consisting of the antisense sequences of Tables 3 and 4.

In some embodiments, an iRNA featured herein can comprise 2'-O-methyl pyrimidines (e.g. 2' O-Methyl C and 2'-O-Methyl U). In some embodiments, an iRNA featured herein comprises 2'-O-methyl pyrimidine modification of every pyrimidine comprised by the iRNA. In some embodiments, an iRNA featured herein can comprise 2'-O-methyl pyrimidine modification of every pyrimidine comprised by one strand (e.g. the sense or the antisense strand) of the iRNA. In some embodiments, an iRNA featured herein can comprise 2'-O-methyl pyrimidine modification of a pyrimidine adjacent to a ribo A nucleoside. In some embodiments, an iRNA featured herein can comprise 2'-O-methyl pyrimidine modification of pyrimidines adjacent to a ribo A nucleoside on one strand of the iRNA. In some embodiments, an iRNA featured herein can comprise 2'-O-methyl pyrimidine modification of a pyrimidine immediately 5' of a ribo A nucleoside. In some embodiments, an iRNA featured herein can comprise 2'-O-methyl pyrimidine modification of pyrimidines immediately 5' of a ribo A nucleoside by the iRNA on one strand of the iRNA. In some embodiments, an iRNA featured herein can comprise a two base dTsdT extension at the 3' end of at least one strand of the iRNA. In some embodiments, an iRNA featured herein can comprise a two base dTsdT extension at the 3' end of both strands of the iRNA.

In one embodiment, the subject is selected, at least in part, on the basis of needing a reduction in misfolded Serpina 1 protein, a reduction in misfolded Serpina 1 protein in the liver, or an increase in wild-type plasma Serpina 1 protein. In certain embodiments, the patient in need of a treatment for a disorder mediated by Serpina 1 expression has the symptoms of, is diagnosed with, and/or is at risk for developing alpha-1 anti-trypsin related liver disease, chronic liver disease, liver inflammation, cirrhosis, liver fibrosis, and/or hepatocellular carcinoma.

In one embodiment, an iRNA as described herein targets a wildtype Serpina 1 RNA transcript, and in another embodiment, the iRNA targets a mutant transcript (e.g., a Serpina 1 RNA carrying an allelic variant). For example, an iRNA of the technology described herein can target a polymorphic variant, such as a single nucleotide polymorphism (SNP) variant, of Serpina 1 (e.g. the PiZ SNP (NCBI ID NO: dbSNP:rs28929474), the PiW SNP (NCBI ID NO: dbSNP: rs1802959, the PiNull(Devon) SNP (NCBI ID NO: dbSNP: rs11558261), and/or the PiNull(Ludwigshafen) SNP (NCBI ID NO: dbSNP:rs28931572). In a further example, an iRNA of the technology described herein can target a polymorphic variant, such as a mutant allele of Serpina 1 that encodes a mutant mRNA (e.g. the PiM(Malton) allele (see Frazier et al., Am J Hum Genet. 1989 44:894-902; Curiel et al., J Biol Chem 1989 264:13938-45; Graham et al., Hum Genet. 1989 84:55-8). In another embodiment, the iRNA targets both a wildtype and a mutant Serpina 1 transcript. In yet another embodiment, the iRNA targets a transcript variant of Serpina 1.

In one embodiment, an iRNA featured in the technology described herein targets a non-coding region of a Serpina 1 RNA transcript, such as the 5' or 3' untranslated region.

In one aspect, the technology described herein provides a cell containing at least one of the iRNAs featured in the technology described herein. The cell is generally a mammalian cell, such as a human cell.

In another aspect, the technology described herein provides a pharmaceutical composition for inhibiting the expression of a Serpina 1 gene in an organism, generally a human subject. The composition typically includes one or more of the iRNAs described herein and a pharmaceutically acceptable carrier or delivery vehicle. In one embodiment, the composition is used for treating a disorder mediated by Serpina 1 expression. In another embodiment, the composition is used for treating alpha-1 anti-trypsin related liver disease. Ian another embodiment, the composition is used to reduce the severity, signs, symptoms, and/or markers of cirrhosis, fibrosis, Serpina 1 accumulation in the liver and/or liver inflammation. In another embodiment, the composition is used to decrease the risk of developing cirrhosis, fibrosis, Serpina 1 accumulation in the liver, hepatocellular carcinoma, and/or liver inflammation.

In another embodiment, the pharmaceutical composition is formulated for administration of a dosage regimen described herein, e.g., not more than once every four weeks, not more than once every three weeks, not more than once every two weeks, or not more than once every week. In another embodiment, the administration of the pharmaceutical composition can be maintained for a month or longer, e.g., one, two, three, or six months, or one year or longer.

In another embodiment, a composition containing an iRNA featured in the technology described herein, e.g., a dsRNA targeting Serpina 1, is administered with a non-iRNA therapeutic agent, such as an agent known to treat a liver disorder, or a symptom of a liver disorder. For example, an iRNA featured in the technology described herein can be administered with an agent for treatment of cirrhosis or other disorders associated with alpha-1 anti-trypsin related liver disease.

In another embodiment, a Serpina 1 iRNA is administered to a patient, and then the non-iRNA agent is administered to the patient (or vice versa). In another embodiment, a Serpina 1 iRNA and the non-iRNA therapeutic agent are administered at the same time.

In another aspect, the technology described herein provides a method for inhibiting the expression of a Serpina 1 gene in a cell by performing the following steps:

(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding Serpina 1, and where the region of complementarity is 30 nucleotides or less, i.e., 15-30 nucleotides in length, and generally 19-24 nucleotides in length, and where the dsRNA, upon contact with a cell expressing Serpina 1, inhibits expression of a Serpina 1 gene by at least 10%, preferably at least 20%, at least 30%, at least 40% or more; and (b) maintaining the cell produced in step (a) for a time sufficient to obtain degradation of the mRNA transcript of the Serpina 1 gene, thereby inhibiting expression of a Serpina 1 gene in the cell.

In another aspect, the technology described herein provides methods and compositions useful for activating expression of a Serpina 1 gene in a cell or mammal.

In another aspect, the technology described herein provides a method for modulating the expression of a Serpina 1 gene in a cell by performing the following steps:

(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding Serpina 1, and where the region of complementarity is 30 nucleotides or less, i.e., 15-30 nucleotides in length, and generally 19-24 nucleotides in length, and where the dsRNA, upon contact with a cell expressing Serpina 1, inhibits expression of a Serpina 1 gene by at least 10%, preferably at least 20%, at least 30%, at least 40% or more; and (b) maintaining the cell produced in step (a) for a time sufficient to obtain degradation or protection of the mRNA transcript of the Serpina 1 gene, thereby modulating expression of a Serpina 1 gene in the cell.

In one embodiment, the method is for inhibiting gene expression in a liver cell, a monocyte, an alveolar macrophage, an enterocyte, and/or a myeloid cell. In another embodiment, the method is for activating gene expression in a liver cell, a monocyte, an alveolar macrophage, an enterocyte, and/or a myeloid cell.

In other aspects, the technology described herein provides methods for treating, preventing or managing pathological processes mediated by Serpina 1 expression, such as an alpha-1 anti-trypsin deficiency liver disease. In one embodiment, the method includes administering to a patient in need of such treatment, prevention or management a therapeutically or prophylactically effective amount of one or more of the iRNAs featured in the technology described herein. In one embodiment the patient has chronic liver disease. In another embodiment, administration of the iRNA targeting Serpina 1 alleviates or relieves the severity of at least one symptom of a Serpina 1-mediated disorder in the patient, such as liver inflammation.

In one aspect, the technology described herein provides a vector for inhibiting the expression of a Serpina 1 gene in a cell. In one embodiment, the vector includes at least one regulatory sequence operably linked to a nucleotide sequence that encodes at least one strand of an iRNA as described herein.

In another aspect, the technology described herein provides a cell containing a vector for inhibiting the expression of a Serpina 1 gene in a cell. The vector includes a regulatory sequence operably linked to a nucleotide sequence that encodes at least one strand of one of the iRNAs as described herein.

In yet another aspect, the technology described herein provides a composition containing a Serpina 1 iRNA, in combination with a second iRNA targeting a second gene involved in a pathological disease, and useful for treating the disease, e.g., a liver disorder.

The details of various embodiments of the invention are set forth in the description below. Other features, objects, and advantages of the invention will be apparent from the description and the drawings, and from the claims.

BRIEF DESCRIPTION OF THE DRAWINGS

FIG. 6A is a Western blot detecting AAT monomer levels. FIG. 6B is a graph of the level of AAT monomer for each experimental group.

FIG. 7A is a Western blot detecting AAT polymer levels. FIG. 7B is a graph of the level of AAT polymer for each experimental group. The values shown above the bars in 7B are the relative densities of each spot wherein the Luc control is set to an arbitrary value of 100.

FIG. 8A is a Western blot detecting AAT monomer levels. FIG.

8B is a Western blot detecting AAT polymer levels. FIG. 8C is a graph of the ratio of AAT monomer:AAT polymer for each experimental group.

FIG. 9A is a graph of the level of AAT mRNA in the livers of the animals. FIG. 9B is a graph of the level of AAT protein in the serum of the animals.

FIG. 10A is a diagram of the experimental procedure. Sac=sacrifice. FIG. 10B is a graph representing AAT mRNA levels in the livers of transgenic animals after intravenous administration of iRNAs. FIG. 10C is a graph representing quantitation of Western blots measuring the level of AAT in the serum of transgenic animals after intravenous administration of iRNAs. PBS=phosphate buffered saline control; Control or siLUC=AD-1955 iRNA control, siAAT or “drug”=AD-44715 iRNA; mpk=mg/kg; RDU=relative densiometric units.

FIGS. 11A-11E depict a diagram and graphs of a multiple-dose AAT iRNA dosing experiment and graphs and Western blots showing the results thereof. FIG. 11A is a diagram of the experimental procedure. Sac=sacrifice. FIG. 11B is a graph representing quantitation of Western blots measuring the level of AAT momomeric form in the livers of transgenic animals administered control and AAT-specific siRNA formulations after sacrifice under the experimental protocol set out in FIG. 11A. Units on the y-axis are RDU (relative densiometric units). FIG. 11C shows a Western blot for the monomeric form of AAT in the liver at the time of sacrifice. FIG. 11D is a graph representing quantitation of Western blots measuring the level of AAT polymeric form in the livers of transgenic animals administered control and AAT-specific iRNA formulations after sacrifice under the experimental protocol set out in FIG. 11A. Units on the y-axis are RDU (relative densiometric units). FIG. 11E shows a Western blot for the polymeric form of AAT in the liver at the time of sacrifice. Control or siLUC=AD-1955 iRNA control, siAAT or “drug”=AD-44715 iRNA.

FIGS. 12A-12C depict levels of AAT after a duration study with a single IV injection of control (Factor VII siRNA; LUC control) or AAT-specific (AD-44715 and AAT 1) iRNAs. iRNAs were administered at a dose of 0.3 mg/kg. Animals were sacrificed and liver and serum samples analyzed at day 2 and day 10 for the control-treated group and days 2, 4, 7, 10, and 14 for the AAT-specific group. Each bar represent the average of three animals. FIG. 12A depicts the level of AAT protein present in the serum (mg/L). FIG. 12B depicts the level of hAAT mRNA in the liver, normalized to mGAPDH. FIG. 12C depicts the level of mouse Factor VII (mVII) mRNA in the liver normalized to mouse GAPDH.

FIG. 13A depicts the experimental protocol with dosing every other week at 0.3 mg/kg with either LNP-AAT specific for human AAT or control LNP-Luc. FIG. 13B is a graph of human AAT mRNA levels mouse livers following long-term dosing with LNP-AAT or LNP-Luc. Each bar represents the average of 6 animals.

FIG. 14A depicts the results of a western blot with human-specific antibody with each lane representing one animal. FIG. 14B a graph quantitating the level of the monomeric protein (in RDU) detected in FIG. 14A while FIG. 14C is a graph quantitating the level of the polymeric protein detected in FIG. 14A.

DETAILED DESCRIPTION

Figure 1:
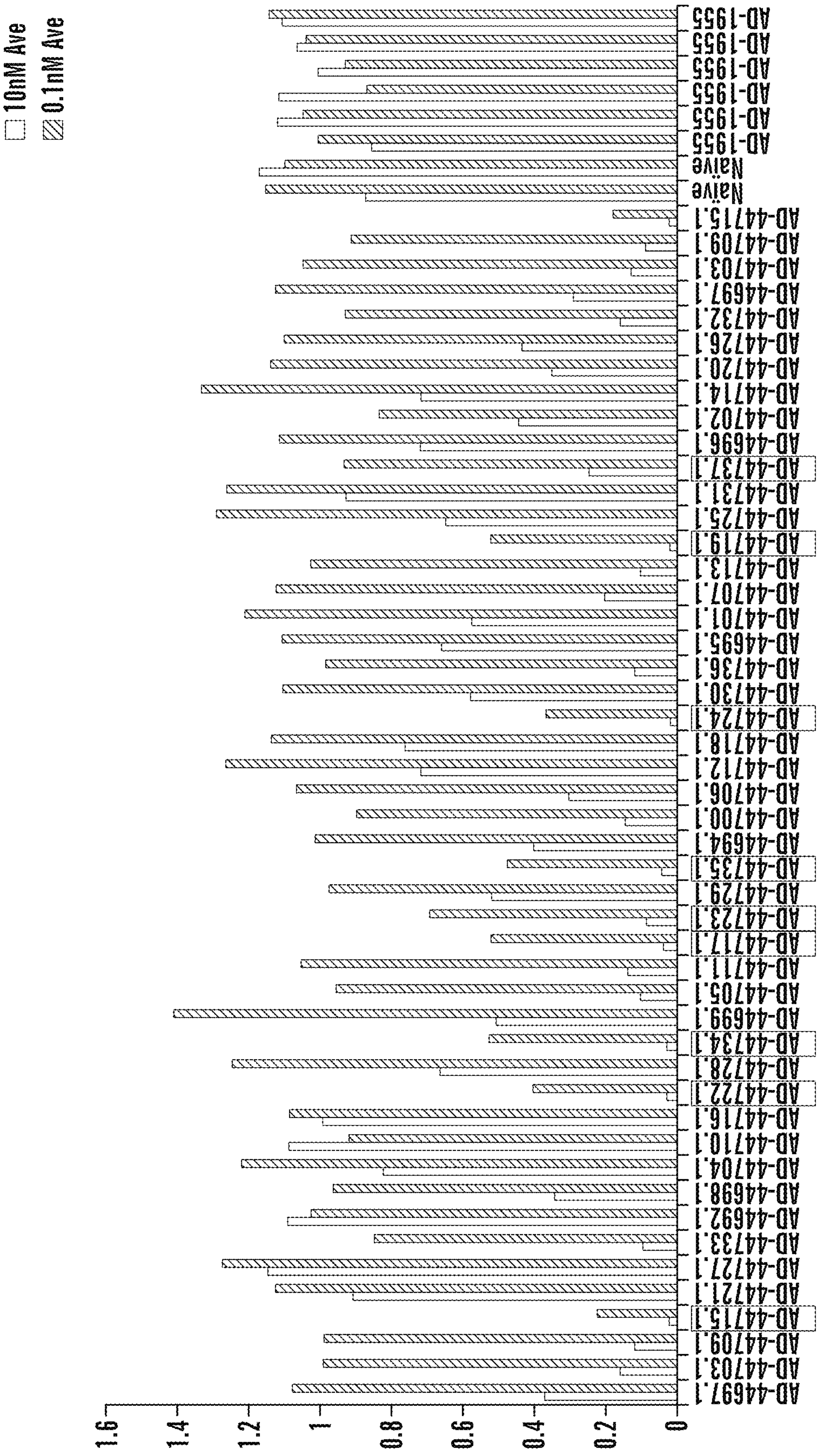
FIG. 1 is a graph showing the inhibition of Serpina 1 expression in Hep3B cells following a single dose of the indicated iRNAs. Duplex IDs are shown on the x-axis and expression normalized to cells transfected with mock-inoculated and cells inoculated with the AD-1955 (10 nM) control is shown on the y-axis. Duplex IDs in the shaded boxes were selected for $IC_{50}$ tests.

Described herein are iRNAs and methods of using them for inhibiting the expression of a Serpina 1 gene in a cell or a mammal where the iRNA targets a Serpina 1 gene. Also provided are compositions and methods for treating pathological conditions and diseases, such as a liver disorder, in a mammal caused by the expression of a Serpina 1 gene. iRNA directs the sequence-specific degradation of mRNA through a process known as RNA interference (RNAi).

The iRNAs of the compositions featured herein include an RNA strand (the antisense strand) having a region which is 30 nucleotides or less in length, i.e., 15-30 nucleotides in length, generally 19-24 nucleotides in length, which region is substantially complementary to at least part of an mRNA transcript of a Serpina 1 gene. The use of these iRNAs enables the targeted degradation of mRNAs of genes that are implicated in pathologies associated with Serpina 1 expression in mammals. Very low dosages of Serpina 1 iRNAs in particular can specifically and efficiently mediate RNAi, resulting in significant inhibition of expression of a Serpina 1 gene. Using cell-based assays, the present inventors have demonstrated that iRNAs targeting Serpina 1 can mediate RNAi, resulting in significant inhibition of expression of a Serpina 1 gene. Thus, methods and compositions including these iRNAs are useful for treating pathological processes caused by accumulation of Serpina 1 protein, such as alpha-1 anti-trypsin liver disease. The following detailed description discloses how to make and use compositions containing iRNAs to inhibit the expression of a Serpina 1 gene, as well as compositions and methods for treating diseases and disorders caused by the expression of this gene. Embodiments of the pharmaceutical compositions featured in the technology described herein include an iRNA having an antisense strand comprising a region which is 30 nucleotides or less in length, generally 19-24 nucleotides in length, which region is substantially complementary to at least part of an RNA transcript of a Serpina 1 gene, together with a pharmaceutically acceptable carrier. Embodiments of compositions featured in the technology described herein also include an iRNA having an antisense strand having a region of complementarity which is 30 nucleotides or less in length, generally 19-24 nucleotides in length, and is substantially complementary to at least part of an RNA transcript of a Serpina 1 gene.

Accordingly, in some aspects, pharmaceutical compositions containing a Serpina 1 iRNA and a pharmaceutically acceptable carrier, methods of using the compositions to inhibit expression of a Serpina 1 gene, and methods of using the pharmaceutical compositions to treat diseases caused by expression of a Serpina 1 gene are featured in the technology described herein.

Liver disease related to Serpina 1 deficiency results not strictly from a lack of the wildtype protein in the liver, but rather, from an accumulation of misfolded Serpina 1 in the liver, which interferes with hepatic function, leading to chronic liver disease. It can be useful to target the mutant or variant Serpina 1 trancripts in individuals to prevent the accumulation of misfolded protein. In addition, without wishing to be bound by theory, it is believed that a therapeutic benefit can also be provided by inhibiting the expression of the wildtype gene in individuals affected by the disease. Without wishing to be bound by theory, it is thought that reducing expression of wildtype protein, with or without selective reduction in mutant or variant expression, can influence the accumulation of misfolded Serpina 1 protein. Thus, while it can, in some instances, be difficult to selectively target a mutant transcript, a therapeutic benefit can be gained for individuals with, or at risk of, alpha-1 anti-trypsin related liver disease via iRNA mediated inhibition of wildtype and/or mutant Serpina 1 expression.

It is also noted that where delivery of iRNA formulations to the liver is relatively straightforward and selective, administration of an iRNA that targets wildtype Serpina 1 would be expected to exert its primary effect in the liver.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the technology described herein by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the technology described herein.

As used herein, "Serpina 1" refers to a particular polypeptide expressed in a cell. Serpina 1 is also known as α-1 antitrypsin or AAT. The sequence of a human Serpina 1 mRNA transcript can be found at NM_000295.4 (SEQ ID NO: 01), NM_001002235.2 (SEQ ID NO: 02), NM_001002236.2 (SEQ ID NO: 03), NM_001127700.1 (SEQ ID NO: 04), NM_001127701.1 (SEQ ID NO: 05), NM_001127702.1 (SEQ ID NO: 06), NM_001127703.1 (SEQ ID NO: 07), NM_001127704.1 (SEQ ID NO: 08), NM_001127705.1 (SEQ ID NO: 09), NM_001127706.1 (SEQ ID NO: 10), and/or NM_001127707.1 (SEQ ID NO: 11). The sequence of rhesus Serpina 1 mRNA can be found at XM_001099255.2 (SEQ ID NO: 12) and/or XM_001099044.2 (SEQ ID NO: 13). Over 80 alleles have been identified and the "M" allele is considered the wildtype or "normal" allele.

As used herein, "Z-AAT" referes to a mutant allele of Serpina 1 in which the $342^{nd}$ amino acid of the protein is changed from a glutamine to a lysine as a result of the relevant codon being changed from GAG to AAG. A subject homozygous for a Z allele can be referred to as "PIZZ." Z-AAT mutations account for 95% of Serpina 1 deficiency patients and is estimated to be present in 100,000 Americans and ~3 million individuals worldwide. Z-AAT does not fold correctly in the endoplasmic reticulum, leading to loop-sheet polymers which aggregate and reduce secretion, elicitation of the unfolded protein response, apoptosis, endoplasmic reticulum overload response, autophagy, mitochondrial stress, and altered hepatocyte function.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of Serpina 1 expression. Alternatively, in another embodiment, an iRNA as described herein activates Serpina 1 expression.

As used herein, "target sequence" refers to a contiguous portion of the nucleotide sequence of an mRNA molecule formed during the transcription of a Serpina 1 gene, including mRNA that is a product of RNA processing of a primary transcription product. The target portion of the sequence will be at least long enough to serve as a substrate for iRNA-directed cleavage at or near that portion. For example, the target sequence will generally be from 9-36 nucleotides in length, e.g., 15-30 nucleotides in length, including all sub-ranges there between. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as “fully complementary” with respect to each other herein. However, where a first sequence is referred to as “substantially complementary” with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as “fully complementary” for the purposes described herein.

“Complementary” sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms “complementary,” “fully complementary” and “substantially complementary” herein can be used with respect to the base matching between the sense strand and the antisense strand of a dsRNA, or between the antisense strand of an iRNA agent and a target sequence, as will be understood from the context of their use.

As used herein, a polynucleotide that is “substantially complementary to at least part of” a messenger RNA (mRNA) refers to a polynucleotide that is substantially complementary to a contiguous portion of the mRNA of interest (e.g., an mRNA encoding Serpina 1). For example, a polynucleotide is complementary to at least a part of a Serpina 1 mRNA if the sequence is substantially complementary to a non-interrupted portion of an mRNA encoding Serpina 1.

The term “double-stranded RNA” or “dsRNA,” as used herein, refers to an iRNA that includes an RNA molecule or complex of molecules having a hybridized duplex region that comprises two anti-parallel and substantially complementary nucleic acid strands, which will be referred to as having “sense” and “antisense” orientations with respect to a target RNA. The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range there between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a “hairpin loop”) between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a “linker.” The term “siRNA” is also used herein to refer to a dsRNA as described above.

The skilled artisan will recognize that the term “RNA molecule” or “ribonucleic acid molecule” encompasses not only RNA molecules as expressed or found in nature, but also analogs and derivatives of RNA comprising one or more ribonucleotide/ribonucleoside analogs or derivatives as described herein or as known in the art. Strictly speaking, a “ribonucleoside” includes a nucleoside base and a ribose sugar, and a “ribonucleotide” is a ribonucleoside with one, two or three phosphate moieties. However, the terms “ribonucleoside” and “ribonucleotide” can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

In one aspect, a modified ribonucleoside includes a deoxyribonucleoside. For example, an iRNA agent can comprise one or more deoxynucleosides, including, for example, a deoxynucleoside overhang(s), or one or more deoxynucleosides within the double stranded portion of a dsRNA. However, it is self evident that under no circumstances is a double stranded DNA molecule encompassed by the term "iRNA."

In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect the technology described herein relates to a single stranded RNA that promotes the formation of a RISC complex to effect silencing of the target gene.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5' end, 3' end or both ends of either an antisense or sense strand of a dsRNA.

In another aspect, the agent is a single-stranded antisense RNA molecule. The antisense RNA molecule can have 15-30 nucleotides complementary to the target. For example, the antisense RNA molecule has a sequence of at least 15, 16, 17, 18, 19, 20, or more contiguous nucleotides from one of the antisense sequences of Tables 3 and/or 4.

In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5' and/or 3' terminus.

The term "sense strand," or "passenger strand" as used herein, refers to the strand of an iRNA that includes a region that is substantially complementary to a region of the antisense strand as that term is defined herein.

As used herein, in one embodiment, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817. These applications are incorporated herein by reference in their entirety. Examples of "SNALP" formulations are described elsewhere herein.

"Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA can also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781 which are hereby incorporated by reference in their entirety. In vitro introduction into a cell includes methods known in the art such as electroporation and lipofection. Further approaches are described herein below or are known in the art.

As used herein, the term "inhibit the expression of," refers to at an least partial reduction of Serpina 1 gene expression in a cell treated with an iRNA composition as described herein compared to the expression of Serpina 1 in an untreated cell.

The terms "silence," "inhibit the expression of," "down-regulate the expression of," "suppress the expression of," and the like, in so far as they refer to a Serpina 1 gene, herein refer to the at least partial suppression of the expression of a Serpina 1 gene, as manifested by a reduction of the amount of Serpina 1 mRNA which can be isolated from or detected in a first cell or group of cells in which a Serpina 1 gene is transcribed and which has or have been treated such that the expression of a Serpina 1 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition can be given in terms of a reduction of a parameter that is functionally linked to Serpina 1 gene expression, e.g., the amount of protein encoded by a Serpina 1 gene, or the number of cells displaying a certain phenotype, e.g., altered hepatocyte function. In principle, Serpina 1 gene silencing can be determined in any cell expressing Serpina 1, either constitutively or by genomic engineering, and by any appropriate assay. However, when a reference is needed in order to determine whether a given iRNA inhibits the expression of the Serpina 1 gene by a certain degree and therefore is encompassed by the instant invention, the assays provided in the Examples below shall serve as such reference.

For example, in certain instances, expression of a Serpina 1 gene is suppressed by at least about 10%, 15%, 20%, 25%, 30%, 35%, 40%, 45%, or 50% by administration of an iRNA featured herein. In some embodiments, a Serpina 1 gene is suppressed by at least about 60%, 70%, or 80% by administration of an iRNA featured herein. In some embodiments, a Serpina 1 gene is suppressed by at least about 85%, 90%, 95%, 98%, 99% or more by administration of an iRNA as described herein.

As used herein in the context of Serpina 1 expression, the terms "treat," "treatment," and the like, refer to relief from or alleviation of pathological processes mediated by Serpina 1 expression. In some embodiments, the terms "treat," "treatment," and the like mean to relieve or alleviate at least one symptom associated with such condition, or to slow or reverse the progression or anticipated progression of such condition, such as slowing the progression of a liver disorder, such as liver inflammation or cirrhosis.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, "prevention" or "preventing," when used in reference to a disease, disorder or symptoms thereof, refers to a reduction in the likelihood that an individual will develop a disease of disorder, e.g., a respiratory disorder. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

As used herein, the phrases "therapeutically effective amount" and "prophylactically effective amount" refer to an amount that provides a therapeutic benefit in the treatment, prevention, or management of pathological processes mediated by Serpina 1 expression or an overt symptom of pathological processes mediated by Serpina 1 expression. The specific amount that is therapeutically effective can be readily determined by an ordinary medical practitioner, and can vary depending on factors known in the art, such as, for example, the type of pathological processes mediated by Serpina 1 expression, the patient's history and age, the stage of pathological processes mediated by Serpina 1 expression, and the administration of other agents that inhibit pathological processes mediated by Serpina 1 expression.

As used herein, a "pharmaceutical composition" comprises a pharmacologically effective amount of an iRNA and a pharmaceutically acceptable carrier. As used herein, "pharmacologically effective amount," "therapeutically effective amount" or simply "effective amount" refers to that amount of an iRNA effective to produce the intended pharmacological, therapeutic or preventive result. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. For example, a therapeutically effective amount of an iRNA targeting Serpina 1 can reduce Serpina 1 protein levels by at least 10%.

As used herein, the term "alpha-1 anti-trypsin liver disease" refers to a condition in which Serpina 1 protein accumulates in the liver, resulting in liver injury and inflammation. Alpha-1 anti-trypsin liver disease can be hereditary and is known to occur more often in subjects with one or more copies of certain alleles (e.g. the PiZ, PiS, or PiM (Malton) alleles). Without wishing to be bound by theory, it is thought that alleles associated with a greater risk of developing alpha-1 anti-trypsin liver disease encode forms of Serpina 1 which are subject to misfolding and are not properly secreted from the hepatocytes. The cellular responses to these misfolded proteins can include the unfolded protein response, ERAD, apoptosis, ER overload response, autophagy, mitochondrial stress and altered hepatocyte function. The injuries to the hepatocytes can lead to symptoms such as, but not limited to, inflammation, cholestasis, fibrosis, cirrhosis, prolonged obstructive jaundice, increased transaminases, portal hypertension and/or hepatocellular carcinoma. Without wishing to be bound by theory, the highly variable clinical course of this disease is suggestive of modifiers or "second hits" as contributors to developing symptoms or progressing in severity. For example, subjects with a PiZ allele can be more sensitive to Hepatitis C infections or alcohol abuse and more likely to develop a liver disorder if exposed to such factors. A deficiency of alpha-1 antitrypsin can also cause or contribute to the development of early onset emphysema, necrotizing panniculitis, bronchiectasis, and/or prolonged neonatal jaundice. Some patients having or at risk of having a deficiency of alpha-1 antitrypsin are identified by screening when they have family members affected by an alpha-1 antitrypsin deficiency.

As used herein, the terms "liver disease" and "liver disorder" are used interchangeably and refer to any disorder which impairs liver function. A liver disorder can arise from one or more sources, which include but are not limited to, accumulation of Serpina 1 protein in the liver and/or liver cells, viral infections, parasitic infections, genetic predisposition, autoimmune diseases, exposure to radiation, exposure to hepatotoxic compounds, mechanical injuries, various environmental toxins, alcohol, acetaminophen, a combination of alcohol and acetaminophen, inhalation anesthetics, niacin, chemotherapeutics, antibiotics, analgesics, antiemetics and the herbal supplement kava. Symptoms of a liver disorder include, but are not limited to, inflammation, cirrhosis, fibrosis, hepatocellular carcinoma, necrosis, steatosis, fibrosis, cholestatis and/or reduction and/or loss of hepatocyte function. Liver disorders often lead to cirrhosis. Cirrhosis is a pathological condition associated with chronic liver damage that includes extensive fibrosis and regenerative nodules. “Fibrosis” as used herein refers to the proliferation of fibroblasts and the formation of scar tissue in the liver.

The phrase “liver function” refers to one or more of the many physiological functions performed by the liver. Such functions include, but are not limited to, regulating blood sugar levels, endocrine regulation, enzyme systems, interconversion of metabolites (e.g., ketone bodies, sterols and steroids and amino acids); manufacturing blood proteins such as fibrinogen, serum albumin, and cholinesterase, erythropoietic function, detoxification, bile formation, and vitamin storage. Several tests to examine liver function are known in the art, including, for example, measuring alanine amino transferase (ALT), alkaline phosphatase, bilirubin, prothrombin, and albumin.

The term “pharmaceutically acceptable carrier” refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents can include starch and gelatin, while the lubricating agent, if present, will generally be magnesium stearate, stearic acid or talc. If desired, the tablets can be coated with a material such as glyceryl monostearate or glyceryl distearate, to delay absorption in the gastrointestinal tract. Agents included in drug formulations are described further herein below.

As used herein, a therapeutic that “prevents” a liver disease is a composition that, in a statistical sample, reduces the occurrence of liver diseases or symptoms of liver disease in the treated sample relative to an untreated control sample, or delays the onset or reduces the severity of one or more symptoms of the disorder or condition relative to the untreated control sample.

As used herein, a “subject” is a mammal, e. g. a dog, horse, cat, and other non-human primates. In a preferred embodiment, a subject is a human.

As used herein, the term “LNPXX”, wherein the “XX” are numerals, is also referred to as “AFXX” herein. For example, LNP09 is also referred to AF09 and LNP12 is also known as or referred to as AF12.

As used herein, the term “comprising” or “comprises” is used in reference to compositions, methods, and respective component(s) thereof, that are essential to the invention, yet open to the inclusion of unspecified elements, whether essential or not.

As used herein, the term “consisting essentially of” refers to those elements required for a given embodiment. The term permits the presence of elements that do not materially affect the basic and novel or functional characteristic(s) of that embodiment of the invention.

The term “consisting of” refers to compositions, methods, and respective components thereof as described herein, which are exclusive of any element not recited in that description of the embodiment.

Double-Stranded Ribonucleic Acid (dsRNA)

Described herein are iRNA agents that inhibit the expression of the Serpina 1 gene. In one embodiment, the iRNA agent includes double-stranded ribonucleic acid (dsRNA) molecules for inhibiting the expression of a Serpina 1 gene in a cell or mammal, e.g., in a human having a lipid disorder, where the dsRNA includes an antisense strand having a region of complementarity which is complementary to at least a part of an mRNA formed in the expression of a Serpina 1 gene, and where the region of complementarity is 30 nucleotides or less in length, generally 19-24 nucleotides in length, and where the dsRNA, upon contact with a cell expressing the Serpina 1 gene, inhibits the expression of the Serpina 1 gene by at least 10% as assayed by, for example, a PCR or branched DNA (bDNA)-based method, or by a protein-based method, such as by Western blot. In one embodiment, the iRNA agent activates the expression of a Serpina 1 gene in a cell or mammal. Expression of a Serpina 1 gene in cell culture, such as in COS cells, HeLa cells, primary hepatocytes, HepG2 cells, primary cultured cells or in a biological sample from a subject, can be assayed by measuring Serpina 1 mRNA levels, such as by bDNA or TaqMan assay, or by measuring protein levels, such as by immunofluorescence analysis, using, for example, Western Blotting or flowcytometric techniques A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a Serpina 1 gene. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a “part” of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, then, a miRNA is a dsRNA. In another embodiment, a dsRNA is not a naturally occurring miRNA. In another embodiment, an iRNA agent useful to target Serpina 1 expression is not generated in the target cell by cleavage of a larger dsRNA.

A dsRNA as described herein can further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc. In one embodiment, a Serpina 1 gene is a human Serpina 1 gene. In another embodiment, the Serpina 1 gene is a rhesus Serpina 1 gene. In another embodiment the Serpina 1 gene is a mouse or a rat Serpina 1 gene. In specific embodiments, the first sequence is a sense strand of a dsRNA that includes a sense sequence from one of Tables 3 and 4, and the second sequence is selected from the group consisting of the anti-sense sequences of one of Tables 3 and 4. Alternative dsRNA agents that target elsewhere in the target sequence provided in Tables 3 and 4 can readily be determined using the target sequence and the flanking Serpina 1 sequence.

In one aspect, a dsRNA will include at least two nucleotide sequences, a sense and an anti-sense sequence, whereby the sense strand is selected from the groups of sequences provided in Tables 3 and 4, and the corresponding antisense strand of the sense strand selected from Tables 3 and 4. In this aspect, one of the two sequences is complementary to the other of the two sequences, with one of the sequences being substantially complementary to a sequence of an mRNA generated in the expression of a Serpina 1 gene. As such, in this aspect, a dsRNA will include two oligonucleotides, where one oligonucleotide is described as the sense strand in Tables 3 and 4, and the second oligonucleotide is described as the corresponding antisense strand of the sense strand in Tables 3 and 4. As described elsewhere herein and as known in the art, the complementary sequences of a dsRNA can also be contained as self-complementary regions of a single nucleic acid molecule, as opposed to being on separate oligonucleotides.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer RNA duplex structures can be effective as well. In the embodiments described above, by virtue of the nature of the oligonucleotide sequences provided in Tables 3 and 4 dsRNAs described herein can include at least one strand of a length of minimally 21 nt. It can be reasonably expected that shorter duplexes having one of the sequences of Tables 3 and 4 minus only a few nucleotides on one or both ends can be similarly effective as compared to the dsRNAs described above. Hence, dsRNAs having a partial sequence of at least 15, 16, 17, 18, 19, 20, or more contiguous nucleotides from one of the sequences of Tables 3 and 4, and differing in their ability to inhibit the expression of a Serpina 1 gene by not more than 5, 10, 15, 20, 25, or 30% inhibition from a dsRNA comprising the full sequence, are contemplated according to the technology described herein.

In addition, the RNAs provided in Tables 3 and 4 identify a site in a Serpina 1 transcript that is susceptible to RISC-mediated cleavage. As such, the technology described herein further features iRNAs that target within one of such sequences. As used herein, an iRNA is said to target within a particular site of an RNA transcript if the iRNA promotes cleavage of the transcript anywhere within that particular site. Such an iRNA will generally include at least 15 contiguous nucleotides from one of the sequences provided in Tables 3 and 4 coupled to additional nucleotide sequences taken from the region contiguous to the selected sequence in a Serpina 1 gene.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in Tables 3 and 4 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in Tables 3 and 4, further optimization could be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of iRNAs based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch not be located in the center of the region of complementarity. If the antisense strand of the iRNA contains mismatches to the target sequence, it is preferable that the mismatch be restricted to be within the last 5 nucleotides from either the 5' or 3' end of the region of complementarity. For example, for a 23 nucleotide iRNA agent RNA strand which is complementary to a region of a Serpina 1 gene, the RNA strand generally does not contain any mismatch within the central 13 nucleotides. The methods described herein or methods known in the art can be used to determine whether an iRNA containing a mismatch to a target sequence is effective in inhibiting the expression of a Serpina 1 gene. Consideration of the efficacy of iRNAs with mismatches in inhibiting expression of a Serpina 1 gene is important, especially if the particular region of complementarity in a Serpina 1 gene is known to have polymorphic sequence variation within the population.

In one embodiment, at least one end of a dsRNA has a single-stranded nucleotide overhang of 1 to 4, generally 1 or 2 nucleotides. dsRNAs having at least one nucleotide overhang can have unexpectedly superior inhibitory properties relative to their blunt-ended counterparts. In yet another embodiment, the RNA of an iRNA, e.g., a dsRNA, is chemically modified to enhance stability or other beneficial characteristics. The nucleic acids featured in the technology described herein can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other embodiments, suitable RNA mimetics suitable are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the technology described herein include RNAs with phosphorothioate backbones and oligonucleosides with heteroatom backbones, and in particular $—CH_2—NH—CH_2—$, $—CH_2—N(CH_3)—O—CH_2—$[known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2—$[wherein the native phosphodiester backbone is represented as $—O—P—O—CH_2—$] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)._nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10.

In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the technology described herein. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the technology described herein involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethylammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic (PK) modulator. As used herein, a "PK modulator" refers to a pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the technology described herein as ligands (e.g. as PK modulating ligands). In addition, aptamers that bind serum components (e.g. serum proteins) are also suitable for use as PK modulating ligands in the embodiments described herein.

Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

Cell Permeation Peptide and Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 25). An RFGF analogue (e.g., amino acid sequence AALLPVLLAAP (SEQ ID NO: 26) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 27) and the *Drosophila* Antennapedia protein (RQIKIWFQNRRMKWKK (SEQ ID NO: 28) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of a dsRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing avB3 (Haubner et al., Jour. Nucl. Med., 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., β-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

Carbohydrate Conjugates

In some embodiments, the iRNA oligonucleotides described herein further comprise carbohydrate conjugates. The carbohydrate conjugates are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include C5 and above (preferably C5-C8) sugars; di- and trisaccharides include sugars having two or three monosaccharide units (preferably C5-C8).

In one embodiment, the carbohydrate conjugate is selected from the group consisting of:
Formula II
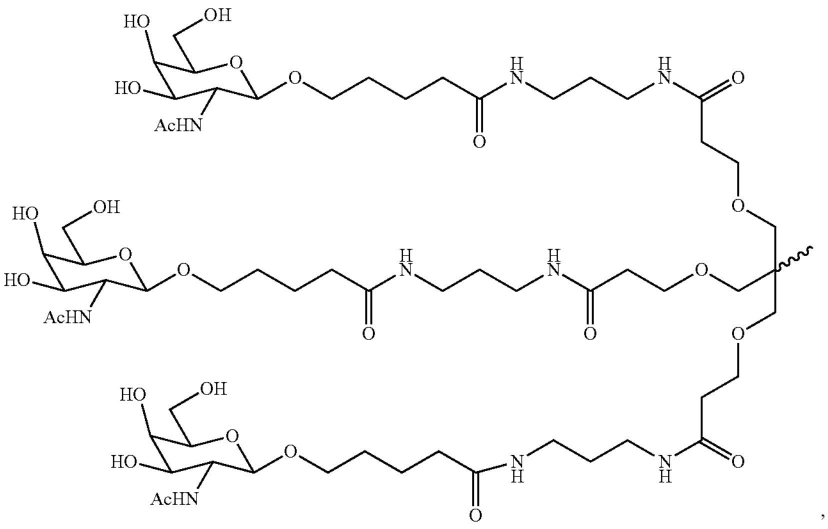
,
Formula III
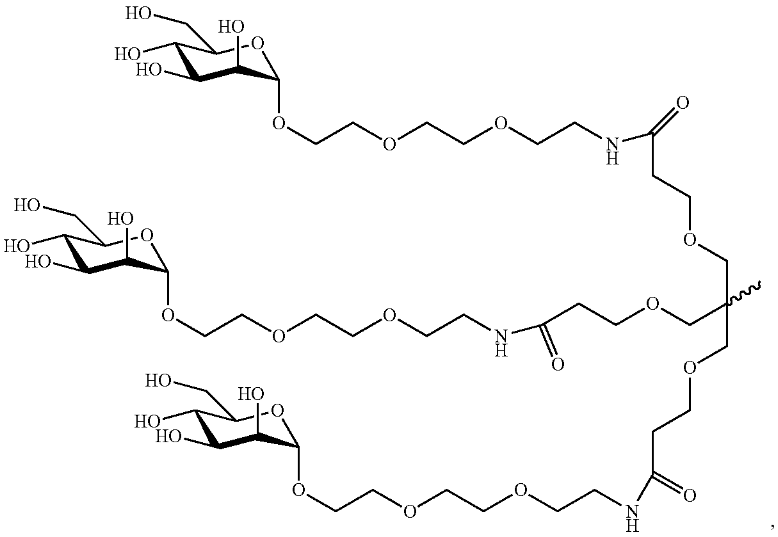
,
Formula IV
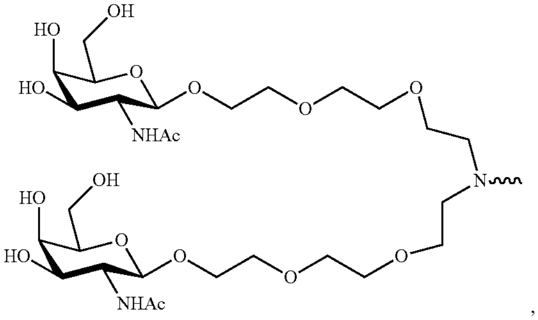
,
Formula V
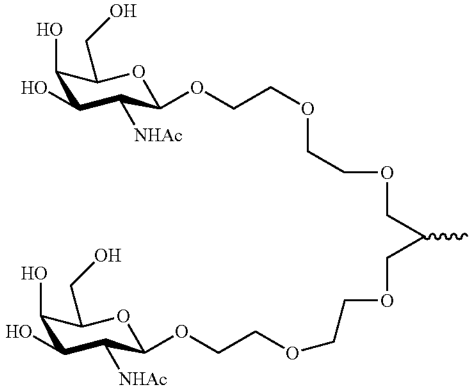
, -continued
Formula VI
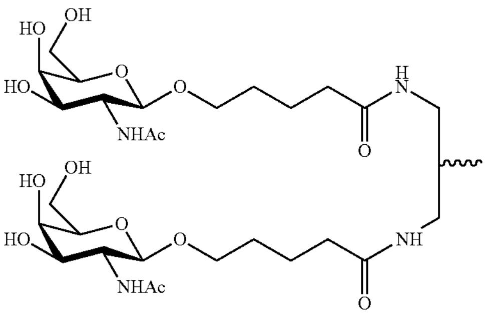
,
Formula VII
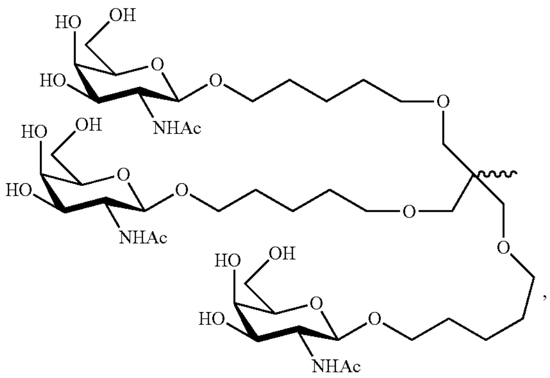
,
Formula VIII
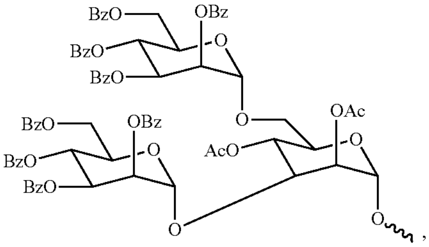
,
Formula IX
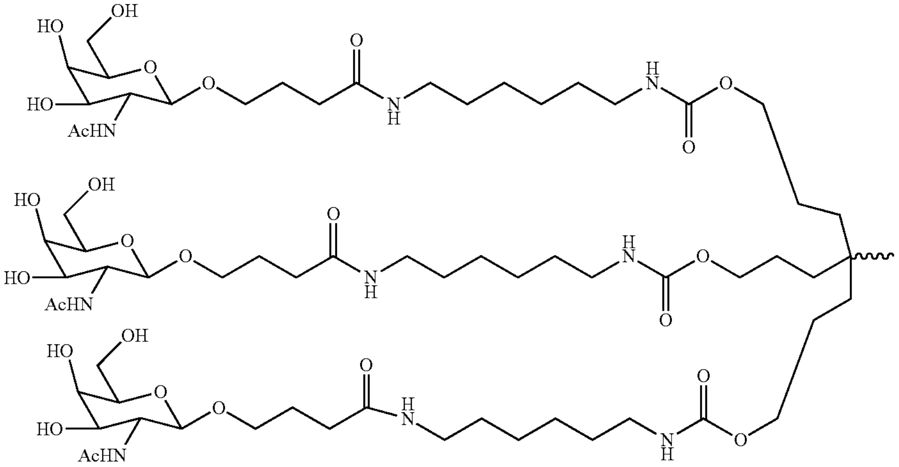
,
Formula X
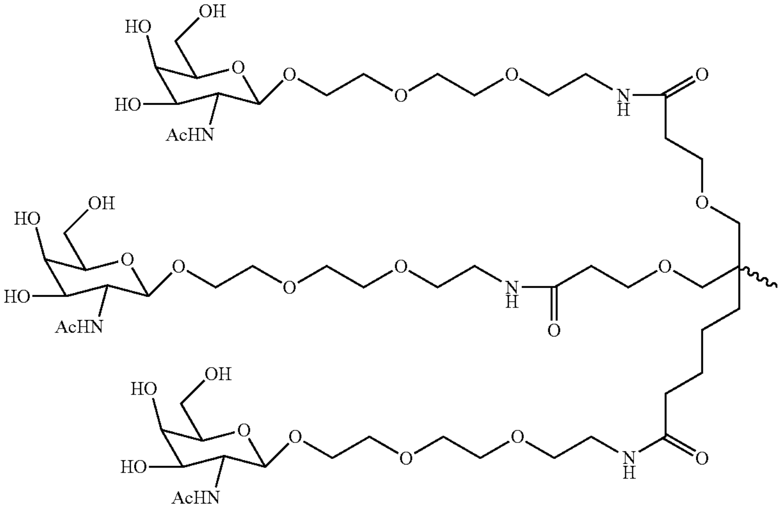
, -continued
Formula XI
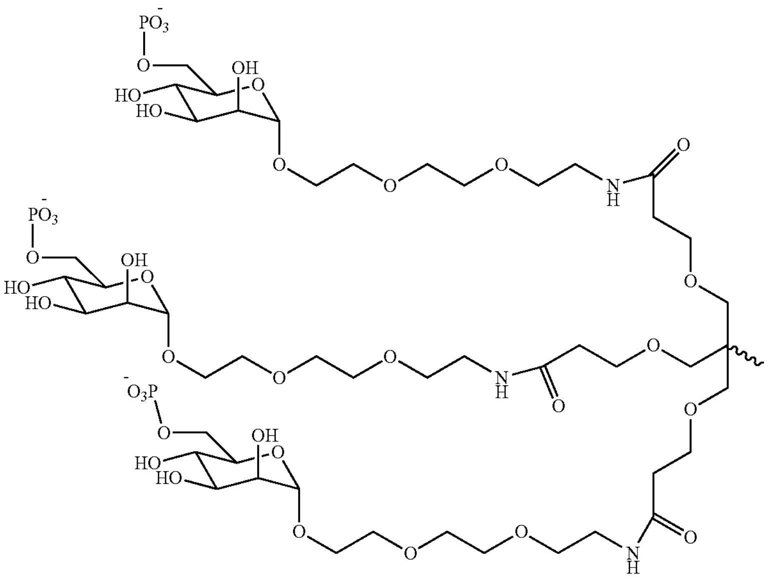
,
Formula XII
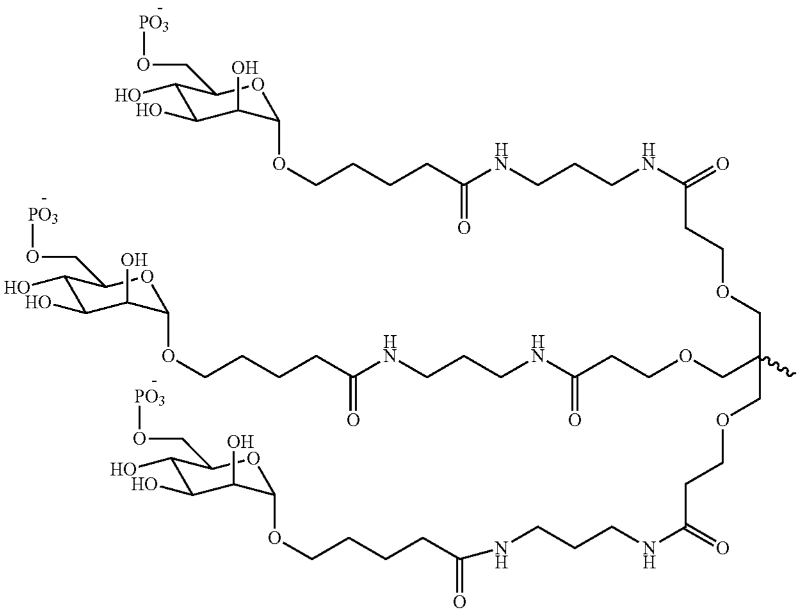
,
Formula XIII
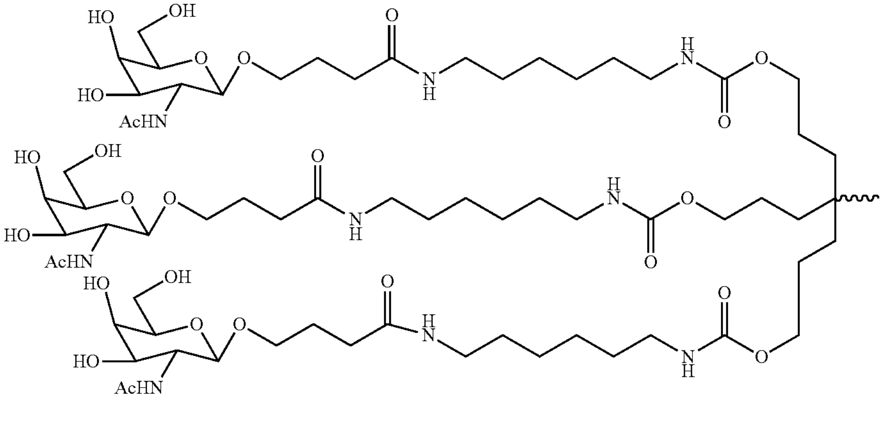
, -continued
Formula XIV
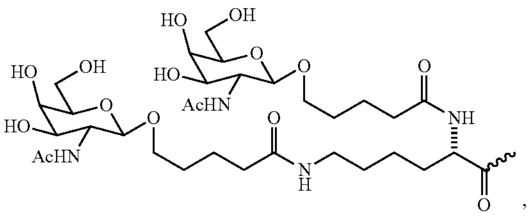
,
Formula XV
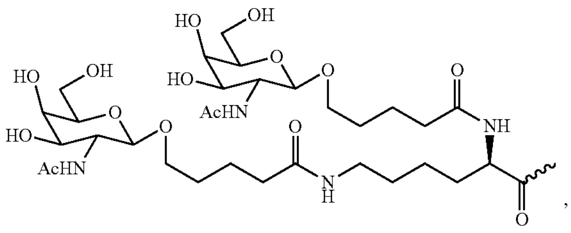
,
Formula XVI
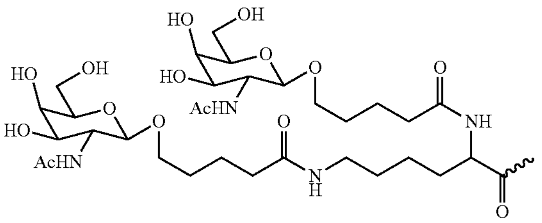
,
Formula XVII
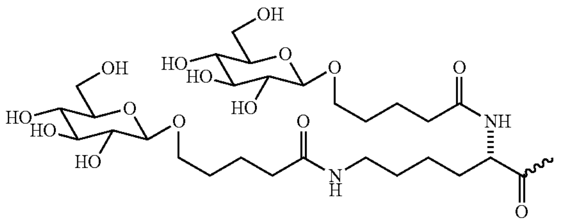
,
Formula XVIII
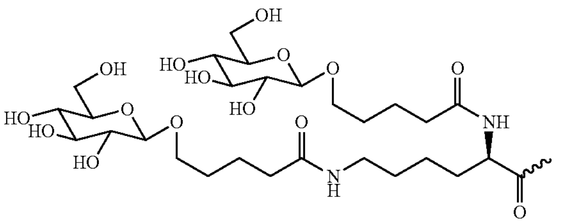
,
Formula XIX
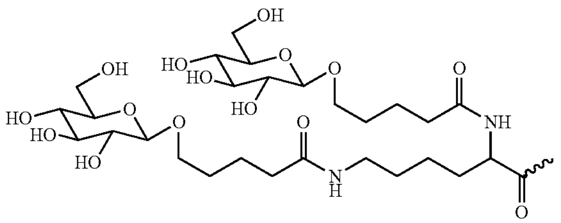
,
Formula XX
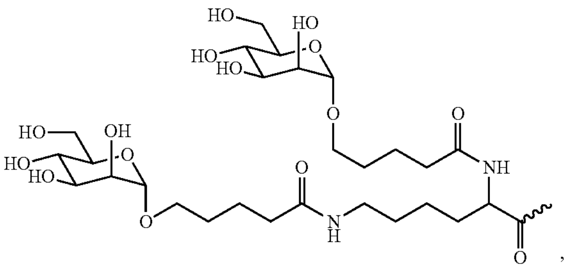
,
Formula XXI
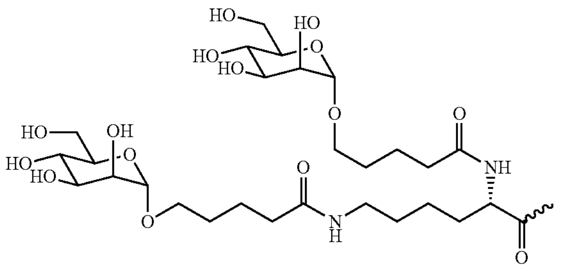
,
Formula XXII
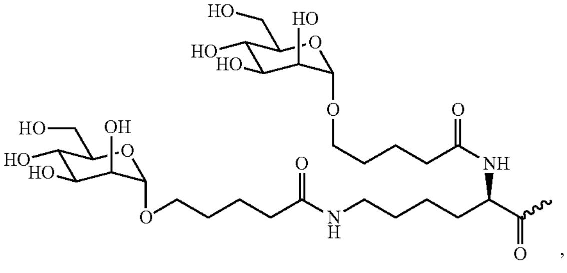
, i.e., Formula II-Formula XXII.

Another representative carbohydrate conjugate for use in the embodiments described herein includes, but is not limited to, (Formula XXIII)

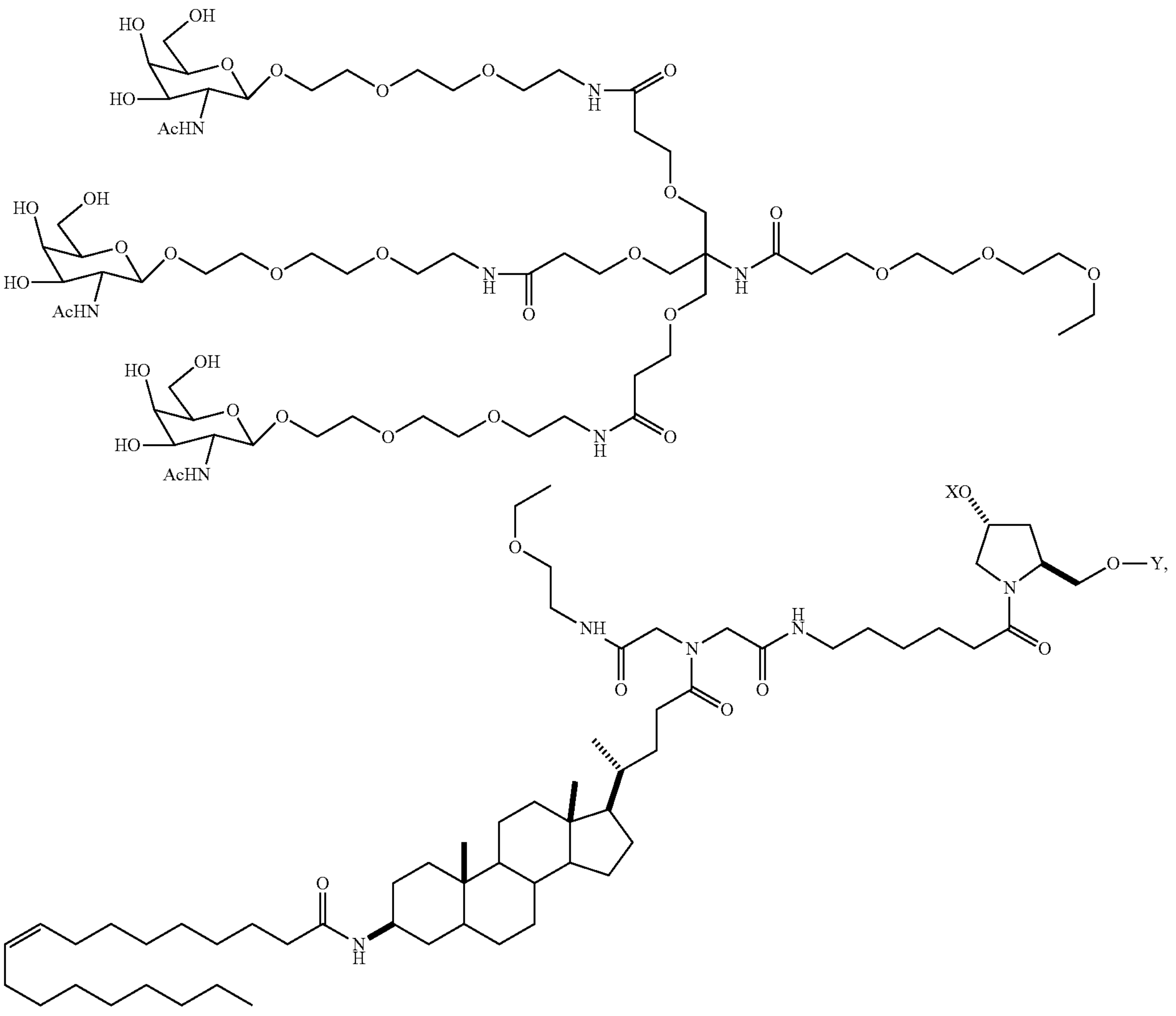

when one of X or Y is an oligonucleotide, the other is a hydrogen.

In some embodiments, the carbohydrate conjugate further comprises other ligand such as, but not limited to, PK modulator, endosomolytic ligand, and cell permeation peptide.

Linkers

In some embodiments, the conjugates described herein can be attached to the iRNA oligonucleotide with various linkers that can be cleavable or non cleavable.

The term "linker" or "linking group" means an organic moiety that connects two parts of a compound. Linkers typically comprise a direct bond or an atom such as oxygen or sulfur, a unit such as NRB, C(O), C(O)NH, SO, SO2, SO2NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO2, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula NHCHRAC(O)NHCHRBC(O)—, where RA and RB are the R groups of the two adjacent amino acids. These candidates can be evaluated using methods analogous to those described above.

Representative carbohydrate conjugates with linkers include, but are not limited to, (Formula XXIV)

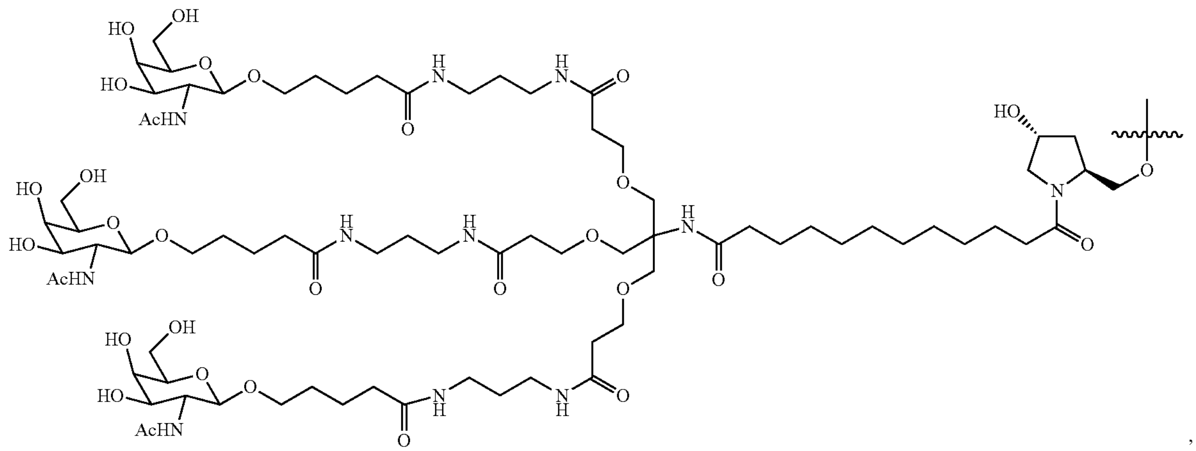

, (Formula XXV)

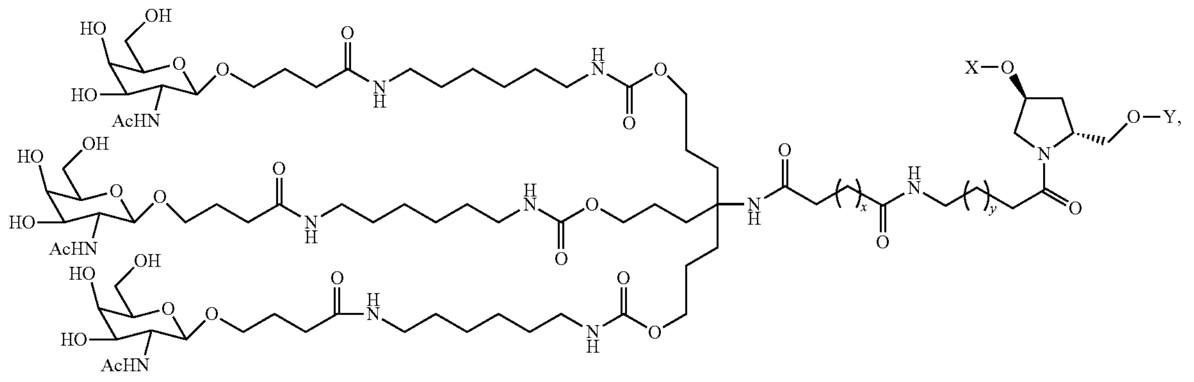

x = 1-30
y = 1-15

(Formula XXVI)

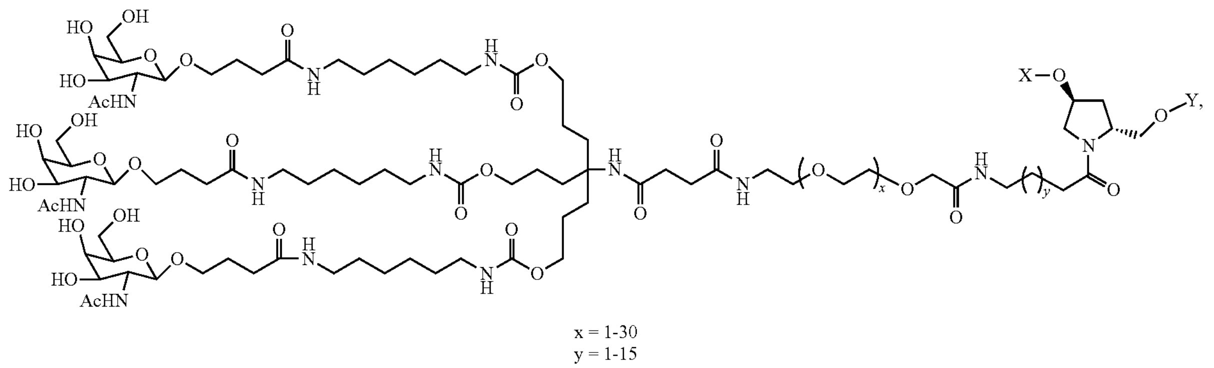

x = 1-30
y = 1-15

-continued
(Formula XXVII)
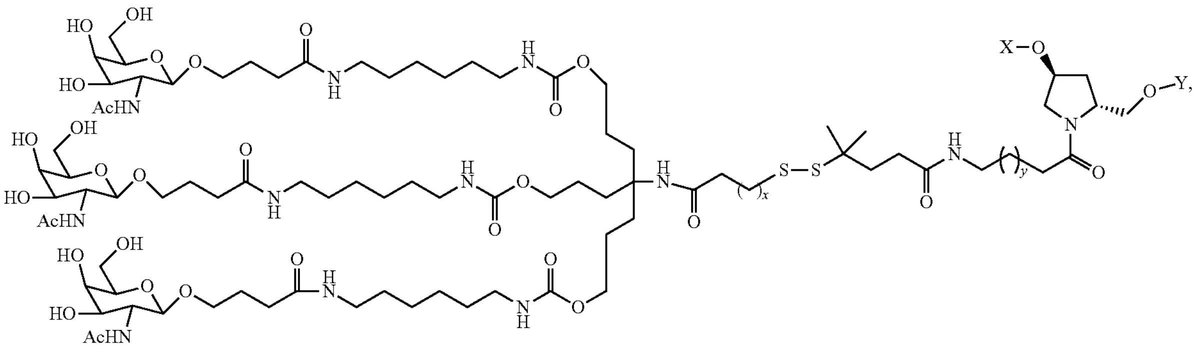
x = 0-30
y = 1-15
(Formula XXVIII)
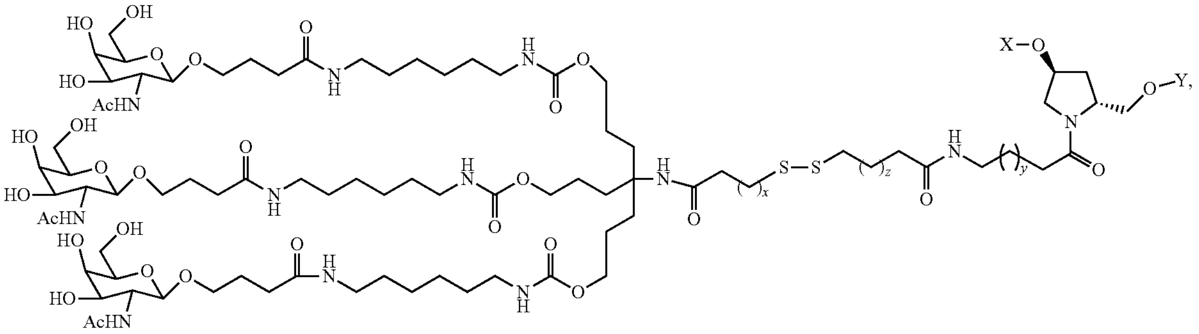
x = 0-30
y = 1-15
z = 1-20
(Formula XXIX)
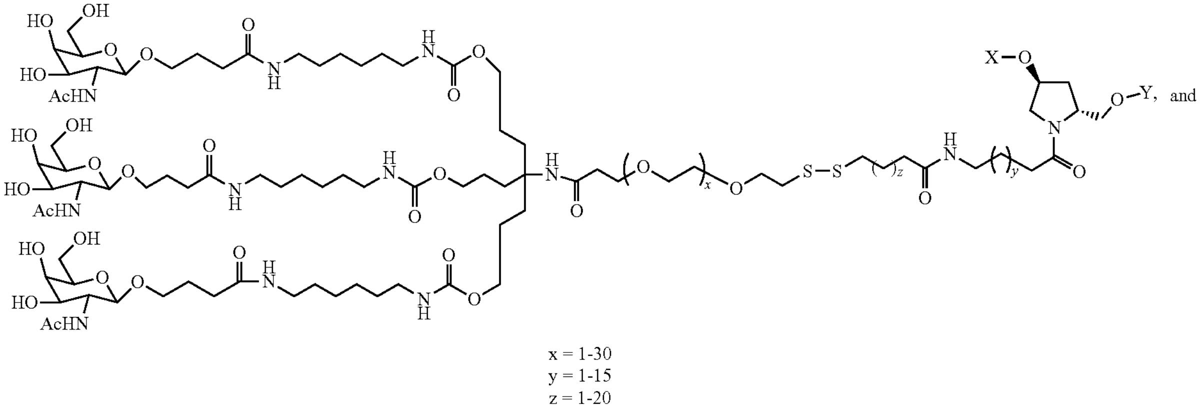
and
x = 1-30
y = 1-15
z = 1-20

-continued (Formula XXX)

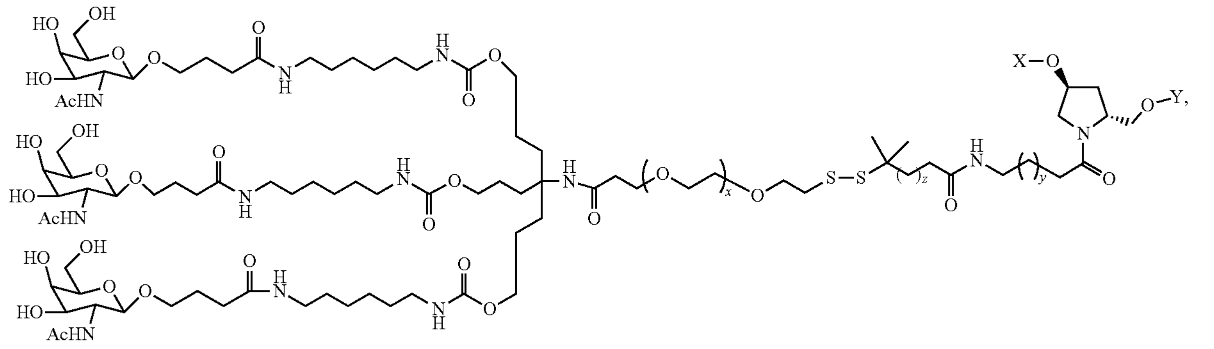

x = 1-30
y = 1-15
z = 1-20 when one of X or Y is an oligonucleotide, the other is a hydrogen.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference.

It is not necessary for all positions in a given compound to be uniformly modified, and in fact more than one of the aforementioned modifications can be incorporated in a single compound or even at a single nucleoside within an iRNA. The technology described herein also includes iRNA compounds that are chimeric compounds. "Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

Delivery of iRNA

The delivery of an iRNA to a subject in need thereof can be achieved in a number of different ways. In vivo delivery can be performed directly by administering a composition comprising an iRNA, e.g. a dsRNA, to a subject. Alternatively, delivery can be performed indirectly by administering one or more vectors that encode and direct the expression of the iRNA. These alternatives are discussed further below.

Delivery of an iRNA Composition

In general, any method of delivering a nucleic acid molecule can be adapted for use with an iRNA (see e.g., Akhtar S. and Julian R L. (1992) Trends Cell. Biol. 2(5): 139-144 and WO94/02595, which are incorporated herein by reference in their entireties). However, there are three factors that are important to consider in order to successfully deliver an iRNA molecule in vivo: (a) biological stability of the delivered molecule, (2) preventing non-specific effects, and (3) accumulation of the delivered molecule in the target tissue. The non-specific effects of an iRNA can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) Journal of Controlled Release 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) J. Mol. Biol 327:761-766; Verma, UN., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, UN., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

Vector Encoded dsRNAs

In another aspect, iRNA targeting the Serpina 1 gene can be expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding an iRNA can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding an iRNA are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing an iRNA featured in the technology described herein, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the technology described herein, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Pharmaceutical Compositions Containing iRNA

In one embodiment, provided herein are pharmaceutical compositions containing an iRNA, as described herein, and a pharmaceutically acceptable carrier. The pharmaceutical composition containing the iRNA is useful for treating a disease or disorder associated with the expression or activity of a Serpina 1 gene, e.g. alpha-1 anti-trypsin deficiency liver disease. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

The pharmaceutical compositions featured herein are administered in dosages sufficient to inhibit expression of Serpina 1 genes. In general, a suitable dose of iRNA will be in the range of 0.001 to 200.0 milligrams per kilogram body weight of the recipient per day, generally in the range of 1 to 50 mg per kilogram body weight per day. For example, the dsRNA can be administered at 0.01 mg/kg, 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the technology described herein. In this embodiment, the dosage unit contains a corresponding multiple of the daily dose.

The effect of a single dose on Serpina 1 levels can be long lasting, such that subsequent doses are administered at not more than 3, 4, or 5 day intervals, or at not more than 1, 2, 3, or 4 week intervals.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the technology described herein can be made using conventional methodologies or on the basis of in vivo testing using an appropriate animal model, as described elsewhere herein.

Advances in mouse genetics have generated a number of mouse models for the study of various human diseases, such as pathological processes mediated by Serpina 1 expression. Such models can be used for in vivo testing of iRNA, as well as for determining a therapeutically effective dose. A suitable mouse model is, for example, a mouse containing a transgene expressing human Serpina 1 , e.g., an allele prone to misfolding.

The technology described herein also includes pharmaceutical compositions and formulations which include the iRNA compounds featured in the technology described herein. The pharmaceutical compositions of the technology described herein can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the technology described herein are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the technology described herein can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the technology described herein, the term “liposome” means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to traverse intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent can act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight nucleic acid into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged nucleic acid molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap nucleic acids rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. S.T.P. Pharma. Sci., 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describes PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes can include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a Serpina 1 dsRNA featured in the technology described herein is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the technology described herein typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the technology described herein are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, di stearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

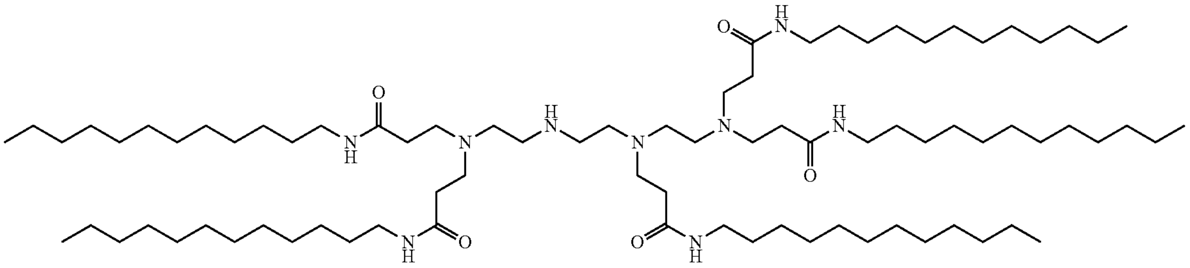

ND98 Isomer I

LNP01 formulations are described, e.g., in International Application Publication No. WO 2008/042973, which is hereby incorporated by reference.

Additional exemplary lipid-dsRNA formulations are as follows:

TABLE 1

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 Lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, Lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |

TABLE 1-continued

| | Ionizable/Cationic Lipid | cationic lipid/non-cationic lipid/cholesterol/PEG-lipid conjugate Lipid:siRNA ratio |
|---|---|---|
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: di stearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Provisional Ser. No. 61/244,834, filed Sep. 22, 2009, U.S. Provisional Ser. No. 61/185,800, filed Jun. 10, 2009, and International Application No. PCT/US10/28224, filed Jun. 10, 2010, which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the technology described herein can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(═O)alkyl, —C(═O)alkenyl, and —C(═O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (═O) two hydrogen atoms are replaced. In this regard, substituents include oxo, halogen, heterocycle, —CN, —ORx, —NRxRy, —NRxC(═O)Ry, —NRxSO2Ry, —C(═O)Rx, —C(═O)ORx, —C(═O)NRxRy, SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(═O)Ry, —NRxSO2Ry, —C(═O)Rx, —C(═O)ORx, —C(═O)NRxRy, —SOnRx and —SOnNRxRy.

"Halogen" means fluoro, chloro, bromo and iodo.

In some embodiments, the methods of the technology described herein can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of the technology described herein are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the technology described herein are formulated using a cationic lipid of formula A:

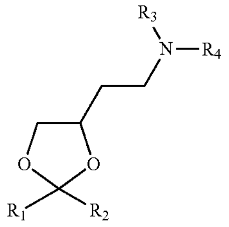

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

Scheme 1

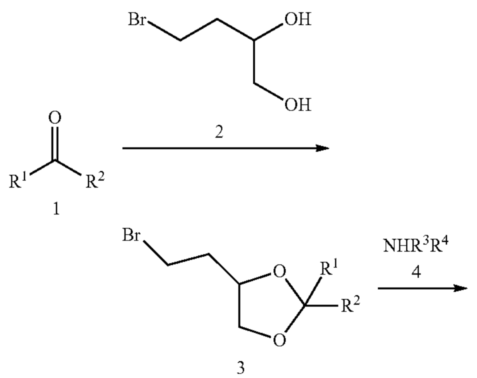

-continued

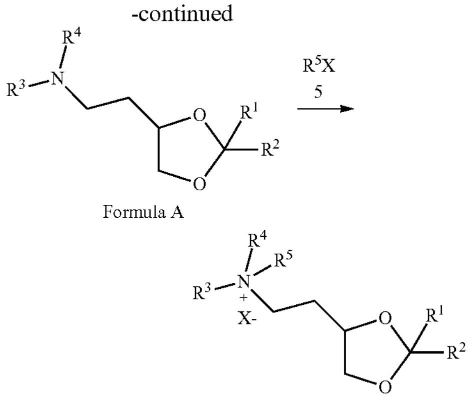

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

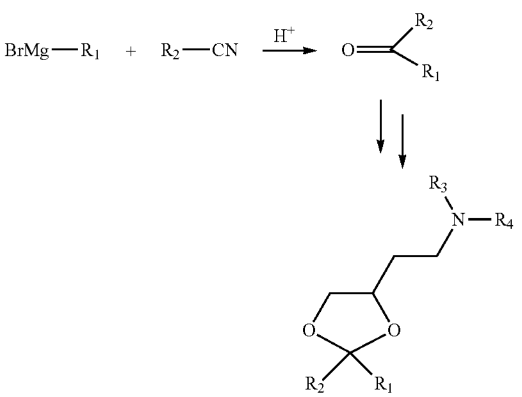

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino) butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

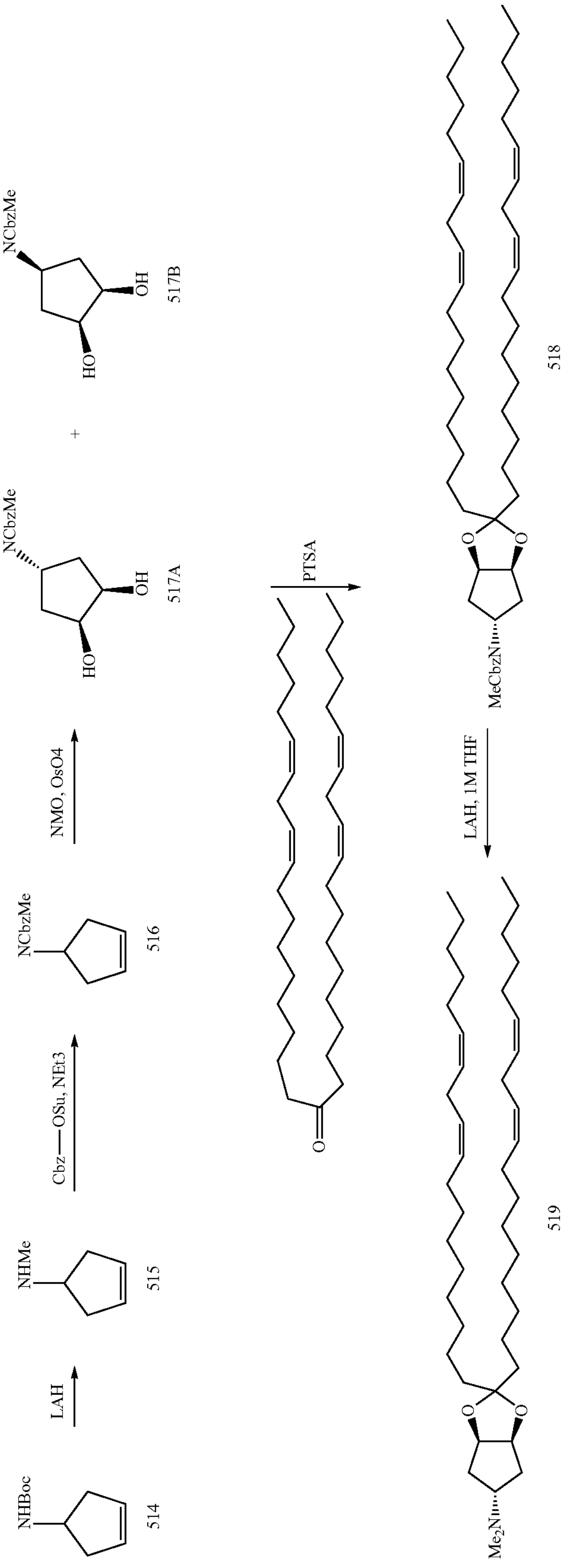
514 515 516 517A 517B 518 519

Synthesis of 515

To a stirred suspension of LiA1H4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated $NaHCO_3$ solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OSO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated $NaHCO_3$(1×50 mL) solution, water (1×30 mL) and finally with brine (lx 50 mL). Organic phase was dried over an.Na2SO4 and solvent was removed in vacuum. Silica gel column chromatographic purification of the crude material was afforded a mixture of diastereomers, which were separated by prep HPLC. Yield:−6 g crude 517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H]-266.3, [M+$NH_4$+]-283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR □=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the technology described herein are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the technology described herein can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the technology described herein include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the technology described herein, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the technology described herein can be formulated into any of many possible dosage forms such as, but not limited to, tablets, capsules, gel capsules, liquid syrups, soft gels, suppositories, and enemas. The compositions of the technology described herein can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

Additional Formulations

Emulsions

The compositions of the technology described herein can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.;

Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the technology described herein, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (M0310), hexaglycerol monooleate (P0310), hexaglycerol pentaoleate (P0500), decaglycerol monocaprate (MCA750), decaglycerol monooleate (M0750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the technology described herein will facilitate the increased systemic absorption of iRNAs and nucleic acids from the gastrointestinal tract, as well as improve the local cellular uptake of iRNAs and nucleic acids.

Microemulsions of the technology described herein can also contain additional components and additives such as sorbitan monostearate (Grill 3), Labrasol, and penetration enhancers to improve the properties of the formulation and to enhance the absorption of the iRNAs and nucleic acids of the technology described herein. Penetration enhancers used in the microemulsions of the technology described herein can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the technology described herein employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants: In connection with the technology described herein, surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the technology described herein, can be defined as compounds that remove metallic ions from solution by forming complexes therewith, with the result that absorption of iRNAs through the mucosa is enhanced. With regards to their use as penetration enhancers in the technology described herein, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the technology described herein. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass[a] D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the technology described herein also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the technology described herein. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the technology described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the technology described herein, such as dyes, flavoring agents, preservatives, antioxidants, opacifiers, thickening agents and stabilizers. However, such materials, when added, should not unduly interfere with the biological activities of the components of the compositions of the technology described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the technology described herein include (a) one or more iRNA compounds and (b) one or more agents which function by a non-RNAi mechanism and which are useful in treating a liver disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Agents which can be useful in treating alpha-1 anti-trypsin liver disorder include, but are not limited to, tauro-doexycholic acid, selenium, PBA chaperone protein and/or compositions which increase the expression of PBA chaperone protein, Prolastin®, and/or rAAV-AAT administration (Brantly et al., Hum Gene Ther 1177-86).

Agents useful in treating alcoholic liver disease include, but are not limited to, oxandrolone and propylthiouracil.

Agents useful in treating chronic viral hepatitis include, but are not limited to, alpha interferon, peginterferon, ribavirin, lamivudine, and adefovir dipivoxil.

Agents useful in treating autoimmune liver diseases include, but are not limited to, prednisone and azathioprine.

Agents useful in treating steatorrhoeic hepatosis and non-alcoholic steatohepatities include, but are not limited to, metformin and thiazolidinones such as pioglitazone, troglitizone, and rosiglitazone.

Agents useful in treating hepatic cancer include, but are not limited to, chemotherapy and radiation. Accordingly, a treatment can include, for example, chemotherapy (for example, chlorambucil, prednisone, prednisolone, vincristine, cytarabine, clofarabine, farnesyl transferase inhibitors, decitabine, inhibitors of MDR1), rituximab, interferon-α, anthracycline drugs (such as daunorubicin or idarubicin), L-asparaginase, doxorubicin, cyclophosphamide, doxorubicin, bleomycin, fludarabine, etoposide, pentostatin, or cladribine), bone marrow transplant, stem cell transplant, anti-metabolite drugs (methotrexate and 6-mercaptopurine), or any combination thereof.

Chemotherapy is the treatment of cancer with drugs that can destroy cancer cells. In current usage, the term “chemotherapy” usually refers to cytotoxic drugs which affect rapidly dividing cells in general, in contrast with targeted therapy. Chemotherapy drugs interfere with cell division in various possible ways, e.g. with the duplication of DNA or the separation of newly formed chromosomes. Most forms of chemotherapy target all rapidly dividing cells and are not specific to cancer cells, although some degree of specificity can come from the inability of many cancer cells to repair DNA damage, while normal cells generally can. Most chemotherapy regimens are given in combination. Exemplary chemotherapeutic agents include, but are not limited to, 5-FU Enhancer, 9-AC, AG2037, AG3340, Aggrecanase Inhibitor, Aminoglutethimide, Amsacrine (m-AMSA), Asparaginase, Azacitidine, Batimastat (BB94), BAY 12-9566, BCH-4556, Bis-Naphtalimide, Busulfan, Capecitabine, Carboplatin, Carmustaine+Polifepr Osan, cdk4/cdk2 inhibitors, Chlorombucil, CI-994, Cisplatin, Cladribine, CS-682, Cytarabine HCl, D2163, Dactinomycin, Daunorubicin HCl, DepoCyt, Dexifosamide, Docetaxel, Dolastain, Doxifluridine, Doxorubicin, DX8951f, E 7070, EGFR, Epirubicin, Erythropoietin, Estramustine phosphate sodium, Etoposide (VP16-213), Farnesyl Transferase Inhibitor, FK 317, Flavopiridol, Floxuridine, Fludarabine, Fluorouracil (5-FU), Flutamide, Fragyline, Gemcitabine, Hexamethylmelamine (HMM), Hydroxyurea (hydroxycarbamide), Ifosfamide, Interferon Alfa-2a, Interferon Alfa-2b, Interleukin-2, Irinotecan, ISI 641, Krestin, Lemonal DP 2202, Leuprolide acetate (LHRH-releasing factor analogue), Levamisole, LiGLA (lithium-gamma linolenate), Lodine Seeds, Lometexol, Lomustine (CCNU), Marimistat, Mechlorethamine HCl (nitrogen mustard), Megestrol acetate, Meglamine GLA, Mercaptopurine, Mesna, Mitoguazone (methyl-GAG; methyl glyoxal bis-guanylhydrazone; MGBG), Mitotane (o.p'-DDD), Mitoxantrone, Mitoxantrone HCl, MMI 270, MMP, MTA/LY 231514, Octreotide, ODN 698, OK-432, Oral Platinum, Oral Taxoid, Paclitaxel (TAXOL®), PARP Inhibitors, PD 183805, Pentostatin (2' deoxycoformycin), PKC 412, Plicamycin, Procarbazine HCl, PSC 833, Ralitrexed, RAS Farnesyl Transferase Inhibitor, RAS Oncogene Inhibitor, Semustine (methyl-CCNU), Streptozocin, Suramin, Tamoxifen citrate, Taxane Analog, Temozolomide, Teniposide (VM-26), Thioguanine, Thiotepa, Topotecan, Tyrosine Kinase, UFT (Tegafur/Uracil), Valrubicin, Vinblastine sulfate, Vindesine sulfate, VX-710, VX-853, YM 116, ZD 0101, ZD 0473/Anormed, ZD 1839, ZD 9331

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the technology described herein lies generally within a range of circulating concentrations that include the ED50 with little or no toxicity. The dosage can vary within this range depending upon the dosage form employed and the route of administration utilized. For any compound used in the methods featured in the technology described herein, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the technology described herein can be administered in combination with other known agents effective in treatment of pathological processes mediated by Serpina 1 expression. In any event, the administering physician can adjust the amount and timing of iRNA administration on the basis of results observed using standard measures of efficacy known in the art or described herein.

Methods for Treating or Preventing Diseases Caused by Expression of a Serpina 1 Gene The technology described herein relates to the use of an iRNA targeting Serpina 1 and compositions containing at least one such iRNA for the treatment or prevention of a Serpina 1-mediated disorder or disease. For example, a composition containing an iRNA targeting a Serpina 1 gene is used for treatment or prevention of liver disorders such as alpha-1 anti-trypsin deficiency liver disease, chronic liver disease, liver inflammation, cirrhosis, liver fibrosis, and/or hepatocellular carcinoma.

The technology described herein further relates to the use of an iRNA or a pharmaceutical composition thereof, e.g., for treating a liver disorder, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting Serpina 1 is administered in combination with, e.g., an agent useful in treating a liver disorder as described elsewhere herein.

The iRNA and an additional therapeutic agent can be administered in the same combination, e.g., parenterally, or the additional therapeutic agent can be administered as part of a separate composition or by another method known in the art or described herein.

The technology described herein features a method of administering an iRNA agent targeting Serpina 1 to a patient having a disease or disorder mediated by Serpina 1 expression, such as a liver disorder. Administration of the dsRNA can resulting in a reduction of the severity, signs, symptoms, and/or markers of such diseases or disorders in a patient with a liver disorder. By "reduction" in this context is meant a statistically significant decrease in such level. The reduction can be, for example, at least 10%, at least 20%, at least 30%, at least 40% or more, and is preferably reduced to a level accepted as within the range of normal for an individual without such disorder.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of liver fibrosis or amelioration of liver fibrosis can be assessed, for example by periodic monitoring of liver fibrosis markers: α-2-macroglobulin (a-MA), transferrin, apolipoproteinA1, hyaluronic acid (HA), laminin, N-terminal procollagen III(PIIINP), 7S collagen IV (7S-IV), total bilirubin, indirect bilirubin, alanine aminotransferase (ALT), aspartate aminotransferase (AST), AST/ALT, g-glutamyl transpeptidase (GGT), alkaline phosphatase (ALP), albumin, albumin/globulin, blood urea nitrogen (BUN), creatinine (Cr), triglyceride, cholersterol, high density lipoprotein and low density lipoprotein and liver puncture biopsy. Liver fibrosis markers can be measured and/or liver puncture biopsy can be performed before treatment (initial readings) and subsequently (later readings) during the treatment regimen. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting Serpina 1 or pharmaceutical composition thereof, "effective against" a hepatic fibrosis condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating liver fibrosis and the related causes.

The iRNA treatments described herein can be used to treat individuals having the signs, symptoms and/or markers of, or being diagnosed with, or being a risk of having alpha-1 anti-trypsin deficiency liver disorder, liver inflammation, cirrhosis, liver fibrosis, and/or hepatoceullar carcinoma. One of skill in the art can easily monitor the signs, symptoms, and/or makers of such disorders in subjects receiving treatment with iRNA as described herein and assay for a reduction in these signs, symptoms and/or makers of at least 10% and preferably to a clinical level representing a low risk of liver disease.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, for certain indications, the efficacy can be measured by an increase in serum levels of Serpina 1 protein. As an example, an increase of serum levels of properly folded Serpina 1 of at least 10%, at least 20%, at least 50%, at least 100%, at least 200% more can be indicative of effective treatment.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). In this example, prognosis of chronic liver disease, mainly cirrhosis, is measured by an aggregate score of five clinical measures, billirubin, serum albumin, INR, ascites, and hepatic encephalopathy. Each marker is assigned a value from 1-3, and the total value is used to provide a score categorized as A (5-6 points), B (7-9 points), or C (10-15 points), which can be correlated with one and two year survival rates. Methods for determination and analysis of Child-Pugh scores are well known in the art (Farnsworth et al., Am J Surgery 2004 188:580-583; Child and Turcotte. Surgery and portal hypertension. In: The liver and portal hypertension. Edited by CG Child. Philadelphia: Saunders 1964:50-64; Pugh et al., Br J Surg 1973; 60:648-52). Efficacy can be measured in this example by the movement of a patient from e.g., a "B" to an "A." Any positive change resulting in e.g., lessening of severity of disease measured using the appropriate scale, represents adequate treatment using an iRNA or iRNA formulation as described herein.

Patients can be administered a therapeutic amount of iRNA, such as 0.01 mg/kg, 0.05 mg/kg, 0.1 mg/kg, 0.5 mg/kg, 1.0 mg/kg, 1.5 mg/kg, 2.0 mg/kg, or 2.5 mg/kg dsRNA. The iRNA can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the iRNA can reduce Serpina 1 levels, e.g., in a cell, tissue, blood, urine or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alpha-1 anti-trypsin deficiency liver disease can be hereditary. Therefore, a patient in need of a Serpina 1 iRNA can be identified by taking a family history. A healthcare provider, such as a doctor, nurse, or family member, can take a family history before prescribing or administering a Serpina 1 dsRNA. A DNA test can also be performed on the patient to identify a mutation in the Serpina 1 gene, before a Serpina 1 dsRNA is administered to the patient.

Owing to the inhibitory effects on Serpina 1 expression, a composition according to the technology described herein or a pharmaceutical composition prepared therefrom can enhance the quality of life.

Methods for Inhibiting Expression of a Serpina 1 Gene

In one aspect, provided herein is a method of inhibiting Serpina 1 expression in a cell, the method comprising: (a) introducing into the cell a dsRNA that targets a Serpina 1 gene in the cell; and (b) maintaining the cell produced in step (a) for a time sufficient to obtain degradation of the mRNA transcript of a Serpina 1 gene, thereby inhibiting expression of the Serpina 1 gene in the cell. Reduction in gene expression can be assessed by any methods known it the art and by methods, e. g. qRT-PCR, described herein.

In one embodiment, the cell is a mammalian cell, preferably a human cell. In another embodiment, the cell is a mammalian liver cell.

In one embodiment, the dsRNA is introduced to the cell, preferably, in a liposome, e.g. a LNP-formulated liposome known in the art and/or described herein. In one embodiment, the LNP is formulated to target a specific cell such as a hepatocyte.

In one embodiment, the Serpina 1 expression is inhibited by at least, 10%, 20%, 30%, 40%, 50%, 60%, 70%, 80%, 90%, 95%, or even 100%.

In one aspect, provided herein is a method for inhibiting the expression of a Serpina 1 gene in a mammal, the method comprising (a) administering to the mammal a composition comprising a dsRNA that targets a Serpina 1 gene in a cell of the mammal; and (b) maintaining the mammal of step (a) for a time sufficient to obtain degradation of the mRNA transcript of a Serpina 1 gene respectively, thereby inhibiting expression of the Serpina 1 gene in the cell. Reduction in gene expression can be assessed by any methods known it the art and by methods, e. g. qRT-PCR, described herein. In one embodiment, a puncture liver biopsy sample serves as the tissue material for monitoring the reduction in the target gene expression.

In one embodiment, the method includes administering a composition featured herein to the mammal such that expression of the target Serpina 1 gene is decreased, such as for an extended duration, e.g., at least two, three, four days or more, e.g., one week, two weeks, three weeks, or four weeks or longer.

Preferably, the iRNAs useful for the methods and compositions featured herein specifically target RNAs (primary or processed) of the target Serpina 1 gene. Compositions and methods for inhibiting the expression of these genes using iRNAs can be prepared and performed as described elsewhere herein.

In one embodiment of the aspects described herein, the method includes administering a composition containing an iRNA, where the iRNA includes a nucleotide sequence that is complementary to at least a part of an RNA transcript of the Serpina 1 gene of the mammal to be treated. When the organism to be treated is a mammal such as a human, the composition can be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Some of the embodiments of the technology described herein can be defined according to any of the following numbered paragraphs:

1. A double-stranded ribonucleic acid (dsRNA) for inhibiting expression of Serpina 1, wherein said dsRNA comprises a sense strand and an antisense strand, wherein the sense strand comprises at least 15 contiguous nucleotides differing by no more than 3 nucleotides from any of the nucleotide sequence of SEQ ID NO: 01 to SEQ ID NO:11 and the antisense strand comprises at least 15 contiguous nucleotides differing by no more than 3 nucleotides from any of the nucleotide sequence of SEQ ID NO: 14 to SEQ ID NO: 24.
2. A double-stranded ribonucleic acid (dsRNA) for inhibiting expression of Serpina 1, wherein said dsRNA comprises a sense strand and an antisense strand, the antisense strand comprising a region of complementarity which comprises at least 15 contiguous nucleotides differing by no more than 3 nucleotides from one of the antisense sequences listed in Tables 3 and 4.
3. The dsRNA of paragraph 2, wherein the sense and antisense strands comprise sequences selected from the group composed of AD-44715.1, AD-44722.1, AD-44734.1, AD-44717.1, AD-44723.1, AD-44735.1, AD-44724.1, AD-44719.1, and AD-44737.1 of Table 3.
4. The dsRNA of paragraph 1 or 2, wherein said dsRNA comprises at least one modified nucleotide.
5. The dsRNA of paragraph 4, wherein at least one of said modified nucleotides is chosen from the group of: a 2'-O-methyl modified nucleotide, a nucleotide comprising a 5'-phosphorothioate group, and a terminal nucleotide linked to a cholesteryl derivative or dodecanoic acid bisdecylamide group.
6. The dsRNA of paragraph 4, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

The dsRNA of paragraph 2, wherein the region of complementarity is at least 17 nucleotides in length.

8. The dsRNA of paragraph 2, wherein the region of complementarity is between 19 and 21 nucleotides in length.
9. The dsRNA of paragraph 8, wherein the region of complementarity is 19 nucleotides in length.
10. The dsRNA of paragraph 1 or 2, wherein each strand is no more than 30 nucleotides in length.
11. The dsRNA of paragraph 1 or 2, wherein at least one strand comprises a 3' overhang of at least 1 nucleotide.
12. The dsRNA of paragraph 1 or 2, wherein at least one strand comprises a 3' overhang of at least 2 nucleotides.
13. The dsRNA of paragraph 1 or 2, further comprising a ligand.
14 The dsRNA of paragraph 13, wherein the ligand is conjugated to the 3' end of the sense strand of the dsRNA.
15. The dsRNA of paragraph 2, wherein the region of complementarity consists of one of the antisense sequences of Tables 3 and 4.
16. The dsRNA of paragraph 2, wherein the sense strand is consists of any of SEQ ID NO: 01 to SEQ ID NO:11 and the antisense strand consists of any of SEQ ID NO: 14 to SEQ ID NO: 24.
17. The dsRNA of paragraph 1 or 2, wherein the dsRNA comprises a sense strand consisting of a sense strand sequence selected from Tables 3 and 4, and an antisense strand consisting of an antisense sequence selected from Tables 3 and 4
18. A cell containing the dsRNA of paragraph 1 or 2.
19. A vector encoding at least one strand of a dsRNA, wherein said dsRNA comprises a region of complementarity to at least a part of an mRNA encoding Serpina 1, wherein said dsRNA is 30 base pairs or less in length, and wherein said dsRNA targets a said mRNA for cleavage.
20. The vector of paragraph 19, wherein the region of complementarity is at least 15 nucleotides in length.
21. The vector of paragraph 19, wherein the region of complementarity is 19 to 21 nucleotides in length.
22. A cell comprising the vector of paragraph 19.
23. A pharmaceutical composition for inhibiting expression of a Serpina 1 gene comprising the dsRNA of paragraph 1 or 2 or the vector of paragraph 19.
24. The pharmaceutical composition of paragraph 23, further comprising a lipid formulation.
25. The pharmaceutical composition of paragraph 23, wherein the lipid formulation is a SNALP, or XTC formulation.
26. A method of inhibiting Serpina 1 expression in a cell, the method comprising:
    (a) introducing into the cell the dsRNA of paragraph 1 or 2 or the vector of paragraph 19; and
    (b) maintaining the cell produced in step (a) for a time sufficient to obtain degradation of the mRNA transcript of a Serpina 1 gene, thereby inhibiting expression of the Serpina 1 gene in the cell.
27. The method of paragraph 26, wherein the Serpina 1 expression is inhibited by at least 30%.
28. A method of treating a disorder mediated by Serpina 1 expression comprising administering to a patient in need of such treatment a therapeutically effective amount of the dsRNA of paragraph 1 or 2 or the vector of paragraph 19.

29. The method of paragraph 28, wherein the disorder is Alpha 1 anti-trypsin deficiency liver disease.
30. The method of paragraph 28, wherein the administration of the dsRNA to the subject causes a decrease in cirrohsis, fibrosis, and/or Serpina 1 protein accumulation in the liver.
31. The method of paragraph 28, wherein the dsRNA is administered at a concentration of 0.01 mg/kg-5 mg/kg bodyweight of the patient.
32. A method of reducing the likelihood of hepatocellular carcinoma in a patient, wherein the method comprises administering to a patient in need of such treatment a therapeutically effective amount of the dsRNA of paragraph 1 or 2 or the vector of paragraph 19.
33. The method of paragraph 32, wherein the likelihood of developing hepatocellular carcinoma is reduced by a statistically significant amount.
34. The method of paragraph 32, wherein the dsRNA is administered at a concentration of 0.01 mg/kg-5 mg/kg bodyweight of the patient.
35. A method of reducing the accumulation of misfolded Serpina 1 protein in the liver of a patient, wherein the method comprises administering to a patient in need of such treatment a therapeutically effective amount of the dsRNA of paragraph 1 or 2 or the vector of paragraph 19.
36. The method of paragraph 35, wherein the dsRNA is administered at a concentration of 0.01 mg/kg-5 mg/kg bodyweight of the patient.
37. A method of inhibiting the expression of Serpina 1 in a patient, wherein the method comprises administering to a patient in need of such treatment a therapeutically effective amount of the dsRNA of paragraph 1 or 2 or the vector of paragraph 19.
38. The method of paragraph 37, wherein the dsRNA is administered at a concentration of 0.01 mg/kg-5 mg/kg bodyweight of the patient.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

iRNA Design

The Serpina 1 gene has multiple, alternate transcripts. siRNA design was carried out to identify siRNAs targeting all human and rhesus (*Macaca mulatta*) Serpina 1 transcripts annotated in the NCBI Gene database (http://www.ncbi.nlm.nih.gov/gene/). Design used the following transcripts from the NCBI RefSeq collection: Human—NM_000295.4, NM_001002235.2, NM_001002236.2, NM_001127700.1, NM_001127701.1, NM_001127702.1, NM_001127703.1, NM_001127704.1, NM_001127705.1, NM_001127706.1, NM_001127707.1; Rhesus—XM_001098533.1, XM_001098837.1, XM_001098941.1, XM_001099044.1, XM_001099150.1, XM_0010992551 All siRNA duplexes were designed that shared 100% identity with all listed human and rhesus transcripts.

Four hundred seventeen candidate siRNAs were used in a comprehensive search against the human transcriptome (defined as the set of NM_ and XM_records within the human NCBI Refseq set). A total of 48 sense and 48 antisense derived siRNA oligos were synthesized and formed into duplexes.

iRNA Synthesis

Serpina 1 tiled sequences were synthesized on MerMade 192 synthesizer at 0.2 umol scale. Sequences that are mus specific and cross reactive in hum rhe and mus rat were synthesized. For all the sequences in the list, 'endolight' chemistry was applied as detailed herein. All pyrimidines (cytosine and uridine) in the sense strand contained 2'-O-Methyl bases (2' O-Methyl C and 2'-O-Methyl U). In the antisense strand, pyrimidines adjacent to (towards 5' position) ribo A nucleoside were replaced with their corresponding 2-0-Methyl nucleosides. A two base dTsdT extension at 3' end of both sense and anti sense sequences was then introduced. The sequence file was then converted to a text file to make it compatible for loading in the MerMade 192 synthesis software The synthesis of Serpina 1 sequences used solid supported oligonucleotide synthesis using phosphoramidite chemistry. The synthesis of the sequences described herein was performed at lum scale in 96 well plates. The amidite solutions were prepared at 0.1M concentration and ethyl thio tetrazole (0.6M in Acetonitrile) was used as activator.

The synthesized sequences were cleaved and deprotected in 96 well plates, using methylamine in the first step and fluoride reagent in the second step. The crude sequences were precipitated using acetone:ethanol (80:20) mix and the pellet were re-suspended in 0.2M sodium acetate buffer. Samples from each sequence were analyzed by LC-MS to confirm the identity, UV for quantification and a selected set of samples by IEX chromatography to determine purity.

Serpina 1 tiled sequences were precipitated and purified on AKTA Purifier system using Sephadex column. The process was run at ambient temperature. Sample injection and collection was performed in 96 well (1.8 mL-deep well) plates. A single peak corresponding to the full length sequence was collected in the eluent. The desalted Serpina 1 sequences were analyzed for concentration (by UV measurement at A260) and purity (by ion exchange HPLC). The complementary single strands were then combined in a 1:1 stoichiometric ratio to form siRNA duplexes. A detailed list of Serpina 1 single strands and duplexes are shown in Tables 3 and 4.

Example 2. In Vitro Screening

HeLa or Hep3B cells (ATCC, Manassas, Va.) were grown to near confluence at 37° C. in an atmosphere of 5% $CO_2$ in X (ATCC) supplemented with 10% FBS, streptomycin, and glutamine (ATCC) before being released from the plate by trypsinization. Transfection was carried out by adding 14.8 μl of Opti-MEM plus 0.2 μl of Lipofectamine RNAiMax per well (Invitrogen, Carlsbad Calif. cat #13778-150) to 5 μl of siRNA duplexes per well into a 96-well plate and incubated at room temperature for 15 minutes. 80 μl of complete growth media without antibiotic containing ~$2\times10^4$ HeLa or Hep3B cells were then added to the siRNA mixture. Cells were incubated for either 24 or 120 hours prior to RNA purification. Single dose experiments were performed at 10 nM and 0.1 nM final duplex concentration and dose response experiments were done at 10, 1, 0.5, 0.1, 0.05, 0.01, 0.005, 0.001, 0.0005, 0.0001, 0.00005, 0.00001 nM final duplex concentration.

Total RNA was isolated using a Dynabeads® mRNA Isolation Kit (Invitrogen, part #610-12). Cells were harvested and lysed in 150 μl of Lysis/Binding Buffer then mixed for 5 minutes at 850 rpm using an Eppendorf Thermomixer (the mixing speed was the same throughout the process). Ten microliters of magnetic beads and 80 μl Lysis/Binding Buffer mixture were added to a round bottom plate and mixed for 1 minute. Magnetic beads were captured using a magnetic stand and the supernatant was removed without disturbing the beads. After removing supernatant, the lysed cells were added to the remaining beads and mixed for 5 minutes. After removing supernatant, magnetic beads were washed 2 times with 150 μl Wash Buffer A and mixed for 1 minute. Beads were captured again and supernatant removed. Beads were then washed with 150 μl Wash Buffer B, captured and supernatant was removed. Beads were next washed with 150 μl Elution Buffer, captured and supernatant removed. Beads were allowed to dry for 2 minutes. After drying, 50 μl of Elution Buffer was added and mixed for 5 minutes at 70° C. Beads were captured on magnet for 5 minutes. 40 μl of supernatant was removed and added to another 96 well plate.

cDNA synthesis was performed using ABI High capacity cDNA reverse transcription kit (Applied Biosystems, Foster City, Calif., Cat #4368813). A master mix of 2 μl 10× Buffer, 0.8 μl 25× dNTPs, 2 μl Random primers, 1 μl Reverse Transcriptase, 1 μl RNase inhibitor and 3.41 of H2O per reaction were added into 10 μl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

To perform real-time PCR, 41 of cDNA were added to a master mix containing 0.5 μl GAPDH TaqMan Probe (Applied Biosystems Cat #4326317E), 0.5 μl Serpina 1 TaqMan probe (Applied Biosystems cat #Hs00165475_ml) and 5 μl Lightcycler 480 probe master mix (Roche Cat #04887301001) per well in a 384 well 50 plates (Roche cat #04887301001). Real time PCR was done in an ABI 7900HT Real Time PCR system (Applied Biosystems) using the ΔΔCt (RQ) assay. Each duplex was tested in two independent transfections and each transfection was assayed in duplicate, unless otherwise noted in the summary tables.

To calculate relative fold change, real time data were analyzed using the ΔΔCt method and normalized to assays performed with cells transfected with 10 nM AD-1955, or mock transfected cells (FIG. 1 and Table 5). IC50s were calculated using a 4 parameter fit model using XLFit and normalized to cells transfected with AD-1955 over the same dose range, or to its own lowest dose (Tables 6 and 7). In Table 7, two repetitions are shown.

Figure 2:
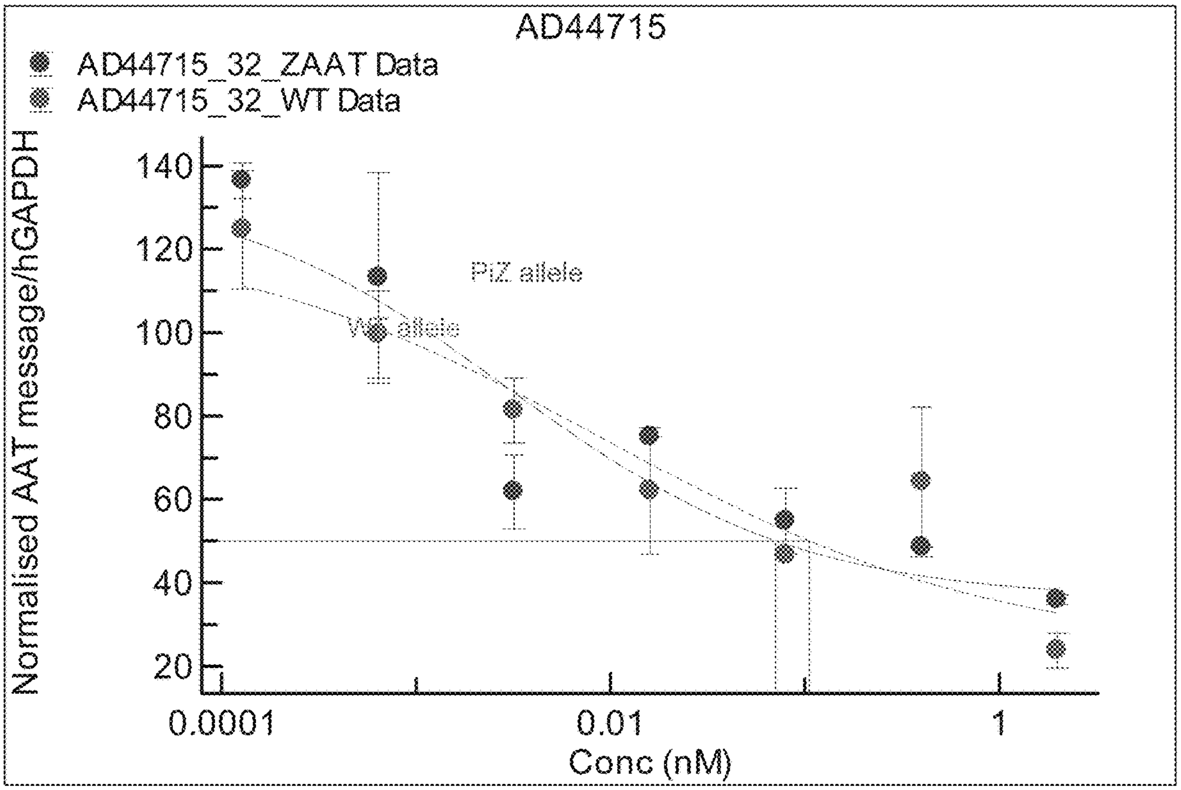
FIG. 2 is a graph comparing inhibition of expression of wild-type Serpina 1 and the PiZ allele in 293T cells. Duplex AD-44715 was used at the concentrations shown on the x-axis. Serpina 1 expression is show in arbitrary units after normalizing to GAPDH expression

To determine the effect of the iRNAs described herein on expression of mutant Serpina 1 alleles, the inhibitory effect of AD-44715 on the PiZ allele was determined. The wildtype allele of Serpina 1 (WT-hAAT) was mutated to incorporate the E443K mutation that distinguishes the PiZ allele from the wildtype allele. 293T cells were transfected with plasmids expressing wildtype or PiZ Serpina 1. After 4 hours, cells were transfected with AD-44715. Twenty-four hours later, RNA was isolated and quantitative PCR performed as described herein. Data were normalized to the expression level of hGAPDH in the 293T cells and are presented in arbitrary units (FIG. 2). The results indicate that the PiZ allele is subject to silencing by AD-44715.

Example 3. In Vivo Tests

Figure 3:
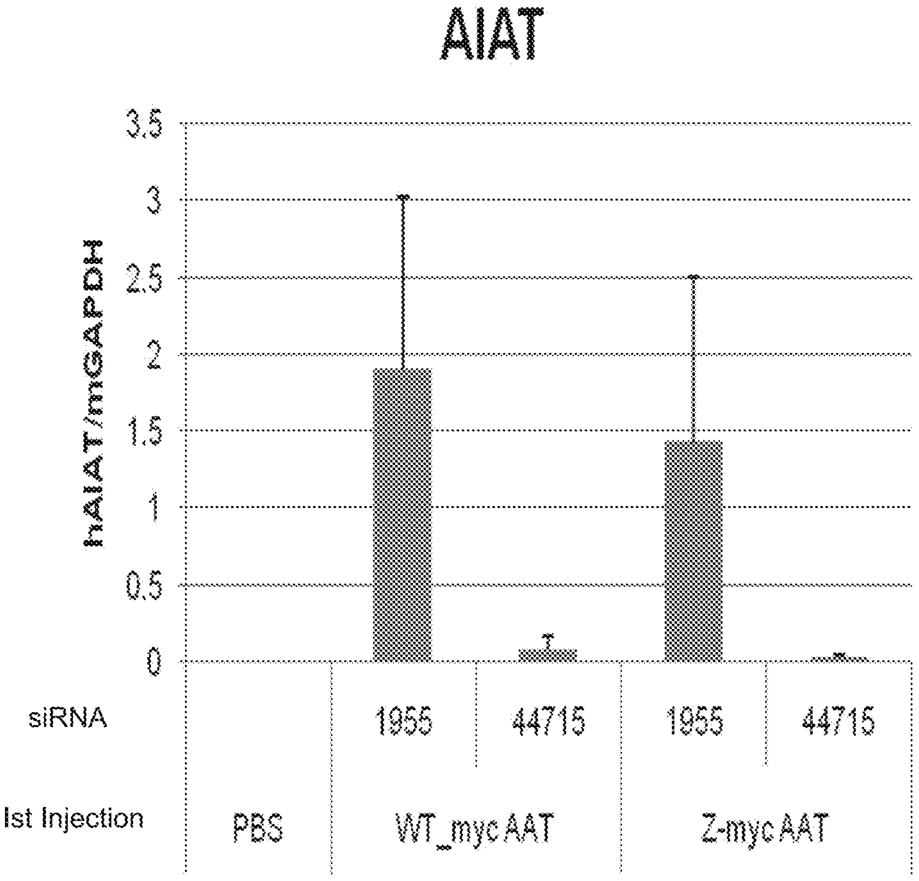
FIG. 3 is a graph of in vivo tests of Serpina 1 expression inhibition using Duplex AD-44715. After a first injection of plasmids expressing human Serpina 1 (wildtype (WT_mycAAT) or PiZ (Z-mycAAT)) or a control, AD-44715 and AD-1955 control iRNAs were delivered to mice intravenously and expression of Serpina 1 detected after 48 hours. Treatments are indicated on the x-axis while the y-axis shows Serpina 1 expression in arbitrary units following normalization to GAPDH.

In vivo tests of the AD-44715 were then performed. CD1 mice received a 3 mL hydrodynamic intravenous injection of PBS or a plamid expressing either myc-tagged wildtype Serpina 1 (WT_mycAAT) or a myc-tagged PiZ allele of Serpina 1 (Z-mycAAT) on day 1. On day 4, the mice were given an intravenous injection of PBS, or the AF11 LNP formulation of AD-44715 or AD-1955 iRNAs at 1 mg/kg (the AF11 LNP formulation was used throughout these animal studies). On day 6 the mice were sacrificed and expression of Serpina 1 mRNA was determined as described herein. FIG. 3 shows the expression of human Serpina 1 in arbitrary units, normalized to mouse GAPDH. The results indicate that the AD-44715 duplex inhibits expression of both wildtype and mutant Serpina 1 transcripts in vivo.

Figure 4:
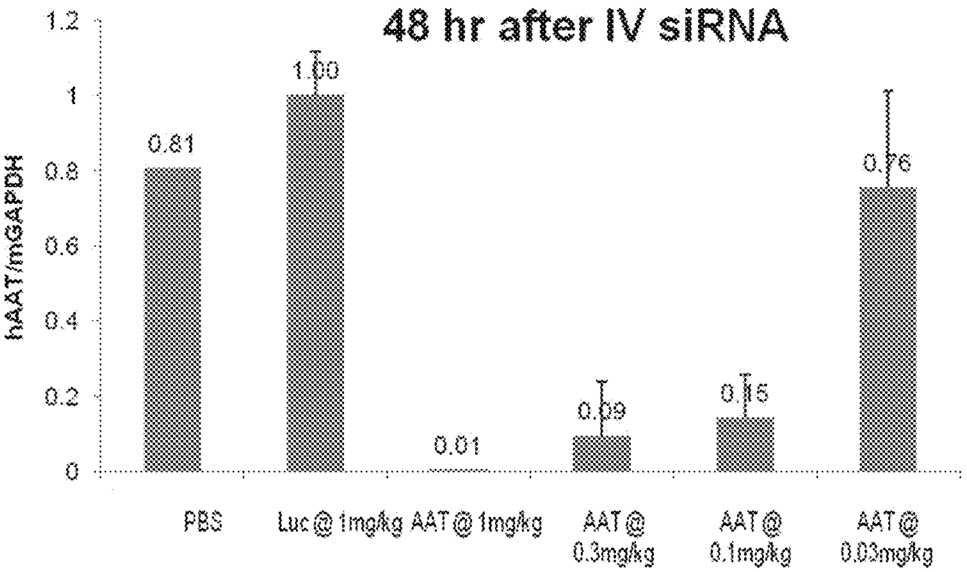
FIG. 4 depicts a graph of the normalized serum level of Z-AAT in transgenic animals 48 hours after intravenous administration of iRNAs. PBS=phosphate buffered saline control; LUC=AD-1955 iRNA control, AAT=AD-44715 iRNA. Doses as shown. The y-axes show the level of human AAT mRNA normalized to mouse GAPDH mRNA. The value of each bar is the average level for that experimental group. The value of each bar is shown above the bar.
Figure 5:
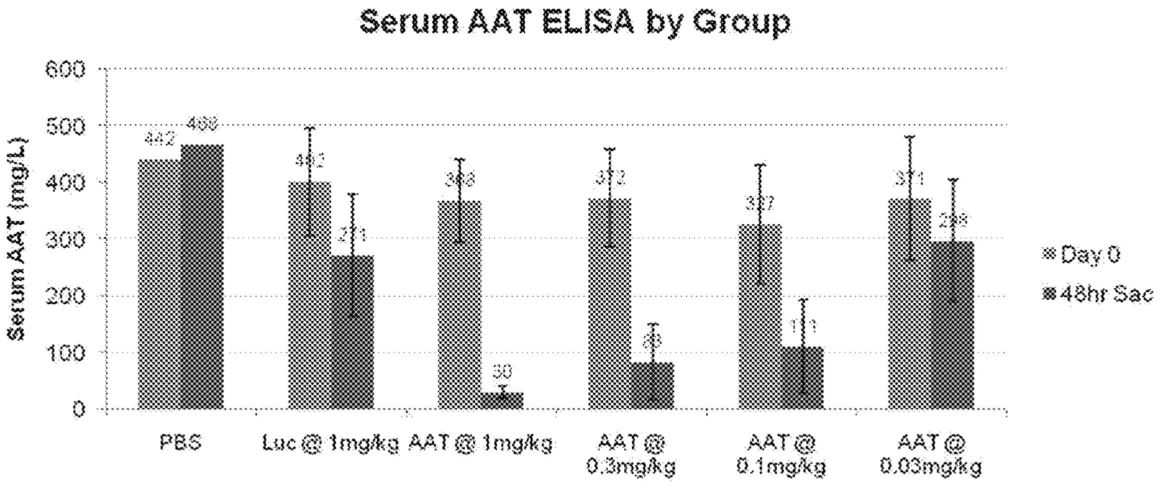
FIG. 5 depict a graph of the normalized serum level of Z-AAT in transgenic animals 48 hours after intravenous administration of iRNAs. PBS=phosphate buffered saline control; LUC=AD-1955 iRNA control, AAT=AD-44715 iRNA. Doses as shown. The y-axes show the level of human AAT protein in mg/L.

Transgenic mice expressing the Z-AAT form of human AAT were used to examine the effect of the iRNAs. The level of serum AAT mRNA and protein was measured 48 hours after intravenous administration of AD-44715 at doses of 1, 0.3, 0.1 and 0.03 mg/kg and AD-1955 at 1 mg/kg (FIG. 4 (mRNA); FIG. 5 (protein)). The siRNAs were administered as AF11 LNP formulations as described herein. Levels of serum AAT were measured on Day 0 and at 48 hours after administration, following sacrifice of the animals. A decrease in both mRNA and protein levels of AAT is observed at 48 hours in a dose-dependent manner following administration of AD-44715.

Figure 6A:
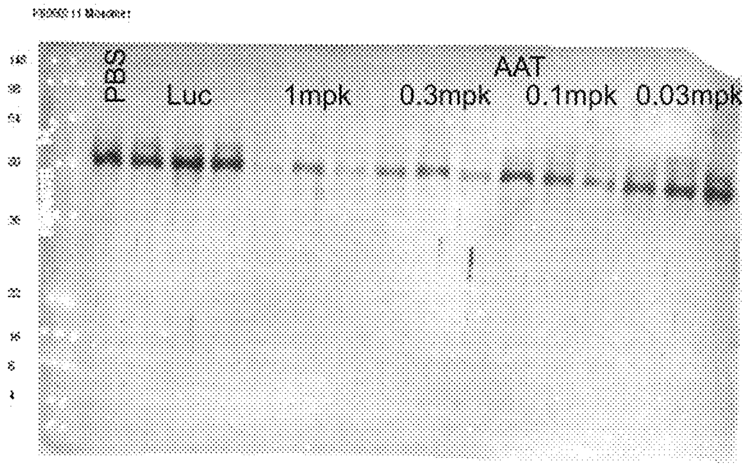
FIGS. 6A-6B depict a Western blot and graph representing quantitation of the Western blot of the level of AAT monomer in the livers of transgenic animals 48 hours after intravenous administration of iRNAs. PBS=phosphate buffered saline control; LUC=AD-1955 iRNA control, AAT=AD-44715 iRNA; mpk=mg/kg; RDU=relative denisometric units.
Figure 6B:
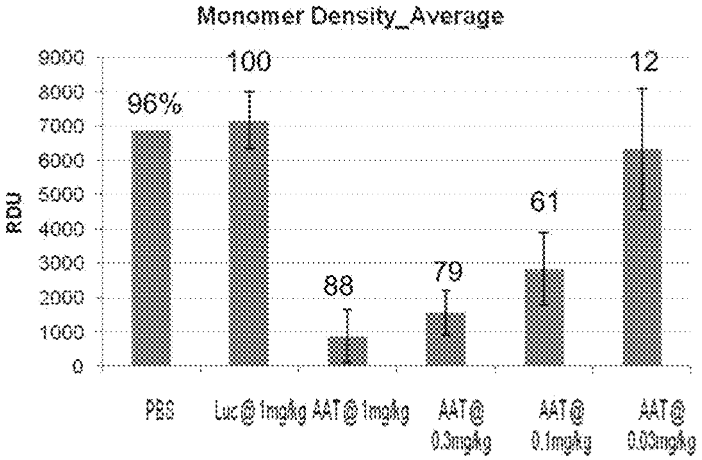
Figure 7A:
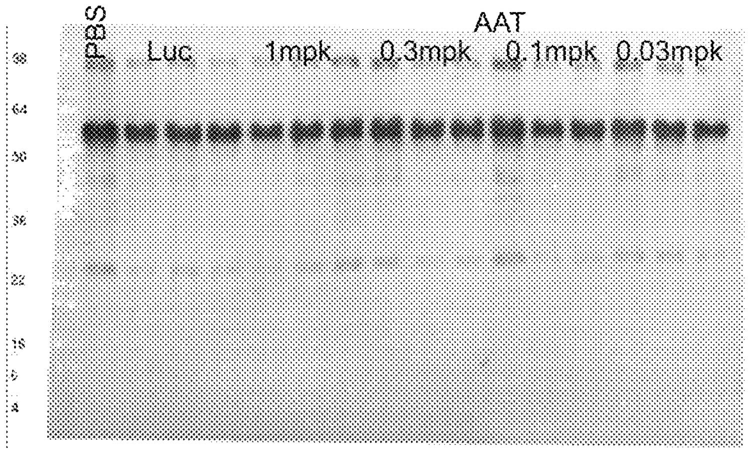
FIGS. 7A-7B depict a Western blot and graph representing quantitation of the Western blot of the level of AAT polymer in the livers of transgenic animals 48 hours after intravenous administration of iRNAs. PBS=phosphate buffered saline control; LUC=AD-1955 iRNA control, AAT=AD-44715 iRNA; mpk=mg/kg; RDU=relative denisometric units.
Figure 7B:
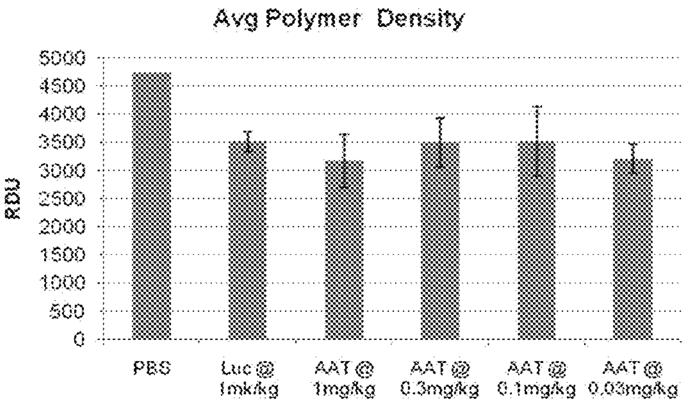
Figures 8A, 8B, 8C:
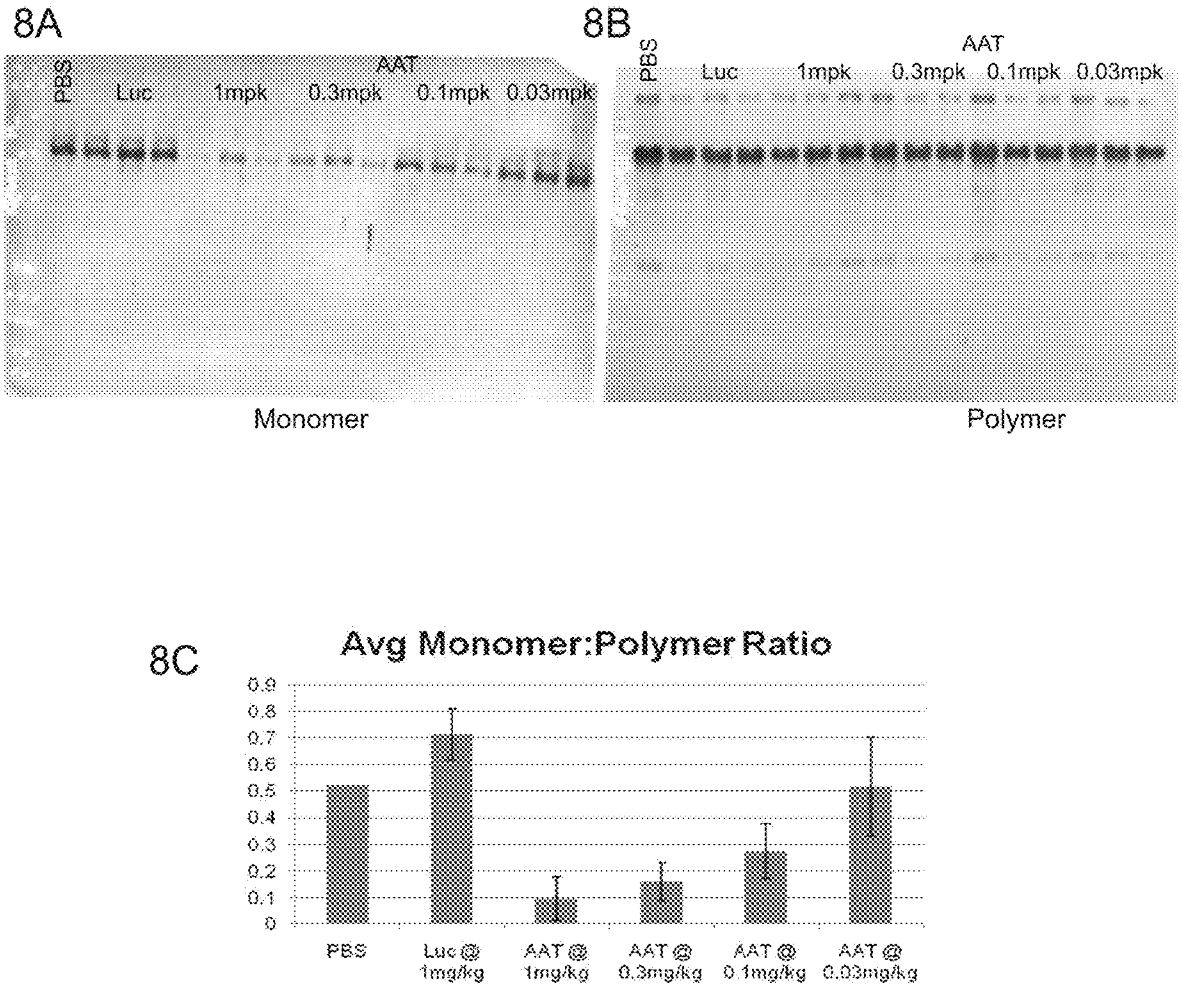
FIGS. 8A-8C depict Western blots and graphs representing quantitation of the Western blots of the level of AAT in the livers of transgenic animals 48 hours after intravenous administration of iRNAs. PBS=phosphate buffered saline control; LUC=AD-1955 iRNA control, AAT=AD-44715 iRNA; mpk=mg/kg; RDU=relative denisometric units.

Levels of AAT protein in the liver of the animals were also determined at 48 hours (FIGS. 6A-6B). FIGS. 6A-6B show the level of AAT monomer present in the liver samples. The monomer is obtained from the soluble fraction of liver homogenate and a decrease in monomer levels is observed at 48 hours in a dose-dependent manner following administration of an AF11 LNP formulation of AD-44715. FIGS. 7A-7B show the level of AAT polymer present in the liver samples. No change in polymer AAT levels was observed in this single, short-term timepoint experiment. FIGS. 8A-8C show monomer and polymer forms of AAT at various dosages of AF11 LNP formulations of AD-44715 (FIGS. 8A and 8B, respectively) and the ratio of monomer to polymer AAT (FIG. 8C) in the liver samples. The $ED_{50}$ in mice was 0.03-0.1 mg/kg.

Figure 9A:
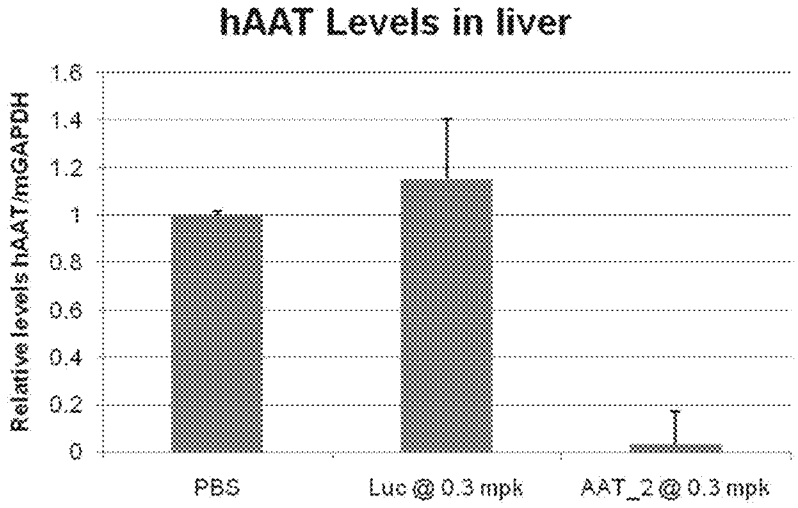
FIGS. 9A-9B depict graphs representing quantitation by RT-PCR and Western blots measuring the level of AAT in the serum and livers of transgenic animals 48 hours after intravenous administration of iRNAs. PBS=phosphate buffered saline control; LUC=AD-1955 iRNA control, AAT_2=AD-44724 iRNA; mpk=mg/kg; RDU=relative densitometric units.
Figure 9B:
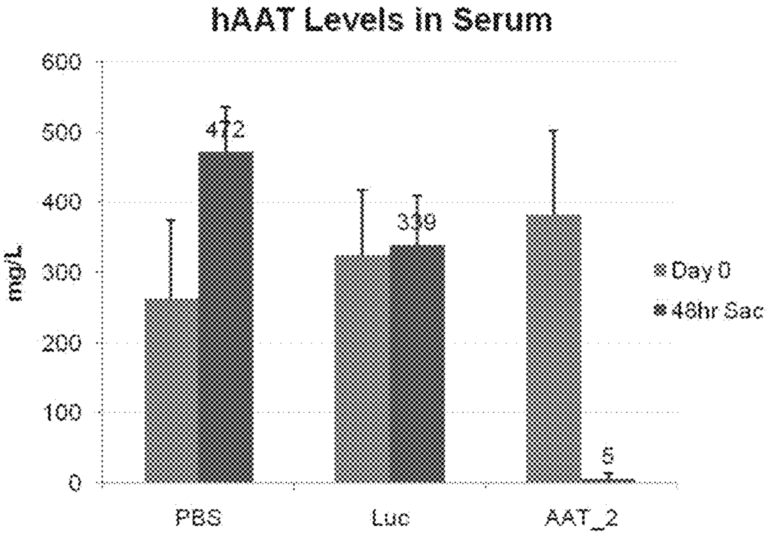

A second iRNA demonstrated similar results when administered to female transgenic mice expressing the Z-AAT form of human AAT. The levels of AAT protein in the serum and the mRNA levels of AAT in the livers of the mice were measured 48 hours after intravenous administration of PBS or an AF11 LNP formulation of AD-44724 at a dose of 0.3 mg/kg or AD-1955 luciferase control at 0.3 mg/kg (FIGS. 9A-9B). Levels of serum AAT were measured on Day 0 and at 48 hours after administration, following sacrifice of the animals. Each experimental group contained 3 animals. A decrease of more than 90% in both serum and liver levels of AAT was observed at 48 hours following administration of AD-44724.

Figures 10A, 10B, 10C:
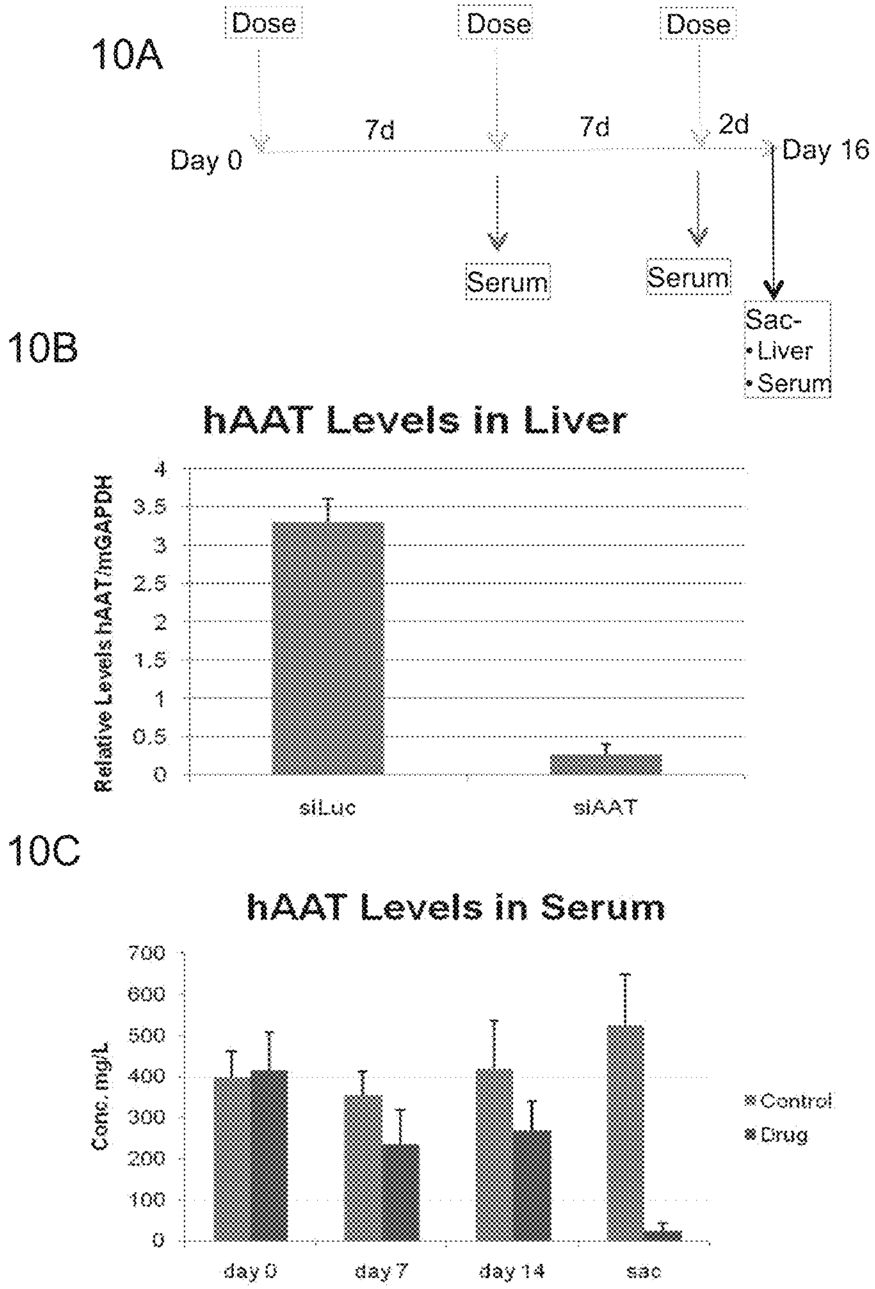
FIGS. 10A-10C depict a diagram and graphs of a multiple-dose iRNA experiment.

A multi-dose experiment was conducted in male transgenic mice expressing the Z-AAT form of human AAT. Mice were given 3 weekly doses of iRNA as an AF11 LNP formulation; either AD-44715 or AD-1955 luciferase control at 0.3 mg/kg (FIG. 10A). Each experimental group consisted of five animals. Serum levels of AAT protein were measured at the time of each dose of iRNA. Forty-eight hours after the third dose was administered, animals were sacrificed and serum protein and liver mRNA levels of AAT were measured (FIGS. 10B-10C). AD-44715 decreased AAT levels at all timepoints after administration. The decrease of AAT mRNA in both the liver and serum at the time of sacrifice was approximately 90%.

Another multi-dose experiment was conducted in male transgenic mice expressing the Z-AAT form of human AAT to investigate the effect of longer term dosage on momomer and polymer forms of AAT in the liver. Mice were given 3 weekly doses of either AD44715 AAT iRNA or AD1955 luciferase control iRNA at 0.3 mg/kg as AF11 LNP formulations (FIG. 11A). Each experimental group consisted of five animals. Forty-eight hours after the third dose was administered, animals were sacrificed and monomeric and polymeric levels of AAT protein in the liver were measured by Western blot. FIGS. 11B and 11C show a summary graph and Western blot, respectively, showing monomeric AAT levels in the livers of animals treated with siLuc control and AAT iRNA at the time of sacrifice. Administration of AD-44715 decreased AAT monomers by approximately 90%.

FIGS. 11D and 11E show a summary graph and Western blot respectively for polymeric AAT levels in the animals treated according to the regimen in FIG. 11A. AAT polymer in the livers was decreased at the time of sacrifice by approximately 20%.

In order to examine the effects of longer-term AAT inhibition, liver sections obtained from mice treated according to the dosing scheme shown in FIG. 11A were stained with periodic acid-Schiff stain, in which polymer globules appear pink. Sections from tissue obtained 48 hours after the last dose were examined. When viewed at 200× magnification, much less pink stain was visible in sections from animals receiving the AAT-specific (AD-44715) iRNA as compared to sections from animals in the control group (siLUC; AD-1955).

A duration study was conducted, in which mice received a single dose of AAT-specific (AD-44715) or control siRNA (Factor VII siRNA) as AF11 LNP formulations at a dosage of 0.3 mg/kg and samples were analyzed through 14 days post treatment. AAT levels were measured as serum protein (FIG. 12A) and mRNA in the liver (FIG. 12B). The level of AAT decreased by more than 95% on Day 2 and began to rise thereafter. On Day 4, AAT was decreased approximately 90%, on Day 7 30-50%, and by Day 10 was at normal levels. FIG. 12C shows the level of knockdown of Factor VII. The control doses of Factor VII-specific siRNA reduced Factor VII expression by the percentage expected at the administered dose.

Example 4: Extended Dosing Regimes

AAT-specific iRNAs can be administered at 0.3 mg/kg over the course of several weeks, including dosing every other week for a total of 6 doses. The effect of iRNA administration is assayed by weekly serum bleeds to measure serum mRNA, protein levels of AAT and conduct liver function tests. Additional analysis for effects on liver function can include, for example, analysis of liver tissue to measure AAT mRNA, AAT protein, liver monomer, and liver polymer at the time of sacrifice; staining of liver tissue with PAS to measure globules or staining with Sirius red or H&E to examine liver histology at the time of sacrifice; and the use of BrdU incorporation to examine cell proliferation.

Example 5: Administration of siRNAs to Subjects with Liver Disease

AAT-specific siRNAs can be administered to mice displaying symptoms of alpha-1 anti-trypsin related liver disease. The effect of siRNAs on cell proliferation and/or cell division in these mice is examined by staining, for example, for Ki-67, PCNA, or BrdU incorporation. The dose response of a diseased liver to AAT-specific siRNA is measured by assaying the expression of AAT protein and/or mRNA or using any parameter of liver function known in the art, including liver function tests or histological examination as described above herein.

Example 6: Long Term Dosing

Figures 13A, 13B:
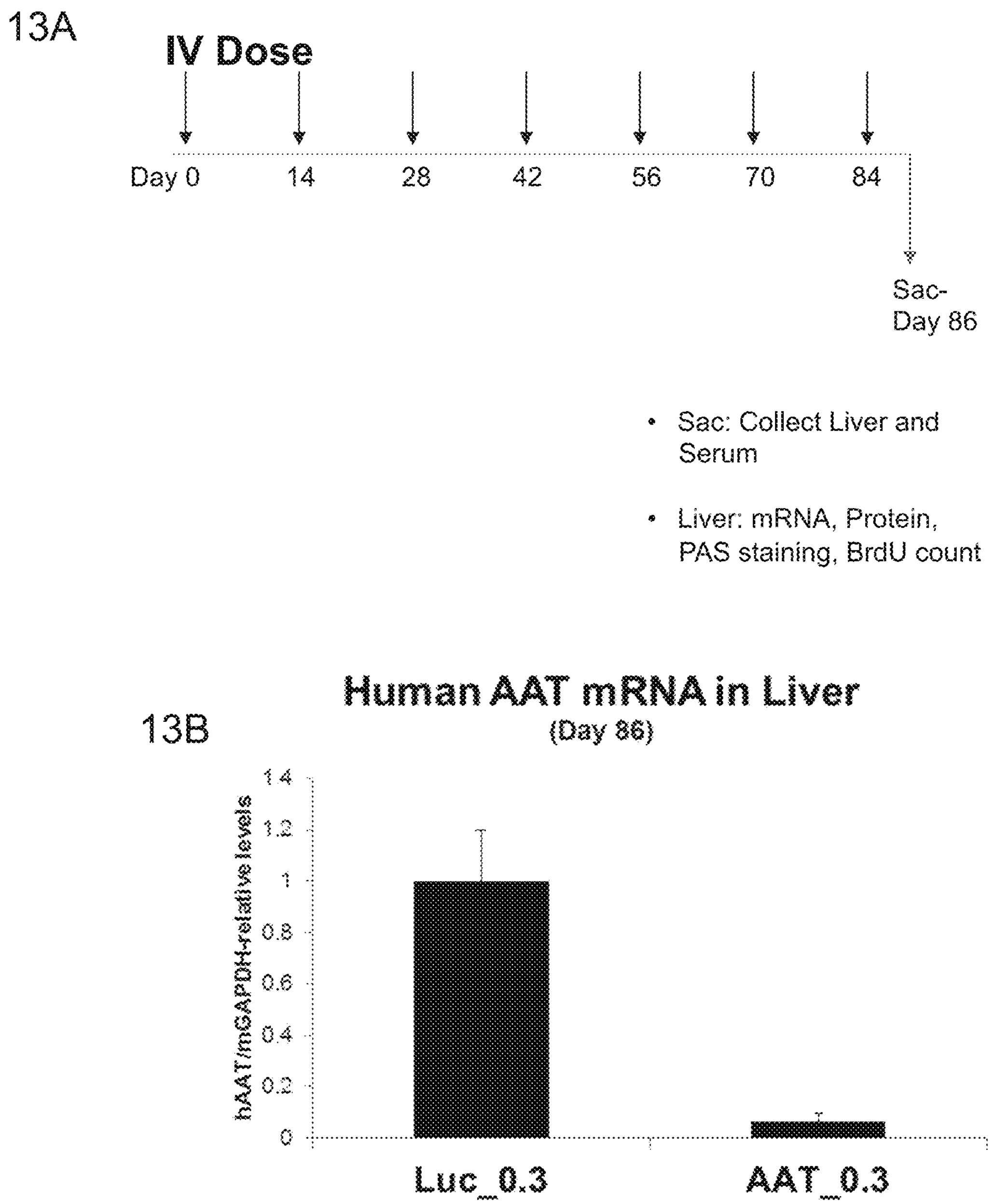
FIGS. 13A-13B depict a long term-dosing experiment with AAT siRNA.

AAT-specific siRNAs were administered to mice displaying symptoms of alpha-1 anti-trypsin related liver disease for extended dosing regimes. The experimental design is depicted in FIG. 13A. Transgenic male mice expressing Z-AAT were administered 0.3 mg/kg doses of siRNA (either LNP-AAT or control LNP-Luc; N=6 for each group) every other week for a total of 7 doses. The experiment was conducted with human AAT-specific reagents. On day 86 the mice were sacrificed. Liver and serum samples were collected and liver samples were subjected to mRNA, protein, PAS stain, and BrdU analysis.

Figures 14A, 14B, 14C:
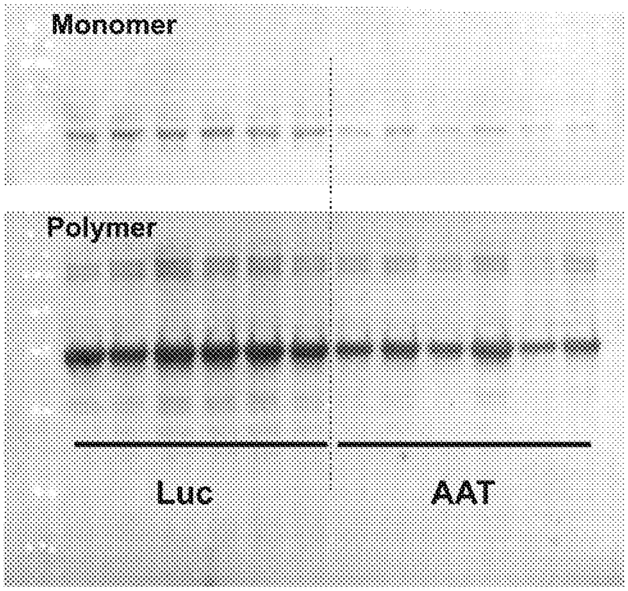
FIGS. 14A-14C depict the levels of human AAT in the mice of FIGS. 13A-13B.

Analysis of human AAT mRNA levels in liver samples demonstrated that the LNP-AAT treated mice displayed lower levels of AAT expression (FIG. 13B). Analysis of human AAT protein levels likewise indicated reduced levels of both monomer and polymer forms of AAT in LNP-AAT treated mice as compared to controls (FIGS. 14A-14C).

Figure 15:
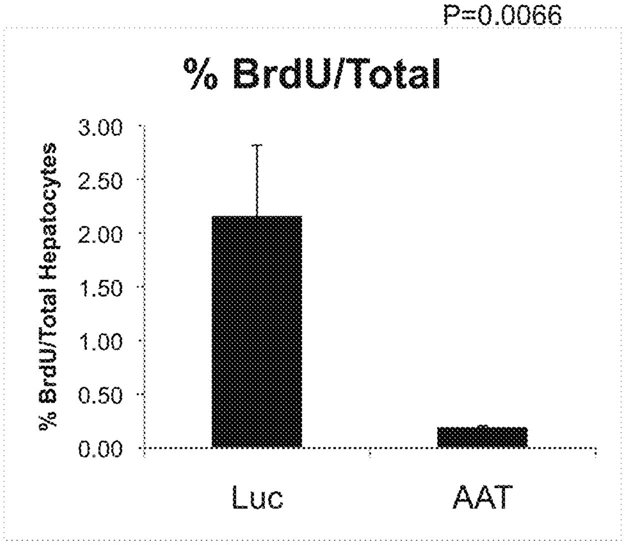
FIG. 15 depicts the measurement of liver cell injury in the mice of FIGS. 13A-13B. The graph displays the percentage of hepatocytes which incorporated BrdU in the livers of mice treated with either LNP-AAT or LNP-Luc. Each bar represents the average of 3 animals.

Cell division is a means by which the liver replaces injured hepatocytes. BrdU pumps were implanted in 3 mice from each treatment group at day 83 and BrdU incorporation in the liver samples of these animals was determined. The LNP-AAT treated mice demonstrated lower levels of BrdU incorporation, indicating that treatment with LNP-AAT was beneficial to the health of the liver (FIG. 15).

Figure 16:
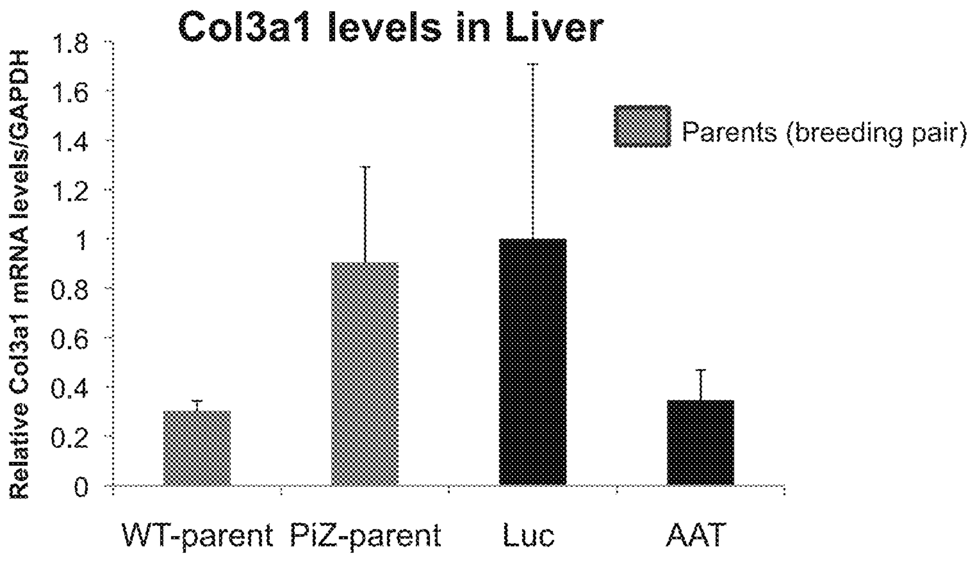
FIG. 16 depicts level of Col3a1 mRNA in the livers of the mice of FIGS. 13A-13B. The mice treated with either LNP-AAT or LNP-Luc are heterozygotes. The graph also displays the level of collagen found in the livers of both wt and PiZ parents.

Collagen levels in the liver of the mice were also examined by determining mRNA levels. Col1A1, Col1a2 (data not shown) and Col3a1 (FIG. 16) were expressed at lower levels in the livers of LNP-AAT treated mice as compared to control LNP-Luc treated mice and was comparable to the level of expression in wild-type parent animals. Decreased collagen expression is indicative of reduced fibrosis.

Figure 17:
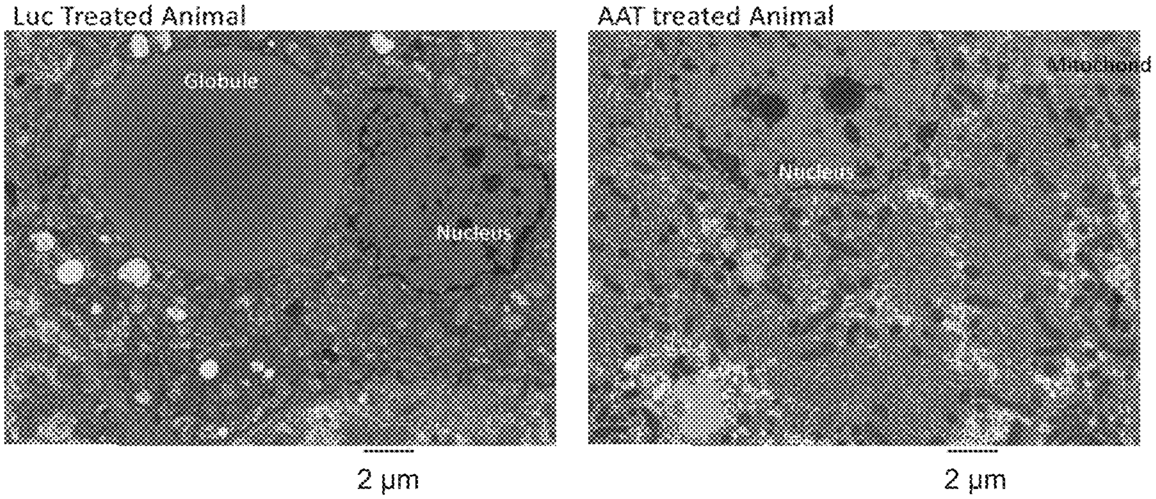
FIG. 17 depicts electron micrograph images of liver cells of the mice of FIGS. 13A-13B. The left micrograph image depicts a cell of a mouse treated with LNP-Luc while the right micrograph depicts a cell of a mouse treated by LNP-AAT.

Liver cells of LNP-Luc treated mice and LNP-AAT treated mice were also examined by electron microscopy (FIG. 17). Animals treated with LNP-AAT had cells with smaller and fewer globules, less ER dilation, fewer autophagic vacuoles, and less mitochondrial injury. Liver ultrastructure was also observed to be markedly improved after LNP-AAT treatment.

This long term dosing experiment demonstrates that LNP-AAT dosing on alternate weeks, at low dosage, is very effective in decreasing disease phenotypes. In LNP-AAT treated mice, levels of AAT mRNA and protein in the liver were decreased, PAS stain (data not shown) decreased, liver damage, as measured by BrdU incorporation was lower, and fibrosis was reduced.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | adenosine |
| C | cytidine |
| G | guanosine |
| T | thymidine |
| U | uridine |
| N | any nucleotide (G, A, C, T or U) |
| a | 2'-O-methyladenosine |
| c | 2'-O-methylcytidine |
| g | 2'-O-methylguanosine |
| u | 2'-O-methyluridine |
| dT | 2'-deoxythymidine |
| s | phosphorothioate linkage |

TABLE 3

Unmodified Sense and antisense strand sequences of Serpinal dsRNAs

| Duplex ID | Sense ID | Sense sequence (SEQ ID NOS 29-72, respectively, in order of appearance) | Antisense ID | Antisensesequence (SEQ ID NOS 73-116, respectively, in order of appearance) | Position relative to NM_000295.4 |
|---|---|---|---|---|---|
| AD-44697.1 | A-93465.1 | CUGGCACACCAGUCCAACA | A-93466.1 | UGUUGGACUGGUGUGCCAG | 454-472 |
| AD-44703.1 | A-93467.1 | AGUCCAACAGCACCAAUAU | A-93468.1 | AUAUUGGUGCUGUUGGACU | 464-482 |
| AD-44709.1 | A-93469.1 | UCCAACAGCACCAAUAUCU | A-93470.1 | AGAUAUUGGUGCUGUUGGA | 466-484 |
| AD-44715.1 | A-93471.1 | CCAACAGCACCAAUAUCUU | A-93472.1 | AAGAUAUUGGUGCUGUUGG | 467-485 |
| AD-44721.1 | A-93473.1 | AACAGCACCAAUAUCUUCU | A-93474.1 | AGAAGAUAUUGGUGCUGUU | 469-487 |
| AD-44727.1 | A-93475.1 | CUCCCCAGUGAGCAUCGCU | A-93476.1 | AGCGAUGCUCACUGGGGAG | 489-507 |
| AD-44733.1 | A-93477.1 | CCCAGUGAGCAUCGCUACA | A-93478.1 | UGUAGCGAUGCUCACUGGG | 492-510 |
| AD-44692.1 | A-93479.1 | GUGAGCAUCGCUACAGCCU | A-93480.1 | AGGCUGUAGCGAUGCUCAC | 496-514 |
| AD-44698.1 | A-93481.1 | UGAGCAUCGCUACAGCCUU | A-93482.1 | AAGGCUGUAGCGAUGCUCA | 497-515 |
| AD-44704.1 | A-93483.1 | GAGCAUCGCUACAGCCUUU | A-93484.1 | AAAGGCUGUAGCGAUGCUC | 498-516 |
| AD-44710.1 | A-93485.1 | CAUCGCUACAGCCUUUGCA | A-93486.1 | UGCAAAGGCUGUAGCGAUG | 501-519 |
| AD-44716.1 | A-93487.1 | CUACAGCCUUUGCAAUGCU | A-93488.1 | AGCAUUGCAAAGGCUGUAG | 506-524 |
| AD-44722.1 | A-93489.1 | GGACCAAGGCUGACACUCA | A-93490.1 | UGAGUGUCAGCCUUGGUCC | 533-551 |
| AD-44728.1 | A-93491.1 | AUCCUGGAGGGCCUGAAUU | A-93492.1 | AAUUCAGGCCCUCCAGGAU | 559-577 |
| AD-44734.1 | A-93493.1 | UCCUGGAGGGCCUGAAUUU | A-93494.1 | AAAUUCAGGCCCUCCAGGA | 560-578 |
| AD-44699.1 | A-93497.1 | UGGAUAAGUUUUUGGAGGA | A-93498.1 | UCCUCCAAAAACUUAUCCA | 713-731 |
| AD-44705.1 | A-93499.1 | GGAUAAGUUUUUGGAGGAU | A-93500.1 | AUCCUCCAAAAACUUAUCC | 714-732 |
| AD-44711.1 | A-93501.1 | GACACCGAAGAGGCCAAGA | A-93502.1 | UCUUGGCCUCUUCGGUGUC | 778-796 |
| AD-44717.1 | A-93503.1 | ACACCGAAGAGGCCAAGAA | A-93504.1 | UUCUUGGCCUCUUCGGUGU | 779-797 |
| AD-44723.1 | A-93505.1 | CACCGAAGAGGCCAAGAAA | A-93506.1 | UUUCUUGGCCUCUUCGGUG | 780-798 |
| AD-44729.1 | A-93507.1 | AAGAGGCCAAGAAACAGAU | A-93508.1 | AUCUGUUUCUUGGCCUCUU | 785-803 |
| AD-44735.1 | A-93509.1 | GAGGCCAAGAAACAGAUCA | A-93510.1 | UGAUCUGUUUCUUGGCCUC | 787-805 |
| AD-44694.1 | A-93511.1 | AUUUGGUCAAGGAGCUUGA | A-93512.1 | UCAAGCUCCUUGACCAAAU | 845-863 |
| AD-44700.1 | A-93513.1 | GGUCAAGGAGCUUGACAGA | A-93514.1 | UCUGUCAAGCUCCUUGACC | 849-867 |
| AD-44706.1 | A-93515.1 | GGAGCUUGACAGAGACACA | A-93516.1 | UGUGUCUCUGUCAAGCUCC | 855-873 |
| AD-44712.1 | A-93517.1 | AGCUUGACAGAGACACAGU | A-93518.1 | ACUGUGUCUCUGUCAAGCU | 857-875 |
| AD-44718.1 | A-93519.1 | ACAGUUUUUGCUCUGGUGA | A-93520.1 | UCACCAGAGCAAAAACUGU | 871-889 |
| AD-44724.1 | A-93521.1 | CAGUUUUUGCUCUGGUGAA | A-93522.1 | UUCACCAGAGCAAAAACUG | 872-890 |
| AD-44730.1 | A-93523.1 | UUUGCUCUGGUGAAUUACA | A-93524.1 | UGUAAUUCACCAGAGCAAA | 877-895 |
| AD-44736.1 | A-93525.1 | UUGCUCUGGUGAAUUACAU | A-93526.1 | AUGUAAUUCACCAGAGCAA | 878-896 |
| AD-44695.1 | A-93527.1 | UACAUCUUCUUUAAAGGCA | A-93528.1 | UGCCUUUAAAGAAGAUGUA | 892-910 |
| AD-44701.1 | A-93529.1 | AAUGGGAGAGACCCUUUGA | A-93530.1 | UCAAAGGGUCUCUCCCAUU | 911-929 |
| AD-44707.1 | A-93531.1 | AGGAAGAGGACUUCCACGU | A-93532.1 | ACGUGGAAGUCCUCUUCCU | 944-962 |
| AD-44713.1 | A-93533.1 | CGUUUAGGCAUGUUUAACA | A-93534.1 | UGUUAAACAUGCCUAAACG | 1000-1018 |
| AD-44719.1 | A-93535.1 | GUUUAGGCAUGUUUAACAU | A-93536.1 | AUGUUAAACAUGCCUAAAC | 1001-1019 |
| AD-44725.1 | A-93537.1 | UGGGUGCUGCUGAUGAAAU | A-93538.1 | AUUUCAUCAGCAGCACCCA | 1045-1063 |
| AD-44731.1 | A-93539.1 | UUCCUGCCUGAUGAGGGGA | A-93540.1 | UCCCCUCAUCAGGCAGGAA | 1090-1108 |

TABLE 3-continued

Unmodified Sense and antisense strand sequences of Serpinal dsRNAs

| Duplex ID | Sense ID | Sense sequence (SEQ ID NOS 29-72, respectively, in order of appearance) | Antisense ID | Antisensesequence (SEQ ID NOS 73-116, respectively, in order of appearance) | Position relative to NM_000295.4 |
|---|---|---|---|---|---|
| AD-44737.1 | A-93541.1 | CCUGCCUGAUGAGGGGAAA | A-93542.1 | UUUCCCCUCAUCAGGCAGG | 1092-1110 |
| AD-44696.1 | A-93543.1 | AGCACCUGGAAAAUGAACU | A-93544.1 | AGUUCAUUUUCCAGGUGCU | 1115-1133 |
| AD-44702.1 | A-93545.1 | UGGAAAAUGAACUCACCCA | A-93546.1 | UGGGUGAGUUCAUUUUCCA | 1121-1139 |
| AD-44714.1 | A-93549.1 | CCAUUACUGGAACCUAUGA | A-93550.1 | UCAUAGGUUCCAGUAAUGG | 1208-1226 |
| AD-44720.1 | A-93551.1 | CAUUACUGGAACCUAUGAU | A-93552.1 | AUCAUAGGUUCCAGUAAUG | 1209-1227 |
| AD-44726.1 | A-93553.1 | UUACUGGAACCUAUGAUCU | A-93554.1 | AGAUCAUAGGUUCCAGUAA | 1211-1229 |
| AD-44732.1 | A-93555.1 | ACUGGAACCUAUGAUCUGA | A-93556.1 | UCAGAUCAUAGGUUCCAGU | 1213-1231 |

TABLE 4

Modified Sense and antisense strand sequences of Serpinal dsRNAs

| Duplex ID | Sense strand ID | Sense strand sequence (SEQ ID NOS 117-160, respectively, in order of appearance) | Antisense ID | Antisense sequence (SEQ ID NOS 161-204, respectively, in order of appearance) |
|---|---|---|---|---|
| AD-44697.1 | A-93465.1 | cuGGcAcAccAGuccAAcAdTsdT | A-93466.1 | UGUUGGACUGGUGUGCcAGdTsdT |
| AD-44703.1 | A-93467.1 | AGuccAAcAGcAccAAuAudTsdT | A-93468.1 | AuAUUGGUGCUGUUGGACUdTsdT |
| AD-44709.1 | A-93469.1 | uccAAcAGcAccAAuAucudTsdT | A-93470.1 | AGAuAUUGGUGCUGUUGGAdTsdT |
| AD-44715.1 | A-93471.1 | ccAAcAGcAccAAuAucuudTsdT | A-93472.1 | AAGAuAUUGGUGCUGUUGGdTsdT |
| AD-44721.1 | A-93473.1 | AAcAGcAccAAuAucuucudTsdT | A-93474.1 | AGAAGAuAUUGGUGCUGUUdTsdT |
| AD-44727.1 | A-93475.1 | cuccccAGuGAGcAucGcudTsdT | A-93476.1 | AGCGAUGCUcACUGGGGAGdTsdT |
| AD-44733.1 | A-93477.1 | cccAGuGAGcAucGcuAcAdTsdT | A-93478.1 | UGuAGCGAUGCUcACUGGGdTsdT |
| AD-44692.1 | A-93479.1 | GuGAGcAucGcuAcAGccudTsdT | A-93480.1 | AGGCUGuAGCGAUGCUcACdTsdT |
| AD-44698.1 | A-93481.1 | uGAGcAucGcuAcAGccuudTsdT | A-93482.1 | AAGGCUGuAGCGAUGCUcAdTsdT |
| AD-44704.1 | A-93483.1 | GAGcAucGcuAcAGccuuudTsdT | A-93484.1 | AAAGGCUGuAGCGAUGCUCdTsdT |
| AD-44710.1 | A-93485.1 | cAucGcuAcAGccuuuGcAdTsdT | A-93486.1 | UGcAAAGGCUGuAGCGAUGdTsdT |
| AD-44716.1 | A-93487.1 | cuAcAGccuuuGcAAuGcudTsdT | A-93488.1 | AGcAUUGcAAAGGCUGuAGdTsdT |
| AD-44722.1 | A-93489.1 | GGAccAAGGcuGAcAcucAdTsdT | A-93490.1 | UGAGUGUcAGCCUUGGUCCdTsdT |
| AD-44728.1 | A-93491.1 | AuccuGGAGGGccuGAAuudTsdT | A-93492.1 | AAUUcAGGCCCUCcAGGAUdTsdT |
| AD-44734.1 | A-93493.1 | uccuGGAGGGccuGAAuuudTsdT | A-93494.1 | AAAUUcAGGCCCUCcAGGAdTsdT |
| AD-44699.1 | A-93497.1 | uGGAuAAGuuuuuGGAGGAdTsdT | A-93498.1 | UCCUCcAAAAACUuAUCcAdTsdT |
| AD-44705.1 | A-93499.1 | GGAuAAGuuuuuGGAGGAudTsdT | A-93500.1 | AUCCUCcAAAAACUuAUCCdTsdT |
| AD-44711.1 | A-93501.1 | GAcAccGAAGAGGccAAGAdTsd | A-93502.1 | UCUUGGCCUCUUCGGUGUCdTsdT |
| AD-44717.1 | A-93503.1 | AcAccGAAGAGGccAAGAAdTsd | A-93504.1 | UUCUUGGCCUCUUCGGUGUdTsdT |
| AD-44723.1 | A-93505.1 | cAccGAAGAGGccAAGAAAdTsd | A-93506.1 | UUUCUUGGCCUCUUCGGUGdTsdT |
| AD-44729.1 | A-93507.1 | AAGAGGccAAGAAAcAGAudTsd | A-93508.1 | AUCUGUUUCUUGGCCUCUUdTsdT |
| AD-44735.1 | A-93509.1 | GAGGccAAGAAAcAGAucAdTsd | A-93510.1 | UGAUCUGUUUCUUGGCCUCdTsdT |
| AD-44694.1 | A-93511.1 | AuuuGGucAAGGAGcuuGAdTsdT | A-93512.1 | UcAAGCUCCUUGACcAAAUdTsdT |
| AD-44700.1 | A-93513.1 | GGucAAGGAGcuuGAcAGAdTsdT | A-93514.1 | UCUGUcAAGCUCCUUGACCdTsdT |
| AD-44706.1 | A-93515.1 | GGAGcuuGAcAGAGAcAcAdTsdT | A-93516.1 | UGUGUCUCUGUcAAGCUCCdTsdT |

TABLE 4-continued

Modified Sense and antisense strand sequences of Serpinal dsRNAs

| Duplex ID | Sense strand ID | Sense strand sequence (SEQ ID NOS 117-160, respectively, in order of appearance) | Antisense ID | Antisense sequence (SEQ ID NOS 161-204, respectively, in order of appearance) |
|---|---|---|---|---|
| AD-44712.1 | A-93517.1 | AGcuuGAcAGAGAcAcAGudTsdT | A-93518.1 | ACUGUGUCUCUGUcAAGCUdTsdT |
| AD-44718.1 | A-93519.1 | AcAGuuuuuGcucuGGuGAdTsdT | A-93520.1 | UcACcAGAGcAAAAACUGUdTsdT |
| AD-44724.1 | A-93521.1 | cAGuuuuuGcucuGGuGAAdTsdT | A-93522.1 | UUcACcAGAGcAAAAACUGdTsdT |
| AD-44730.1 | A-93523.1 | uuuGcucuGGuGAAuuAcAdTsdT | A-93524.1 | UGuAAUUcACcAGAGcAAAdTsdT |
| AD-44736.1 | A-93525.1 | uuGcucuGGuGAAuuAcAudTsdT | A-93526.1 | AUGuAAUUcACcAGAGcAAdTsdT |
| AD-44695.1 | A-93527.1 | uAcAucuucuuuAAAGGcAdTsdT | A-93528.1 | UGCCUUuAAAGAAGAUGuAdTsdT |
| AD-44701.1 | A-93529.1 | AAuGGGAGAGAcccuuuGAdTsdT | A-93530.1 | UcAAAGGGUCUCUCCcAUUdTsdT |
| AD-44707.1 | A-93531.1 | AGGAAGAGGAcuuccAcGudTsdT | A-93532.1 | ACGUGGAAGUCCUCUUCCUdTsdT |
| AD-44713.1 | A-93533.1 | cGuuuAGGcAuGuuuAAcAdTsdT | A-93534.1 | UGUuAAAcAUGCCuAAACGdTsdT |
| AD-44719.1 | A-93535.1 | GuuuAGGcAuGuuuAAcAudTsdT | A-93536.1 | AUGUuAAAcAUGCCuAAACdTsdT |
| AD-44725.1 | A-93537.1 | uGGGuGcuGcuGAuGAAAudTsdT | A-93538.1 | AUUUcAUcAGcAGcACCcAdTsdT |
| AD-44731.1 | A-93539.1 | uuccuGccuGAuGAGGGGAdTsdT | A-93540.1 | UCCCCUcAUcAGGcAGGAAdTsdT |
| AD-44737.1 | A-93541.1 | ccuGccuGAuGAGGGGAAAdTsdT | A-93542.1 | UUUCCCCUcAUcAGGcAGGdTsdT |
| AD-44696.1 | A-93543.1 | AGcAccuGGAAAAuGAAcudTsdT | A-93544.1 | AGUUcAUUUUCcAGGUGCUdTsdT |
| AD-44702.1 | A-93545.1 | uGGAAAAuGAAcucAcccAdTsdT | A-93546.1 | UGGGUGAGUUcAUUUUCcAdTsdT |
| AD-44714.1 | A-93549.1 | ccAuuAcuGGAAccuAuGAdTsdT | A-93550.1 | UcAuAGGUUCcAGuAAUGGdTsdT |
| AD-44720.1 | A-93551.1 | cAuuAcuGGAAccuAuGAudTsdT | A-93552.1 | AUcAuAGGUUCcAGuAAUGdTsdT |
| AD-44726.1 | A-93553.1 | uuAcuGGAAccuAuGAucudTsdT | A-93554.1 | AGAUcAuAGGUUCcAGuAAdTsdT |
| AD-44732.1 | A-93555.1 | AcuGGAAccuAuGAucuGAdTsdT | A-93556.1 | UcAGAUcAuAGGUUCcAGUdTsdT |

TABLE 5

Serpina1 single dose screen

| | 10 nM Average | 0.1 nM Average |
|---|---|---|
| AD-44692.1 | 1.09 | 1.03 |
| AD-44694.1 | 0.40 | 1.01 |
| AD-44695.1 | 0.67 | 1.12 |
| AD-44696.1 | 0.73 | 1.11 |
| AD-44697.1 | 0.37 | 1.08 |
| AD-44697.1 | 0.29 | 1.13 |
| AD-44698.1 | 0.35 | 0.97 |
| AD-44699.1 | 0.51 | 1.41 |
| AD-44700.1 | 0.15 | 0.90 |
| AD-44701.1 | 0.58 | 1.22 |
| AD-44702.1 | 0.45 | 0.84 |
| AD-44703.1 | 0.16 | 0.99 |
| AD-44703.1 | 0.13 | 1.05 |
| AD-44704.1 | 0.82 | 1.22 |
| AD-44705.1 | 0.10 | 0.95 |
| AD-44706.1 | 0.31 | 1.07 |
| AD-44707.1 | 0.21 | 1.13 |
| AD-44709.1 | 0.09 | 0.92 |
| AD-44709.1 | 0.12 | 0.99 |
| AD-44710.1 | 1.09 | 0.92 |
| AD-44711.1 | 0.14 | 1.05 |
| AD-44712.1 | 0.72 | 1.26 |
| AD-44713.1 | 0.10 | 1.04 |
| AD-44714.1 | 0.72 | 1.34 |
| AD-44715.1 | 0.02 | 0.18 |
| AD-44715.1 | 0.03 | 0.23 |

TABLE 5-continued

Serpina1 single dose screen

| | 10 nM Average | 0.1 nM Average |
|---|---|---|
| AD-44716.1 | 0.99 | 1.08 |
| AD-44717.1 | 0.04 | 0.52 |
| AD-44718.1 | 0.76 | 1.14 |
| AD-44719.1 | 0.03 | 0.53 |
| AD-44720.1 | 0.36 | 1.14 |
| AD-44721.1 | 0.91 | 1.12 |
| AD-44722.1 | 0.03 | 0.40 |
| AD-44723.1 | 0.09 | 0.70 |
| AD-44724.1 | 0.02 | 0.37 |
| AD-44725.1 | 0.65 | 1.29 |
| AD-44726.1 | 0.44 | 1.11 |
| AD-44727.1 | 1.15 | 1.27 |
| AD-44728.1 | 0.67 | 1.24 |
| AD-44729.1 | 0.52 | 0.97 |
| AD-44730.1 | 0.58 | 1.11 |
| AD-44731.1 | 0.93 | 1.26 |
| AD-44732.1 | 0.16 | 0.94 |
| AD-44733.1 | 0.10 | 0.85 |
| AD-44734.1 | 0.03 | 0.52 |
| AD-44735.1 | 0.04 | 0.48 |
| AD-44736.1 | 0.12 | 0.99 |
| AD-44737.1 | 0.25 | 0.94 |
| Mock | 1.17 | 1.10 |
| Mock | 0.87 | 1.15 |
| AD-1955 | 1.12 | 0.87 |
| AD-1955 | 1.01 | 0.93 |

TABLE 5-continued

| Serpina1 single dose screen | | |
|---|---|---|
| | 10 nM Average | 0.1 nM Average |
| AD-1955 | 0.86 | 1.01 |
| AD-1955 | 1.06 | 1.04 |
| AD-1955 | 1.12 | 1.05 |
| AD-1955 | 1.11 | 1.14 |

TABLE 6

Serpina1 $IC_{50}$ Data

| | IC50 24 hrs (nM) | | IC50 120 hrs (nM) | |
|---|---|---|---|---|
| Duplex ID | Normalized to AD-1955 | Normalized to low dose | Normalized to AD-1955 | Normalized to low dose |
| AD-44715.1 | 0.041 | 0.033 | 0.004 | 0.005 |
| AD-44722.1 | 0.097 | 0.075 | 0.006 | 0.008 |
| AD-44734.1 | 0.237 | 0.237 | 0.008 | 0.01 |
| AD-44717.1 | 0.172 | 0.167 | 0.008 | 0.012 |
| AD-44723.1 | 0.303 | 0.352 | 0.017 | 0.025 |
| AD-44735.1 | 0.082 | 0.076 | 0.011 | 0.01 |
| AD-44724.1 | 0.086 | 0.098 | 0.003 | 0.005 |

TABLE 6-continued

Serpina1 $IC_{50}$ Data

| | IC50 24 hrs (nM) | | IC50 120 hrs (nM) | |
|---|---|---|---|---|
| Duplex ID | Normalized to AD-1955 | Normalized to low dose | Normalized to AD-1955 | Normalized to low dose |
| AD-44719.1 | 0.337 | 0.289 | 0.009 | 0.018 |
| AD-44737.1 | 20.511 | 20.828 | 0.052 | 0.07 |

TABLE 7

Serpina1 $IC_{50}$ Data from Hep3B cells 24 hours after treatment

| Duplex ID | IC50 I (nM) | IC50 II (nM) |
|---|---|---|
| AD-44715.1 | 0.040 | 0.043 |
| AD-44722.1 | 0.094 | 0.103 |
| AD-44734.1 | 0.244 | 0.225 |
| AD-44717.1 | 0.163 | 0.185 |
| AD-44723.1 | 0.280 | 0.335 |
| AD-44735.1 | 0.082 | 0.083 |
| AD-44724.1 | 0.085 | 0.090 |
| AD-44719.1 | 0.351 | 0.342 |
| AD-44737.1 | 23.169 | 24.430 |

Other embodiments are in the claims.

```
SEQ ID NO: 01: Human Serpina1 mRNA, transcript variant1 (NM_000295.4)
    1 acaatgactc ctttcggtaa gtgcagtgga agctgtacac tgcccaggca aagcgtccgg

   61 gcagcgtagg cgggcgactc agatcccagc cagtggactt agcccctgtt tgctcctccg

  121 ataactgggg tgaccttggt taatattcac cagcagcctc ccccgttgcc cctctggatc

  181 cactgcttaa atacggacga ggacagggcc ctgtctcctc agcttcaggc accaccactg

  241 acctgggaca gtgaatcgac aatgccgtct tctgtctcgt ggggcatcct cctgctggca

  301 ggcctgtgct gcctggtccc tgtctccctg gctgaggatc cccagggaga tgctgcccag

  361 aagacagata catcccacca tgatcaggat cacccaacct tcaacaagat cacccccaac

  421 ctggctgagt tcgccttcag cctataccgc cagctggcac accagtccaa cagcaccaat

  481 atcttcttct ccccagtgag catcgctaca gcctttgcaa tgctctccct ggggaccaag

  541 gctgacactc acgatgaaat cctggagggc ctgaatttca acctcacgga gattccggag

  601 gctcagatcc atgaaggctt ccaggaactc ctccgtaccc tcaaccagcc agacagccag

  661 ctccagctga ccaccggcaa tggcctgttc ctcagcgagg gcctgaagct agtggataag

  721 tttttggagg atgttaaaaa gttgtaccac tcagaagcct tcactgtcaa cttcggggac

  781 accgaagagg ccaagaaaca gatcaacgat tacgtggaga agggtactca agggaaaatt

  841 gtggatttgg tcaaggagct tgacagagac acagtttttg ctctggtgaa ttacatcttc

  901 tttaaaggca aatgggagag accctttgaa gtcaaggaca ccgaggaaga ggacttccac

  961 gtggaccagg tgaccaccgt gaaggtgcct atgatgaagc gtttaggcat gtttaacatc

 1021 cagcactgta agaagctgtc cagctgggtg ctgctgatga aatacctggg caatgccacc

 1081 gccatcttct tcctgcctga tgaggggaaa ctacagcacc tggaaaatga actcacccac

 1141 gatatcatca ccaagttcct ggaaaatgaa gacagaaggt ctgccagctt acatttaccc

 1201 aaactgtcca ttactggaac ctatgatctg aagagcgtcc tgggtcaact gggcatcact

 1261 aaggtcttca gcaatggggc tgacctctcc ggggtcacag aggaggcacc cctgaagctc

 1321 tccaaggccg tgcataaggc tgtgctgacc atcgacgaga aagggactga agctgctggg

 1381 gccatgtttt tagaggccat acccatgtct atcccccccg aggtcaagtt caacaaaccc
```

-continued

```
1441 tttgtcttct taatgattga acaaaatacc aagtctcccc tcttcatggg aaaagtggtg
1501 aatcccaccc aaaaataact gcctctcgct cctcaacccc tcccctccat ccctggcccc
1561 ctccctggat gacattaaag aagggttgag ctggtccctg cctgcatgtg actgtaaatc
1621 cctcccatgt tttctctgag tctccctttg cctgctgagg ctgtatgtgg gctccaggta
1681 acagtgctgt cttcgggccc cctgaactgt gttcatggag catctggctg ggtaggcaca
1741 tgctgggctt gaatccaggg gggactgaat cctcagctta cggacctggg cccatctgtt
1801 tctggagggc tccagtcttc cttgtcctgt cttggagtcc ccaagaagga atcacagggg
1861 aggaaccaga taccagccat gaccccaggc tccaccaagc atcttcatgt ccccctgctc
1921 atcccccact cccccccacc cagagttgct catcctgcca gggctggctg tgcccacccc
1981 aaggctgccc tcctgggggc cccagaactg cctgatcgtg ccgtggccca gttttgtggc
2041 atctgcagca acacaagaga gaggacaatg tcctcctctt gacccgctgt cacctaacca
2101 gactcgggcc ctgcacctct caggcacttc tggaaaatga ctgaggcaga ttcttcctga
2161 agcccattct ccatggggca acaaggacac ctattctgtc cttgtccttc catcgctgcc
2221 ccagaaagcc tcacatatct ccgtttagaa tcaggtccct tctccccaga tgaagaggag
2281 ggtctctgct ttgttttctc tatctcctcc tcagacttga ccaggcccag caggccccag
2341 aagaccatta ccctatatcc cttctcctcc ctagtcacat ggccataggc ctgctgatgg
2401 ctcaggaagg ccattgcaag gactcctcag ctatgggaga ggaagcacat cacccattga
2461 cccccgcaac ccctcccttt cctcctctga gtcccgactg gggccacatg cagcctgact
2521 tctttgtgcc tgttgctgtc cctgcagtct tcagagggcc accgcagctc cagtgccacg
2581 gcaggaggct gttcctgaat agcccctgtg gtaagggcca ggagagtcct tccatcctcc
2641 aaggccctgc taaaggacac agcagccagg aagtcccctg ggcccctagc tgaaggacag
2701 cctgctccct ccgtctctac caggaatggc cttgtcctat ggaaggcact gccccatccc
2761 aaactaatct aggaatcact gtctaaccac tcactgtcat gaatgtgtac ttaaaggatg
2821 aggttgagtc ataccaaata gtgatttcga tagttcaaaa tggtgaaatt agcaattcta
2881 catgattcag tctaatcaat ggataccgac tgtttcccac acaagtctcc tgttctctta
2941 agcttactca ctgacagcct ttcactctcc acaaatacat taaagatatg gccatcacca
3001 agccccctag gatgacacca gacctgagag tctgaagacc tggatccaag ttctgacttt
3061 tccccctgac agctgtgtga ccttcgtgaa gtcgccaaac ctctctgagc cccagtcatt
3121 gctagtaaga cctgcctttg agttggtatg atgttcaagt tagataacaa aatgtttata
3181 cccattagaa cagagaataa atagaactac atttcttgca
```

SEQ ID NO: 02: Human Serpina1 mRNA, transcript variant 3
(NM_001002235.2)

```
  1 tgggcaggaa ctgggcactg tgcccagggc atgcactgcc tccacgcagc aaccctcaga
 61 gtcctgagct gaaccaagaa ggaggagggg gtcgggcctc cgaggaaggc ctagccgctg
121 ctgctgccag gaattccagg ttggaggggc ggcaacctcc tgccagcctt caggccactc
181 tcctgtgcct gccagaagag acagagcttg aggagagctt gaggagagca ggaaaggaca
241 atgccgtctt ctgtctcgtg ggcatcctcc ctgctggcag gcctgtgctg cctggtccct
301 gtctccctgg ctgaggatcc ccagggagat gctgcccaga agacagatac atcccaccat
361 gatcaggatc acccaacctt caacaagatc acccccaacc tggctgagtt cgccttcagc
421 ctataccgcc agctggcaca ccagtccaac agcaccaata tcttcttctc cccagtgagc
481 atcgctacag cctttgcaat gctctccctg gggaccaagg ctgacactca cgatgaaatc
```

-continued 541 ctggagggcc tgaatttcaa cctcacggag attccggagg ctcagatcca tgaaggcttc 601 caggaactcc tccgtaccct caaccagcca gacagccagc tccagctgac caccggcaat 661 ggcctgttcc tcagcgaggg cctgaagcta gtggataagt tttggagga tgttaaaaag 721 ttgtaccact cagaagcctt cactgtcaac ttcggggaca ccgaagaggc caagaaacag 781 atcaacgatt acgtggagaa gggtactcaa gggaaaattg tggatttggt caaggagctt 841 gacagagaca cagtttttgc tctggtgaat tacatcttct ttaaaggcaa atgggagaga 901 ccctttgaag tcaaggacac cgaggaagag gacttccacg tggaccaggt gaccaccgtg 961 aaggtgccta tgatgaagcg tttaggcatg tttaacatcc agcactgtaa gaagctgtcc 1021 agctgggtgc tgctgatgaa atacctgggc aatgccaccg ccatcttctt cctgcctgat 1081 gaggggaaac tacagcacct ggaaaatgaa ctcacccacg atatcatcac caagttcctg 1141 gaaaatgaag acagaaggtc tgccagctta catttaccca aactgtccat tactggaacc 1201 tatgatctga agagcgtcct gggtcaactg ggcatcacta aggtcttcag caatggggct 1261 gacctctccg gggtcacaga ggaggcaccc ctgaagctct ccaaggccgt gcataaggct 1321 gtgctgacca tcgacgagaa agggactgaa gctgctgggg ccatgttttt agaggccata 1381 cccatgtcta tccccccccga ggtcaagttc aacaaaccct ttgtcttctt aatgattgaa 1441 caaaatacca agtctcccct cttcatggga aaagtggtga atcccaccca aaaataactg 1501 cctctcgctc ctcaacccct cccctccatc cctggccccc tccctggatg acattaaaga 1561 agggttgagc tggtccctgc ctgcatgtga ctgtaaatcc ctcccatgtt ttctctgagt 1621 ctccctttgc ctgctgaggc tgtatgtggg ctccaggtaa cagtgctgtc ttcgggcccc 1681 ctgaactgtg ttcatggagc atctggctgg gtaggcacat gctgggcttg aatccagggg 1741 ggactgaatc ctcagcttac ggacctgggc ccatctgttt ctggagggct ccagtcttcc 1801 ttgtcctgtc ttggagtccc caagaaggaa tcacagggga ggaaccagat accagccatg 1861 accccaggct ccaccaagca tcttcatgtc cccctgctca tcccccactc ccccccaccc 1921 agagttgctc atcctgccag ggctggctgt gcccacccca aggctgccct cctgggggcc 1981 ccagaactgc ctgatcgtgc cgtggcccag ttttgtggca tctgcagcaa cacaagagag 2041 aggacaatgt cctcctcttg acccgctgtc acctaaccag actcgggccc tgcacctctc 2101 aggcacttct ggaaaatgac tgaggcagat tcttcctgaa gcccattctc catggggcaa 2161 caaggacacc tattctgtcc ttgtccttcc atcgctgccc cagaaagcct cacatatctc 2221 cgtttagaat caggtccctt ctccccagat gaagaggagg gtctctgctt tgttttctct 2281 atctcctcct cagacttgac caggcccagc aggccccaga agaccattac cctatatccc 2341 ttctcctccc tagtcacatg gccataggcc tgctgatggc tcaggaaggc cattgcaagg 2401 actcctcagc tatgggagag gaagcacatc acccattgac cccccgcaacc cctccctttc 2461 ctcctctgag tcccgactgg ggccacatgc agcctgactt ctttgtgcct gttgctgtcc 2521 ctgcagtctt cagagggcca ccgcagctcc agtgccacgg caggaggctg ttcctgaata 2581 gcccctgtgg taagggccag gagagtcctt ccatcctcca aggccctgct aaaggacaca 2641 gcagccagga agtcccctgg gcccctagct gaaggacagc ctgctccctc cgtctctacc 2701 aggaatggcc ttgtcctatg gaaggcactg ccccatccca aactaatcta ggaatcactg 2761 tctaaccact cactgtcatg aatgtgtact taaaggatga ggttgagtca taccaaatag 2821 tgatttcgat agttcaaaat ggtgaaatta gcaattctac atgattcagt ctaatcaatg 2881 gataccgact gtttcccaca caagtctcct gttctcttaa gcttactcac tgacagcctt 2941 tcactctcca caaatacatt aaagatatgg ccatcaccaa gcccccctagg atgacaccag -continued

```
3001 acctgagagt ctgaagacct ggatccaagt tctgactttt ccccctgaca gctgtgtgac
3061 cttcgtgaag tcgccaaacc tctctgagcc ccagtcattg ctagtaagac ctgcctttga
3121 gttggtatga tgttcaagtt agataacaaa atgtttatac ccattagaac agagaataaa
3181 tagaactaca tttcttgca
```

SEQ ID NO: 03: Human Serpina1 mRNA, transcript variant 2 (NM_001002236.2)

```
   1 tgggcaggaa ctgggcactg tgcccagggc atgcactgcc tccacgcagc aaccctcaga
  61 gtcctgagct gaaccaagaa ggaggagggg gtcgggcctc cgaggaaggc ctagccgctg
 121 ctgctgccag gaattccagg ttggaggggc ggcaacctcc tgccagcctt caggccactc
 181 tcctgtgcct gccagaagag acagagcttg aggagagctt gaggagagca ggaaagggcg
 241 gcagtaagtc ttcagcatca ggcattttgg ggtgactcag taaatggtag atcttgctac
 301 cagtggaaca gccactaagg attctgcagt gagagcagag ggccagctaa gtggtactct
 361 cccagagact gtctgactca cgccaccccc tccaccttgg acacaggacg ctgtggtttc
 421 tgagccaggt acaatgactc ctttcgcagc ctcccccgtt gcccctctgg atccactgct
 481 taaatacgga cgaggacagg gccctgtctc ctcagcttca ggcaccacca ctgacctggg
 541 acagtgaatc gacaatgccg tcttctgtct cgtggggcat cctcctgctg gcaggcctgt
 601 gctgcctggt ccctgtctcc ctggctgagg atccccaggg agatgctgcc cagaagacag
 661 atacatccca ccatgatcag gatcacccaa ccttcaacaa gatcaccccc aacctggctg
 721 agttcgcctt cagcctatac cgccagctgg cacaccagtc caacagcacc aatatcttct
 781 tctccccagt gagcatcgct acagcctttg caatgctctc cctggggacc aaggctgaca
 841 ctcacgatga aatcctggag ggcctgaatt tcaacctcac ggagattccg gaggctcaga
 901 tccatgaagg cttccaggaa ctcctccgta ccctcaacca gccagacagc cagctccagc
 961 tgaccaccgg caatggcctg ttcctcagcg agggcctgaa gctagtggat aagtttttgg
1021 aggatgttaa aaagttgtac cactcagaag ccttcactgt caacttcggg gacaccgaag
1081 aggccaagaa acagatcaac gattacgtgg agaagggtac tcaagggaaa attgtggatt
1141 tggtcaagga gcttgacaga gacacagttt ttgctctggt gaattacatc ttctttaaag
1201 gcaaatggga gagacccttt gaagtcaagg acaccgagga agaggacttc cacgtggacc
1261 aggtgaccac cgtgaaggtg cctatgatga agcgtttagg catgtttaac atccagcact
1321 gtaagaagct gtccagctgg gtgctgctga tgaaatacct gggcaatgcc accgccatct
1381 tcttcctgcc tgatgagggg aaactacagc acctggaaaa tgaactcacc cacgatatca
1441 tcaccaagtt cctggaaaat gaagacagaa ggtctgccag cttacattta cccaaactgt
1501 ccattactgg aacctatgat ctgaagagcg tcctgggtca actgggcatc actaaggtct
1561 tcagcaatgg ggctgacctc tccggggtca cagaggaggc acccctgaag ctctccaagg
1621 ccgtgcataa ggctgtgctg accatcgacg agaaagggac tgaagctgct ggggccatgt
1681 ttttagaggc catacccatg tctatccccc ccgaggtcaa gttcaacaaa ccctttgtct
1741 tcttaatgat tgaacaaaat accaagtctc ccctcttcat gggaaaagtg gtgaatccca
1801 cccaaaaata actgcctctc gctcctcaac ccctcccctc catccctggc cccctccctg
1861 gatgacatta aagaagggtt gagctggtcc ctgcctgcat gtgactgtaa atccctccca
1921 tgttttctct gagtctccct ttgcctgctg aggctgtatg tgggctccag gtaacagtgc
1981 tgtcttcggg ccccctgaac tgtgttcatg gagcatctgg ctgggtaggc acatgctggg
2041 cttgaatcca ggggggactg aatcctcagc ttacggacct gggcccatct gtttctggag
```

-continued 2101 ggctccagtc ttccttgtcc tgtcttggag tccccaagaa ggaatcacag gggaggaacc 2161 agataccagc catgacccca ggctccacca agcatcttca tgtccccctg ctcatccccc 2221 actccccccc acccagagtt gctcatcctg ccagggctgg ctgtgcccac cccaaggctg 2281 ccctcctggg ggccccagaa ctgcctgatc gtgccgtggc ccagttttgt ggcatctgca 2341 gcaacacaag agagaggaca atgtcctcct cttgacccgc tgtcacctaa ccagactcgg 2401 gccctgcacc tctcaggcac ttctggaaaa tgactgaggc agattcttcc tgaagcccat 2461 tctccatggg gcaacaagga cacctattct gtccttgtcc ttccatcgct gccccagaaa 2521 gcctcacata tctccgttta gaatcaggtc ccttctcccc agatgaagag gagggtctct 2581 gctttgtttt ctctatctcc tcctcagact tgaccaggcc cagcaggccc cagaagacca 2641 ttaccctata tcccttctcc tccctagtca catggccata ggcctgctga tggctcagga 2701 aggccattgc aaggactcct cagctatggg agaggaagca catcacccat tgacccccgc 2761 aacccctccc tttcctcctc tgagtcccga ctggggccac atgcagcctg acttctttgt 2821 gcctgttgct gtccctgcag tcttcagagg gccaccgcag ctccagtgcc acggcaggag 2881 gctgttcctg aatagcccct gtggtaaggg ccaggagagt ccttccatcc tccaaggccc 2941 tgctaaagga cacagcagcc aggaagtccc ctgggcccct agctgaagga cagcctgctc 3001 cctccgtctc taccaggaat ggccttgtcc tatggaaggc actgccccat cccaaactaa 3061 tctaggaatc actgtctaac cactcactgt catgaatgtg tacttaaagg atgaggttga 3121 gtcataccaa atagtgattt cgatagttca aaatggtgaa attagcaatt ctacatgatt 3181 cagtctaatc aatggatacc gactgtttcc cacacaagtc tcctgttctc ttaagcttac 3241 tcactgacag cctttcactc tccacaaata cattaaagat atggccatca ccaagccccc 3301 taggatgaca ccagacctga gagtctgaag acctggatcc aagttctgac ttttccccct 3361 gacagctgtg tgaccttcgt gaagtcgcca aacctctctg agccccagtc attgctagta 3421 agacctgcct ttgagttggt atgatgttca agttagataa caaaatgttt atacccatta 3481 gaacagagaa taaatagaac tacatttctt gca SEQ ID NO: 04: Human Serpina1 mRNA, transcript variant 4
(NM_001127700.1)

1 tgggcaggaa ctgggcactg tgcccagggc atgcactgcc tccacgcagc aaccctcaga 61 gtcctgagct gaaccaagaa ggaggagggg gtcgggcctc cgaggaaggc ctagccgctg 121 ctgctgccag gaattccagg ttggaggggc ggcaacctcc tgccagcctt caggccactc 181 tcctgtgcct gccagaagag acagagcttg aggagagctt gaggagagca ggaaaggtgg 241 gacattgctg ctgctgctca ctcagttcca caggacaatg ccgtcttctg tctcgtgggg 301 catcctcctg ctggcaggcc tgtgctgcct ggtccctgtc tccctggctg aggatcccca 361 gggagatgct gcccagaaga cagatacatc ccaccatgat caggatcacc caaccttcaa 421 caagatcacc cccaacctgg ctgagttcgc cttcagccta taccgccagc tggcacacca 481 gtccaacagc accaatatct tcttctcccc agtgagcatc gctacagcct ttgcaatgct 541 ctccctgggg accaaggctg acactcacga tgaaatcctg gagggcctga atttcaacct 601 cacggagatt ccggaggctc agatccatga aggcttccag gaactcctcc gtaccctcaa 661 ccagccagac agccagctcc agctgaccac cggcaatggc ctgttcctca gcgagggcct 721 gaagctagtg gataagtttt tggaggatgt taaaaagttg taccactcag aagccttcac 781 tgtcaacttc ggggacaccg aagaggccaa gaaacagatc aacgattacg tggagaaggg 841 tactcaaggg aaaattgtgg atttggtcaa ggagcttgac agagacacag tttttgctct 901 ggtgaattac atcttcttta aaggcaaatg ggagagaccc tttgaagtca aggacaccga -continued

```
 961 ggaagaggac ttccacgtgg accaggtgac caccgtgaag gtgcctatga tgaagcgttt
1021 aggcatgttt aacatccagc actgtaagaa gctgtccagc tgggtgctgc tgatgaaata
1081 cctgggcaat gccaccgcca tcttcttcct gcctgatgag gggaaactac agcacctgga
1141 aaatgaactc acccacgata tcatcaccaa gttcctggaa aatgaagaca gaaggtctgc
1201 cagcttacat ttacccaaac tgtccattac tggaacctat gatctgaaga gcgtcctggg
1261 tcaactgggc atcactaagg tcttcagcaa tggggctgac ctctccgggg tcacagagga
1321 ggcacccctg aagctctcca aggccgtgca taaggctgtg ctgaccatcg acgagaaagg
1381 gactgaagct gctggggcca tgtttttaga ggccataccc atgtctatcc cccccgaggt
1441 caagttcaac aaaccctttg tcttcttaat gattgaacaa aataccaagt ctcccctctt
1501 catgggaaaa gtggtgaatc ccacccaaaa ataactgcct ctcgctcctc aacccctccc
1561 ctccatccct ggccccctcc ctggatgaca ttaaagaagg gttgagctgg tccctgcctg
1621 catgtgactg taaatccctc ccatgttttc tctgagtctc cctttgcctg ctgaggctgt
1681 atgtgggctc caggtaacag tgctgtcttc gggccccctg aactgtgttc atggagcatc
1741 tggctgggta ggcacatgct gggcttgaat ccagggggga ctgaatcctc agcttacgga
1801 cctgggccca tctgtttctg gagggctcca gtcttccttg tcctgtcttg gagtccccaa
1861 gaaggaatca caggggagga accagatacc agccatgacc ccaggctcca ccaagcatct
1921 tcatgtcccc ctgctcatcc cccactcccc cccacccaga gttgctcatc ctgccagggc
1981 tggctgtgcc caccccaagg ctgccctcct gggggcccca gaactgcctg atcgtgccgt
2041 ggcccagttt tgtggcatct gcagcaacac aagagagagg acaatgtcct cctcttgacc
2101 cgctgtcacc taaccagact cgggccctgc acctctcagg cacttctgga aaatgactga
2161 ggcagattct tcctgaagcc cattctccat ggggcaacaa ggacacctat tctgtccttg
2221 tccttccatc gctgccccag aaagcctcac atatctccgt ttagaatcag gtcccttctc
2281 cccagatgaa gaggagggtc tctgctttgt tttctctatc tcctcctcag acttgaccag
2341 gcccagcagg ccccagaaga ccattaccct atatcccttc tcctccctag tcacatggcc
2401 ataggcctgc tgatggctca ggaaggccat tgcaaggact cctcagctat gggagaggaa
2461 gcacatcacc cattgacccc cgcaacccct ccctttcctc ctctgagtcc cgactggggc
2521 cacatgcagc ctgacttctt tgtgcctgtt gctgtccctg cagtcttcag agggccaccg
2581 cagctccagt gccacggcag gaggctgttc ctgaatagcc cctgtggtaa gggccaggag
2641 agtccttcca tcctccaagg ccctgctaaa ggacacagca gccaggaagt cccctgggcc
2701 cctagctgaa ggacagcctg ctccctccgt ctctaccagg aatggccttg tcctatggaa
2761 ggcactgccc catcccaaac taatctagga atcactgtct aaccactcac tgtcatgaat
2821 gtgtacttaa aggatgaggt tgagtcatac caaatagtga tttcgatagt tcaaaatggt
2881 gaaattagca attctacatg attcagtcta atcaatggat accgactgtt tcccacacaa
2941 gtctcctgtt ctcttaagct tactcactga cagcctttca ctctccacaa atacattaaa
3001 gatatggcca tcaccaagcc ccctaggatg acaccagacc tgagagtctg aagacctgga
3061 tccaagttct gacttttccc cctgacagct gtgtgacctt cgtgaagtcg ccaaacctct
3121 ctgagcccca gtcattgcta gtaagacctg cctttgagtt ggtatgatgt tcaagttaga
3181 taacaaaatg tttataccca ttagaacaga gaataaatag aactacattt cttgca
```

SEQ ID NO: 05: Human Serpina1 mRNA, transcript variant 5 (NM_001127701.1)

```
   1 tgggcaggaa ctgggcactg tgcccagggc atgcactgcc tccacgcagc aaccctcaga
```

-continued

```
  61 gtcctgagct gaaccaagaa ggaggagggg gtcgggcctc cgaggaaggc ctagccgctg
 121 ctgctgccag gaattccagg ttggaggggc ggcaacctcc tgccagcctt caggccactc
 181 tcctgtgcct gccagaagag acagagcttg aggagagctt gaggagagca ggaaaggtgg
 241 gacattgctg ctgctgctca ctcagttcca cagggcggca gtaagtcttc agcatcaggc
 301 attttggggt gactcagtaa atggtagatc ttgctaccag tggaacagcc actaaggatt
 361 ctgcagtgag agcagagggc cagctaagtg gtactctccc agagactgtc tgactcacgc
 421 cacccccctcc accttggaca caggacgctg tggtttctga gccagcagcc tcccccgttg
 481 cccctctgga tccactgctt aaatacggac gaggacaggg ccctgtctcc tcagcttcag
 541 gcaccaccac tgacctggga cagtgaatcg acaatgccgt cttctgtctc gtggggcatc
 601 ctcctgctgg caggcctgtg ctgcctggtc cctgtctccc tggctgagga tccccaggga
 661 gatgctgccc agaagacaga tacatcccac catgatcagg atcacccaac cttcaacaag
 721 atcacccccca acctggctga gttcgccttc agcctatacc gccagctggc acaccagtcc
 781 aacagcacca atatcttctt ctccccagtg agcatcgcta cagcctttgc aatgctctcc
 841 ctggggacca aggctgacac tcacgatgaa atcctggagg gcctgaattt caacctcacg
 901 gagattccgg aggctcagat ccatgaaggc ttccaggaac tcctccgtac cctcaaccag
 961 ccagacagcc agctccagct gaccaccggc aatggcctgt tcctcagcga gggcctgaag
1021 ctagtggata agtttttgga ggatgttaaa aagttgtacc actcagaagc cttcactgtc
1081 aacttcgggg acaccgaaga ggccaagaaa cagatcaacg attacgtgga gaagggtact
1141 caagggaaaa ttgtggattt ggtcaaggag cttgacagag acacagtttt tgctctggtg
1201 aattacatct tctttaaagg caaatgggag agaccctttg aagtcaagga caccgaggaa
1261 gaggacttcc acgtggacca ggtgaccacc gtgaaggtgc ctatgatgaa gcgtttaggc
1321 atgtttaaca tccagcactg taagaagctg tccagctggg tgctgctgat gaaatacctg
1381 ggcaatgcca ccgccatctt cttcctgcct gatgagggga aactacagca cctggaaaat
1441 gaactcaccc acgatatcat caccaagttc ctggaaaatg aagacagaag gtctgccagc
1501 ttacatttac ccaaactgtc cattactgga acctatgatc tgaagagcgt cctgggtcaa
1561 ctgggcatca ctaaggtctt cagcaatggg gctgacctct ccggggtcac agaggaggca
1621 cccctgaagc tctccaaggc cgtgcataag gctgtgctga ccatcgacga gaaagggact
1681 gaagctgctg gggccatgtt tttagaggcc atacccatgt ctatcccccc cgaggtcaag
1741 ttcaacaaac cctttgtctt cttaatgatt gaacaaaata ccaagtctcc cctcttcatg
1801 ggaaaagtgg tgaatcccac ccaaaaataa ctgcctctcg ctcctcaacc cctcccctcc
1861 atccctggcc ccctccctgg atgacattaa agaagggttg agctggtccc tgcctgcatg
1921 tgactgtaaa tccctcccat gttttctctg agtctccctt tgcctgctga ggctgtatgt
1981 gggctccagg taacagtgct gtcttcgggc cccctgaact gtgttcatgg agcatctggc
2041 tgggtaggca catgctgggc ttgaatccag gggggactga atcctcagct tacggacctg
2101 ggcccatctg tttctggagg gctccagtct tccttgtcct gtcttggagt ccccaagaag
2161 gaatcacagg ggaggaacca gataccagcc atgaccccag gctccaccaa gcatcttcat
2221 gtcccccctgc tcatccccca ctccccccca cccagagttg ctcatcctgc cagggctggc
2281 tgtgcccacc ccaaggctgc cctcctgggg gccccagaac tgcctgatcg tgccgtggcc
2341 cagttttgtg gcatctgcag caacacaaga gagaggacaa tgtcctcctc ttgacccgct
2401 gtcacctaac cagactcggg ccctgcacct ctcaggcact tctggaaaat gactgaggca
2461 gattcttcct gaagcccatt ctccatgggg caacaaggac acctattctg tccttgtcct
```

-continued 2521 tccatcgctg ccccagaaag cctcacatat ctccgtttag aatcaggtcc cttctcccca 2581 gatgaagagg agggtctctg ctttgttttc tctatctcct cctcagactt gaccaggccc 2641 agcaggcccc agaagaccat taccctatat cccttctcct ccctagtcac atggccatag 2701 gcctgctgat ggctcaggaa ggccattgca aggactcctc agctatggga gaggaagcac 2761 atcacccatt gacccccgca acccctccct ttcctcctct gagtcccgac tggggccaca 2821 tgcagcctga cttctttgtg cctgttgctg tccctgcagt cttcagaggg ccaccgcagc 2881 tccagtgcca cggcaggagg ctgttcctga atagcccctg tggtaagggc caggagagtc 2941 cttccatcct ccaaggccct gctaaaggac acagcagcca ggaagtcccc tgggccccta 3001 gctgaaggac agcctgctcc ctccgtctct accaggaatg gccttgtcct atggaaggca 3061 ctgccccatc ccaaactaat ctaggaatca ctgtctaacc actcactgtc atgaatgtgt 3121 acttaaagga tgaggttgag tcataccaaa tagtgatttc gatagttcaa aatggtgaaa 3181 ttagcaattc tacatgattc agtctaatca atggataccg actgtttccc acacaagtct 3241 cctgttctct taagcttact cactgacagc ctttcactct ccacaaatac attaaagata 3301 tggccatcac caagcccccct aggatgacac cagacctgag agtctgaaga cctggatcca 3361 agttctgact tttccccctg acagctgtgt gaccttcgtg aagtcgccaa acctctctga 3421 gccccagtca ttgctagtaa gacctgcctt tgagttggta tgatgttcaa gttagataac 3481 aaaatgttta tacccattag aacagagaat aaatagaact acatttcttg ca SEQ ID NO: 06: Human Serpina1 mRNA, transcript variant 6
(NM_001127702.1)

1 tgggcaggaa ctgggcactg tgcccagggc atgcactgcc tccacgcagc aaccctcaga 61 gtcctgagct gaaccaagaa ggaggagggg gtcgggcctc cgaggaaggc ctagccgctg 121 ctgctgccag gaattccagg ttggaggggc ggcaacctcc tgccagcctt caggccactc 181 tcctgtgcct gccagaagag acagagcttg aggagagctt gaggagagca ggaaaggtgg 241 gacattgctg ctgctgctca ctcagttcca cagcagcctc ccccgttgcc cctctggatc 301 cactgcttaa atacggacga ggacagggcc ctgtctcctc agcttcaggc accaccactg 361 acctgggaca gtgaatcgac aatgccgtct tctgtctcgt ggggcatcct cctgctggca 421 ggcctgtgct gcctggtccc tgtctccctg gctgaggatc cccagggaga tgctgcccag 481 aagacagata catcccacca tgatcaggat cacccaacct tcaacaagat cacccccaac 541 ctggctgagt tcgccttcag cctataccgc cagctggcac accagtccaa cagcaccaat 601 atcttcttct ccccagtgag catcgctaca gcctttgcaa tgctctccct ggggaccaag 661 gctgacactc acgatgaaat cctggagggc ctgaatttca acctcacgga gattccggag 721 gctcagatcc atgaaggctt ccaggaactc ctccgtaccc tcaaccagcc agacagccag 781 ctccagctga ccaccggcaa tggcctgttc ctcagcgagg gcctgaagct agtggataag 841 tttttggagg atgttaaaaa gttgtaccac tcagaagcct tcactgtcaa cttcggggac 901 accgaagagg ccaagaaaca gatcaacgat tacgtggaga agggtactca agggaaaatt 961 gtggatttgg tcaaggagct tgacagagac acagtttttg ctctggtgaa ttacatcttc 1021 tttaaaggca aatgggagag accctttgaa gtcaaggaca ccgaggaaga ggacttccac 1081 gtggaccagg tgaccaccgt gaaggtgcct atgatgaagc gtttaggcat gtttaacatc 1141 cagcactgta agaagctgtc cagctgggtg ctgctgatga aatacctggg caatgccacc 1201 gccatcttct tcctgcctga tgaggggaaa ctacagcacc tggaaaatga actcacccac 1261 gatatcatca ccaagttcct ggaaaatgaa gacagaaggt ctgccagctt acatttaccc -continued 1321 aaactgtcca ttactggaac ctatgatctg aagagcgtcc tgggtcaact gggcatcact
1381 aaggtcttca gcaatggggc tgacctctcc ggggtcacag aggaggcacc cctgaagctc
1441 tccaaggccg tgcataaggc tgtgctgacc atcgacgaga aagggactga agctgctggg
1501 gccatgtttt tagaggccat acccatgtct atcccccccg aggtcaagtt caacaaaccc
1561 tttgtcttct taatgattga acaaaatacc aagtctcccc tcttcatggg aaaagtggtg
1621 aatcccaccc aaaaataact gcctctcgct cctcaacccc tcccctccat ccctggcccc
1681 ctccctggat gacattaaag aagggttgag ctggtccctg cctgcatgtg actgtaaatc
1741 cctcccatgt tttctctgag tctccctttg cctgctgagg ctgtatgtgg gctccaggta
1801 acagtgctgt cttcgggccc cctgaactgt gttcatggag catctggctg ggtaggcaca
1861 tgctgggctt gaatccaggg gggactgaat cctcagctta cggacctggg cccatctgtt
1921 tctggagggc tccagtcttc cttgtcctgt cttggagtcc ccaagaagga atcacagggg
1981 aggaaccaga taccagccat gaccccaggc tccaccaagc atcttcatgt ccccctgctc
2041 atcccccact ccccccacc cagagttgct catcctgcca gggctggctg tgcccacccc
2101 aaggctgccc tcctgggggc cccagaactg cctgatcgtg ccgtggccca gttttgtggc
2161 atctgcagca acacaagaga gaggacaatg tcctcctctt gacccgctgt cacctaacca
2221 gactcgggcc ctgcacctct caggcacttc tggaaaatga ctgaggcaga ttcttcctga
2281 agcccattct ccatggggca acaaggacac ctattctgtc cttgtccttc catcgctgcc
2341 ccagaaagcc tcacatatct ccgtttagaa tcaggtccct tctccccaga tgaagaggag
2401 ggtctctgct ttgttttctc tatctcctcc tcagacttga ccaggcccag caggccccag
2461 aagaccatta ccctatatcc cttctcctcc ctagtcacat ggccataggc ctgctgatgg
2521 ctcaggaagg ccattgcaag gactcctcag ctatgggaga ggaagcacat cacccattga
2581 cccccgcaac cctcccttt cctcctctga gtcccgactg gggccacatg cagcctgact
2641 tctttgtgcc tgttgctgtc cctgcagtct tcagagggcc accgcagctc cagtgccacg
2701 gcaggaggct gttcctgaat agcccctgtg gtaagggcca ggagagtcct tccatcctcc
2761 aaggccctgc taaaggacac agcagccagg aagtcccctg ggcccctagc tgaaggacag
2821 cctgctccct ccgtctctac caggaatggc cttgtcctat ggaaggcact gccccatccc
2881 aaactaatct aggaatcact gtctaaccac tcactgtcat gaatgtgtac ttaaaggatg
2941 aggttgagtc ataccaaata gtgatttcga tagttcaaaa tggtgaaatt agcaattcta
3001 catgattcag tctaatcaat ggataccgac tgtttcccac acaagtctcc tgttctctta
3061 agcttactca ctgacagcct ttcactctcc acaaatacat taaagatatg gccatcacca
3121 agccccctag gatgacacca gacctgagag tctgaagacc tggatccaag ttctgacttt
3181 tccccctgac agctgtgtga ccttcgtgaa gtcgccaaac ctctctgagc cccagtcatt
3241 gctagtaaga cctgcctttg agttggtatg atgttcaagt tagataacaa aatgtttata
3301 cccattagaa cagagaataa atagaactac atttcttgca SEQ ID NO: 07: Human Serpina1 mRNA, transcript variant 7 (NM_001127703.1)

1 tgggcaggaa ctgggcactg tgcccagggc atgcactgcc tccacgcagc aaccctcaga
61 gtcctgagct gaaccaagaa ggaggagggg gtcgggcctc cgaggaaggc ctagccgctg
121 ctgctgccag gaattccagg ttggaggggc ggcaacctcc tgccagcctt caggccactc
181 tcctgtgcct gccagaagag acagagcttg aggagagctt gaggagagca ggaaagggcg
241 gcagtaagtc ttcagcatca ggcattttgg ggtgactcag taaatggtag atcttgctac
301 cagtggaaca gccactaagg attctgcagt gagagcagag ggccagctaa gtggtactct -continued 361 cccagagact gtctgactca cgccaccccc tccaccttgg acacaggacg ctgtggtttc 421 tgagccagca gcctccccccg ttgcccctct ggatccactg cttaaatacg gacgaggaca 481 gggccctgtc tcctcagctt caggcaccac cactgacctg ggacagtgaa tcgacaatgc 541 cgtcttctgt ctcgtggggc atcctcctgc tggcaggcct gtgctgcctg gtccctgtct 601 ccctggctga ggatccccag ggagatgctg cccagaagac agatacatcc caccatgatc 661 aggatcaccc aaccttcaac aagatcaccc ccaacctggc tgagttcgcc ttcagcctat 721 accgccagct ggcacaccag tccaacagca ccaatatctt cttctcccca gtgagcatcg 781 ctacagcctt tgcaatgctc tccctgggga ccaaggctga cactcacgat gaaatcctgg 841 agggcctgaa tttcaacctc acggagattc cggaggctca gatccatgaa ggcttccagg 901 aactcctccg taccctcaac cagccagaca gccagctcca gctgaccacc ggcaatggcc 961 tgttcctcag cgagggcctg aagctagtgg ataagttttt ggaggatgtt aaaaagttgt 1021 accactcaga agccttcact gtcaacttcg gggacaccga agaggccaag aaacagatca 1081 acgattacgt ggagaagggt actcaaggga aaattgtgga tttggtcaag gagcttgaca 1141 gagacacagt tttgctctg gtgaattaca tcttctttaa aggcaaatgg gagagaccct 1201 ttgaagtcaa ggacaccgag gaagaggact tccacgtgga ccaggtgacc accgtgaagg 1261 tgcctatgat gaagcgttta ggcatgttta acatccagca ctgtaagaag ctgtccagct 1321 gggtgctgct gatgaaatac ctgggcaatg ccaccgccat cttcttcctg cctgatgagg 1381 ggaaactaca gcacctggaa aatgaactca cccacgatat catcaccaag ttcctggaaa 1441 atgaagacag aaggtctgcc agcttacatt tacccaaact gtccattact ggaacctatg 1501 atctgaagag cgtcctgggt caactgggca tcactaaggt cttcagcaat ggggctgacc 1561 tctccggggt cacagaggag gcacccctga agctctccaa ggccgtgcat aaggctgtgc 1621 tgaccatcga cgagaaaggg actgaagctg ctggggccat gtttttagag gccataccca 1681 tgtctatccc ccccgaggtc aagttcaaca aaccctttgt cttcttaatg attgaacaaa 1741 ataccaagtc tcccctcttc atgggaaaag tggtgaatcc cacccaaaaa taactgcctc 1801 tcgctcctca acccctcccc tccatccctg gccccctccc tggatgacat taaagaaggg 1861 ttgagctggt ccctgcctgc atgtgactgt aaatccctcc catgttttct ctgagtctcc 1921 ctttgcctgc tgaggctgta tgtgggctcc aggtaacagt gctgtcttcg ggccccctga 1981 actgtgttca tggagcatct ggctgggtag gcacatgctg ggcttgaatc caggggggac 2041 tgaatcctca gcttacggac ctgggcccat ctgtttctgg agggctccag tcttccttgt 2101 cctgtcttgg agtccccaag aaggaatcac aggggaggaa ccagatacca gccatgaccc 2161 caggctccac caagcatctt catgtccccc tgctcatccc ccactccccc ccacccagag 2221 ttgctcatcc tgccagggct ggctgtgccc accccaaggc tgccctcctg gggggccccag 2281 aactgcctga tcgtgccgtg gcccagtttt gtggcatctg cagcaacaca agagagagga 2341 caatgtcctc ctcttgaccc gctgtcacct aaccagactc gggccctgca cctctcaggc 2401 acttctggaa aatgactgag gcagattctt cctgaagccc attctccatg gggcaacaag 2461 gacacctatt ctgtccttgt ccttccatcg ctgccccaga aagcctcaca tatctccgtt 2521 tagaatcagg tcccttctcc ccagatgaag aggagggtct ctgctttgtt ttctctatct 2581 cctcctcaga cttgaccagg cccagcaggc cccagaagac cattacccta tatcccttct 2641 cctccctagt cacatggcca taggcctgct gatggctcag gaaggccatt gcaaggactc 2701 ctcagctatg ggagaggaag cacatcaccc attgaccccc gcaacccctc cctttcctcc -continued 2761 tctgagtccc gactggggcc acatgcagcc tgacttcttt gtgcctgttg ctgtccctgc 2821 agtcttcaga gggccaccgc agctccagtg ccacggcagg aggctgttcc tgaatagccc 2881 ctgtggtaag ggccaggaga gtccttccat cctccaaggc cctgctaaag gacacagcag 2941 ccaggaagtc ccctgggccc ctagctgaag gacagcctgc tccctccgtc tctaccagga 3001 atggccttgt cctatggaag gcactgcccc atcccaaact aatctaggaa tcactgtcta 3061 accactcact gtcatgaatg tgtacttaaa ggatgaggtt gagtcatacc aaatagtgat 3121 ttcgatagtt caaaatggtg aaattagcaa ttctacatga ttcagtctaa tcaatggata 3181 ccgactgttt cccacacaag tctcctgttc tcttaagctt actcactgac agcctttcac 3241 tctccacaaa tacattaaag atatggccat caccaagccc cctaggatga caccagacct 3301 gagagtctga agacctggat ccaagttctg acttttcccc ctgacagctg tgtgaccttc 3361 gtgaagtcgc caaacctctc tgagccccag tcattgctag taagacctgc ctttgagttg 3421 gtatgatgtt caagttagat aacaaaatgt ttatacccat tagaacagag aataaataga 3481 actacatttc ttgca SEQ ID NO: 08: Human Serpina1 mRNA, transcript variant 8
(NM_001127704.1)

1 tgggcaggaa ctgggcactg tgcccagggc atgcactgcc tccacgcagc aaccctcaga 61 gtcctgagct gaaccaagaa ggaggagggg gtcgggcctc cgaggaaggc ctagccgctg 121 ctgctgccag gaattccagg ttggaggggc ggcaacctcc tgccagcctt caggccactc 181 tcctgtgcct gccagaagag acagagcttg aggagagctt gaggagagca ggaaagggcg 241 gcagtaagtc ttcagcatca ggcattttgg ggtgactcag taaatggtag atcttgctac 301 cagtggaaca gccactaagg attctgcagt gagagcagag ggccagctaa gtggtactct 361 cccagagact gtctgactca cgccaccccc tccaccttgg acacaggacg ctgtggtttc 421 tgagccagcc tccccccgttg cccctctgga tccactgctt aaatacggac gaggacaggg 481 ccctgtctcc tcagcttcag gcaccaccac tgacctggga cagtgaatcg acaatgccgt 541 cttctgtctc gtggggcatc ctcctgctgg caggcctgtg ctgcctggtc cctgtctccc 601 tggctgagga tccccaggga gatgctgccc agaagacaga tacatcccac catgatcagg 661 atcacccaac cttcaacaag atcacccca acctggctga gttcgccttc agcctatacc 721 gccagctggc acaccagtcc aacagcacca atatcttctt ctccccagtg agcatcgcta 781 cagcctttgc aatgctctcc ctggggacca aggctgacac tcacgatgaa atcctggagg 841 gcctgaattt caacctcacg gagattccgg aggctcagat ccatgaaggc ttccaggaac 901 tcctccgtac cctcaaccag ccagacagcc agctccagct gaccaccggc aatggcctgt 961 tcctcagcga gggcctgaag ctagtggata agtttttgga ggatgttaaa aagttgtacc 1021 actcagaagc cttcactgtc aacttcgggg acaccgaaga ggccaagaaa cagatcaacg 1081 attacgtgga gaagggtact caagggaaaa ttgtggattt ggtcaaggag cttgacagag 1141 acacagtttt tgctctggtg aattacatct tctttaaagg caaatgggag agaccctttg 1201 aagtcaagga caccgaggaa gaggacttcc acgtggacca ggtgaccacc gtgaaggtgc 1261 ctatgatgaa gcgtttaggc atgtttaaca tccagcactg taagaagctg tccagctggg 1321 tgctgctgat gaaatacctg ggcaatgcca ccgccatctt cttcctgcct gatgagggga 1381 aactacagca cctggaaaat gaactcaccc acgatatcat caccaagttc ctggaaaatg 1441 aagacagaag gtctgccagc ttacatttac ccaaactgtc cattactgga acctatgatc 1501 tgaagagcgt cctgggtcaa ctgggcatca ctaaggtctt cagcaatggg gctgacctct 1561 ccggggtcac agaggaggca cccctgaagc tctccaaggc cgtgcataag gctgtgctga -continued 1621 ccatcgacga gaaagggact gaagctgctg gggccatgtt tttagaggcc atacccatgt 1681 ctatcccccc cgaggtcaag ttcaacaaac cctttgtctt cttaatgatt gaacaaaata 1741 ccaagtctcc cctcttcatg ggaaaagtgg tgaatcccac ccaaaaataa ctgcctctcg 1801 ctcctcaacc cctcccctcc atccctggcc ccctccctgg atgacattaa agaagggttg 1861 agctggtccc tgcctgcatg tgactgtaaa tccctcccat gttttctctg agtctccctt 1921 tgcctgctga ggctgtatgt gggctccagg taacagtgct gtcttcgggc cccctgaact 1981 gtgttcatgg agcatctggc tgggtaggca catgctgggc ttgaatccag ggggggactga 2041 atcctcagct tacggacctg ggcccatctg tttctggagg gctccagtct tccttgtcct 2101 gtcttggagt ccccaagaag gaatcacagg ggaggaacca gataccagcc atgaccccag 2161 gctccaccaa gcatcttcat gtcccctgc tcatccccca ctcccccccca cccagagttg 2221 ctcatcctgc cagggctggc tgtgcccacc ccaaggctgc cctcctgggg gccccagaac 2281 tgcctgatcg tgccgtggcc cagttttgtg gcatctgcag caacacaaga gagaggacaa 2341 tgtcctcctc ttgacccgct gtcacctaac cagactcggg ccctgcacct ctcaggcact 2401 tctggaaaat gactgaggca gattcttcct gaagcccatt ctccatgggg caacaaggac 2461 acctattctg tccttgtcct tccatcgctg ccccagaaag cctcacatat ctccgtttag 2521 aatcaggtcc cttctcccca gatgaagagg agggtctctg ctttgttttc tctatctcct 2581 cctcagactt gaccaggccc agcaggcccc agaagaccat taccctatat cccttctcct 2641 ccctagtcac atggccatag gcctgctgat ggctcaggaa ggccattgca aggactcctc 2701 agctatggga gaggaagcac atcacccatt gacccccgca acccctccct ttcctcctct 2761 gagtcccgac tggggccaca tgcagcctga cttctttgtg cctgttgctg tccctgcagt 2821 cttcagaggg ccaccgcagc tccagtgcca cggcaggagg ctgttcctga atagcccctg 2881 tggtaagggc caggagagtc cttccatcct ccaaggccct gctaaaggac acagcagcca 2941 ggaagtcccc tgggccccta gctgaaggac agcctgctcc ctccgtctct accaggaatg 3001 gccttgtcct atggaaggca ctgccccatc ccaaactaat ctaggaatca ctgtctaacc 3061 actcactgtc atgaatgtgt acttaaagga tgaggttgag tcataccaaa tagtgatttc 3121 gatagttcaa aatggtgaaa ttagcaattc tacatgattc agtctaatca atggataccg 3181 actgtttccc acacaagtct cctgttctct taagcttact cactgacagc ctttcactct 3241 ccacaaatac attaaagata tggccatcac caagcccccct aggatgacac cagacctgag 3301 agtctgaaga cctggatcca agttctgact tttcccccctg acagctgtgt gaccttcgtg 3361 aagtcgccaa acctctctga gccccagtca ttgctagtaa gacctgcctt tgagttggta 3421 tgatgttcaa gttagataac aaaatgttta tacccattag aacagagaat aaatagaact 3481 acatttcttg ca SEQ ID NO: 09: Human Serpina1 mRNA, transcript variant 9
(NM_001127705.1)

1 tgggcaggaa ctgggcactg tgcccagggc atgcactgcc tccacgcagc aaccctcaga 61 gtcctgagct gaaccaagaa ggaggagggg gtcgggcctc cgaggaaggc ctagccgctg 121 ctgctgccag gaattccagg ttggaggggc ggcaacctcc tgccagcctt caggccactc 181 tcctgtgcct gccagaagag acagagcttg aggagagctt gaggagagca ggaaagggcg 241 gcagtaagtc ttcagcatca ggcattttgg ggtgactcag taaatggtag atcttgctac 301 cagtggaaca gccactaagg attctgcagt gagagcagag ggccagctaa gtggtactct 361 cccagagact gtctgactca cgccaccccc tccaccttgg acacaggacg ctgtggtttc -continued

```
 421 tgagccaggt acaatgactc ctttcgcctc ccccgttgcc cctctggatc cactgcttaa
 481 atacggacga ggacagggcc ctgtctcctc agcttcaggc accaccactg acctgggaca
 541 gtgaatcgac aatgccgtct tctgtctcgt ggggcatcct cctgctggca ggcctgtgct
 601 gcctggtccc tgtctccctg gctgaggatc cccagggaga tgctgcccag aagacagata
 661 catcccacca tgatcaggat cacccaacct tcaacaagat cacccccaac ctggctgagt
 721 tcgccttcag cctataccgc cagctggcac accagtccaa cagcaccaat atcttcttct
 781 ccccagtgag catcgctaca gcctttgcaa tgctctccct ggggaccaag gctgacactc
 841 acgatgaaat cctggagggc ctgaatttca acctcacgga gattccggag gctcagatcc
 901 atgaaggctt ccaggaactc ctccgtaccc tcaaccagcc agacagccag ctccagctga
 961 ccaccggcaa tggcctgttc ctcagcgagg gcctgaagct agtggataag tttttggagg
1021 atgttaaaaa gttgtaccac tcagaagcct tcactgtcaa cttcggggac accgaagagg
1081 ccaagaaaca gatcaacgat tacgtggaga agggtactca agggaaaatt gtggatttgg
1141 tcaaggagct tgacagagac acagtttttg ctctggtgaa ttacatcttc tttaaaggca
1201 aatgggagag accctttgaa gtcaaggaca ccgaggaaga ggacttccac gtggaccagg
1261 tgaccaccgt gaaggtgcct atgatgaagc gtttaggcat gtttaacatc cagcactgta
1321 agaagctgtc cagctgggtg ctgctgatga aatacctggg caatgccacc gccatcttct
1381 tcctgcctga tgaggggaaa ctacagcacc tggaaaatga actcacccac gatatcatca
1441 ccaagttcct ggaaaatgaa gacagaaggt ctgccagctt acatttaccc aaactgtcca
1501 ttactggaac ctatgatctg aagagcgtcc tgggtcaact gggcatcact aaggtcttca
1561 gcaatggggc tgacctctcc ggggtcacag aggaggcacc cctgaagctc tccaaggccg
1621 tgcataaggc tgtgctgacc atcgacgaga aagggactga agctgctggg gccatgtttt
1681 tagaggccat acccatgtct atcccccccg aggtcaagtt caacaaaccc tttgtcttct
1741 taatgattga acaaaatacc aagtctcccc tcttcatggg aaaagtggtg aatcccaccc
1801 aaaaataact gcctctcgct cctcaacccc tcccctccat ccctggcccc ctccctggat
1861 gacattaaag aagggttgag ctggtccctg cctgcatgtg actgtaaatc cctcccatgt
1921 tttctctgag tctccctttg cctgctgagg ctgtatgtgg gctccaggta acagtgctgt
1981 cttcgggccc cctgaactgt gttcatggag catctggctg ggtaggcaca tgctgggctt
2041 gaatccaggg gggactgaat cctcagctta cggacctggg cccatctgtt tctggagggc
2101 tccagtcttc cttgtcctgt cttggagtcc ccaagaagga atcacagggg aggaaccaga
2161 taccagccat gaccccaggc tccaccaagc atcttcatgt ccccctgctc atcccccact
2221 ccccccccacc cagagttgct catcctgcca gggctggctg tgcccacccc aaggctgccc
2281 tcctgggggc cccagaactg cctgatcgtg ccgtggccca gttttgtggc atctgcagca
2341 acacaagaga gaggacaatg tcctcctctt gacccgctgt cacctaacca gactcgggcc
2401 ctgcacctct caggcacttc tggaaaatga ctgaggcaga ttcttcctga agcccattct
2461 ccatggggca acaaggacac ctattctgtc cttgtccttc catcgctgcc ccagaaagcc
2521 tcacatatct ccgtttagaa tcaggtccct tctccccaga tgaagaggag ggtctctgct
2581 ttgttttctc tatctcctcc tcagacttga ccaggcccag caggccccag aagaccatta
2641 ccctatatcc cttctcctcc ctagtcacat ggccataggc ctgctgatgg ctcaggaagg
2701 ccattgcaag gactcctcag ctatgggaga ggaagcacat cacccattga cccccgcaac
2761 ccctcccttt cctcctctga gtcccgactg gggccacatg cagcctgact tctttgtgcc
2821 tgttgctgtc cctgcagtct tcagagggcc accgcagctc cagtgccacg gcaggaggct
```

-continued 2881 gttcctgaat agcccctgtg gtaagggcca ggagagtcct tccatcctcc aaggccctgc 2941 taaaggacac agcagccagg aagtcccctg ggcccctagc tgaaggacag cctgctccct 3001 ccgtctctac caggaatggc cttgtcctat ggaaggcact gccccatccc aaactaatct 3061 aggaatcact gtctaaccac tcactgtcat gaatgtgtac ttaaaggatg aggttgagtc 3121 ataccaaata gtgatttcga tagttcaaaa tggtgaaatt agcaattcta catgattcag 3181 tctaatcaat ggataccgac tgtttcccac acaagtctcc tgttctctta agcttactca 3241 ctgacagcct ttcactctcc acaaatacat taaagatatg gccatcacca agccccctag 3301 gatgacacca gacctgagag tctgaagacc tggatccaag ttctgacttt tcccccctgac 3361 agctgtgtga ccttcgtgaa gtcgccaaac ctctctgagc cccagtcatt gctagtaaga 3421 cctgcctttg agttggtatg atgttcaagt tagataacaa aatgtttata cccattagaa 3481 cagagaataa atagaactac atttcttgca SEQ ID NO: 10: Human Serpina1 mRNA, transcript variant 10
(NM_001127706.1)

1 tgggcaggaa ctgggcactg tgcccagggc atgcactgcc tccacgcagc aaccctcaga 61 gtcctgagct gaaccaagaa ggaggagggg gtcgggcctc cgaggaaggc ctagccgctg 121 ctgctgccag gaattccagg ttggaggggc ggcaacctcc tgccagcctt caggccactc 181 tcctgtgcct gccagaagag acagagcttg aggagagctt gaggagagca ggaaagcagc 241 ctccccccgtt gcccctctgg atccactgct taaatacgga cgaggacagg gccctgtctc 301 ctcagcttca ggcaccacca ctgacctggg acagtgaatc gacaatgccg tcttctgtct 361 cgtggggcat cctcctgctg gcaggcctgt gctgcctggt ccctgtctcc ctggctgagg 421 atccccaggg agatgctgcc cagaagacag atacatccca ccatgatcag gatcacccaa 481 ccttcaacaa gatcaccccc aacctggctg agttcgcctt cagcctatac cgccagctgg 541 cacaccagtc caacagcacc aatatcttct tctccccagt gagcatcgct acagcctttg 601 caatgctctc cctggggacc aaggctgaca ctcacgatga aatcctggag ggcctgaatt 661 tcaacctcac ggagattccg gaggctcaga tccatgaagg cttccaggaa ctcctccgta 721 ccctcaacca gccagacagc cagctccagc tgaccaccgg caatggcctg ttcctcagcg 781 agggcctgaa gctagtggat aagtttttgg aggatgttaa aaagttgtac cactcagaag 841 ccttcactgt caacttcggg gacaccgaag aggccaagaa acagatcaac gattacgtgg 901 agaagggtac tcaagggaaa attgtggatt tggtcaagga gcttgacaga gacacagttt 961 ttgctctggt gaattacatc ttctttaaag gcaaatggga gagacccttt gaagtcaagg 1021 acaccgagga agaggacttc cacgtggacc aggtgaccac cgtgaaggtg cctatgatga 1081 agcgtttagg catgtttaac atccagcact gtaagaagct gtccagctgg gtgctgctga 1141 tgaaatacct gggcaatgcc accgccatct tcttcctgcc tgatgagggg aaactacagc 1201 acctggaaaa tgaactcacc cacgatatca tcaccaagtt cctggaaaat gaagacagaa 1261 ggtctgccag cttacattta cccaaactgt ccattactgg aacctatgat ctgaagagcg 1321 tcctgggtca actgggcatc actaaggtct tcagcaatgg ggctgacctc tccggggtca 1381 cagaggaggc acccctgaag ctctccaagg ccgtgcataa ggctgtgctg accatcgacg 1441 agaaagggac tgaagctgct ggggccatgt ttttagaggc catacccatg tctatccccc 1501 ccgaggtcaa gttcaacaaa ccctttgtct tcttaatgat tgaacaaaat accaagtctc 1561 ccctcttcat gggaaaagtg gtgaatccca cccaaaaata actgcctctc gctcctcaac 1621 ccctcccctc catccctggc cccctccctg gatgacatta aagaagggtt gagctggtcc -continued

```
1681 ctgcctgcat gtgactgtaa atccctccca tgttttctct gagtctccct ttgcctgctg
1741 aggctgtatg tgggctccag gtaacagtgc tgtcttcggg ccccctgaac tgtgttcatg
1801 gagcatctgg ctgggtaggc acatgctggg cttgaatcca ggggggactg aatcctcagc
1861 ttacggacct gggcccatct gtttctggag ggctccagtc ttccttgtcc tgtcttggag
1921 tccccaagaa ggaatcacag gggaggaacc agataccagc catgacccca ggctccacca
1981 agcatcttca tgtcccccctg ctcatccccc actcccccc acccagagtt gctcatcctg
2041 ccagggctgg ctgtgcccac cccaaggctg ccctcctggg ggccccagaa ctgcctgatc
2101 gtgccgtggc ccagttttgt ggcatctgca gcaacacaag agagaggaca atgtcctcct
2161 cttgacccgc tgtcacctaa ccagactcgg gccctgcacc tctcaggcac ttctggaaaa
2221 tgactgaggc agattcttcc tgaagcccat tctccatggg gcaacaagga cacctattct
2281 gtccttgtcc ttccatcgct gccccagaaa gcctcacata tctccgttta gaatcaggtc
2341 ccttctcccc agatgaagag gagggtctct gctttgtttt ctctatctcc tcctcagact
2401 tgaccaggcc cagcaggccc cagaagacca ttaccctata tcccttctcc tccctagtca
2461 catggccata ggcctgctga tggctcagga aggccattgc aaggactcct cagctatggg
2521 agaggaagca catcacccat tgacccccgc aacccctccc tttcctcctc tgagtcccga
2581 ctggggccac atgcagcctg acttctttgt gcctgttgct gtccctgcag tcttcagagg
2641 gccaccgcag ctccagtgcc acggcaggag gctgttcctg aatagcccct gtggtaaggg
2701 ccaggagagt ccttccatcc tccaaggccc tgctaaagga cacagcagcc aggaagtccc
2761 ctgggcccct agctgaagga cagcctgctc cctccgtctc taccaggaat ggccttgtcc
2821 tatggaaggc actgccccat cccaaactaa tctaggaatc actgtctaac cactcactgt
2881 catgaatgtg tacttaaagg atgaggttga gtcataccaa atagtgattt cgatagttca
2941 aaatggtgaa attagcaatt ctacatgatt cagtctaatc aatggatacc gactgtttcc
3001 cacacaagtc tcctgttctc ttaagcttac tcactgacag cctttcactc tccacaaata
3061 cattaaagat atggccatca ccaagccccc taggatgaca ccagacctga gagtctgaag
3121 acctggatcc aagttctgac ttttccccct gacagctgtg tgaccttcgt gaagtcgcca
3181 aacctctctg agccccagtc attgctagta agacctgcct ttgagttggt atgatgttca
3241 agttagataa caaaatgttt atacccatta gaacagagaa taaatagaac tacatttctt
3301 gca
```

SEQ ID NO: 11: Human Serpina1 mRNA, transcript variant 11
(NM_001127707.1)

```
  1 tgggcaggaa ctgggcactg tgcccagggc atgcactgcc tccacgcagc aaccctcaga
 61 gtcctgagct gaaccaagaa ggaggagggg gtcgggcctc cgaggaaggc ctagccgctg
121 ctgctgccag gaattccagg ttggaggggc ggcaacctcc tgccagcctt caggccactc
181 tcctgtgcct gccagaagag acagagcttg aggagagctt gaggagagca ggaaagcctc
241 ccccgttgcc cctctggatc cactgcttaa atacggacga ggacagggcc ctgtctcctc
301 agcttcaggc accaccactg acctgggaca gtgaatcgac aatgccgtct tctgtctcgt
361 ggggcatcct cctgctggca ggcctgtgct gcctggtccc tgtctccctg gctgaggatc
421 cccagggaga tgctgcccag aagacagata catcccacca tgatcaggat cacccaacct
481 tcaacaagat cacccccaac ctggctgagt tcgccttcag cctataccgc cagctggcac
541 accagtccaa cagcaccaat atcttcttct ccccagtgag catcgctaca gcctttgcaa
601 tgctctccct ggggaccaag gctgacactc acgatgaaat cctggagggc ctgaatttca
661 acctcacgga gattccggag gctcagatcc atgaaggctt ccaggaactc ctccgtaccc
```

-continued 721 tcaaccagcc agacagccag ctccagctga ccaccggcaa tggcctgttc ctcagcgagg
781 gcctgaagct agtggataag tttttggagg atgttaaaaa gttgtaccac tcagaagcct
841 tcactgtcaa cttcggggac accgaagagg ccaagaaaca gatcaacgat tacgtggaga
901 agggtactca agggaaaatt gtggatttgg tcaaggagct tgacagagac acagtttttg
961 ctctggtgaa ttacatcttc tttaaaggca aatgggagag accctttgaa gtcaaggaca
1021 ccgaggaaga ggacttccac gtggaccagg tgaccaccgt gaaggtgcct atgatgaagc
1081 gtttaggcat gtttaacatc cagcactgta agaagctgtc cagctgggtg ctgctgatga
1141 aatacctggg caatgccacc gccatcttct tcctgcctga tgaggggaaa ctacagcacc
1201 tggaaaatga actcacccac gatatcatca ccaagttcct ggaaaatgaa gacagaaggt
1261 ctgccagctt acatttaccc aaactgtcca ttactggaac ctatgatctg aagagcgtcc
1321 tgggtcaact gggcatcact aaggtcttca gcaatggggc tgacctctcc ggggtcacag
1381 aggaggcacc cctgaagctc tccaaggccg tgcataaggc tgtgctgacc atcgacgaga
1441 aagggactga agctgctggg gccatgtttt tagaggccat acccatgtct atcccccccg
1501 aggtcaagtt caacaaaccc tttgtcttct taatgattga acaaaatacc aagtctcccc
1561 tcttcatggg aaaagtggtg aatcccaccc aaaaataact gcctctcgct cctcaacccc
1621 tcccctccat ccctggcccc ctccctggat gacattaaag aagggttgag ctggtccctg
1681 cctgcatgtg actgtaaatc cctcccatgt tttctctgag tctccctttg cctgctgagg
1741 ctgtatgtgg gctccaggta acagtgctgt cttcgggccc cctgaactgt gttcatggag
1801 catctggctg ggtaggcaca tgctgggctt gaatccaggg gggactgaat cctcagctta
1861 cggacctggg cccatctgtt tctggagggc tccagtcttc cttgtcctgt cttggagtcc
1921 ccaagaagga atcacagggg aggaaccaga taccagccat gaccccaggc tccaccaagc
1981 atcttcatgt ccccctgctc atcccccact cccccccacc cagagttgct catcctgcca
2041 gggctggctg tgcccacccc aaggctgccc tcctgggggc cccagaactg cctgatcgtg
2101 ccgtggccca gttttgtggc atctgcagca acacaagaga gaggacaatg tcctcctctt
2161 gacccgctgt cacctaacca gactcgggcc ctgcacctct caggcacttc tggaaaatga
2221 ctgaggcaga ttcttcctga agcccattct ccatggggca acaaggacac ctattctgtc
2281 cttgtccttc catcgctgcc ccagaaagcc tcacatatct ccgtttagaa tcaggtccct
2341 tctccccaga tgaagaggag ggtctctgct ttgttttctc tatctcctcc tcagacttga
2401 ccaggcccag caggccccag aagaccatta ccctatatcc cttctcctcc ctagtcacat
2461 ggccataggc ctgctgatgg ctcaggaagg ccattgcaag gactcctcag ctatgggaga
2521 ggaagcacat cacccattga cccccgcaac ccctcccttt cctcctctga gtcccgactg
2581 gggccacatg cagcctgact tctttgtgcc tgttgctgtc cctgcagtct tcagagggcc
2641 accgcagctc cagtgccacg gcaggaggct gttcctgaat agcccctgtg gtaagggcca
2701 ggagagtcct tccatcctcc aaggccctgc taaaggacac agcagccagg aagtcccctg
2761 ggcccctagc tgaaggacag cctgctccct ccgtctctac caggaatggc cttgtcctat
2821 ggaaggcact gccccatccc aaactaatct aggaatcact gtctaaccac tcactgtcat
2881 gaatgtgtac ttaaaggatg aggttgagtc ataccaaata gtgatttcga tagttcaaaa
2941 tggtgaaatt agcaattcta catgattcag tctaatcaat ggataccgac tgtttcccac
3001 acaagtctcc tgttctctta agcttactca ctgacagcct ttcactctcc acaaatacat
3061 taaagatatg gccatcacca agccccctag gatgacacca gacctgagag tctgaagacc -continued 3121 tggatccaag ttctgacttt tccccctgac agctgtgtga ccttcgtgaa gtcgccaaac 3181 ctctctgagc cccagtcatt gctagtaaga cctgcctttg agttggtatg atgttcaagt 3241 tagataacaa aatgtttata cccattagaa cagagaataa atagaactac atttcttgca SEQ ID NO: 12: Rhesus Serpina1 mRNA, transcript variant 6
(XM_001099255.2)

1 gcccagtctt gtgtctgcct ggcaatgggc aaggcccctt cctgcccaag ctccccgccc 61 ctccccaacc tattgcctcc gccacccgcc acccgaggcc aacttcctgg gtgggcagga 121 actgggccct gtgcccaggg cgtgcactgc ctccacgcag caaccctcag agtactgagc 181 tgagcaaagg aggaggaggg gatcagcact ctgaggaagg cctagccact gctgctgcca 241 ggaattccag ggcggcatca gtcttcagca tcaggcattt cggggtgaat tagtaaatgg 301 tagatcttgc taccagtgga acagccgcta aggattctgc agtgagagca gagggccagc 361 aaagtggtac tctcccagcg actggctgac tcacgccacc ccctccacct tggacgcagg 421 acactgtggt ttctgagcca ggtacaatga ctccttttgg tacgtgcagt ggaggctgta 481 tgctgctcag gcagagcgtc cggacagcgt gggcgggcga ctcagcgccc agcctgtgaa 541 cttagtccct gtttgctcct ccggtaactg ggtgatctt ggttaatatt caccagcagc 601 ctccccccgtt gcccctctgc acccactgct taaatacgga caaggacagg gctctgtctc 661 ctcagcctca ggcaccacca ctgacctggg acggtgaatc gacaatgcca tcttctgtct 721 catggggcgt cctcctgctg gcaggcctgt gctgcctgct ccccggctct ctggctgagg 781 atccccaggg agatgctgcc cagaagacgg atacatccca ccatgatcag gaccacccaa 841 ccctcaacaa gatcaccccc agcctggctg agttcggctt cagcctatac cgccagctgg 901 cacaccagtc caacagcacc aatatcttct tctccccagt gagcatcgct acagcctttg 961 caatgctctc cctggggacc aaggctgaca ctcacagtga aatcctggag ggcctgaatt 1021 tcaacgtcac ggagattccg gaggctcagg tccatgaagg cttccaggaa ctcctccata 1081 ccctcaacaa gccagacagc cagctccagc tgaccaccgg caacggcctg ttcctcaaca 1141 agagcctgaa ggtagtggat aagtttttgg aggatgtcaa aaaactgtac cactcagaag 1201 ccttctctgt caactttgag gacaccgaag aggccaagaa acagatcaac aattacgtgg 1261 agaaggaaac tcaagggaaa attgtggatt tggtcaagga gcttgacaga gacacagttt 1321 ttgctctggt gaattacatc ttctttaaag gcaaatggga gagacccttt gacgttgagg 1381 ccaccaagga agaggacttc cacgtggacc aggcgaccac cgtgaaggtg cccatgatga 1441 ggcgtttagg catgtttaac atctaccact gtgagaagct gtccagctgg gtgctgctga 1501 tgaaatacct gggcaatgcc accgccatct tcttcctgcc tgatgagggg aaactgcagc 1561 acctggaaaa tgaactcacc catgatatca tcaccaagtt cctggaaaat gaaaacagca 1621 ggtctgccaa cttacattta cccagactgg ccattactgg aacctatgat ctgaagacag 1681 tcctgggcca cctgggtatc actaaggtct tcagcaatgg ggctgacctc tcggggatca 1741 cggaggaggc acccctgaag ctctccaagg ccgtgcataa ggctgtgctg accatcgatg 1801 agaaagggac tgaagctgct ggggccatgt ttttagaggc catacccatg tctattcccc 1861 ccgaggtcaa gttcaacaaa ccctttgtct tcttaatgat tgaacaaaat accaagtctc 1921 ccctcttcat gggaaaagtg gtgaatccca cccagaaata actgcctgtc actcctcagc 1981 ccctcccctc catccctggc cccctccctg aatgacatta aagaagggtt gagctggtcc 2041 ctgcctgcgt gtgtgactgc aaac SEQ ID NO: 13: Rhesus Serpina1 mRNA, transcript variant 4
(XM_001099044.2)

1 tcttgtgtct gcctggcaat gggcaaggcc ccttcctgcc caagctcccc gcccctcccc

-continued 61 aacctattgc ctccgccacc cgccacccga ggccaacttc ctgggtgggc aggaactggg
121 ccctgtgccc agggcgtgca ctgcctccac gcagcaaccc tcagagtact gagctgagca
181 aaggaggagg aggggatcag cactctgagg aaggcctagc cactgctgct gccaggaatt
241 ccaggacaat gccatcttct gtctcatggg gcgtcctcct gctggcaggc ctgtgctgcc
301 tgctccccgg ctctctggct gaggatcccc agggagatgc tgcccagaag acggatacat
361 cccaccatga tcaggaccac ccaaccctca acaagatcac ccccagcctg gctgagttcg
421 gcttcagcct ataccgccag ctggcacacc agtccaacag caccaatatc ttcttctccc
481 cagtgagcat cgctacagcc tttgcaatgc tctccctggg gaccaaggct gacactcaca
541 gtgaaatcct ggagggcctg aatttcaacg tcacggagat tccggaggct caggtccatg
601 aaggcttcca ggaactcctc cataccctca acaagccaga cagccagctc cagctgacca
661 ccggcaacgg cctgttcctc aacaagagcc tgaaggtagt ggataagttt ttggaggatg
721 tcaaaaaact gtaccactca gaagccttct ctgtcaactt tgaggacacc gaagaggcca
781 agaaacagat caacaattac gtggagaagg aaactcaagg gaaaattgtg gatttggtca
841 aggagcttga cagagacaca gtttttgctc tggtgaatta catcttcttt aaaggcaaat
901 gggagagacc ctttgacgtt gaggccacca aggaagagga cttccacgtg gaccaggcga
961 ccaccgtgaa ggtgcccatg atgaggcgtt taggcatgtt taacatctac cactgtgaga
1021 agctgtccag ctgggtgctg ctgatgaaat acctgggcaa tgccaccgcc atcttcttcc
1081 tgcctgatga ggggaaactg cagcacctgg aaaatgaact cacccatgat atcatcacca
1141 agttcctgga aaatgaaaac agcaggtctg ccaacttaca tttacccaga ctggccatta
1201 ctggaaccta tgatctgaag acagtcctgg gccacctggg tatcactaag gtcttcagca
1261 atggggctga cctctcgggg atcacggagg aggcacccct gaagctctcc aaggccgtgc
1321 ataaggctgt gctgaccatc gatgagaaag ggactgaagc tgctggggcc atgtttttag
1381 aggccatacc catgtctatt ccccccgagg tcaagttcaa caaacccttt gtcttcttaa
1441 tgattgaaca aaataccaag tctcccctct tcatgggaaa agtggtgaat cccacccaga
1501 aataactgcc tgtcactcct cagcccctcc cctccatccc tggcccccct cctgaatgac
1561 attaaagaag ggttgagctg gtccctgcct gcgtgtgtga ctgcaaac SEQ ID NO: 14: Reverse complement of SEQ ID NO: 01
tgcaagaaatgtagttctatttattctctgttctaatgggtataaacattttgttatctaacttgaacatcatac
caactcaaaggcaggtcttactagcaatgactggggctcagagaggtttggcgacttcacgaaggtcacacagct
gtcaggggggaaaagtcagaacttggatccaggtcttcagactctcaggtctggtgtcatcctagggggcttggtg
atggccatatctttaatgtatttgtggagagtgaaaggctgtcagtgagtaagcttaagagaacaggagacttgt
gtgggaaacagtcggtatccattgattagactgaatcatgtagaattgctaatttcaccattttgaactatcgaa
atcactatttggtatgactcaacctcatcctttaagtacacattcatgacagtgagtggttagacagtgattcct
agattagtttgggatggggcagtgccttccataggacaaggccattcctggtagagacggagggagcaggctgtc
cttcagctaggggcccaggggacttcctggctgctgtgtcctttagcagggccttggaggatggaaggactctcc
tggcccttaccacaggggctattcaggaacagcctcctgccgtggcactggagctgcggtggccctctgaagact
gcagggacagcaacaggcacaaagaagtcaggctgcatgtggccccagtcgggactcagaggaggaaagggaggg
gttgcggggggtcaatgggtgatgtgcttcctctcccatagctgaggagtccttgcaatggccttcctgagccatc
agcaggcctatggccatgtgactagggaggagaagggatatagggtaatggtcttctggggcctgctgggcctgg
tcaagtctgaggaggagatagagaaaacaaagcagagaccctcctcttcatctggggagaagggacctgattcta
aacggagatatgtgaggctttctggggcagcgatggaaggacaaggacagaataggtgtccttgttgccccatgg -continued agaatgggcttcaggaagaatctgcctcagtcattttccagaagtgcctgagaggtgcagggcccgagtctggtt aggtgacagcgggtcaagaggaggacattgtcctctctcttgtgttgctgcagatgccacaaaactgggccacgg cacgatcaggcagttctggggcccccaggagggcagccttggggtgggcacagccagccctggcaggatgagcaa ctctgggtggggggggagtgggggatgagcagggggacatgaagatgcttggtggagcctggggtcatggctggta tctggttcctcccctgtgattccttcttggggactccaagacaggacaaggaagactggagccctccagaaacag atgggcccaggtccgtaagctgaggattcagtccccccctggattcaagcccagcatgtgcctacccagccagatg ctccatgaacacagttcaggggggcccgaagacagcactgttacctggagcccacatacagcctcagcaggcaaag ggagactcagagaaaacatgggagggatttacagtcacatgcaggcagggaccagctcaacccttctttaatgtc atccagggagggggccagggatggaggggaggggttgaggagcgagaggcagttatttttgggtgggattcacca cttttcccatgaagaggggagacttggtattttgttcaatcattaagaagacaaagggtttgttgaacttgacct cgggggggatagacatgggtatggcctctaaaaacatggccccagcagcttcagtccctttctcgtcgatggtca gcacagccttatgcacggccttggagagcttcaggggtgcctcctctgtgaccccggagaggtcagccccattgc tgaagaccttagtgatgcccagttgacccaggacgctcttcagatcataggttccagtaatggacagtttgggta aatgtaagctggcagaccttctgtcttcattttccaggaacttggtgatgatatcgtgggtgagttcattttcca ggtgctgtagtttcccctcatcaggcaggaagaagatggcggtggcattgcccaggtatttcatcagcagcaccc agctggacagcttcttacagtgctggatgttaaacatgcctaaacgcttcatcataggcaccttcacggtggtca cctggtccacgtggaagtcctcttcctcggtgtccttgacttcaaagggtctctcccatttgcctttaaagaaga tgtaattcaccagagcaaaaactgtgtctctgtcaagctccttgaccaaatccacaattttcccttgagtaccct tctccacgtaatcgttgatctgtttcttggcctcttcggtgtccccgaagttgacagtgaaggcttctgagtggt acaactttttaacatcctccaaaaacttatccactagcttcaggccctcgctgaggaacaggccattgccggtgg tcagctggagctggctgtctggctggttgagggtacggaggagttcctggaagccttcatggatctgagcctccg gaatctccgtgaggttgaaattcaggccctccaggatttcatcgtgagtgtcagccttggtccccagggagagca ttgcaaaggctgtagcgatgctcactggggagaagaagatattggtgctgttggactggtgtgccagctggcggt ataggctgaaggcgaactcagccaggttgggggtgatcttgttgaaggttgggtgatcctgatcatggtgggatg tatctgtcttctgggcagcatctccctggggatcctcagccagggagacagggaccaggcagcacaggcctgcca gcaggaggatgccccacgagacagaagacggcattgtcgattcactgtcccaggtcagtggtggtgcctgaagct gaggagacagggccctgtcctcgtccgtatttaagcagtggatccagaggggcaacgggggaggctgctggtgaa tattaaccaaggtcaccccagttatcggaggagcaaacaggggctaagtccactggctgggatctgagtcgcccg cctacgctgcccggacgctttgcctgggcagtgtacagcttccactgcacttaccgaaaggagtcattgt SEQ ID NO: 15: Reverse complement of SEQ ID NO: 02
tgcaagaaatgtagttctatttattctctgttctaatgggtataaacattttgttatctaacttgaa catcataccaactcaaaggcaggtcttactagcaatgactggggctcagagaggtttggcgacttcacgaaggtc acacagctgtcaggggggaaaagtcagaacttggatccaggtcttcagactctcaggtctggtgtcatcctagggg gcttggtgatggccatatctttaatgtatttgtggagagtgaaaggctgtcagtgagtaagcttaagagaacagg agacttgtgtgggaaacagtcggtatccattgattagactgaatcatgtagaattgctaatttcaccattttgaa ctatcgaaatcactatttggtatgactcaacctcatcctttaagtacacattcatgacagtgagtggttagacag tgattcctagattagtttgggatggggcagtgccttccataggacaaggccattcctggtagagacggagggagc aggctgtccttcagctaggggcccaggggacttcctggctgctgtgtcctttagcagggccttggaggatggaag gactctcctggcccttaccacaggggctattcaggaacagcctcctgccgtggcactggagctgcggtggccctc tgaagactgcagggacagcaacaggcacaaagaagtcaggctgcatgtggccccagtcgggactcagaggaggaa agggaggggttgcgggggtcaatgggtgatgtgcttcctctcccatagctgaggagtccttgcaatggccttcct -continued gagccatcagcaggcctatggccatgtgactagggaggagaagggatatagggtaatggtcttctggggcctgct gggcctggtcaagtctgaggaggagatagagaaaacaaagcagagaccctcctcttcatctggggagaagggacc tgattctaaacggagatatgtgaggctttctggggcagcgatggaaggacaaggacagaataggtgtccttgttg ccccatggagaatgggcttcaggaagaatctgcctcagtcattttccagaagtgcctgagaggtgcagggcccga gtctggttaggtgacagcgggtcaagaggaggacattgtcctctctcttgtgttgctgcagatgccacaaaactg ggccacggcacgatcaggcagttctggggcccccaggagggcagccttggggtgggcacagccagccctggcagg atgagcaactctgggtgggggggagtgggggatgagcagggggacatgaagatgcttggtggagcctggggtcat ggctggtatctggttcctcccctgtgattccttcttggggactccaagacaggacaaggaagactggagccctcc agaaacagatgggcccaggtccgtaagctgaggattcagtccccccctggattcaagcccagcatgtgcctaccca gccagatgctccatgaacacagttcagggggcccgaagacagcactgttacctggagcccacatacagcctcagc aggcaaagggagactcagagaaaacatgggagggatttacagtcacatgcaggcagggaccagctcaacccttct ttaatgtcatccagggagggggccagggatggaggggaggggttgaggagcgagaggcagttatttttgggtggg attcaccacttttcccatgaagaggggagacttggtattttgttcaatcattaagaagacaaagggtttgttgaa cttgacctcggggggggatagacatgggtatggcctctaaaaacatggccccagcagcttcagtccctttctcgtc gatggtcagcacagccttatgcacggccttggagagcttcaggggtgcctcctctgtgaccccggagaggtcagc cccattgctgaagaccttagtgatgcccagttgacccaggacgctcttcagatcataggttccagtaatggacag tttgggtaaatgtaagctggcagaccttctgtcttcattttccaggaacttggtgatgatatcgtgggtgagttc attttccaggtgctgtagtttcccctcatcaggcaggaagaagatggcggtggcattgcccaggtatttcatcag cagcacccagctggacagcttcttacagtgctggatgttaaacatgcctaaacgcttcatcataggcaccttcac ggtggtcacctggtccacgtggaagtcctcttcctcggtgtccttgacttcaaagggtctctcccatttgccttt aaagaagatgtaattcaccagagcaaaaactgtgtctctgtcaagctccttgaccaaatccacaattttcccttg agtacccttctccacgtaatcgttgatctgtttcttggcctcttcggtgtccccgaagttgacagtgaaggcttc tgagtggtacaactttttaacatcctccaaaaacttatccactagcttcaggccctcgctgaggaacaggccatt gccggtggtcagctggagctggctgtctggctggttgagggtacggaggagttcctggaagccttcatggatctg agcctccggaatctccgtgaggttgaaattcaggccctccaggatttcatcgtgagtgtcagccttggtccccag ggagagcattgcaaaggctgtagcgatgctcactggggagaagaagatattggtgctgttggactggtgtgccag ctggcggtataggctgaaggcgaactcagccaggttgggggtgatcttgttgaaggttgggtgatcctgatcatg gtgggatgtatctgtcttctgggcagcatctccctggggatcctcagccagggagacagggaccaggcagcacag gcctgccagcaggaggatgccccacgagacagaagacggcattgtcctttcctgctctcctcaagctctcctcaa gctctgtctcttctggcaggcacaggagagtggcctgaaggctggcaggaggttgccgcccctccaacctggaat tcctggcagcagcagcggctaggccttcctcggaggcccgacccctcctccttcttggttcagctcaggactct gagggttgctgcgtggaggcagtgcatgccctgggcacagtgcccagttcctgccca SEQ ID NO: 16: Reverse complement of SEQ ID NO: 03
tgcaagaaatgtagttctatttattctctgttctaatgggtataaacattttgttatctaacttgaa catcataccaactcaaaggcaggtcttactagcaatgactggggctcagagaggtttggcgacttcacgaaggtc acacagctgtcaggggggaaaagtcagaacttggatccaggtcttcagactctcaggtctggtgtcatcctagggg gcttggtgatggccatatctttaatgtatttgtggagagtgaaaggctgtcagtgagtaagcttaagagaacagg agacttgtgtgggaaacagtcggtatccattgattagactgaatcatgtagaattgctaatttcaccattttgaa ctatcgaaatcactatttggtatgactcaacctcatcctttaagtacacattcatgacagtgagtggttagacag tgattcctagattagtttgggatggggcagtgccttccataggacaaggccattcctggtagagacggagggagc aggctgtccttcagctaggggcccaggggacttcctggctgctgtgtcctttagcagggccttggaggatggaag -continued gactctcctggcccttaccacaggggctattcaggaacagcctcctgccgtggcactggagctgcggtggccctc tgaagactgcagggacagcaacaggcacaaagaagtcaggctgcatgtggccccagtcgggactcagaggaggaa agggaggggttgcgggggtcaatgggtgatgtgcttcctctcccatagctgaggagtccttgcaatggccttcct gagccatcagcaggcctatggccatgtgactagggaggagaagggatatagggtaatggtcttctggggcctgct gggcctggtcaagtctgaggaggagatagagaaaacaaagcagagaccctcctcttcatctggggagaagggacc tgattctaaacggagatatgtgaggctttctggggcagcgatggaaggacaaggacagaataggtgtccttgttg ccccatggagaatgggcttcaggaagaatctgcctcagtcattttccagaagtgcctgagaggtgcagggcccga gtctggttaggtgacagcgggtcaagaggaggacattgtcctctctcttgtgttgctgcagatgccacaaaactg ggccacggcacgatcaggcagttctggggcccccaggagggcagccttggggtgggcacagccagccctggcagg atgagcaactctgggtggggggggagtgggggatgagcaggggggacatgaagatgcttggtggagcctggggtcat ggctggtatctggttcctcccctgtgattccttcttggggactccaagacaggacaaggaagactggagccctcc agaaacagatgggcccaggtccgtaagctgaggattcagtccccccctggattcaagcccagcatgtgcctaccca gccagatgctccatgaacacagttcagggggcccgaagacagcactgttacctggagcccacatacagcctcagc aggcaaagggagactcagagaaaacatgggagggatttacagtcacatgcaggcagggaccagctcaacccttct ttaatgtcatccagggagggggccagggatggaggggaggggttgaggagcgagaggcagttatttttgggtggg attcaccacttttcccatgaagaggggagacttggtattttgttcaatcattaagaagacaaagggtttgttgaa cttgacctcggggggggatagacatgggtatggcctctaaaaacatggccccagcagcttcagtccctttctcgtc gatggtcagcacagccttatgcacggccttggagagcttcaggggtgcctcctctgtgaccccggagaggtcagc cccattgctgaagaccttagtgatgcccagttgacccaggacgctcttcagatcataggttccagtaatggacag tttgggtaaatgtaagctggcagaccttctgtcttcattttccaggaacttggtgatgatatcgtgggtgagttc attttccaggtgctgtagtttcccctcatcaggcaggaagaagatggcggtggcattgcccaggtatttcatcag cagcacccagctggacagcttcttacagtgctggatgttaaacatgcctaaacgcttcatcataggcaccttcac ggtggtcacctggtccacgtggaagtcctcttcctcggtgtccttgacttcaaagggtctctcccatttgccttt aaagaagatgtaattcaccagagcaaaaactgtgtctctgtcaagctccttgaccaaatccacaattttcccttg agtacccttctccacgtaatcgttgatctgtttcttggcctcttcggtgtccccgaagttgacagtgaaggcttc tgagtggtacaactttttaacatcctccaaaaacttatccactagcttcaggccctcgctgaggaacaggccatt gccggtggtcagctggagctggctgtctggctggttgagggtacggaggagttcctggaagccttcatggatctg agcctccggaatctccgtgaggttgaaattcaggccctccaggatttcatcgtgagtgtcagccttggtccccag ggagagcattgcaaaggctgtagcgatgctcactggggagaagaagatattggtgctgttggactggtgtgccag ctggcggtataggctgaaggcgaactcagccaggttgggggtgatcttgttgaaggttgggtgatcctgatcatg gtgggatgtatctgtcttctgggcagcatctccctggggatcctcagccagggagacagggaccaggcagcacag gcctgccagcaggaggatgccccacgagacagaagacggcattgtcgattcactgtcccaggtcagtggtggtgc ctgaagctgaggagacagggccctgtcctcgtccgtatttaagcagtggatccagaggggcaacgggggaggctg cgaaaggagtcattgtacctggctcagaaaccacagcgtcctgtgtccaaggtggagggggtggcgtgagtcaga cagtctctgggagagtaccacttagctggccctctgctctcactgcagaatccttagtggctgttccactggtag caagatctaccatttactgagtcaccccaaaatgcctgatgctgaagacttactgccgccctttcctgctctcct caagctctcctcaagctctgtctcttctggcaggcacaggagagtggcctgaaggctggcaggaggttgccgccc ctccaacctggaattcctggcagcagcagcggctaggccttcctcggaggcccgacccccctcctccttcttggtt cagctcaggactctgagggttgctgcgtggaggcagtgcatgccctgggcacagtgcccagttcctgccca SEQ ID NO: 17: Reverse complement of SEQ ID NO: 04
tgcaagaaatgtagttctatttattctctgttctaatgggtataaacattttgttatctaacttgaacatcataccaactcaaaggcaggtct -continued tactagcaatgactggggctcagagaggtttggcgacttcacgaaggtcacacagctgtcaggggggaaaagtcagaacttggatccaggt cttcagactctcaggtctggtgtcatcctagggggcttggtgatggccatatctttaatgtatttgtggagagtgaaaggctgtcagtgagt aagcttaagagaacaggagacttgtgtgggaaacagtcggtatccattgattagactgaatcatgtagaattgctaatttcaccattttgaa ctatcgaaatcactatttggtatgactcaacctcatcctttaagtacacattcatgacagtgagtggttagacagtgattcctagattagtttg ggatggggcagtgccttccataggacaaggccattcctggtagagacggagggagcaggctgtccttcagctaggggcccagggg acttcctggctgctgtgtcctttagcagggccttggaggatggaaggactctcctggcccttaccacaggggctattcaggaacagcct cctgccgtggcactggagctgcggtggccctctgaagactgcagggacagcaacaggcacaaagaagtcaggctgcatgtggccc cagtcgggactcagaggaggaaagggaggggttgcgggggtcaatgggtgatgtgcttcctctcccatagctgaggagtccttgcaa tggccttcctgagccatcagcaggcctatggccatgtgactagggaggagaagggatatagggtaatggtcttctggggcctgctggg cctggtcaagtctgaggaggagatagagaaaacaaagcagagaccctcctcttcatctggggagaagggacctgattctaaacggag atatgtgaggctttctggggcagcgatggaaggacaaggacagaataggtgtccttgttgccccatggagaatgggcttcaggaaga atctgcctcagtcattttccagaagtgcctgagaggtgcagggcccgagtctggttaggtgacagcgggtcaagaggaggacattgtc ctctctcttgtgttgctgcagatgccacaaaactgggccacggcacgatcaggcagttctggggcccccaggagggcagccttgggg tgggcacagccagccctggcaggatgagcaactctgggtgggggggagtgggggatgagcagggggacatgaagatgcttggtg gagcctggggtcatggctggtatctggttcctcccctgtgattccttcttggggactccaagacaggacaaggaagactggagccctcc agaaacagatgggcccaggtccgtaagctgaggattcagtccccccctggattcaagcccagcatgtgcctacccagccagatgctcc atgaacacagttcagggggcccgaagacagcactgttacctggagcccacatacagcctcagcaggcaaagggagactcagagaa aacatgggagggatttacagtcacatgcaggcagggaccagctcaacccttctttaatgtcatccagggagggggccagggatggag gggaggggttgaggagcgagaggcagttatttttgggtgggattcaccacttttcccatgaagaggggagacttggtattttgttcaatc attaagaagacaaagggtttgttgaacttgacctcgggggggatagacatgggtatggcctctaaaaacatggccccagcagcttcag tccctttctcgtcgatggtcagcacagccttatgcacggccttggagagcttcaggggtgcctcctctgtgaccccggagaggtcagcc ccattgctgaagaccttagtgatgcccagttgacccaggacgctcttcagatcataggttccagtaatggacagtttgggtaaatgtaag ctggcagaccttctgtcttcattttccaggaacttggtgatgatatcgtgggtgagttcattttccaggtgctgtagtttcccctcatcaggca ggaagaagatggcggtggcattgcccaggtatttcatcagcagcacccagctggacagcttcttacagtgctggatgttaaacatgcct aaacgcttcatcataggcaccttcacggtggtcacctggtccacgtggaagtcctcttcctcggtgtccttgacttcaaagggtctctccc atttgcctttaaagaagatgtaattcaccagagcaaaaactgtgtctctgtcaagctccttgaccaaatccacaattttcccttgagtaccct tctccacgtaatcgttgatctgtttcttggcctcttcggtgtccccgaagttgacagtgaaggcttctgagtggtacaactttttaacatcctc caaaaacttatccactagcttcaggccctcgctgaggaacaggccattgccggtggtcagctggagctggctgtctggctggttgagg gtacggaggagttcctggaagccttcatggatctgagcctccggaatctccgtgaggttgaaattcaggccctccaggatttcatcgtga gtgtcagccttggtccccagggagagcattgcaaaggctgtagcgatgctcactggggagaagaagatattggtgctgttggactggt gtgccagctggcggtataggctgaaggcgaactcagccaggttgggggtgatcttgttgaaggttgggtgatcctgatcatggtggga tgtatctgtcttctgggcagcatctccctggggatcctcagccagggagacagggaccaggcagcacaggcctgccagcaggagga tgccccacgagacagaagacggcattgtcctgtggaactgagtgagcagcagcagcaatgtcccacctttcctgctctcctcaagctct cctcaagctctgtctcttctggcaggcacaggagagtggcctgaaggctggcaggaggttgccgcccctccaacctggaattcctggc agcagcagcggctaggccttcctcggaggcccgacccccctcctccttcttggttcagctcaggactctgagggttgctgcgtggaggc agtgcatgccctgggcacagtgcccagttcctgccca SEQ ID NO: 18: Reverse complement of SEQ ID NO: 05 tgcaagaaatgtagttctatttattctctgttctaatgggtataaacattttgttatctaacttgaacatcatac caactcaaaggcaggtcttactagcaatgactggggctcagagaggtttggcgacttcacgaaggtcacacagct gtcaggggggaaaagtcagaacttggatccaggtcttcagactctcaggtctggtgtcatcctagggggcttggtg atggccatatctttaatgtatttgtggagagtgaaaggctgtcagtgagtaagcttaagagaacaggagacttgt -continued gtgggaaacagtcggtatccattgattagactgaatcatgtagaattgctaatttcaccattttgaactatcgaa
atcactatttggtatgactcaacctcatcctttaagtacacattcatgacagtgagtggttagacagtgattcct
agattagtttgggatggggcagtgccttccataggacaaggccattcctggtagagacggagggagcaggctgtc
cttcagctaggggcccaggggacttcctggctgctgtgtcctttagcagggccttggaggatggaaggactctcc
tggcccttaccacaggggctattcaggaacagcctcctgccgtggcactggagctgcggtggccctctgaagact
gcagggacagcaacaggcacaaagaagtcaggctgcatgtggccccagtcgggactcagaggaggaaagggaggg
gttgcgggggtcaatgggtgatgtgcttcctctcccatagctgaggagtccttgcaatggccttcctgagccatc
agcaggcctatggccatgtgactagggaggagaagggatatagggtaatggtcttctggggcctgctgggcctgg
tcaagtctgaggaggagatagagaaaacaaagcagagaccctcctcttcatctggggagaagggacctgattcta
aacggagatatgtgaggctttctggggcagcgatggaaggacaaggacagaataggtgtccttgttgccccatgg
agaatgggcttcaggaagaatctgcctcagtcattttccagaagtgcctgagaggtgcagggcccgagtctggtt
aggtgacagcgggtcaagaggaggacattgtcctctctcttgtgttgctgcagatgccacaaaactgggccacgg
cacgatcaggcagttctggggcccccaggagggcagccttggggtgggcacagccagccctggcaggatgagcaa
ctctgggtggggggggagtgggggatgagcagggggacatgaagatgcttggtggagcctggggtcatggctggta
tctggttcctcccctgtgattccttcttggggactccaagacaggacaaggaagactggagccctccagaaacag
atgggcccaggtccgtaagctgaggattcagtccccccctggattcaagcccagcatgtgcctacccagccagatg
ctccatgaacacagttcaggggggcccgaagacagcactgttacctggagcccacatacagcctcagcaggcaaag
ggagactcagagaaaacatgggagggatttacagtcacatgcaggcagggaccagctcaacccttctttaatgtc
atccagggagggggccagggatggagggggaggggttgaggagcgagaggcagttatttttgggtgggattcacca
cttttcccatgaagaggggagacttggtattttgttcaatcattaagaagacaaagggtttgttgaacttgacct
cggggggggatagacatgggtatggcctctaaaaacatggccccagcagcttcagtccctttctcgtcgatggtca
gcacagccttatgcacggccttggagagcttcaggggtgcctcctctgtgaccccggagaggtcagccccattgc
tgaagaccttagtgatgcccagttgacccaggacgctcttcagatcataggttccagtaatggacagtttgggta
aatgtaagctggcagaccttctgtcttcattttccaggaacttggtgatgatatcgtgggtgagttcatttttcca
ggtgctgtagtttcccctcatcaggcaggaagaagatggcggtggcattgcccaggtatttcatcagcagcaccc
agctggacagcttcttacagtgctggatgttaaacatgcctaaacgcttcatcataggcaccttcacggtggtca
cctggtccacgtggaagtcctcttcctcggtgtccttgacttcaaagggtctctcccatttgcctttaaagaaga
tgtaattcaccagagcaaaaactgtgtctctgtcaagctccttgaccaaatccacaattttcccttgagtaccct
tctccacgtaatcgttgatctgtttcttggcctcttcggtgtccccgaagttgacagtgaaggcttctgagtggt
acaactttttaacatcctccaaaaacttatccactagcttcaggccctcgctgaggaacaggccattgccggtgg
tcagctggagctggctgtctggctggttgagggtacggaggagttcctggaagccttcatggatctgagcctccg
gaatctccgtgaggttgaaattcaggccctccaggatttcatcgtgagtgtcagccttggtccccagggagagca
ttgcaaaggctgtagcgatgctcactggggagaagaagatattggtgctgttggactggtgtgccagctggcggt
ataggctgaaggcgaactcagccaggttgggggtgatcttgttgaaggttgggtgatcctgatcatggtgggatg
tatctgtcttctgggcagcatctccctggggatcctcagccagggagacagggaccaggcagcacaggcctgcca
gcaggaggatgccccacgagacagaagacggcattgtcgattcactgtcccaggtcagtggtggtgcctgaagct
gaggagacagggccctgtcctcgtccgtatttaagcagtggatccagaggggcaacgggggaggctgctggctca
gaaaccacagcgtcctgtgtccaaggtggaggggggtggcgtgagtcagacagtctctgggagagtaccacttagc
tggccctctgctctcactgcagaatccttagtggctgttccactggtagcaagatctaccatttactgagtcacc
ccaaaatgcctgatgctgaagacttactgccgccctgtggaactgagtgagcagcagcagcaatgtcccaccttt -continued cctgctctcctcaagctctcctcaagctctgtctcttctggcaggcacaggagagtggcctgaaggctggcagga ggttgccgcccctccaacctggaattcctggcagcagcagcggctaggccttcctcggaggcccgaccccctcct ccttcttggttcagctcaggactctgagggttgctgcgtggaggcagtgcatgccctgggcacagtgcccagttc ctgccca SEQ ID NO: 19: Reverse complement of SEQ ID NO: 06 tgcaagaaatgtagttctatttattctctgttctaatgggtataaacattttgttatctaacttgaacatcatac caactcaaaggcaggtcttactagcaatgactggggctcagagaggtttggcgacttcacgaaggtcacacagct gtcaggggggaaaagtcagaacttggatccaggtcttcagactctcaggtctggtgtcatcctaggggggcttggtg atggccatatctttaatgtatttgtggagagtgaaaggctgtcagtgagtaagcttaagagaacaggagacttgt gtgggaaacagtcggtatccattgattagactgaatcatgtagaattgctaatttcaccattttgaactatcgaa atcactatttggtatgactcaacctcatcctttaagtacacattcatgacagtgagtggttagacagtgattcct agattagtttgggatggggcagtgccttccataggacaaggccattcctggtagagacggagggagcaggctgtc cttcagctaggggcccaggggacttcctggctgctgtgtcctttagcagggccttggaggatggaaggactctcc tggcccttaccacaggggctattcaggaacagcctcctgccgtggcactggagctgcggtggccctctgaagact gcagggacagcaacaggcacaaagaagtcaggctgcatgtggccccagtcgggactcagaggaggaaagggaggg gttgcgggggtcaatgggtgatgtgcttcctctcccatagctgaggagtccttgcaatggccttcctgagccatc agcaggcctatggccatgtgactagggaggagaagggatatagggtaatggtcttctggggcctgctgggcctgg tcaagtctgaggaggagatagagaaaacaaagcagagaccctcctcttcatctggggagaagggacctgattcta aacggagatatgtgaggctttctggggcagcgatggaaggacaaggacagaataggtgtccttgttgccccatgg agaatgggcttcaggaagaatctgcctcagtcattttccagaagtgcctgagaggtgcagggcccgagtctggtt aggtgacagcgggtcaagaggaggacattgtcctctctcttgtgttgctgcagatgccacaaaactgggccacgg cacgatcaggcagttctggggcccccaggagggcagccttggggtgggcacagccagccctggcaggatgagcaa ctctgggtgggggggagtgggggatgagcaggggggacatgaagatgcttggtggagcctggggtcatggctggta tctggttcctcccctgtgattccttcttggggactccaagacaggacaaggaagactggagccctccagaaacag atgggcccaggtccgtaagctgaggattcagtccccccctggattcaagcccagcatgtgcctacccagccagatg ctccatgaacacagttcaggggggcccgaagacagcactgttacctggagcccacatacagcctcagcaggcaaag ggagactcagagaaaacatgggagggatttacagtcacatgcaggcagggaccagctcaacccttctttaatgtc atccagggagggggccagggatggaggggaggggttgaggagcgagaggcagttatttttgggtgggattcacca cttttcccatgaagaggggagacttggtattttgttcaatcattaagaagacaaagggtttgttgaacttgacct cggggggggatagacatgggtatggcctctaaaaacatggccccagcagcttcagtccctttctcgtcgatggtca gcacagccttatgcacggccttggagagcttcaggggtgcctcctctgtgaccccggagaggtcagccccattgc tgaagaccttagtgatgcccagttgacccaggacgctcttcagatcataggttccagtaatggacagtttgggta aatgtaagctggcagaccttctgtcttcattttccaggaacttggtgatgatatcgtgggtgagttcattttcca ggtgctgtagtttcccctcatcaggcaggaagaagatggcggtggcattgcccaggtatttcatcagcagcaccc agctggacagcttcttacagtgctggatgttaaacatgcctaaacgcttcatcataggcaccttcacggtggtca cctggtccacgtggaagtcctcttcctcggtgtccttgacttcaaagggtctctcccatttgcctttaaagaaga tgtaattcaccagagcaaaaactgtgtctctgtcaagctccttgaccaaatccacaattttcccttgagtaccct tctccacgtaatcgttgatctgtttcttggcctcttcggtgtccccgaagttgacagtgaaggcttctgagtggt acaacttttttaacatcctccaaaaacttatccactagcttcaggccctcgctgaggaacaggccattgccggtgg tcagctggagctggctgtctggctggttgagggtacggaggagttcctggaagccttcatggatctgagcctccg gaatctccgtgaggttgaaattcaggccctccaggatttcatcgtgagtgtcagccttggtccccagggagagca -continued ttgcaaaggctgtagcgatgctcactggggagaagaagatattggtgctgttggactggtgtgccagctggcggt ataggctgaaggcgaactcagccaggttgggggtgatcttgttgaaggttgggtgatcctgatcatggtgggatg tatctgtcttctgggcagcatctccctggggatcctcagccagggagacagggaccaggcagcacaggcctgcca gcaggaggatgccccacgagacagaagacggcattgtcgattcactgtcccaggtcagtggtggtgcctgaagct gaggagacagggccctgtcctcgtccgtatttaagcagtggatccagaggggcaacgggggaggctgctgtggaa ctgagtgagcagcagcagcaatgtcccacctttcctgctctcctcaagctctcctcaagctctgtctcttctggc aggcacaggagagtggcctgaaggctggcaggaggttgccgcccctccaacctggaattcctggcagcagcagcg gctaggccttcctcggaggcccgacccccctcctccttcttggttcagctcaggactctgagggttgctgcgtgga ggcagtgcatgccctgggcacagtgcccagttcctgccca SEQ ID NO: 20: Reverse complement of SEQ ID NO: 07 tgcaagaaatgtagttctatttattctctgttctaatgggtataaacattttgttatctaacttgaacatcataccaactcaaaggcaggtct tactagcaatgactggggctcagagaggtttggcgacttcacgaaggtcacacagctgtcaggggggaaaagtcagaacttggatccaggt cttcagactctcaggtctggtgtcatcctaggggggcttggtgatggccatatctttaatgtatttgtggagagtgaaaggctgtcagtgagt aagcttaagagaacaggagacttgtgtgggaaacagtcggtatccattgattagactgaatcatgtagaattgctaatttcaccattttgaa ctatcgaaatcactatttggtatgactcaacctcatcctttaagtacacattcatgacagtgagtggttagacagtgattcctagattagtttg ggatggggcagtgccttccataggacaaggccattcctggtagagacggagggagcaggctgtccttcagctaggggcccagggg acttcctggctgctgtgtcctttagcagggccttggaggatggaaggactctcctggcccttaccacaggggctattcaggaacagcct cctgccgtggcactggagctgcggtggccctctgaagactgcagggacagcaacaggcacaaagaagtcaggctgcatgtggccc cagtcgggactcagaggaggaaagggaggggttgcgggggtcaatgggtgatgtgcttcctctcccatagctgaggagtccttgcaa tggccttcctgagccatcagcaggcctatggccatgtgactagggaggagaaggatatagggtaatggtcttctggggcctgctggg cctggtcaagtctgaggaggagatagagaaaacaaagcagagaccctcctcttcatctggggagaagggacctgattctaaacggag atatgtgaggctttctggggcagcgatggaaggacaaggacagaataggtgtccttgttgccccatggagaatgggcttcaggaaga atctgcctcagtcattttccagaagtgcctgagaggtgcagggcccgagtctggttaggtgacagcgggtcaagaggaggacattgtc ctctctcttgtgttgctgcagatgccacaaaactgggccacggcacgatcaggcagttctggggcccccaggagggcagccttgggg tgggcacagccagccctggcaggatgagcaactctgggtggggggagtgggggatgagcagggggacatgaagatgcttggtg gagcctggggtcatggctggtatctggttcctcccctgtgattccttcttggggactccaagacaggacaaggaagactggagccctcc agaaacagatgggcccaggtccgtaagctgaggattcagtccccctggattcaagcccagcatgtgcctacccagccagatgctcc atgaacacagttcagggggcccgaagacagcactgttacctggagcccacatacagcctcagcaggcaaagggagactcagagaa aacatgggagggatttacagtcacatgcaggcagggaccagctcaacccttctttaatgtcatccagggagggggccagggatggag gggaggggttgaggagcgagaggcagttatttttgggtgggattcaccacttttcccatgaagaggggagacttggtattttgttcaatc attaagaagacaaagggtttgttgaacttgacctcgggggggatagacatgggtatggcctctaaaaacatggccccagcagcttcag tccctttctcgtcgatggtcagcacagccttatgcacggccttggagagcttcaggggtgcctcctctgtgaccccggagaggtcagcc ccattgctgaagaccttagtgatgcccagttgacccaggacgctcttcagatcataggttccagtaatggacagtttgggtaaatgtaag ctggcagaccttctgtcttcattttccaggaacttggtgatgatatcgtgggtgagttcattttccaggtgctgtagtttcccctcatcaggca ggaagaagatggcggtggcattgcccaggtatttcatcagcagcacccagctggacagcttcttacagtgctggatgttaaacatgcct aaacgcttcatcataggcaccttcacggtggtcacctggtccacgtggaagtcctcttcctcggtgtccttgacttcaaagggtctctccc atttgcctttaaagaagatgtaattcaccagagcaaaaactgtgtctctgtcaagctccttgaccaaatccacaattttcccttgagtaccct tctccacgtaatcgttgatctgtttcttggcctcttcggtgtccccgaagttgacagtgaaggcttctgagtggtacaactttttaacatcctc caaaaacttatccactagcttcaggccctcgctgaggaacaggccattgccggtggtcagctggagctggctgtctggctggttgagg gtacggaggagttcctggaagccttcatggatctgagcctccggaatctccgtgaggttgaaattcaggccctccaggatttcatcgtga gtgtcagccttggtccccagggagagcattgcaaaggctgtagcgatgctcactggggagaagaagatattggtgctgttggactggt -continued gtgccagctggcggtataggctgaaggcgaactcagccaggttgggggtgatcttgttgaaggttgggtgatcctgatcatggtggga tgtatctgtcttctgggcagcatctccctggggatcctcagccagggagacagggaccaggcagcacaggcctgccagcaggagga tgccccacgagacagaagacggcattgtcgattcactgtcccaggtcagtggtggtgcctgaagctgaggagacagggccctgtcct cgtccgtatttaagcagtggatccagaggggcaacgggggaggctgctggctcagaaaccacagcgtcctgtgtccaaggtggagg gggtggcgtgagtcagacagtctctgggagagtaccacttagctggccctctgctctcactgcagaatccttagtggctgttccactggt agcaagatctaccatttactgagtcaccccaaaatgcctgatgctgaagacttactgccgccctttcctgctctcctcaagctctcctcaa gctctgtctcttctggcaggcacaggagagtggcctgaaggctggcaggaggttgccgcccctccaacctggaattcctggcagcag cagcggctaggccttcctcggaggcccgaccccctcctccttcttggttcagctcaggactctgagggttgctgcgtggaggcagtgc atgccctgggcacagtgcccagttcctgccca SEQ ID NO: 21: Reverse complement of SEQ ID NO: 08 tgcaagaaatgtagttctatttattctctgttctaatgggtataaacattttgttatctaacttgaacatcatac caactcaaaggcaggtcttactagcaatgactggggctcagagaggtttggcgacttcacgaaggtcacacagct gtcaggggggaaaagtcagaacttggatccaggtcttcagactctcaggtctggtgtcatcctagggggcttggtg atggccatatctttaatgtatttgtggagagtgaaaggctgtcagtgagtaagcttaagagaacaggagacttgt gtgggaaacagtcggtatccattgattagactgaatcatgtagaattgctaatttcaccattttgaactatcgaa atcactatttggtatgactcaacctcatcctttaagtacacattcatgacagtgagtggttagacagtgattcct agattagtttgggatggggcagtgccttccataggacaaggccattcctggtagagacggagggagcaggctgtc cttcagctaggggcccaggggacttcctggctgctgtgtcctttagcagggccttggaggatggaaggactctcc tggcccttaccacaggggctattcaggaacagcctcctgccgtggcactggagctgcggtggccctctgaagact gcagggacagcaacaggcacaaagaagtcaggctgcatgtggccccagtcgggactcagaggaggaaagggaggg gttgcgggggtcaatgggtgatgtgcttcctctcccatagctgaggagtccttgcaatggccttcctgagccatc agcaggcctatggccatgtgactagggaggagaagggatatagggtaatggtcttctggggcctgctgggcctgg tcaagtctgaggaggagatagagaaaacaaagcagagaccctcctcttcatctggggagaagggacctgattcta aacggagatatgtgaggctttctggggcagcgatggaaggacaaggacagaataggtgtccttgttgccccatgg agaatgggcttcaggaagaatctgcctcagtcattttccagaagtgcctgagaggtgcagggcccgagtctggtt aggtgacagcgggtcaagaggaggacattgtcctctctcttgtgttgctgcagatgccacaaaactgggccacgg cacgatcaggcagttctggggcccccaggagggcagccttggggtgggcacagccagccctggcaggatgagcaa ctctgggtggggggggagtgggggatgagcagggggacatgaagatgcttggtggagcctggggtcatggctggta tctggttcctcccctgtgattccttcttggggactccaagacaggacaaggaagactggagccctccagaaacag atgggcccaggtccgtaagctgaggattcagtccccccctggattcaagcccagcatgtgcctacccagccagatg ctccatgaacacagttcagggggcccgaagacagcactgttacctggagcccacatacagcctcagcaggcaaag ggagactcagagaaaacatgggagggatttacagtcacatgcaggcagggaccagctcaacccttctttaatgtc atccagggagggggccagggatggaggggaggggttgaggagcgagaggcagttatttttgggtgggattcacca cttttcccatgaagaggggagacttggtattttgttcaatcattaagaagacaaagggtttgttgaacttgacct cggggggggatagacatgggtatggcctctaaaaacatggccccagcagcttcagtccctttctcgtcgatggtca gcacagccttatgcacggccttggagagcttcaggggtgcctcctctgtgaccccggagaggtcagccccattgc tgaagaccttagtgatgcccagttgacccaggacgctcttcagatcataggttccagtaatggacagtttgggta aatgtaagctggcagaccttctgtcttcattttccaggaacttggtgatgatatcgtgggtgagttcattttcca ggtgctgtagtttcccctcatcaggcaggaagaagatggcggtggcattgcccaggtatttcatcagcagcaccc agctggacagcttcttacagtgctggatgttaaacatgcctaaacgcttcatcataggcaccttcacggtggtca cctggtccacgtggaagtcctcttcctcggtgtccttgacttcaaagggtctctcccatttgcctttaaagaaga -continued tgtaattcaccagagcaaaaactgtgtctctgtcaagctccttgaccaaatccacaattttcccttgagtaccct tctccacgtaatcgttgatctgtttcttggcctcttcggtgtccccgaagttgacagtgaaggcttctgagtggt acaacttttttaacatcctccaaaaacttatccactagcttcaggccctcgctgaggaacaggccattgccggtgg tcagctggagctggctgtctggctggttgagggtacggaggagttcctggaagccttcatggatctgagcctccg gaatctccgtgaggttgaaattcaggccctccaggatttcatcgtgagtgtcagccttggtccccagggagagca ttgcaaaggctgtagcgatgctcactggggagaagaagatattggtgctgttggactggtgtgccagctggcggt ataggctgaaggcgaactcagccaggttgggggtgatcttgttgaaggttgggtgatcctgatcatggtgggatg tatctgtcttctgggcagcatctccctggggatcctcagccagggagacagggaccaggcagcacaggcctgcca gcaggaggatgccccacgagacagaagacggcattgtcgattcactgtcccaggtcagtggtggtgcctgaagct gaggagacagggccctgtcctcgtccgtatttaagcagtggatccagaggggcaacgggggaggctggctcagaa accacagcgtcctgtgtccaaggtggagggggtggcgtgagtcagacagtctctgggagagtaccacttagctgg ccctctgctctcactgcagaatccttagtggctgttccactggtagcaagatctaccatttactgagtcacccca aaatgcctgatgctgaagacttactgccgccctttcctgctctcctcaagctctcctcaagctctgtctcttctg gcaggcacaggagagtggcctgaaggctggcaggaggttgccgcccctccaacctggaattcctggcagcagcag cggctaggccttcctcggaggcccgaccccctcctccttcttggttcagctcaggactctgagggttgctgcgtg gaggcagtgcatgccctgggcacagtgcccagttcctgccca SEQ ID NO: 22: Reverse complement of SEQ ID NO: 09
tgcaagaaatgtagttctatttattctctgttctaatgggtataaacattttgttatctaacttgaa catcataccaactcaaaggcaggtcttactagcaatgactggggctcagagaggtttggcgacttcacgaaggtc acacagctgtcaggggggaaaagtcagaacttggatccaggtcttcagactctcaggtctggtgtcatcctagggg gcttggtgatggccatatctttaatgtatttgtggagagtgaaaggctgtcagtgagtaagcttaagagaacagg agacttgtgtgggaaacagtcggtatccattgattagactgaatcatgtagaattgctaatttcaccattttgaa ctatcgaaatcactatttggtatgactcaacctcatcctttaagtacacattcatgacagtgagtggttagacag tgattcctagattagtttgggatggggcagtgccttccataggacaaggccattcctggtagagacggagggagc aggctgtccttcagctaggggcccaggggacttcctggctgctgtgtcctttagcagggccttggaggatggaag gactctcctggcccttaccacaggggctattcaggaacagcctcctgccgtggcactggagctgcggtggccctc tgaagactgcagggacagcaacaggcacaaagaagtcaggctgcatgtggccccagtcgggactcagaggaggaa agggaggggttgcgggggtcaatgggtgatgtgcttcctctcccatagctgaggagtccttgcaatggccttcct gagccatcagcaggcctatggccatgtgactagggaggagaagggatatagggtaatggtcttctggggcctgct gggcctggtcaagtctgaggaggagatagagaaaacaaagcagagaccctcctcttcatctggggagaagggacc tgattctaaacggagatatgtgaggctttctggggcagcgatggaaggacaaggacagaataggtgtccttgttg ccccatggagaatgggcttcaggaagaatctgcctcagtcattttccagaagtgcctgagaggtgcagggcccga gtctggttaggtgacagcgggtcaagaggaggacattgtcctctctcttgtgttgctgcagatgccacaaaactg ggccacggcacgatcaggcagttctggggcccccaggagggcagccttggggtgggcacagccagccctggcagg atgagcaactctgggtgggggggagtgggggatgagcagggggacatgaagatgcttggtggagcctggggtcat ggctggtatctggttcctcccctgtgattccttcttggggactccaagacaggacaaggaagactggagccctcc agaaacagatgggcccaggtccgtaagctgaggattcagtccccccctggattcaagcccagcatgtgcctaccca gccagatgctccatgaacacagttcagggggcccgaagacagcactgttacctggagcccacatacagcctcagc aggcaaagggagactcagagaaaacatgggagggatttacagtcacatgcaggcagggaccagctcaacccttct ttaatgtcatccagggagggggccagggatggagggggaggggttgaggagcgagaggcagttatttttgggtggg attcaccacttttcccatgaagaggggagacttggtattttgttcaatcattaagaagacaaagggtttgttgaa -continued cttgacctcgggggggatagacatgggtatggcctctaaaaacatggccccagcagcttcagtccctttctcgtc gatggtcagcacagccttatgcacggccttggagagcttcaggggtgcctcctctgtgaccccggagaggtcagc cccattgctgaagaccttagtgatgcccagttgacccaggacgctcttcagatcataggttccagtaatggacag tttgggtaaatgtaagctggcagaccttctgtcttcattttccaggaacttggtgatgatatcgtgggtgagttc attttccaggtgctgtagtttcccctcatcaggcaggaagaagatggcggtggcattgcccaggtatttcatcag cagcacccagctggacagcttcttacagtgctggatgttaaacatgcctaaacgcttcatcataggcaccttcac ggtggtcacctggtccacgtggaagtcctcttcctcggtgtccttgacttcaaagggtctctcccatttgccttt aaagaagatgtaattcaccagagcaaaaactgtgtctctgtcaagctccttgaccaaatccacaattttcccttg agtacccttctccacgtaatcgttgatctgtttcttggcctcttcggtgtccccgaagttgacagtgaaggcttc tgagtggtacaactttttaacatcctccaaaaacttatccactagcttcaggccctcgctgaggaacaggccatt gccggtggtcagctggagctggctgtctggctggttgagggtacggaggagttcctggaagccttcatggatctg agcctccggaatctccgtgaggttgaaattcaggccctccaggatttcatcgtgagtgtcagccttggtccccag ggagagcattgcaaaggctgtagcgatgctcactggggagaagaagatattggtgctgttggactggtgtgccag ctggcggtataggctgaaggcgaactcagccaggttgggggtgatcttgttgaaggttgggtgatcctgatcatg gtgggatgtatctgtcttctgggcagcatctccctggggatcctcagccagggagacagggaccaggcagcacag gcctgccagcaggaggatgccccacgagacagaagacggcattgtcgattcactgtcccaggtcagtggtggtgc ctgaagctgaggagacagggccctgtcctcgtccgtatttaagcagtggatccagaggggcaacgggggaggcga aaggagtcattgtacctggctcagaaaccacagcgtcctgtgtccaaggtggagggggtggcgtgagtcagacag tctctgggagagtaccacttagctggccctctgctctcactgcagaatccttagtggctgttccactggtagcaa gatctaccatttactgagtcaccccaaaatgcctgatgctgaagacttactgccgccctttcctgctctcctcaa gctctcctcaagctctgtctcttctggcaggcacaggagagtggcctgaaggctggcaggaggttgccgcccctc caacctggaattcctggcagcagcagcggctaggccttcctcggaggcccgacccccctcctccttcttggttcag ctcaggactctgagggttgctgcgtggaggcagtgcatgccctgggcacagtgcccagttcctgccca SEQ ID NO: 23: Reverse complement of SEQ ID NO: 10
tgcaagaaatgtagttctatttattctctgttctaatgggtataaacattttgttatctaacttgaa catcataccaactcaaaggcaggtcttactagcaatgactggggctcagagaggtttggcgacttcacgaaggtc acacagctgtcaggggggaaaagtcagaacttggatccaggtcttcagactctcaggtctggtgtcatcctagggg gcttggtgatggccatatctttaatgtatttgtggagagtgaaaggctgtcagtgagtaagcttaagagaacagg agacttgtgtgggaaacagtcggtatccattgattagactgaatcatgtagaattgctaatttcaccattttgaa ctatcgaaatcactatttggtatgactcaacctcatcctttaagtacacattcatgacagtgagtggttagacag tgattcctagattagtttgggatggggcagtgccttccataggacaaggccattcctggtagagacggagggagc aggctgtccttcagctaggggcccaggggacttcctggctgctgtgtcctttagcagggccttggaggatggaag gactctcctggcccttaccacaggggctattcaggaacagcctcctgccgtggcactggagctgcggtggccctc tgaagactgcagggacagcaacaggcacaaagaagtcaggctgcatgtggccccagtcgggactcagaggaggaa agggaggggttgcgggggtcaatgggtgatgtgcttcctctcccatagctgaggagtccttgcaatggccttcct gagccatcagcaggcctatggccatgtgactagggaggagaagggatatagggtaatggtcttctggggcctgct gggcctggtcaagtctgaggaggagatagagaaaacaaagcagagaccctcctcttcatctggggagaaggcacc tgattctaaacggagatatgtgaggctttctggggcagcgatggaaggacaaggacagaataggtgtccttgttg ccccatggagaatgggcttcaggaagaatctgcctcagtcattttccagaagtgcctgagaggtgcagggcccga gtctggttaggtgacagcgggtcaagaggaggacattgtcctctctcttgtgttgctgcagatgccacaaaactg ggccacggcacgatcaggcagttctggggccccccaggagggcagccttggggtgggcacagccagccctggcagg -continued atgagcaactctgggtgggggggagtgggggatgagcaggggggacatgaagatgcttggtggagcctggggtcat ggctggtatctggttcctcccctgtgattccttcttggggactccaagacaggacaaggaagactggagccctcc agaaacagatgggcccaggtccgtaagctgaggattcagtccccccctggattcaagcccagcatgtgcctaccca gccagatgctccatgaacacagttcagggggcccgaagacagcactgttacctggagcccacatacagcctcagc aggcaaagggagactcagagaaaacatgggagggatttacagtcacatgcaggcagggaccagctcaacccttct ttaatgtcatccagggagggggccagggatggaggggaggggttgaggagcgagaggcagttatttttgggtggg attcaccacttttcccatgaagaggggagacttggtattttgttcaatcattaagaagacaaagggtttgttgaa cttgacctcgggggggatagacatgggtatggcctctaaaaacatggccccagcagcttcagtccctttctcgtc gatggtcagcacagccttatgcacggccttggagagcttcaggggtgcctcctctgtgaccccggagaggtcagc cccattgctgaagaccttagtgatgcccagttgacccaggacgctcttcagatcataggttccagtaatggacag tttgggtaaatgtaagctggcagaccttctgtcttcattttccaggaacttggtgatgatatcgtgggtgagttc attttccaggtgctgtagtttcccctcatcaggcaggaagaagatggcggtggcattgcccaggtatttcatcag cagcacccagctggacagcttcttacagtgctggatgttaaacatgcctaaacgcttcatcataggcaccttcac ggtggtcacctggtccacgtggaagtcctcttcctcggtgtccttgacttcaaagggtctctcccatttgccttt aaagaagatgtaattcaccagagcaaaaactgtgtctctgtcaagctccttgaccaaatccacaattttcccttg agtacccttctccacgtaatcgttgatctgtttcttggcctcttcggtgtccccgaagttgacagtgaaggcttc tgagtggtacaactttttaacatcctccaaaaacttatccactagcttcaggccctcgctgaggaacaggccatt gccggtggtcagctggagctggctgtctggctggttgagggtacggaggagttcctggaagccttcatggatctg agcctccggaatctccgtgaggttgaaattcaggccctccaggatttcatcgtgagtgtcagccttggtccccag ggagagcattgcaaaggctgtagcgatgctcactggggagaagaagatattggtgctgttggactggtgtgccag ctggcggtataggctgaaggcgaactcagccaggttgggggtgatcttgttgaaggttgggtgatcctgatcatg gtgggatgtatctgtcttctgggcagcatctccctggggatcctcagccagggagacagggaccaggcagcacag gcctgccagcaggaggatgccccacgagacagaagacggcattgtcgattcactgtcccaggtcagtggtggtgc ctgaagctgaggagacagggccctgtcctcgtccgtatttaagcagtggatccagaggggcaacgggggaggctg ctttcctgctctcctcaagctctcctcaagctctgtctcttctggcaggcacaggagagtggcctgaaggctggc aggaggttgccgcccctccaacctggaattcctggcagcagcagcggctaggccttcctcggaggcccgaccccc tcctccttcttggttcagctcaggactctgagggttgctgcgtggaggcagtgcatgccctgggcacagtgccca gttcctgccca SEQ ID NO: 24: Reverse complement of SEQ ID NO: 11 tgcaagaaatgtagttctatttattctctgttctaatgggtataaacattttgttatctaacttgaacatcatac caactcaaaggcaggtcttactagcaatgactggggctcagagaggtttggcgacttcacgaaggtcacacagct gtcaggggggaaaagtcagaacttggatccaggtcttcagactctcaggtctggtgtcatcctagggggcttggtg atggccatatctttaatgtatttgtggagagtgaaaggctgtcagtgagtaagcttaagagaacaggagacttgt gtgggaaacagtcggtatccattgattagactgaatcatgtagaattgctaatttcaccattttgaactatcgaa atcactatttggtatgactcaacctcatcctttaagtacacattcatgacagtgagtggttagacagtgattcct agattagtttgggatggggcagtgccttccataggacaaggccattcctggtagagacggagggagcaggctgtc cttcagctaggggcccaggggacttcctggctgctgtgtcctttagcagggccttggaggatggaaggactctcc tggcccttaccacaggggctattcaggaacagcctcctgccgtggcactggagctgcggtggccctctgaagact gcagggacagcaacaggcacaaagaagtcaggctgcatgtggccccagtcgggactcagaggaggaaagggaggg gttgcgggggtcaatgggtgatgtgcttcctctcccatagctgaggagtccttgcaatggccttcctgagccatc agcaggcctatggccatgtgactagggaggagaagggatatagggtaatggtcttctggggcctgctgggcctgg -continued tcaagtctgaggaggagatagagaaaacaaagcagagaccctcctcttcatctggggagaagggacctgattcta aacggagatatgtgaggctttctggggcagcgatggaaggacaaggacagaataggtgtccttgttgccccatgg agaatgggcttcaggaagaatctgcctcagtcattttccagaagtgcctgagaggtgcagggcccgagtctggtt aggtgacagcgggtcaagaggaggacattgtcctctctcttgtgttgctgcagatgccacaaaactgggccacgg cacgatcaggcagttctggggcccccaggagggcagccttggggtgggcacagccagccctggcaggatgagcaa ctctgggtgggggggagtgggggatgagcaggggggacatgaagatgcttggtggagcctggggtcatggctggta tctggttcctcccctgtgattccttcttggggactccaagacaggacaaggaagactggagccctccagaaacag atgggcccaggtccgtaagctgaggattcagtccccccctggattcaagcccagcatgtgcctacccagccagatg ctccatgaacacagttcaggggggcccgaagacagcactgttacctggagcccacatacagcctcagcaggcaaag ggagactcagagaaaacatgggagggatttacagtcacatgcaggcagggaccagctcaacccttctttaatgtc atccagggagggggccagggatggagggggaggggttgaggagcgagaggcagttatttttgggtgggattcacca cttttcccatgaagaggggagacttggtattttgttcaatcattaagaagacaaagggtttgttgaacttgacct cggggggggatagacatgggtatggcctctaaaaacatggccccagcagcttcagtccctttctcgtcgatggtca gcacagccttatgcacggccttggagagcttcaggggtgcctcctctgtgaccccggagaggtcagccccattgc tgaagaccttagtgatgcccagttgacccaggacgctcttcagatcataggttccagtaatggacagtttgggta aatgtaagctggcagaccttctgtcttcattttccaggaacttggtgatgatatcgtgggtgagttcattttcca ggtgctgtagtttcccctcatcaggcaggaagaagatggcggtggcattgcccaggtatttcatcagcagcaccc agctggacagcttcttacagtgctggatgttaaacatgcctaaacgcttcatcataggcaccttcacggtggtca cctggtccacgtggaagtcctcttcctcggtgtccttgacttcaaagggtctctcccatttgcctttaaagaaga tgtaattcaccagagcaaaaactgtgtctctgtcaagctccttgaccaaatccacaattttcccttgagtaccct tctccacgtaatcgttgatctgtttcttggcctcttcggtgtccccgaagttgacagtgaaggcttctgagtggt acaactttttaacatcctccaaaaacttatccactagcttcaggccctcgctgaggaacaggccattgccggtgg tcagctggagctggctgtctggctggttgagggtacggaggagttcctggaagccttcatggatctgagcctccg gaatctccgtgaggttgaaattcaggccctccaggatttcatcgtgagtgtcagccttggtccccagggagagca ttgcaaaggctgtagcgatgctcactggggagaagaagatattggtgctgttggactggtgtgccagctggcggt ataggctgaaggcgaactcagccaggttgggggtgatcttgttgaaggttgggtgatcctgatcatggtgggatg tatctgtcttctgggcagcatctccctggggatcctcagccagggagacagggaccaggcagcacaggcctgcca gcaggaggatgccccacgagacagaagacggcattgtcgattcactgtcccaggtcagtggtggtgcctgaagct gaggagacagggccctgtcctcgtccgtatttaagcagtggatccagaggggcaacgggggaggctttcctgctc tcctcaagctctcctcaagctctgtctcttctggcaggcacaggagagtggcctgaaggctggcaggaggttgcc gcccctccaacctggaattcctggcagcagcagcggctaggccttcctcggaggcccgacccccctcctccttctt ggttcagctcaggactctgagggttgctgcgtggaggcagtgcatgccctgggcacagtgcccagttcctgccca

SEQ ID NO: 25
AAVALLPAVLLALLAP

SEQ ID NO: 26
AALLPVLLAAP

SEQ ID NO: 27 HIV Tat peptide
GRKKRRQRRRPPQ

SEQ ID NO: 28 *Drosophila* Antennapedia peptide
RQIKIWFQNRRMKWKK

---

What is claimed herein is:

1. A method of inhibiting Serpina 1 expression in a cell, the method comprising:

(a) introducing into the cell a Serpina-1 inhibiting double stranded ribonucleic acid (dsRNA) comprising:

i. a sense strand molecule which is 19-23 nucleotides in length comprising at least 19 contiguous nucleotides of SEQ ID NO:62, said sense strand comprising at least 10 nucleotides comprising a 2'-O-methyl modification;

ii. a separate antisense strand molecule which is 19-23 nucleotides in length comprising at least 19 contiguous nucleotides of SEQ ID NO: 106, said antisense strand comprising at least 3 nucleotides comprising a 2'O-methyl modification; and iii. at least 19 of the nucleotides in each strand are modified; and wherein the sense strand and antisense strand are two separate molecules; and (b) maintaining the cell produced in step (a) for a time sufficient to obtain degradation of the mRNA transcript of a Serpina 1 gene, thereby inhibiting expression of the Serpina 1 gene in the cell.

2. The method of claim 1, wherein the nucleotides in said antisense strand are all modified nucleotides.

3. The method of claim 1, wherein said modified nucleotides comprise a modification selected from the group consisting of: 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

4. The method of claim 1, wherein said sense strand comprises at least one phosphorothioate linkage.

5. The method of claim 4, wherein said sense strand comprises three phosphorothioate linkages.

6. The method of claim 1, wherein said antisense strand comprises at least one phosphorothioate linkage.

7. The method of claim 6, wherein said antisense strand comprises three phosphorothioate linkages.

8. The method of claim 1, wherein said dsRNA comprises a ligand.

9. The method of claim 8, wherein said ligand comprises at least one carbohydrate conjugate.

10. The method of claim 8, wherein said ligand is attached to the 5' end of said sense strand.

11. The method of claim 1, wherein said sense strand comprises at least one inverted nucleotide linkage.

12. The method of claim 11, wherein said sense strand comprises at least two inverted nucleotide linkages.

13. A method of inhibiting Serpina 1 expression in a cell, the method comprising:

(a) introducing into the cell a Serpina-1 inhibiting double stranded ribonucleic acid (dsRNA) comprising:

i. a sense strand molecule which is 19-23 nucleotides in length comprising:

A. at least 19 contiguous nucleotides of SEQ ID NO:62;

B. three phosphorothioate linkages;

C. a ligand attached to the 5' end wherein said ligand comprises at least one carbohydrate conjugate;

D. at least one inverted base;

E. all modified nucleotides;

F. at least 10 nucleotides comprising a 2'-O-methyl modification; and ii. a separate antisense strand molecule which is 19-23 nucleotides in length comprising:

A. at least 19 contiguous nucleotides of SEQ ID NO: 106;

B. three phosphorothioate linkages;

C. all modified nucleotides;

D. at least 3 nucleotides comprising a 2'-O-methyl modification; and wherein the sense strand and antisense strand are two separate molecules; and (b) maintaining the cell produced in step (a) for a time sufficient to obtain degradation of the mRNA transcript of a Serpina 1 gene, thereby inhibiting expression of the Serpina 1 gene in the cell.

14. A method of treating a disorder mediated by Serpina 1 expression comprising administering to a patient in need of such treatment a therapeutically effective amount of a Serpina-1 inhibiting double stranded ribonucleic acid (dsRNA) comprising:

i. a sense strand molecule which is 19-23 nucleotides in length comprising at least 19 contiguous nucleotides of SEQ ID NO:62, wherein at least 10 nucleotides comprise a 2'-O-methyl modification;

ii. a separate antisense strand molecule which is 19-23 nucleotides in length comprising at least 19 contiguous nucleotides of SEQ ID NO: 106, wherein at least 3 nucleotides comprise a 2'-O-methyl modification; and iii. at least 19 of the nucleotides in each strand are modified wherein the sense strand and antisense strand are two separate molecule.

15. The method of claim 14, wherein the disorder is Alpha 1 anti-trypsin deficiency liver disease.

16. The method of claim 14, wherein the administration of the dsRNA to the patient causes a decrease in cirrhosis, fibrosis, and/or Serpina 1 protein accumulation in the liver.

17. The method of claim 14, wherein the likelihood of hepatocellular carcinoma occurring in the patient is reduced.

18. The method of claim 14, wherein the dsRNA is administered at a concentration of 0.01 mg/kg 5 mg/kg body-weight of the patient.

19. A method of treating a disorder mediated by Serpina 1 expression comprising administering to a patient in need of such treatment a therapeutically effective amount of a Serpina-1 inhibiting double stranded ribonucleic acid (dsRNA) comprising:

i. a sense strand molecule which is 19-23 nucleotides in length comprising:
   A. at least 19 contiguous nucleotides of SEQ ID NO:62;
   B. three phosphorothioate linkages;
   C. a ligand attached to the 5' end wherein said ligand comprises at least one carbohydrate conjugate;
   D. at least one inverted base;
   E. all modified nucleotides;
   F. at least 10 nucleotides comprising a 2'-O-methyl modification; and ii. a separate antisense strand molecule which is 19-23 nucleotides in length comprising:
   A. at least 19 contiguous nucleotides of SEQ ID NO: 106;
   B. three phosphorothioate linkages;
   C. all modified nucleotides;
   D. at least 10 nucleotides comprising a 2'-O-methyl modification; and wherein the sense strand and antisense strand are two separate molecules.

20. The method of claim 19, wherein the disorder is Alpha 1 anti-trypsin deficiency liver disease.

21. The method of claim 19, wherein the administration of the dsRNA to the patient causes a decrease in cirrhosis or fibrosis.

22. The method of claim 19, wherein the likelihood of hepatocellular carcinoma occurring in the patient is reduced.

23. The method of claim 19, wherein the dsRNA is administered at a concentration of 0.01 mg/kg 5 mg/kg body-weight of the patient.

24. The method of claim 1, wherein said sense strand comprises a 2'-O-methyl modified nucleotide at positions 1, 3, 4, 5, 9, 11, 13, 14, 15, and 18 of the 19 contiguous nucleotides of SEQ ID NO 62.

25. The method of claim 1, wherein said antisense strand comprises a 2'-O-methyl modified nucleotide at position 8 of the 19 contiguous nucleotides of SEQ ID NO:106.

26. The method of claim 1, wherein all uridine nucleotides of the sense strand comprise a 2'-O-methyl modification.

27. The method of claim 1, wherein all adenine nucleotides of the sense strand comprise a 2'-O-methyl modification.

28. The method of claim 1, wherein said expression of the Serpina 1 gene is inhibited by at least 30%.

29. The method of claim 19, wherein the administration of the dsRNA to the patient causes a decrease in Serpina 1 protein accumulation in the liver.

* * * * *

SEQUENCE LISTING

<160> NUMBER OF SEQ ID NOS: 204

<210> SEQ ID NO 1
<211> LENGTH: 3220
<212> TYPE: DNA
<213> ORGANISM: Homo sapiens

<400> SEQUENCE: 1

```
acaatgactc ctttcggtaa gtgcagtgga agctgtacac tgcccaggca aagcgtccgg      60
gcagcgtagg cgggcgactc agatcccagc cagtggactt agcccctgtt tgctcctccg     120
ataactgggg tgaccttggt taatattcac cagcagcctc cccgttgcc cctctggatc     180
cactgcttaa atacggacga ggacagggcc ctgtctcctc agcttcaggc accaccactg     240
acctgggaca gtgaatcgac aatgccgtct tctgtctcgt ggggcatcct cctgctggca     300
ggcctgtgct gcctggtccc tgtctccctg gctgaggatc cccagggaga tgctgcccag     360
aagacagata catcccacca tgatcaggat cacccaacct tcaacaagat cacccccaac     420
ctggctgagt tcgccttcag cctataccgc cagctggcac accagtccaa cagcaccaat     480
atcttcttct ccccagtgag catcgctaca gcctttgcaa tgctctccct ggggaccaag     540
gctgacactc acgatgaaat cctggagggc ctgaatttca acctcacgga gattccggag     600
gctcagatcc atgaaggctt ccaggaactc ctccgtaccc tcaaccagcc agacagccag     660
ctccagctga ccaccggcaa tggcctgttc ctcagcgagg gcctgaagct agtggataag     720
tttttggagg atgttaaaaa gttgtaccac tcagaagcct tcactgtcaa cttcggggac     780
accgaagagg ccaagaaaca gatcaacgat tacgtggaga agggtactca agggaaaatt     840
gtggatttgg tcaaggagct tgacagagac acagtttttg ctctggtgaa ttacatcttc     900
tttaaaggca aatgggagag accctttgaa gtcaaggaca ccgaggaaga ggacttccac     960
gtggaccagg tgaccaccgt gaaggtgcct atgatgaagc gtttaggcat gtttaacatc    1020
cagcactgta agaagctgtc cagctgggtg ctgctgatga aatacctggg caatgccacc    1080
gccatcttct tcctgcctga tgaggggaaa ctacagcacc tggaaaatga actcacccac    1140
gatatcatca ccaagttcct ggaaaatgaa gacagaaggt ctgccagctt acatttaccc    1200
aaactgtcca ttactggaac ctatgatctg aagagcgtcc tgggtcaact gggcatcact    1260
aaggtcttca gcaatggggc tgacctctcc ggggtcacag aggaggcacc cctgaagctc    1320
tccaaggccg tgcataaggc tgtgctgacc atcgacgaga aagggactga agctgctggg    1380
gccatgtttt tagaggccat acccatgtct atcccccccg aggtcaagtt caacaaaccc    1440
tttgtcttct taatgattga acaaaatacc aagtctcccc tcttcatggg aaaagtggtg    1500
aatcccaccc aaaaataact gcctctcgct cctcaacccc tcccctccat ccctggcccc    1560
ctccctggat gacattaaag aagggttgag ctggtccctg cctgcatgtg actgtaaatc    1620
cctcccatgt tttctctgag tctccctttg cctgctgagg ctgtatgtgg gctccaggta    1680
acagtgctgt cttcgggccc cctgaactgt gttcatggag catctggctg ggtaggcaca    1740
tgctgggctt gaatccaggg gggactgaat cctcagctta cggacctggg cccatctgtt    1800
tctggagggc tccagtcttc cttgtcctgt cttggagtcc ccaagaagga atcacagggg    1860
aggaaccaga taccagccat gaccccaggc tccaccaagc atcttcatgt ccccctgctc    1920
atcccccact ccccccacc cagagttgct catcctgcca gggctggctg tgcccacccc    1980
aaggctgccc tcctgggggc cccagaactg cctgatcgtg ccgtggccca gttttgtggc    2040
atctgcagca acacaagaga gaggacaatg tcctcctctt gacccgctgt cacctaacca    2100
```

-continued gactcgggcc ctgcacctct caggcacttc tggaaaatga ctgaggcaga ttcttcctga 2160
agcccattct ccatggggca acaaggacac ctattctgtc cttgtccttc catcgctgcc 2220
ccagaaagcc tcacatatct ccgtttagaa tcaggtccct tctccccaga tgaagaggag 2280
ggtctctgct ttgttttctc tatctcctcc tcagacttga ccaggcccag caggccccag 2340
aagaccatta ccctatatcc cttctcctcc ctagtcacat ggccataggc ctgctgatgg 2400
ctcaggaagg ccattgcaag gactcctcag ctatgggaga ggaagcacat cacccattga 2460
cccccgcaac ccctcccttt cctcctctga gtcccgactg gggccacatg cagcctgact 2520
tctttgtgcc tgttgctgtc cctgcagtct tcagagggcc accgcagctc cagtgccacg 2580
gcaggaggct gttcctgaat agcccctgtg gtaagggcca ggagagtcct tccatcctcc 2640
aaggccctgc taaaggacac agcagccagg aagtcccctg ggcccctagc tgaaggacag 2700
cctgctccct ccgtctctac caggaatggc cttgtcctat ggaaggcact gccccatccc 2760
aaactaatct aggaatcact gtctaaccac tcactgtcat gaatgtgtac ttaaaggatg 2820
aggttgagtc ataccaaata gtgatttcga tagttcaaaa tggtgaaatt agcaattcta 2880
catgattcag tctaatcaat ggataccgac tgtttcccac acaagtctcc tgttctctta 2940
agcttactca ctgacagcct ttcactctcc acaaatacat taaagatatg gccatcacca 3000
agccccctag gatgacacca gacctgagag tctgaagacc tggatccaag ttctgacttt 3060
tccccctgac agctgtgtga ccttcgtgaa gtcgccaaac ctctctgagc cccagtcatt 3120
gctagtaaga cctgcctttg agttggtatg atgttcaagt tagataacaa aatgtttata 3180
cccattagaa cagagaataa atagaactac atttcttgca 3220

<210> SEQ ID NO 2
<211> LENGTH: 3199
<212> TYPE: DNA
<213> ORGANISM: Homo sapiens

<400> SEQUENCE: 2
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaaggaca 240
atgccgtctt ctgtctcgtg gggcatcctc ctgctggcag gcctgtgctg cctggtccct 300
gtctccctgg ctgaggatcc ccagggagat gctgcccaga agacagatac atcccaccat 360
gatcaggatc acccaacctt caacaagatc acccccaacc tggctgagtt cgccttcagc 420
ctataccgcc agctggcaca ccagtccaac agcaccaata tcttcttctc cccagtgagc 480
atcgctacag cctttgcaat gctctccctg gggaccaagg ctgacactca cgatgaaatc 540
ctggagggcc tgaatttcaa cctcacggag attccggagg ctcagatcca tgaaggcttc 600
caggaactcc tccgtaccct caaccagcca gacagccagc tccagctgac caccggcaat 660
ggcctgttcc tcagcgaggg cctgaagcta gtggataagt tttggaggga tgttaaaaag 720
ttgtaccact cagaagcctt cactgtcaac ttcggggaca ccgaagaggc caagaaacag 780
atcaacgatt acgtggagaa gggtactcaa gggaaaattg tggatttggt caaggagctt 840
gacagagaca cagtttttgc tctggtgaat tacatcttct ttaaaggcaa atgggagaga 900
ccctttgaag tcaaggacac cgaggaagag gacttccacg tggaccaggt gaccaccgtg 960
aaggtgccta tgatgaagcg tttaggcatg tttaacatcc agcactgtaa gaagctgtcc 1020
agctgggtgc tgctgatgaa atacctgggc aatgccaccg ccatcttctt cctgcctgat 1080
gaggggaaac tacagcacct ggaaaatgaa ctcacccacg atatcatcac caagttcctg 1140
gaaaatgaag acagaaggtc tgccagctta catttaccca aactgtccat tactggaacc 1200
tatgatctga agagcgtcct gggtcaactg ggcatcacta aggtcttcag caatggggct 1260
gacctctccg gggtcacaga ggaggcaccc ctgaagctct ccaaggccgt gcataaggct 1320
gtgctgacca tcgacgagaa agggactgaa gctgctgggg ccatgttttt agaggccata 1380
cccatgtcta tccccccga ggtcaagttc aacaaaccct ttgtcttctt aatgattgaa 1440
caaaatacca agtctcccct cttcatggga aaagtggtga atcccaccca aaaataactg 1500
cctctcgctc ctcaacccct cccctccatc cctggccccc tccctggatg acattaaaga 1560
agggttgagc tggtccctgc ctgcatgtga ctgtaaatcc ctcccatgtt ttctctgagt 1620
ctccctttgc ctgctgaggc tgtatgtggg ctccaggtaa cagtgctgtc ttcgggcccc 1680
ctgaactgtg ttcatggagc atctggctgg gtaggcacat gctgggcttg aatccagggg 1740
ggactgaatc ctcagcttac ggacctgggc ccatctgttt ctggagggct ccagtcttcc 1800
ttgtcctgtc ttggagtccc caagaaggaa tcacagggga ggaaccagat accagccatg 1860
accccaggct ccaccaagca tcttcatgtc cccctgctca tcccccactc ccccccaccc 1920
agagttgctc atcctgccag ggctggctgt gcccacccca aggctgccct cctgggggcc 1980
ccagaactgc ctgatcgtgc cgtggcccag ttttgtggca tctgcagcaa cacaagagag 2040
aggacaatgt cctcctcttg acccgctgtc acctaaccag actcgggccc tgcacctctc 2100
aggcacttct ggaaaatgac tgaggcagat tcttcctgaa gcccattctc catggggcaa 2160
caaggacacc tattctgtcc ttgtccttcc atcgctgccc cagaaagcct cacatatctc 2220
cgtttagaat caggtccctt ctccccagat gaagaggagg gtctctgctt tgttttctct 2280
atctcctcct cagacttgac caggcccagc aggccccaga agaccattac cctatatccc 2340
ttctcctccc tagtcacatg gccataggcc tgctgatggc tcaggaaggc cattgcaagg 2400
actcctcagc tatgggagag gaagcacatc acccattgac cccgcaacc cctccctttc 2460
ctcctctgag tcccgactgg ggccacatgc agcctgactt ctttgtgcct gttgctgtcc 2520
ctgcagtctt cagagggcca ccgcagctcc agtgccacgg caggaggctg ttcctgaata 2580
gcccctgtgg taagggccag gagagtcctt ccatcctcca aggccctgct aaaggacaca 2640
gcagccagga agtcccctgg gcccctagct gaaggacagc ctgctccctc cgtctctacc 2700
aggaatggcc ttgtcctatg gaaggcactg ccccatccca aactaatcta ggaatcactg 2760
tctaaccact cactgtcatg aatgtgtact taaaggatga ggttgagtca taccaaatag 2820
tgatttcgat agttcaaaat ggtgaaatta gcaattctac atgattcagt ctaatcaatg 2880
gataccgact gtttcccaca caagtctcct gttctcttaa gcttactcac tgacagcctt 2940
tcactctcca caaatacatt aaagatatgg ccatcaccaa gccccctagg atgacaccag 3000
acctgagagt ctgaagacct ggatccaagt tctgactttt ccccctgaca gctgtgtgac 3060
cttcgtgaag tcgccaaacc tctctgagcc ccagtcattg ctagtaagac ctgcctttga 3120
gttggtatga tgttcaagtt agataacaaa atgtttatac ccattagaac agagaataaa 3180
tagaactaca tttcttgca 3199

<210> SEQ ID NO 3
<211> LENGTH: 3513

-continued

<212> TYPE: DNA
<213> ORGANISM: Homo sapiens

<400> SEQUENCE: 3
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaagggcg 240
gcagtaagtc ttcagcatca ggcattttgg ggtgactcag taaatggtag atcttgctac 300
cagtggaaca gccactaagg attctgcagt gagagcagag ggccagctaa gtggtactct 360
cccagagact gtctgactca cgccaccccc tccaccttgg acacaggacg ctgtggtttc 420
tgagccaggt acaatgactc ctttcgcagc ctcccccgtt gcccctctgg atccactgct 480
taaatacgga cgaggacagg gccctgtctc ctcagcttca ggcaccacca ctgacctggg 540
acagtgaatc gacaatgccg tcttctgtct cgtggggcat cctcctgctg gcaggcctgt 600
gctgcctggt ccctgtctcc ctggctgagg atccccaggg agatgctgcc cagaagacag 660
atacatccca ccatgatcag gatcacccaa ccttcaacaa gatcaccccc aacctggctg 720
agttcgcctt cagcctatac cgccagctgg cacaccagtc caacagcacc aatatcttct 780
tctccccagt gagcatcgct acagcctttg caatgctctc cctggggacc aaggctgaca 840
ctcacgatga aatcctggag ggcctgaatt tcaacctcac ggagattccg gaggctcaga 900
tccatgaagg cttccaggaa ctcctccgta ccctcaacca gccagacagc cagctccagc 960
tgaccaccgg caatggcctg ttcctcagcg agggcctgaa gctagtggat aagtttttgg 1020
aggatgttaa aaagttgtac cactcagaag ccttcactgt caacttcggg gacaccgaag 1080
aggccaagaa acagatcaac gattacgtgg agaagggtac tcaagggaaa attgtggatt 1140
tggtcaagga gcttgacaga gacacagttt ttgctctggt gaattacatc ttctttaaag 1200
gcaaatggga gagacccttt gaagtcaagg acaccgagga agaggacttc cacgtggacc 1260
aggtgaccac cgtgaaggtg cctatgatga agcgtttagg catgtttaac atccagcact 1320
gtaagaagct gtccagctgg gtgctgctga tgaaatacct gggcaatgcc accgccatct 1380
tcttcctgcc tgatgagggg aaactacagc acctggaaaa tgaactcacc cacgatatca 1440
tcaccaagtt cctggaaaat gaagacagaa ggtctgccag cttacattta cccaaactgt 1500
ccattactgg aacctatgat ctgaagagcg tcctgggtca actgggcatc actaaggtct 1560
tcagcaatgg ggctgacctc tccggggtca cagaggaggc acccctgaag ctctccaagg 1620
ccgtgcataa ggctgtgctg accatcgacg agaaagggac tgaagctgct ggggccatgt 1680
ttttagaggc catacccatg tctatccccc ccgaggtcaa gttcaacaaa ccctttgtct 1740
tcttaatgat tgaacaaaat accaagtctc ccctcttcat gggaaaagtg gtgaatccca 1800
cccaaaaata actgcctctc gctcctcaac ccctcccctc catccctggc cccctccctg 1860
gatgacatta aagaagggtt gagctggtcc ctgcctgcat gtgactgtaa atccctccca 1920
tgttttctct gagtctccct ttgcctgctg aggctgtatg tgggctccag gtaacagtgc 1980
tgtcttcggg ccccctgaac tgtgttcatg gagcatctgg ctgggtaggc acatgctggg 2040
cttgaatcca gggggactg aatcctcagc ttacggacct gggcccatct gtttctggag 2100
ggctccagtc ttccttgtcc tgtcttggag tccccaagaa ggaatcacag gggaggaacc 2160
agataccagc catgacccca ggctccacca agcatcttca tgtcccctg ctcatcccc 2220

```
actccccccc acccagagtt gctcatcctg ccagggctgg ctgtgcccac cccaaggctg   2280
ccctcctggg ggccccagaa ctgcctgatc gtgccgtggc ccagttttgt ggcatctgca   2340
gcaacacaag agagaggaca atgtcctcct cttgacccgc tgtcacctaa ccagactcgg   2400
gccctgcacc tctcaggcac ttctggaaaa tgactgaggc agattcttcc tgaagcccat   2460
tctccatggg gcaacaagga cacctattct gtccttgtcc ttccatcgct gccccagaaa   2520
gcctcacata tctccgttta gaatcaggtc ccttctcccc agatgaagag gagggtctct   2580
gctttgtttt ctctatctcc tcctcagact tgaccaggcc cagcaggccc cagaagacca   2640
ttaccctata tcccttctcc tccctagtca catggccata ggcctgctga tggctcagga   2700
aggccattgc aaggactcct cagctatggg agaggaagca catcacccat tgaccccccgc  2760
aacccctccc tttcctcctc tgagtcccga ctggggccac atgcagcctg acttctttgt   2820
gcctgttgct gtccctgcag tcttcagagg gccaccgcag ctccagtgcc acggcaggag   2880
gctgttcctg aatagcccct gtggtaaggg ccaggagagt ccttccatcc tccaaggccc   2940
tgctaaagga cacagcagcc aggaagtccc ctgggcccct agctgaagga cagcctgctc   3000
cctccgtctc taccaggaat ggccttgtcc tatggaaggc actgccccat cccaaactaa   3060
tctaggaatc actgtctaac cactcactgt catgaatgtg tacttaaagg atgaggttga   3120
gtcataccaa atagtgattt cgatagttca aaatggtgaa attagcaatt ctacatgatt   3180
cagtctaatc aatggatacc gactgtttcc cacacaagtc tcctgttctc ttaagcttac   3240
tcactgacag cctttcactc tccacaaata cattaaagat atggccatca ccaagccccc   3300
taggatgaca ccagacctga gagtctgaag acctggatcc aagttctgac ttttccccct   3360
gacagctgtg tgaccttcgt gaagtcgcca aacctctctg agccccagtc attgctagta   3420
agacctgcct ttgagttggt atgatgttca agttagataa caaaatgttt atacccatta   3480
gaacagagaa taaatagaac tacatttctt gca                                3513
```

<210> SEQ ID NO 4
<211> LENGTH: 3236
<212> TYPE: DNA
<213> ORGANISM: Homo sapiens

<400> SEQUENCE: 4

```
tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaaggtgg    240
gacattgctg ctgctgctca ctcagttcca caggacaatg ccgtcttctg tctcgtgggg    300
catcctcctg ctggcaggcc tgtgctgcct ggtccctgtc tccctggctg aggatcccca    360
gggagatgct gcccagaaga cagatacatc ccaccatgat caggatcacc caaccttcaa    420
caagatcacc cccaacctgg ctgagttcgc cttcagccta taccgccagc tggcacacca    480
gtccaacagc accaatatct tcttctcccc agtgagcatc gctacagcct ttgcaatgct    540
ctccctgggg accaaggctg acactcacga tgaaatcctg gagggcctga atttcaacct    600
cacggagatt ccggaggctc agatccatga aggcttccag gaactcctcc gtaccctcaa    660
ccagccagac agccagctcc agctgaccac cggcaatggc ctgttcctca gcgagggcct    720
gaagctagtg gataagtttt tggaggatgt taaaaagttg taccactcag aagccttcac    780
tgtcaacttc ggggacaccg aagaggccaa gaaacagatc aacgattacg tggagaaggg    840
```

-continued

```
tactcaaggg aaaattgtgg atttggtcaa ggagcttgac agagacacag tttttgctct    900
ggtgaattac atcttcttta aaggcaaatg ggagagaccc tttgaagtca aggacaccga    960
ggaagaggac ttccacgtgg accaggtgac caccgtgaag gtgcctatga tgaagcgttt   1020
aggcatgttt aacatccagc actgtaagaa gctgtccagc tgggtgctgc tgatgaaata   1080
cctgggcaat gccaccgcca tcttcttcct gcctgatgag gggaaactac agcacctgga   1140
aaatgaactc acccacgata tcatcaccaa gttcctggaa aatgaagaca gaaggtctgc   1200
cagcttacat ttacccaaac tgtccattac tggaacctat gatctgaaga gcgtcctggg   1260
tcaactgggc atcactaagg tcttcagcaa tggggctgac ctctccgggg tcacagagga   1320
ggcacccctg aagctctcca aggccgtgca taaggctgtg ctgaccatcg acgagaaagg   1380
gactgaagct gctggggcca tgtttttaga ggccataccc atgtctatcc cccccgaggt   1440
caagttcaac aaaccctttg tcttcttaat gattgaacaa aataccaagt ctcccctctt   1500
catgggaaaa gtggtgaatc ccacccaaaa ataactgcct ctcgctcctc aacccctccc   1560
ctccatccct ggccccctcc ctggatgaca ttaaagaagg gttgagctgg tccctgcctg   1620
catgtgactg taaatccctc ccatgttttc tctgagtctc cctttgcctg ctgaggctgt   1680
atgtgggctc caggtaacag tgctgtcttc gggccccctg aactgtgttc atggagcatc   1740
tggctgggta ggcacatgct gggcttgaat ccagggggga ctgaatcctc agcttacgga   1800
cctgggccca tctgtttctg gagggctcca gtcttccttg tcctgtcttg gagtccccaa   1860
gaaggaatca caggggagga accagatacc agccatgacc ccaggctcca ccaagcatct   1920
tcatgtcccc ctgctcatcc cccactcccc cccacccaga gttgctcatc ctgccagggc   1980
tggctgtgcc caccccaagg ctgccctcct gggggcccca gaactgcctg atcgtgccgt   2040
ggcccagttt tgtggcatct gcagcaacac aagagagagg acaatgtcct cctcttgacc   2100
cgctgtcacc taaccagact cgggccctgc acctctcagg cacttctgga aaatgactga   2160
ggcagattct tcctgaagcc cattctccat ggggcaacaa ggacacctat tctgtccttg   2220
tccttccatc gctgccccag aaagcctcac atatctccgt ttagaatcag gtcccttctc   2280
cccagatgaa gaggagggtc tctgctttgt tttctctatc tcctcctcag acttgaccag   2340
gcccagcagg ccccagaaga ccattaccct atatcccttc tcctccctag tcacatggcc   2400
ataggcctgc tgatggctca ggaaggccat tgcaaggact cctcagctat gggagaggaa   2460
gcacatcacc cattgacccc cgcaacccct ccctttcctc ctctgagtcc cgactggggc   2520
cacatgcagc ctgacttctt tgtgcctgtt gctgtccctg cagtcttcag agggccaccg   2580
cagctccagt gccacggcag gaggctgttc ctgaatagcc cctgtggtaa gggccaggag   2640
agtccttcca tcctccaagg ccctgctaaa ggacacagca gccaggaagt cccctgggcc   2700
cctagctgaa ggacagcctg ctccctccgt ctctaccagg aatggccttg tcctatggaa   2760
ggcactgccc catcccaaac taatctagga atcactgtct aaccactcac tgtcatgaat   2820
gtgtacttaa aggatgaggt tgagtcatac caaatagtga tttcgatagt tcaaaatggt   2880
gaaattagca attctacatg attcagtcta atcaatggat accgactgtt tcccacacaa   2940
gtctcctgtt ctcttaagct tactcactga cagcctttca ctctccacaa atacattaaa   3000
gatatggcca tcaccaagcc ccctaggatg acaccagacc tgagagtctg aagacctgga   3060
tccaagttct gacttttccc cctgacagct gtgtgacctt cgtgaagtcg ccaaacctct   3120
ctgagcccca gtcattgcta gtaagacctg cctttgagtt ggtatgatgt tcaagttaga   3180
```

-continued

```
taacaaaatg tttataccca ttagaacaga gaataaatag aactacattt cttgca      3236


<210> SEQ ID NO 5
<211> LENGTH: 3532
<212> TYPE: DNA
<213> ORGANISM: Homo sapiens

<400> SEQUENCE: 5

tgggcaggaa ctgggcactg tgcccagggc atgcactgcc tccacgcagc aaccctcaga     60

gtcctgagct gaaccaagaa ggaggagggg gtcgggcctc cgaggaaggc ctagccgctg    120

ctgctgccag gaattccagg ttggaggggc ggcaacctcc tgccagcctt caggccactc    180

tcctgtgcct gccagaagag acagagcttg aggagagctt gaggagagca ggaaaggtgg    240

gacattgctg ctgctgctca ctcagttcca cagggcggca gtaagtcttc agcatcaggc    300

attttggggt gactcagtaa atggtagatc ttgctaccag tggaacagcc actaaggatt    360

ctgcagtgag agcagagggc cagctaagtg gtactctccc agagactgtc tgactcacgc    420

caccccctcc accttggaca caggacgctg tggtttctga gccagcagcc tcccccgttg    480

cccctctgga tccactgctt aaatacggac gaggacaggg ccctgtctcc tcagcttcag    540

gcaccaccac tgacctggga cagtgaatcg acaatgccgt cttctgtctc gtggggcatc    600

ctcctgctgg caggcctgtg ctgcctggtc cctgtctccc tggctgagga tccccaggga    660

gatgctgccc agaagacaga tacatcccac catgatcagg atcacccaac cttcaacaag    720

atcaccccca acctggctga gttcgccttc agcctatacc gccagctggc acaccagtcc    780

aacagcacca atatcttctt ctccccagtg agcatcgcta cagcctttgc aatgctctcc    840

ctggggacca aggctgacac tcacgatgaa atcctggagg gcctgaattt caacctcacg    900

gagattccgg aggctcagat ccatgaaggc ttccaggaac tcctccgtac cctcaaccag    960

ccagacagcc agctccagct gaccaccggc aatggcctgt tcctcagcga gggcctgaag   1020

ctagtggata agtttttgga ggatgttaaa aagttgtacc actcagaagc cttcactgtc   1080

aacttcgggg acaccgaaga ggccaagaaa cagatcaacg attacgtgga gaagggtact   1140

caagggaaaa ttgtggattt ggtcaaggag cttgacagag acacagtttt tgctctggtg   1200

aattacatct tctttaaagg caaatgggag agaccctttg aagtcaagga caccgaggaa   1260

gaggacttcc acgtggacca ggtgaccacc gtgaaggtgc ctatgatgaa gcgtttaggc   1320

atgtttaaca tccagcactg taagaagctg tccagctggg tgctgctgat gaaatacctg   1380

ggcaatgcca ccgccatctt cttcctgcct gatgagggga aactacagca cctggaaaat   1440

gaactcaccc acgatatcat caccaagttc ctggaaaatg aagacagaag gtctgccagc   1500

ttacatttac ccaaactgtc cattactgga acctatgatc tgaagagcgt cctgggtcaa   1560

ctgggcatca ctaaggtctt cagcaatggg gctgacctct ccggggtcac agaggaggca   1620

cccctgaagc tctccaaggc cgtgcataag gctgtgctga ccatcgacga gaaagggact   1680

gaagctgctg gggccatgtt tttagaggcc atacccatgt ctatcccccc cgaggtcaag   1740

ttcaacaaac cctttgtctt cttaatgatt gaacaaaata ccaagtctcc cctcttcatg   1800

ggaaaagtgg tgaatcccac ccaaaaataa ctgcctctcg ctcctcaacc cctcccctcc   1860

atccctggcc ccctccctgg atgacattaa agaagggttg agctggtccc tgcctgcatg   1920

tgactgtaaa tccctcccat gttttctctg agtctccctt tgcctgctga ggctgtatgt   1980

gggctccagg taacagtgct gtcttcgggc cccctgaact gtgttcatgg agcatctggc   2040

tgggtaggca catgctgggc ttgaatccag gggggactga atcctcagct tacggacctg   2100
```

ggcccatctg tttctggagg gctccagtct tccttgtcct gtcttggagt ccccaagaag 2160
gaatcacagg ggaggaacca gataccagcc atgaccccag gctccaccaa gcatcttcat 2220
gtccccctgc tcatccccca ctcccccca cccagagttg ctcatcctgc cagggctggc 2280
tgtgcccacc ccaaggctgc cctcctgggg gccccagaac tgcctgatcg tgccgtggcc 2340
cagttttgtg gcatctgcag caacacaaga gagaggacaa tgtcctcctc ttgacccgct 2400
gtcacctaac cagactcggg ccctgcacct ctcaggcact tctggaaaat gactgaggca 2460
gattcttcct gaagcccatt ctccatgggg caacaaggac acctattctg tccttgtcct 2520
tccatcgctg ccccagaaag cctcacatat ctccgtttag aatcaggtcc cttctcccca 2580
gatgaagagg agggtctctg ctttgttttc tctatctcct cctcagactt gaccaggccc 2640
agcaggcccc agaagaccat taccctatat cccttctcct ccctagtcac atggccatag 2700
gcctgctgat ggctcaggaa ggccattgca aggactcctc agctatggga gaggaagcac 2760
atcacccatt gacccccgca acccctccct ttcctcctct gagtcccgac tggggccaca 2820
tgcagcctga cttctttgtg cctgttgctg tccctgcagt cttcagaggg ccaccgcagc 2880
tccagtgcca cggcaggagg ctgttcctga atagcccctg tggtaagggc caggagagtc 2940
cttccatcct ccaaggccct gctaaaggac acagcagcca ggaagtcccc tgggccccta 3000
gctgaaggac agcctgctcc ctccgtctct accaggaatg gccttgtcct atggaaggca 3060
ctgccccatc ccaaactaat ctaggaatca ctgtctaacc actcactgtc atgaatgtgt 3120
acttaaagga tgaggttgag tcataccaaa tagtgatttc gatagttcaa aatggtgaaa 3180
ttagcaattc tacatgattc agtctaatca atggataccg actgtttccc acacaagtct 3240
cctgttctct taagcttact cactgacagc ctttcactct ccacaaatac attaaagata 3300
tggccatcac caagcccccct aggatgacac cagacctgag agtctgaaga cctggatcca 3360
agttctgact tttcccctg acagctgtgt gaccttcgtg aagtcgccaa acctctctga 3420
gccccagtca ttgctagtaa gacctgcctt tgagttggta tgatgttcaa gttagataac 3480
aaaatgttta tacccattag aacagagaat aaatagaact acatttcttg ca 3532

<210> SEQ ID NO 6
<211> LENGTH: 3340
<212> TYPE: DNA
<213> ORGANISM: Homo sapiens

<400> SEQUENCE: 6
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaaggtgg 240
gacattgctg ctgctgctca ctcagttcca cagcagcctc cccgttgcc cctctggatc 300 cactgcttaa atacggacga ggacagggcc ctgtctcctc agcttcaggc accaccactg 360
acctgggaca gtgaatcgac aatgccgtct tctgtctcgt ggggcatcct cctgctggca 420
ggcctgtgct gcctggtccc tgtctccctg gctgaggatc cccagggaga tgctgcccag 480
aagacagata catcccacca tgatcaggat cacccaacct tcaacaagat cacccccaac 540
ctggctgagt tcgccttcag cctataccgc cagctggcac accagtccaa cagcaccaat 600
atcttcttct ccccagtgag catcgctaca gcctttgcaa tgctctccct ggggaccaag 660

-continued

```
gctgacactc acgatgaaat cctggagggc ctgaatttca acctcacgga gattccggag    720
gctcagatcc atgaaggctt ccaggaactc ctccgtaccc tcaaccagcc agacagccag    780
ctccagctga ccaccggcaa tggcctgttc ctcagcgagg gcctgaagct agtggataag    840
tttttggagg atgttaaaaa gttgtaccac tcagaagcct tcactgtcaa cttcggggac    900
accgaagagg ccaagaaaca gatcaacgat tacgtggaga agggtactca agggaaaatt    960
gtggatttgg tcaaggagct tgacagagac acagtttttg ctctggtgaa ttacatcttc   1020
tttaaaggca aatgggagag accctttgaa gtcaaggaca ccgaggaaga ggacttccac   1080
gtggaccagg tgaccaccgt gaaggtgcct atgatgaagc gtttaggcat gtttaacatc   1140
cagcactgta agaagctgtc cagctgggtg ctgctgatga aatacctggg caatgccacc   1200
gccatcttct tcctgcctga tgaggggaaa ctacagcacc tggaaaatga actcacccac   1260
gatatcatca ccaagttcct ggaaaatgaa gacagaaggt ctgccagctt acatttaccc   1320
aaactgtcca ttactggaac ctatgatctg aagagcgtcc tgggtcaact gggcatcact   1380
aaggtcttca gcaatggggc tgacctctcc ggggtcacag aggaggcacc cctgaagctc   1440
tccaaggccg tgcataaggc tgtgctgacc atcgacgaga aagggactga agctgctggg   1500
gccatgtttt tagaggccat acccatgtct atcccccccg aggtcaagtt caacaaaccc   1560
tttgtcttct taatgattga acaaaatacc aagtctcccc tcttcatggg aaaagtggtg   1620
aatcccaccc aaaaataact gcctctcgct cctcaacccc tcccctccat ccctggcccc   1680
ctccctggat gacattaaag aagggttgag ctggtccctg cctgcatgtg actgtaaatc   1740
cctcccatgt tttctctgag tctccctttg cctgctgagg ctgtatgtgg gctccaggta   1800
acagtgctgt cttcgggccc cctgaactgt gttcatggag catctggctg ggtaggcaca   1860
tgctgggctt gaatccaggg gggactgaat cctcagctta cggacctggg cccatctgtt   1920
tctggagggc tccagtcttc cttgtcctgt cttggagtcc ccaagaagga atcacagggg   1980
aggaaccaga taccagccat gaccccaggc tccaccaagc atcttcatgt ccccctgctc   2040
atcccccact ccccccaccc cagagttgct catcctgcca gggctggctg tgcccacccc   2100
aaggctgccc tcctgggggc cccagaactg cctgatcgtg ccgtggccca gttttgtggc   2160
atctgcagca acacaagaga gaggacaatg tcctcctctt gacccgctgt cacctaacca   2220
gactcgggcc ctgcacctct caggcacttc tggaaaatga ctgaggcaga ttcttcctga   2280
agcccattct ccatggggca acaaggacac ctattctgtc cttgtccttc catcgctgcc   2340
ccagaaagcc tcacatatct ccgtttagaa tcaggtccct tctccccaga tgaagaggag   2400
ggtctctgct ttgttttctc tatctcctcc tcagacttga ccaggcccag caggccccag   2460
aagaccatta ccctatatcc cttctcctcc ctagtcacat ggccataggc ctgctgatgg   2520
ctcaggaagg ccattgcaag gactcctcag ctatgggaga ggaagcacat cacccattga   2580
cccccgcaac ccctcccttt cctcctctga gtcccgactg gggccacatg cagcctgact   2640
tctttgtgcc tgttgctgtc cctgcagtct tcagagggcc accgcagctc cagtgccacg   2700
gcaggaggct gttcctgaat agcccctgtg gtaagggcca ggagagtcct tccatcctcc   2760
aaggccctgc taaaggacac agcagccagg aagtcccctg ggcccctagc tgaaggacag   2820
cctgctccct ccgtctctac caggaatggc cttgtcctat ggaaggcact gccccatccc   2880
aaactaatct aggaatcact gtctaaccac tcactgtcat gaatgtgtac ttaaaggatg   2940
aggttgagtc ataccaaata gtgatttcga tagttcaaaa tggtgaaatt agcaattcta   3000
catgattcag tctaatcaat ggataccgac tgtttcccac acaagtctcc tgttctctta   3060
```

```
agcttactca ctgacagcct ttcactctcc acaaatacat taaagatatg gccatcacca   3120

agccccctag gatgacacca gacctgagag tctgaagacc tggatccaag ttctgacttt   3180

tccccctgac agctgtgtga ccttcgtgaa gtcgccaaac ctctctgagc cccagtcatt   3240

gctagtaaga cctgcctttg agttggtatg atgttcaagt tagataacaa aatgtttata   3300

cccattagaa cagagaataa atagaactac atttcttgca                        3340
```

<210> SEQ ID NO 7
<211> LENGTH: 3495
<212> TYPE: DNA
<213> ORGANISM: Homo sapiens

<400> SEQUENCE: 7

```
tgggcaggaa ctgggcactg tgcccagggc atgcactgcc tccacgcagc aaccctcaga     60

gtcctgagct gaaccaagaa ggaggagggg gtcgggcctc cgaggaaggc ctagccgctg    120

ctgctgccag gaattccagg ttggaggggc ggcaacctcc tgccagcctt caggccactc    180

tcctgtgcct gccagaagag acagagcttg aggagagctt gaggagagca ggaaagggcg    240

gcagtaagtc ttcagcatca ggcattttgg ggtgactcag taaatggtag atcttgctac    300

cagtggaaca gccactaagg attctgcagt gagagcagag ggccagctaa gtggtactct    360

cccagagact gtctgactca cgccaccccc tccaccttgg acacaggacg ctgtggtttc    420

tgagccagca gcctcccccg ttgcccctct ggatccactg cttaaatacg gacgaggaca    480

gggccctgtc tcctcagctt caggcaccac cactgacctg ggacagtgaa tcgacaatgc    540

cgtcttctgt ctcgtggggc atcctcctgc tggcaggcct gtgctgcctg gtccctgtct    600

ccctggctga ggatccccag ggagatgctg cccagaagac agatacatcc caccatgatc    660

aggatcaccc aaccttcaac aagatcaccc ccaacctggc tgagttcgcc ttcagcctat    720

accgccagct ggcacaccag tccaacagca ccaatatctt cttctcccca gtgagcatcg    780

ctacagcctt tgcaatgctc tccctgggga ccaaggctga cactcacgat gaaatcctgg    840

agggcctgaa tttcaacctc acggagattc cggaggctca gatccatgaa ggcttccagg    900

aactcctccg taccctcaac cagccagaca gccagctcca gctgaccacc ggcaatggcc    960

tgttcctcag cgagggcctg aagctagtgg ataagttttt ggaggatgtt aaaaagttgt   1020

accactcaga agccttcact gtcaacttcg gggacaccga agaggccaag aaacagatca   1080

acgattacgt ggagaagggt actcaaggga aaattgtgga tttggtcaag gagcttgaca   1140

gagacacagt ttttgctctg gtgaattaca tcttctttaa aggcaaatgg gagagaccct   1200

ttgaagtcaa ggacaccgag gaagaggact tccacgtgga ccaggtgacc accgtgaagg   1260

tgcctatgat gaagcgttta ggcatgttta acatccagca ctgtaagaag ctgtccagct   1320

gggtgctgct gatgaaatac ctgggcaatg ccaccgccat cttcttcctg cctgatgagg   1380

ggaaactaca gcacctggaa aatgaactca cccacgatat catcaccaag ttcctggaaa   1440

atgaagacag aaggtctgcc agcttacatt tacccaaact gtccattact ggaacctatg   1500

atctgaagag cgtcctgggt caactgggca tcactaaggt cttcagcaat ggggctgacc   1560

tctccggggt cacagaggag gcacccctga agctctccaa ggccgtgcat aaggctgtgc   1620

tgaccatcga cgagaaaggg actgaagctg ctggggccat gtttttagag gccataccca   1680

tgtctatccc ccccgaggtc aagttcaaca aaccctttgt cttcttaatg attgaacaaa   1740

ataccaagtc tcccctcttc atgggaaaag tggtgaatcc cacccaaaaa taactgcctc   1800
```

-continued

```
tcgctcctca acccctcccc tccatccctg gccccctccc tggatgacat taaagaaggg   1860

ttgagctggt ccctgcctgc atgtgactgt aaatccctcc catgttttct ctgagtctcc   1920

ctttgcctgc tgaggctgta tgtgggctcc aggtaacagt gctgtcttcg ggccccctga   1980

actgtgttca tggagcatct ggctgggtag gcacatgctg ggcttgaatc caggggggac   2040

tgaatcctca gcttacggac ctgggcccat ctgtttctgg agggctccag tcttccttgt   2100

cctgtcttgg agtccccaag aaggaatcac aggggaggaa ccagatacca gccatgaccc   2160

caggctccac caagcatctt catgtccccc tgctcatccc ccactccccc ccacccagag   2220

ttgctcatcc tgccagggct ggctgtgccc accccaaggc tgccctcctg gggccccag    2280

aactgcctga tcgtgccgtg gcccagtttt gtggcatctg cagcaacaca agagagagga   2340

caatgtcctc ctcttgaccc gctgtcacct aaccagactc gggccctgca cctctcaggc   2400

acttctggaa aatgactgag gcagattctt cctgaagccc attctccatg gggcaacaag   2460

gacacctatt ctgtccttgt ccttccatcg ctgccccaga aagcctcaca tatctccgtt   2520

tagaatcagg tcccttctcc ccagatgaag aggagggtct ctgctttgtt ttctctatct   2580

cctcctcaga cttgaccagg cccagcaggc cccagaagac cattacccta tatcccttct   2640

cctccctagt cacatggcca taggcctgct gatggctcag gaaggccatt gcaaggactc   2700

ctcagctatg ggagaggaag cacatcaccc attgaccccc gcaacccctc cctttcctcc   2760

tctgagtccc gactggggcc acatgcagcc tgacttcttt gtgcctgttg ctgtccctgc   2820

agtcttcaga gggccaccgc agctccagtg ccacggcagg aggctgttcc tgaatagccc   2880

ctgtggtaag ggccaggaga gtccttccat cctccaaggc cctgctaaag gacacagcag   2940

ccaggaagtc ccctgggccc ctagctgaag gacagcctgc tccctccgtc tctaccagga   3000

atggccttgt cctatggaag gcactgcccc atcccaaact aatctaggaa tcactgtcta   3060

accactcact gtcatgaatg tgtacttaaa ggatgaggtt gagtcatacc aaatagtgat   3120

ttcgatagtt caaaatggtg aaattagcaa ttctacatga ttcagtctaa tcaatggata   3180

ccgactgttt cccacacaag tctcctgttc tcttaagctt actcactgac agcctttcac   3240

tctccacaaa tacattaaag atatggccat caccaagccc cctaggatga caccagacct   3300

gagagtctga agacctggat ccaagttctg acttttcccc ctgacagctg tgtgaccttc   3360

gtgaagtcgc caaacctctc tgagccccag tcattgctag taagacctgc ctttgagttg   3420

gtatgatgtt caagttagat aacaaaatgt ttatacccat tagaacagag aataaataga   3480

actacatttc ttgca                                                    3495
```

<210> SEQ ID NO 8
<211> LENGTH: 3492
<212> TYPE: DNA
<213> ORGANISM: Homo sapiens

<400> SEQUENCE: 8

```
tgggcaggaa ctgggcactg tgcccagggc atgcactgcc tccacgcagc aaccctcaga     60

gtcctgagct gaaccaagaa ggaggagggg gtcgggcctc cgaggaaggc ctagccgctg    120

ctgctgccag gaattccagg ttggaggggc ggcaacctcc tgccagcctt caggccactc    180

tcctgtgcct gccagaagag acagagcttg aggagagctt gaggagagca ggaaagggcg    240

gcagtaagtc ttcagcatca ggcattttgg ggtgactcag taaatggtag atcttgctac    300

cagtggaaca gccactaagg attctgcagt gagagcagag ggccagctaa gtggtactct    360

cccagagact gtctgactca cgccaccccc tccaccttgg acacaggacg ctgtggtttc    420
```

-continued

```
tgagccagcc tcccccgttg cccctctgga tccactgctt aaatacggac gaggacaggg    480
ccctgtctcc tcagcttcag gcaccaccac tgacctggga cagtgaatcg acaatgccgt    540
cttctgtctc gtggggcatc ctcctgctgg caggcctgtg ctgcctggtc cctgtctccc    600
tggctgagga tccccaggga gatgctgccc agaagacaga tacatcccac catgatcagg    660
atcacccaac cttcaacaag atcacccccca acctggctga gttcgccttc agcctatacc    720
gccagctggc acaccagtcc aacagcacca atatcttctt ctccccagtg agcatcgcta    780
cagcctttgc aatgctctcc ctggggacca aggctgacac tcacgatgaa atcctggagg    840
gcctgaattt caacctcacg gagattccgg aggctcagat ccatgaaggc ttccaggaac    900
tcctccgtac cctcaaccag ccagacagcc agctccagct gaccaccggc aatggcctgt    960
tcctcagcga gggcctgaag ctagtggata agtttttgga ggatgttaaa aagttgtacc   1020
actcagaagc cttcactgtc aacttcgggg acaccgaaga ggccaagaaa cagatcaacg   1080
attacgtgga gaagggtact caagggaaaa ttgtggattt ggtcaaggag cttgacagag   1140
acacagtttt tgctctggtg aattacatct tctttaaagg caaatgggag agaccctttg   1200
aagtcaagga caccgaggaa gaggacttcc acgtggacca ggtgaccacc gtgaaggtgc   1260
ctatgatgaa gcgtttaggc atgtttaaca tccagcactg taagaagctg tccagctggg   1320
tgctgctgat gaaatacctg ggcaatgcca ccgccatctt cttcctgcct gatgagggga   1380
aactacagca cctggaaaat gaactcaccc acgatatcat caccaagttc ctggaaaatg   1440
aagacagaag gtctgccagc ttacatttac ccaaactgtc cattactgga acctatgatc   1500
tgaagagcgt cctgggtcaa ctgggcatca ctaaggtctt cagcaatggg gctgacctct   1560
ccggggtcac agaggaggca cccctgaagc tctccaaggc cgtgcataag gctgtgctga   1620
ccatcgacga gaaagggact gaagctgctg gggccatgtt tttagaggcc atacccatgt   1680
ctatcccccc cgaggtcaag ttcaacaaac cctttgtctt cttaatgatt gaacaaaata   1740
ccaagtctcc cctcttcatg ggaaaagtgg tgaatcccac ccaaaaataa ctgcctctcg   1800
ctcctcaacc cctcccctcc atccctggcc ccctccctgg atgacattaa agaagggttg   1860
agctggtccc tgcctgcatg tgactgtaaa tccctcccat gttttctctg agtctccctt   1920
tgcctgctga ggctgtatgt gggctccagg taacagtgct gtcttcgggc cccctgaact   1980
gtgttcatgg agcatctggc tgggtaggca catgctgggc ttgaatccag gggggactga   2040
atcctcagct tacggacctg ggcccatctg tttctggagg gctccagtct tccttgtcct   2100
gtcttggagt ccccaagaag gaatcacagg ggaggaacca gataccagcc atgaccccag   2160
gctccaccaa gcatcttcat gtccccctgc tcatccccca ctcccccccca cccagagttg   2220
ctcatcctgc cagggctggc tgtgcccacc ccaaggctgc cctcctgggg gccccagaac   2280
tgcctgatcg tgccgtggcc cagttttgtg gcatctgcag caacacaaga gagaggacaa   2340
tgtcctcctc ttgacccgct gtcacctaac cagactcggg ccctgcacct ctcaggcact   2400
tctggaaaat gactgaggca gattcttcct gaagcccatt ctccatgggg caacaaggac   2460
acctattctg tccttgtcct tccatcgctg ccccagaaag cctcacatat ctccgtttag   2520
aatcaggtcc cttctcccca gatgaagagg agggtctctg ctttgttttc tctatctcct   2580
cctcagactt gaccaggccc agcaggcccc agaagaccat taccctatat cccttctcct   2640
ccctagtcac atggccatag gcctgctgat ggctcaggaa ggccattgca aggactcctc   2700
agctatggga gaggaagcac atcacccatt gacccccgca acccctccct ttcctcctct   2760
```

-continued

```
gagtcccgac tggggccaca tgcagcctga cttctttgtg cctgttgctg tccctgcagt   2820

cttcagaggg ccaccgcagc tccagtgcca cggcaggagg ctgttcctga atagcccctg   2880

tggtaagggc caggagagtc cttccatcct ccaaggccct gctaaaggac acagcagcca   2940

ggaagtcccc tgggccccta gctgaaggac agcctgctcc ctccgtctct accaggaatg   3000

gccttgtcct atggaaggca ctgccccatc ccaaactaat ctaggaatca ctgtctaacc   3060

actcactgtc atgaatgtgt acttaaagga tgaggttgag tcataccaaa tagtgatttc   3120

gatagttcaa aatggtgaaa ttagcaattc tacatgattc agtctaatca atggataccg   3180

actgtttccc acacaagtct cctgttctct taagcttact cactgacagc ctttcactct   3240

ccacaaatac attaaagata tggccatcac caagccccct aggatgacac cagacctgag   3300

agtctgaaga cctggatcca agttctgact tttcccctg acagctgtgt gaccttcgtg   3360

aagtcgccaa acctctctga gccccagtca ttgctagtaa gacctgcctt tgagttggta   3420

tgatgttcaa gttagataac aaaatgttta tacccattag aacagagaat aaatagaact   3480

acatttcttg ca                                                       3492


<210> SEQ ID NO 9
<211> LENGTH: 3510
<212> TYPE: DNA
<213> ORGANISM: Homo sapiens

<400> SEQUENCE: 9

tgggcaggaa ctgggcactg tgcccagggc atgcactgcc tccacgcagc aaccctcaga     60

gtcctgagct gaaccaagaa ggaggagggg gtcgggcctc cgaggaaggc ctagccgctg    120

ctgctgccag gaattccagg ttggaggggc ggcaacctcc tgccagcctt caggccactc    180

tcctgtgcct gccagaagag acagagcttg aggagagctt gaggagagca ggaaagggcg    240

gcagtaagtc ttcagcatca ggcattttgg ggtgactcag taaatggtag atcttgctac    300

cagtggaaca gccactaagg attctgcagt gagagcagag ggccagctaa gtggtactct    360

cccagagact gtctgactca cgccaccccc tccaccttgg acacaggacg ctgtggtttc    420

tgagccaggt acaatgactc ctttcgcctc ccccgttgcc cctctggatc cactgcttaa    480

atacggacga ggacagggcc ctgtctcctc agcttcaggc accaccactg acctgggaca    540

gtgaatcgac aatgccgtct tctgtctcgt ggggcatcct cctgctggca ggcctgtgct    600

gcctggtccc tgtctccctg gctgaggatc cccagggaga tgctgcccag aagacagata    660

catcccacca tgatcaggat cacccaacct tcaacaagat cacccccaac ctggctgagt    720

tcgccttcag cctataccgc cagctggcac accagtccaa cagcaccaat atcttcttct    780

ccccagtgag catcgctaca gcctttgcaa tgctctccct ggggaccaag gctgacactc    840

acgatgaaat cctggagggc ctgaatttca acctcacgga gattccggag gctcagatcc    900

atgaaggctt ccaggaactc ctccgtaccc tcaaccagcc agacagccag ctccagctga    960

ccaccggcaa tggcctgttc ctcagcgagg gcctgaagct agtggataag tttttggagg   1020

atgttaaaaa gttgtaccac tcagaagcct tcactgtcaa cttcggggac accgaagagg   1080

ccaagaaaca gatcaacgat tacgtggaga agggtactca agggaaaatt gtggatttgg   1140

tcaaggagct tgacagagac acagtttttg ctctggtgaa ttacatcttc tttaaaggca   1200

aatgggagag accctttgaa gtcaaggaca ccgaggaaga ggacttccac gtggaccagg   1260

tgaccaccgt gaaggtgcct atgatgaagc gtttaggcat gtttaacatc cagcactgta   1320

agaagctgtc cagctgggtg ctgctgatga aatacctggg caatgccacc gccatcttct   1380
```

-continued

```
tcctgcctga tgaggggaaa ctacagcacc tggaaaatga actcacccac gatatcatca   1440
ccaagttcct ggaaaatgaa gacagaaggt ctgccagctt acatttaccc aaactgtcca   1500
ttactggaac ctatgatctg aagagcgtcc tgggtcaact gggcatcact aaggtcttca   1560
gcaatggggc tgacctctcc ggggtcacag aggaggcacc cctgaagctc tccaaggccg   1620
tgcataaggc tgtgctgacc atcgacgaga aagggactga agctgctggg gccatgtttt   1680
tagaggccat acccatgtct atcccccccg aggtcaagtt caacaaaccc tttgtcttct   1740
taatgattga acaaaatacc aagtctcccc tcttcatggg aaaagtggtg aatcccaccc   1800
aaaaataact gcctctcgct cctcaacccc tcccctccat ccctggcccc ctccctggat   1860
gacattaaag aagggttgag ctggtccctg cctgcatgtg actgtaaatc cctcccatgt   1920
tttctctgag tctccctttg cctgctgagg ctgtatgtgg gctccaggta acagtgctgt   1980
cttcgggccc cctgaactgt gttcatggag catctggctg ggtaggcaca tgctgggctt   2040
gaatccaggg gggactgaat cctcagctta cggacctggg cccatctgtt tctggagggc   2100
tccagtcttc cttgtcctgt cttggagtcc ccaagaagga atcacagggg aggaaccaga   2160
taccagccat gaccccaggc tccaccaagc atcttcatgt ccccctgctc atcccccact   2220
cccccccacc cagagttgct catcctgcca gggctggctg tgcccacccc aaggctgccc   2280
tcctgggggc cccagaactg cctgatcgtg ccgtggccca gttttgtggc atctgcagca   2340
acacaagaga gaggacaatg tcctcctctt gacccgctgt cacctaacca gactcgggcc   2400
ctgcacctct caggcacttc tggaaaatga ctgaggcaga ttcttcctga agcccattct   2460
ccatggggca acaaggacac ctattctgtc cttgtccttc catcgctgcc ccagaaagcc   2520
tcacatatct ccgtttagaa tcaggtccct tctccccaga tgaagaggag ggtctctgct   2580
ttgttttctc tatctcctcc tcagacttga ccaggcccag caggccccag aagaccatta   2640
ccctatatcc cttctcctcc ctagtcacat ggccataggc ctgctgatgg ctcaggaagg   2700
ccattgcaag gactcctcag ctatgggaga ggaagcacat cacccattga cccccgcaac   2760
ccctcccttt cctcctctga gtcccgactg gggccacatg cagcctgact tctttgtgcc   2820
tgttgctgtc cctgcagtct tcagagggcc accgcagctc cagtgccacg gcaggaggct   2880
gttcctgaat agcccctgtg gtaagggcca ggagagtcct tccatcctcc aaggccctgc   2940
taaaggacac agcagccagg aagtcccctg ggcccctagc tgaaggacag cctgctccct   3000
ccgtctctac caggaatggc cttgtcctat ggaaggcact gccccatccc aaactaatct   3060
aggaatcact gtctaaccac tcactgtcat gaatgtgtac ttaaaggatg aggttgagtc   3120
ataccaaata gtgatttcga tagttcaaaa tggtgaaatt agcaattcta catgattcag   3180
tctaatcaat ggataccgac tgtttcccac acaagtctcc tgttctctta agcttactca   3240
ctgacagcct ttcactctcc acaaatacat taaagatatg gccatcacca agccccctag   3300
gatgacacca gacctgagag tctgaagacc tggatccaag ttctgacttt tccccctgac   3360
agctgtgtga ccttcgtgaa gtcgccaaac ctctctgagc cccagtcatt gctagtaaga   3420
cctgcctttg agttggtatg atgttcaagt tagataacaa aatgtttata cccattagaa   3480
cagagaataa atagaactac atttcttgca                                    3510
```

<210> SEQ ID NO 10
<211> LENGTH: 3303
<212> TYPE: DNA
<213> ORGANISM: Homo sapiens

<400> SEQUENCE: 10

```
tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaagcagc    240
ctcccccgtt gcccctctgg atccactgct taaatacgga cgaggacagg gccctgtctc    300
ctcagcttca ggcaccacca ctgacctggg acagtgaatc gacaatgccg tcttctgtct    360
cgtggggcat cctcctgctg gcaggcctgt gctgcctggt ccctgtctcc ctggctgagg    420
atccccaggg agatgctgcc cagaagacag atacatccca ccatgatcag gatcacccaa    480
ccttcaacaa gatcaccccc aacctggctg agttcgcctt cagcctatac cgccagctgg    540
cacaccagtc caacagcacc aatatcttct tctccccagt gagcatcgct acagcctttg    600
caatgctctc cctggggacc aaggctgaca ctcacgatga aatcctggag ggcctgaatt    660
tcaacctcac ggagattccg gaggctcaga tccatgaagg cttccaggaa ctcctccgta    720
ccctcaacca gccagacagc cagctccagc tgaccaccgg caatggcctg ttcctcagcg    780
agggcctgaa gctagtggat aagtttttgg aggatgttaa aaagttgtac cactcagaag    840
ccttcactgt caacttcggg gacaccgaag aggccaagaa acagatcaac gattacgtgg    900
agaagggtac tcaagggaaa attgtggatt tggtcaagga gcttgacaga gacacagttt    960
ttgctctggt gaattacatc ttctttaaag gcaaatggga gagacccttt gaagtcaagg   1020
acaccgagga agaggacttc cacgtggacc aggtgaccac cgtgaaggtg cctatgatga   1080
agcgtttagg catgtttaac atccagcact gtaagaagct gtccagctgg gtgctgctga   1140
tgaaatacct gggcaatgcc accgccatct tcttcctgcc tgatgagggg aaactacagc   1200
acctggaaaa tgaactcacc cacgatatca tcaccaagtt cctggaaaat gaagacagaa   1260
ggtctgccag cttacattta cccaaactgt ccattactgg aacctatgat ctgaagagcg   1320
tcctgggtca actgggcatc actaaggtct tcagcaatgg ggctgacctc tccggggtca   1380
cagaggaggc acccctgaag ctctccaagg ccgtgcataa ggctgtgctg accatcgacg   1440
agaaagggac tgaagctgct ggggccatgt ttttagaggc catacccatg tctatccccc   1500
ccgaggtcaa gttcaacaaa ccctttgtct tcttaatgat tgaacaaaat accaagtctc   1560
ccctcttcat gggaaaagtg gtgaatccca cccaaaaata actgcctctc gctcctcaac   1620
ccctcccctc catccctggc cccctccctg gatgacatta aagaagggtt gagctggtcc   1680
ctgcctgcat gtgactgtaa atccctccca tgttttctct gagtctccct ttgcctgctg   1740
aggctgtatg tgggctccag gtaacagtgc tgtcttcggg ccccctgaac tgtgttcatg   1800
gagcatctgg ctgggtaggc acatgctggg cttgaatcca gggggggactg aatcctcagc   1860
ttacggacct gggcccatct gtttctggag ggctccagtc ttccttgtcc tgtcttggag   1920
tccccaagaa ggaatcacag gggaggaacc agataccagc catgacccca ggctccacca   1980
agcatcttca tgtcccctg ctcatccccc actccccccc acccagagtt gctcatcctg   2040
ccagggctgg ctgtgcccac cccaaggctg ccctcctggg ggccccagaa ctgcctgatc   2100
gtgccgtggc ccagttttgt ggcatctgca gcaacacaag agagaggaca atgtcctcct   2160
cttgacccgc tgtcacctaa ccagactcgg gccctgcacc tctcaggcac ttctggaaaa   2220
tgactgaggc agattcttcc tgaagcccat tctccatggg gcaacaagga cacctattct   2280
gtccttgtcc ttccatcgct gccccagaaa gcctcacata tctccgttta gaatcaggtc   2340
```

ccttctcccc agatgaagag gagggtctct gctttgtttt ctctatctcc tcctcagact 2400
tgaccaggcc cagcaggccc cagaagacca ttaccctata tcccttctcc tccctagtca 2460
catggccata ggcctgctga tggctcagga aggccattgc aaggactcct cagctatggg 2520
agaggaagca catcacccat tgacccccgc aacccctccc tttcctcctc tgagtcccga 2580
ctggggccac atgcagcctg acttctttgt gcctgttgct gtccctgcag tcttcagagg 2640
gccaccgcag ctccagtgcc acggcaggag gctgttcctg aatagcccct gtggtaaggg 2700
ccaggagagt ccttccatcc tccaaggccc tgctaaagga cacagcagcc aggaagtccc 2760
ctgggcccct agctgaagga cagcctgctc cctccgtctc taccaggaat ggccttgtcc 2820
tatggaaggc actgccccat cccaaactaa tctaggaatc actgtctaac cactcactgt 2880
catgaatgtg tacttaaagg atgaggttga gtcataccaa atagtgattt cgatagttca 2940
aaatggtgaa attagcaatt ctacatgatt cagtctaatc aatggatacc gactgtttcc 3000
cacacaagtc tcctgttctc ttaagcttac tcactgacag cctttcactc tccacaaata 3060
cattaaagat atggccatca ccaagccccc taggatgaca ccagacctga gagtctgaag 3120
acctggatcc aagttctgac ttttccccct gacagctgtg tgaccttcgt gaagtcgcca 3180
aacctctctg agccccagtc attgctagta agacctgcct ttgagttggt atgatgttca 3240
agttagataa caaaatgttt atacccatta gaacagagaa taaatagaac tacatttctt 3300
gca 3303

<210> SEQ ID NO 11
<211> LENGTH: 3300
<212> TYPE: DNA
<213> ORGANISM: Homo sapiens

<400> SEQUENCE: 11
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaagcctc 240
ccccgttgcc cctctggatc cactgcttaa atacggacga ggacagggcc ctgtctcctc 300
agcttcaggc accaccactg acctgggaca gtgaatcgac aatgccgtct tctgtctcgt 360
ggggcatcct cctgctggca ggcctgtgct gcctggtccc tgtctccctg gctgaggatc 420
cccagggaga tgctgcccag aagacagata catcccacca tgatcaggat cacccaacct 480
tcaacaagat cacccccaac ctggctgagt tcgccttcag cctataccgc cagctggcac 540
accagtccaa cagcaccaat atcttcttct ccccagtgag catcgctaca gcctttgcaa 600
tgctctccct ggggaccaag gctgacactc acgatgaaat cctggagggc ctgaatttca 660
acctcacgga gattccggag gctcagatcc atgaaggctt ccaggaactc ctccgtaccc 720
tcaaccagcc agacagccag ctccagctga ccaccggcaa tggcctgttc ctcagcgagg 780
gcctgaagct agtggataag tttttggagg atgttaaaaa gttgtaccac tcagaagcct 840
tcactgtcaa cttcggggac accgaagagg ccaagaaaca gatcaacgat tacgtggaga 900
agggtactca agggaaaatt gtggatttgg tcaaggagct tgacagagac acagtttttg 960
ctctggtgaa ttacatcttc tttaaaggca aatgggagag accctttgaa gtcaaggaca 1020
ccgaggaaga ggacttccac gtggaccagg tgaccaccgt gaaggtgcct atgatgaagc 1080

```
gtttaggcat gtttaacatc cagcactgta agaagctgtc cagctgggtg ctgctgatga   1140
aatacctggg caatgccacc gccatcttct tcctgcctga tgaggggaaa ctacagcacc   1200
tggaaaatga actcacccac gatatcatca ccaagttcct ggaaaatgaa gacagaaggt   1260
ctgccagctt acatttaccc aaactgtcca ttactggaac ctatgatctg aagagcgtcc   1320
tgggtcaact gggcatcact aaggtcttca gcaatggggc tgacctctcc ggggtcacag   1380
aggaggcacc cctgaagctc tccaaggccg tgcataaggc tgtgctgacc atcgacgaga   1440
aagggactga agctgctggg gccatgtttt tagaggccat acccatgtct atcccccccg   1500
aggtcaagtt caacaaaccc tttgtcttct taatgattga acaaaatacc aagtctcccc   1560
tcttcatggg aaaagtggtg aatcccaccc aaaaataact gcctctcgct cctcaacccc   1620
tcccctccat ccctggcccc ctccctggat gacattaaag aagggttgag ctggtccctg   1680
cctgcatgtg actgtaaatc cctcccatgt tttctctgag tctccctttg cctgctgagg   1740
ctgtatgtgg gctccaggta acagtgctgt cttcgggccc cctgaactgt gttcatggag   1800
catctggctg ggtaggcaca tgctgggctt gaatccaggg gggactgaat cctcagctta   1860
cggacctggg cccatctgtt tctggagggc tccagtcttc cttgtcctgt cttggagtcc   1920
ccaagaagga atcacagggg aggaaccaga taccagccat gaccccaggc tccaccaagc   1980
atcttcatgt ccccctgctc atcccccact cccccccacc cagagttgct catcctgcca   2040
gggctggctg tgcccacccc aaggctgccc tcctgggggc cccagaactg cctgatcgtg   2100
ccgtggccca gttttgtggc atctgcagca acacaagaga gaggacaatg tcctcctctt   2160
gacccgctgt cacctaacca gactcgggcc ctgcacctct caggcacttc tggaaaatga   2220
ctgaggcaga ttcttcctga agcccattct ccatggggca acaaggacac ctattctgtc   2280
cttgtccttc catcgctgcc ccagaaagcc tcacatatct ccgtttagaa tcaggtccct   2340
tctccccaga tgaagaggag ggtctctgct ttgttttctc tatctcctcc tcagacttga   2400
ccaggcccag caggccccag aagaccatta ccctatatcc cttctcctcc ctagtcacat   2460
ggccataggc ctgctgatgg ctcaggaagg ccattgcaag gactcctcag ctatgggaga   2520
ggaagcacat cacccattga cccccgcaac ccctcccttt cctcctctga gtcccgactg   2580
gggccacatg cagcctgact tctttgtgcc tgttgctgtc cctgcagtct tcagagggcc   2640
accgcagctc cagtgccacg gcaggaggct gttcctgaat agcccctgtg gtaagggcca   2700
ggagagtcct tccatcctcc aaggccctgc taaaggacac agcagccagg aagtcccctg   2760
ggcccctagc tgaaggacag cctgctccct ccgtctctac caggaatggc cttgtcctat   2820
ggaaggcact gccccatccc aaactaatct aggaatcact gtctaaccac tcactgtcat   2880
gaatgtgtac ttaaaggatg aggttgagtc ataccaaata gtgatttcga tagttcaaaa   2940
tggtgaaatt agcaattcta catgattcag tctaatcaat ggataccgac tgtttcccac   3000
acaagtctcc tgttctctta agcttactca ctgacagcct ttcactctcc acaaatacat   3060
taaagatatg gccatcacca agccccctag gatgacacca gacctgagag tctgaagacc   3120
tggatccaag ttctgacttt tccccctgac agctgtgtga ccttcgtgaa gtcgccaaac   3180
ctctctgagc cccagtcatt gctagtaaga cctgcctttg agttggtatg atgttcaagt   3240
tagataacaa aatgtttata cccattagaa cagagaataa atagaactac atttcttgca   3300
```

<210> SEQ ID NO 12
<211> LENGTH: 2064
<212> TYPE: DNA
<213> ORGANISM: Macaca mulatta

<400> SEQUENCE: 12

```
gcccagtctt gtgtctgcct ggcaatgggc aaggcccctt cctgcccaag ctccccgccc     60
ctccccaacc tattgcctcc gccacccgcc acccgaggcc aacttcctgg gtgggcagga    120
actgggccct gtgcccaggg cgtgcactgc ctccacgcag caaccctcag agtactgagc    180
tgagcaaagg aggaggaggg gatcagcact ctgaggaagg cctagccact gctgctgcca    240
ggaattccag ggcggcatca gtcttcagca tcaggcattt cggggtgaat tagtaaatgg    300
tagatcttgc taccagtgga acagccgcta aggattctgc agtgagagca gagggccagc    360
aaagtggtac tctcccagcg actggctgac tcacgccacc ccctccacct tggacgcagg    420
acactgtggt ttctgagcca ggtacaatga ctccttttgg tacgtgcagt ggaggctgta    480
tgctgctcag gcagagcgtc cggacagcgt gggcgggcga ctcagcgccc agcctgtgaa    540
cttagtccct gtttgctcct ccggtaactg gggtgatctt ggttaatatt caccagcagc    600
ctcccccgtt gcccctctgc acccactgct taaatacgga caaggacagg gctctgtctc    660
ctcagcctca ggcaccacca ctgacctggg acggtgaatc gacaatgcca tcttctgtct    720
catggggcgt cctcctgctg gcaggcctgt gctgcctgct ccccggctct ctggctgagg    780
atccccaggg agatgctgcc cagaagacgg atacatccca ccatgatcag gaccacccaa    840
ccctcaacaa gatcaccccc agcctggctg agttcggctt cagcctatac cgccagctgg    900
cacaccagtc caacagcacc aatatcttct tctccccagt gagcatcgct acagcctttg    960
caatgctctc cctggggacc aaggctgaca ctcacagtga aatcctggag ggcctgaatt   1020
tcaacgtcac ggagattccg gaggctcagg tccatgaagg cttccaggaa ctcctccata   1080
ccctcaacaa gccagacagc cagctccagc tgaccaccgg caacggcctg ttcctcaaca   1140
agagcctgaa ggtagtggat aagtttttgg aggatgtcaa aaaactgtac cactcagaag   1200
ccttctctgt caactttgag gacaccgaag aggccaagaa acagatcaac aattacgtgg   1260
agaaggaaac tcaagggaaa attgtggatt tggtcaagga gcttgacaga gacacagttt   1320
ttgctctggt gaattacatc ttctttaaag gcaaatggga gagacccttt gacgttgagg   1380
ccaccaagga agaggacttc cacgtggacc aggcgaccac cgtgaaggtg cccatgatga   1440
ggcgtttagg catgtttaac atctaccact gtgagaagct gtccagctgg gtgctgctga   1500
tgaaatacct gggcaatgcc accgccatct tcttcctgcc tgatgagggg aaactgcagc   1560
acctggaaaa tgaactcacc catgatatca tcaccaagtt cctggaaaat gaaaacagca   1620
ggtctgccaa cttacattta cccagactgg ccattactgg aacctatgat ctgaagacag   1680
tcctgggcca cctgggtatc actaaggtct tcagcaatgg ggctgacctc tcggggatca   1740
cggaggaggc acccctgaag ctctccaagg ccgtgcataa ggctgtgctg accatcgatg   1800
agaaagggac tgaagctgct ggggccatgt ttttagaggc catacccatg tctattcccc   1860
ccgaggtcaa gttcaacaaa ccctttgtct tcttaatgat tgaacaaaat accaagtctc   1920
ccctcttcat gggaaaagtg gtgaatccca cccagaaata actgcctgtc actcctcagc   1980
ccctcccctc catccctggc cccctccctg aatgacatta aagaagggtt gagctggtcc   2040
ctgcctgcgt gtgtgactgc aaac                                          2064
```

<210> SEQ ID NO 13
<211> LENGTH: 1608
<212> TYPE: DNA
<213> ORGANISM: Macaca mulatta

<400> SEQUENCE: 13

```
tcttgtgtct gcctggcaat gggcaaggcc ccttcctgcc caagctcccc gcccctcccc      60
aacctattgc ctccgccacc cgccacccga ggccaacttc ctgggtgggc aggaactggg     120
ccctgtgccc agggcgtgca ctgcctccac gcagcaaccc tcagagtact gagctgagca     180
aaggaggagg aggggatcag cactctgagg aaggcctagc cactgctgct gccaggaatt     240
ccaggacaat gccatcttct gtctcatggg gcgtcctcct gctggcaggc ctgtgctgcc     300
tgctccccgg ctctctggct gaggatcccc agggagatgc tgcccagaag acggatacat     360
cccaccatga tcaggaccac ccaaccctca acaagatcac cccccagcctg gctgagttcg    420
gcttcagcct ataccgccag ctggcacacc agtccaacag caccaatatc ttcttctccc     480
cagtgagcat cgctacagcc tttgcaatgc tctccctggg gaccaaggct gacactcaca     540
gtgaaatcct ggagggcctg aatttcaacg tcacggagat tccggaggct caggtccatg     600
aaggcttcca ggaactcctc cataccctca acaagccaga cagccagctc cagctgacca     660
ccggcaacgg cctgttcctc aacaagagcc tgaaggtagt ggataagttt ttggaggatg     720
tcaaaaaact gtaccactca gaagccttct ctgtcaactt tgaggacacc gaagaggcca     780
agaaacagat caacaattac gtggagaagg aaactcaagg gaaaattgtg gatttggtca     840
aggagcttga cagagacaca gtttttgctc tggtgaatta catcttcttt aaaggcaaat     900
gggagagacc ctttgacgtt gaggccacca aggaagagga cttccacgtg gaccaggcga     960
ccaccgtgaa ggtgcccatg atgaggcgtt taggcatgtt taacatctac cactgtgaga    1020
agctgtccag ctgggtgctg ctgatgaaat acctgggcaa tgccaccgcc atcttcttcc    1080
tgcctgatga ggggaaactg cagcacctgg aaaatgaact cacccatgat atcatcacca    1140
agttcctgga aaatgaaaac agcaggtctg ccaacttaca tttacccaga ctggccatta    1200
ctggaaccta tgatctgaag acagtcctgg gccacctggg tatcactaag gtcttcagca    1260
atggggctga cctctcgggg atcacggagg aggcacccct gaagctctcc aaggccgtgc    1320
ataaggctgt gctgaccatc gatgagaaag ggactgaagc tgctggggcc atgtttttag    1380
aggccatacc catgtctatt ccccccgagg tcaagttcaa caaaccctt gtcttcttaa     1440
tgattgaaca aaataccaag tctcccctct tcatgggaaa agtggtgaat cccacccaga    1500
aataactgcc tgtcactcct cagcccctcc cctccatccc tggcccccctc cctgaatgac   1560
attaaagaag ggttgagctg gtccctgcct gcgtgtgtga ctgcaaac                 1608
```

<210> SEQ ID NO 14
<211> LENGTH: 3220
<212> TYPE: DNA
<213> ORGANISM: Homo sapiens

<400> SEQUENCE: 14

```
tgcaagaaat gtagttctat ttattctctg ttctaatggg tataaacatt ttgttatcta      60
acttgaacat cataccaact caaaggcagg tcttactagc aatgactggg gctcagagag     120
gtttggcgac ttcacgaagg tcacacagct gtcaggggga aaagtcagaa cttggatcca     180
ggtcttcaga ctctcaggtc tggtgtcatc ctagggggct tggtgatggc catatcttta     240
atgtatttgt ggagagtgaa aggctgtcag tgagtaagct taagagaaca ggagacttgt     300
gtgggaaaca gtcggtatcc attgattaga ctgaatcatg tagaattgct aatttcacca     360
ttttgaacta tcgaaatcac tatttggtat gactcaacct catcctttaa gtacacattc     420
atgacagtga gtggttagac agtgattcct agattagttt gggatggggc agtgccttcc     480
```

-continued

```
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
```

-continued

```
aggttgggtg atcctgatca tggtgggatg tatctgtctt ctgggcagca tctccctggg   2880

gatcctcagc cagggagaca gggaccaggc agcacaggcc tgccagcagg aggatgcccc   2940

acgagacaga agacggcatt gtcgattcac tgtcccaggt cagtggtggt gcctgaagct   3000

gaggagacag ggccctgtcc tcgtccgtat ttaagcagtg gatccagagg ggcaacgggg   3060

gaggctgctg gtgaatatta accaaggtca ccccagttat cggaggagca aacaggggct   3120

aagtccactg gctgggatct gagtcgcccg cctacgctgc ccggacgctt tgcctgggca   3180

gtgtacagct tccactgcac ttaccgaaag gagtcattgt                         3220


<210> SEQ ID NO 15
<211> LENGTH: 3199
<212> TYPE: DNA
<213> ORGANISM: Homo sapiens

<400> SEQUENCE: 15

tgcaagaaat gtagttctat ttattctctg ttctaatggg tataaacatt ttgttatcta     60

acttgaacat cataccaact caaaggcagg tcttactagc aatgactggg gctcagagag    120

gtttggcgac ttcacgaagg tcacacagct gtcagggggga aaagtcagaa cttggatcca    180

ggtcttcaga ctctcaggtc tggtgtcatc ctagggggct tggtgatggc catatcttta    240

atgtatttgt ggagagtgaa aggctgtcag tgagtaagct taagagaaca ggagacttgt    300

gtgggaaaca gtcggtatcc attgattaga ctgaatcatg tagaattgct aatttcacca    360

ttttgaacta tcgaaatcac tatttggtat gactcaacct catcctttaa gtacacattc    420

atgacagtga gtggttagac agtgattcct agattagttt gggatggggc agtgccttcc    480

ataggacaag gccattcctg gtagagacgg agggagcagg ctgtccttca gctaggggcc    540

caggggactt cctggctgct gtgtccttta gcagggcctt ggaggatgga aggactctcc    600

tggcccttac cacaggggct attcaggaac agcctcctgc cgtggcactg gagctgcggt    660

ggccctctga agactgcagg gacagcaaca ggcacaaaga agtcaggctg catgtggccc    720

cagtcgggac tcagaggagg aaagggaggg gttgcggggg tcaatgggtg atgtgcttcc    780

tctcccatag ctgaggagtc cttgcaatgg ccttcctgag ccatcagcag gcctatggcc    840

atgtgactag ggaggagaag ggatataggg taatggtctt ctggggcctg ctgggcctgg    900

tcaagtctga ggaggagata gagaaaacaa agcagagacc ctcctcttca tctggggaga    960

agggacctga ttctaaacgg agatatgtga ggctttctgg ggcagcgatg gaaggacaag   1020

gacagaatag gtgtccttgt tgccccatgg agaatgggct tcaggaagaa tctgcctcag   1080

tcattttcca gaagtgcctg agaggtgcag ggcccgagtc tggttaggtg acagcgggtc   1140

aagaggagga cattgtcctc tctcttgtgt tgctgcagat gccacaaaac tgggccacgg   1200

cacgatcagg cagttctggg gcccccagga gggcagcctt ggggtgggca cagccagccc   1260

tggcaggatg agcaactctg ggtggggggg agtgggggat gagcaggggg acatgaagat   1320

gcttggtgga gcctggggtc atggctggta tctggttcct cccctgtgat tccttcttgg   1380

ggactccaag acaggacaag gaagactgga gccctccaga aacagatggg cccaggtccg   1440

taagctgagg attcagtccc ccctggattc aagcccagca tgtgcctacc cagccagatg   1500

ctccatgaac acagttcagg gggcccgaag acagcactgt tacctggagc ccacatacag   1560

cctcagcagg caaagggaga ctcagagaaa acatgggagg gatttacagt cacatgcagg   1620

cagggaccag ctcaaccctt ctttaatgtc atccagggag ggggccaggg atggagggga   1680

ggggttgagg agcgagaggc agttattttt gggtgggatt caccactttt cccatgaaga   1740
```

-continued

```
ggggagactt ggtattttgt tcaatcatta agaagacaaa gggtttgttg aacttgacct   1800

cggggggat agacatgggt atggcctcta aaaacatggc cccagcagct tcagtccctt    1860

tctcgtcgat ggtcagcaca gccttatgca cggccttgga gagcttcagg ggtgcctcct   1920

ctgtgacccc ggagaggtca gccccattgc tgaagacctt agtgatgccc agttgaccca   1980

ggacgctctt cagatcatag gttccagtaa tggacagttt gggtaaatgt aagctggcag   2040

accttctgtc ttcattttcc aggaacttgg tgatgatatc gtgggtgagt tcattttcca   2100

ggtgctgtag tttcccctca tcaggcagga agaagatggc ggtggcattg cccaggtatt   2160

tcatcagcag cacccagctg gacagcttct tacagtgctg gatgttaaac atgcctaaac   2220

gcttcatcat aggcaccttc acggtggtca cctggtccac gtggaagtcc tcttcctcgg   2280

tgtccttgac ttcaaagggt ctctcccatt tgcctttaaa gaagatgtaa ttcaccagag   2340

caaaaactgt gtctctgtca agctccttga ccaaatccac aattttccct tgagtaccct   2400

tctccacgta atcgttgatc tgtttcttgg cctcttcggt gtccccgaag ttgacagtga   2460

aggcttctga gtggtacaac tttttaacat cctccaaaaa cttatccact agcttcaggc   2520

cctcgctgag gaacaggcca ttgccggtgg tcagctggag ctggctgtct ggctggttga   2580

gggtacggag gagttcctgg aagccttcat ggatctgagc ctccggaatc tccgtgaggt   2640

tgaaattcag gccctccagg atttcatcgt gagtgtcagc cttggtcccc agggagagca   2700

ttgcaaaggc tgtagcgatg ctcactgggg agaagaagat attggtgctg ttggactggt   2760

gtgccagctg gcggtatagg ctgaaggcga actcagccag gttgggggtg atcttgttga   2820

aggttgggtg atcctgatca tggtgggatg tatctgtctt ctgggcagca tctccctggg   2880

gatcctcagc cagggagaca gggaccaggc agcacaggcc tgccagcagg aggatgcccc   2940

acgagacaga agacggcatt gtcctttcct gctctcctca agctctcctc aagctctgtc   3000

tcttctggca ggcacaggag agtggcctga aggctggcag gaggttgccg cccctccaac   3060

ctggaattcc tggcagcagc agcggctagg ccttcctcgg aggcccgacc ccctcctcct   3120

tcttggttca gctcaggact ctgagggttg ctgcgtggag gcagtgcatg ccctgggcac   3180

agtgcccagt tcctgccca                                                3199
```

<210> SEQ ID NO 16
<211> LENGTH: 3513
<212> TYPE: DNA
<213> ORGANISM: Homo sapiens

<400> SEQUENCE: 16

```
tgcaagaaat gtagttctat ttattctctg ttctaatggg tataaacatt ttgttatcta     60

acttgaacat cataccaact caaaggcagg tcttactagc aatgactggg gctcagagag    120

gtttggcgac ttcacgaagg tcacacagct gtcaggggga aaagtcagaa cttggatcca    180

ggtcttcaga ctctcaggtc tggtgtcatc ctagggggct tggtgatggc catatcttta    240

atgtatttgt ggagagtgaa aggctgtcag tgagtaagct taagagaaca ggagacttgt    300

gtgggaaaca gtcggtatcc attgattaga ctgaatcatg tagaattgct aatttcacca    360

ttttgaacta tcgaaatcac tatttggtat gactcaacct catcctttaa gtacacattc    420

atgacagtga gtggttagac agtgattcct agattagttt gggatggggc agtgccttcc    480

ataggacaag gccattcctg gtagagacgg agggagcagg ctgtccttca gctaggggcc    540

caggggactt cctggctgct gtgtccttta gcagggcctt ggaggatgga aggactctcc    600
```

-continued

```
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
```

```
gaggagacag ggccctgtcc tcgtccgtat ttaagcagtg gatccagagg ggcaacgggg   3060

gaggctgcga aaggagtcat tgtacctggc tcagaaacca cagcgtcctg tgtccaaggt   3120

ggagggggtg gcgtgagtca gacagtctct gggagagtac cacttagctg gccctctgct   3180

ctcactgcag aatccttagt ggctgttcca ctggtagcaa gatctaccat ttactgagtc   3240

accccaaaat gcctgatgct gaagacttac tgccgccctt tcctgctctc ctcaagctct   3300

cctcaagctc tgtctcttct ggcaggcaca ggagagtggc ctgaaggctg gcaggaggtt   3360

gccgcccctc caacctggaa ttcctggcag cagcagcggc taggccttcc tcggaggccc   3420

gaccccctcc tccttcttgg ttcagctcag gactctgagg gttgctgcgt ggaggcagtg   3480

catgccctgg gcacagtgcc cagttcctgc cca                                3513
```

<210> SEQ ID NO 17
<211> LENGTH: 3236
<212> TYPE: DNA
<213> ORGANISM: Homo sapiens

<400> SEQUENCE: 17

```
tgcaagaaat gtagttctat ttattctctg ttctaatggg tataaacatt ttgttatcta     60

acttgaacat cataccaact caaaggcagg tcttactagc aatgactggg gctcagagag    120

gtttggcgac ttcacgaagg tcacacagct gtcaggggga aaagtcagaa cttggatcca    180

ggtcttcaga ctctcaggtc tggtgtcatc ctagggggct tggtgatggc catatcttta    240

atgtatttgt ggagagtgaa aggctgtcag tgagtaagct taagagaaca ggagacttgt    300

gtgggaaaca gtcggtatcc attgattaga ctgaatcatg tagaattgct aatttcacca    360

ttttgaacta tcgaaatcac tatttggtat gactcaacct catcctttaa gtacacattc    420

atgacagtga gtggttagac agtgattcct agattagttt gggatggggc agtgccttcc    480

ataggacaag gccattcctg gtagagacgg agggagcagg ctgtccttca gctaggggcc    540

caggggactt cctggctgct gtgtccttta gcagggcctt ggaggatgga aggactctcc    600

tggcccttac cacaggggct attcaggaac agcctcctgc cgtggcactg gagctgcggt    660

ggccctctga agactgcagg gacagcaaca ggcacaaaga agtcaggctg catgtggccc    720

cagtcgggac tcagaggagg aaagggaggg gttgcggggg tcaatgggtg atgtgcttcc    780

tctcccatag ctgaggagtc cttgcaatgg ccttcctgag ccatcagcag gcctatggcc    840

atgtgactag ggaggagaag ggatataggg taatggtctt ctggggcctg ctgggcctgg    900

tcaagtctga ggaggagata gagaaaacaa agcagagacc ctcctcttca tctggggaga    960

agggacctga ttctaaacgg agatatgtga ggctttctgg ggcagcgatg gaaggacaag   1020

gacagaatag gtgtccttgt tgccccatgg agaatgggct tcaggaagaa tctgcctcag   1080

tcattttcca gaagtgcctg agaggtgcag ggcccgagtc tggttaggtg acagcgggtc   1140

aagaggagga cattgtcctc tctcttgtgt tgctgcagat gccacaaaac tgggccacgg   1200

cacgatcagg cagttctggg gcccccagga gggcagcctt ggggtgggca cagccagccc   1260

tggcaggatg agcaactctg ggtggggggg agtgggggat gagcaggggg acatgaagat   1320

gcttggtgga gcctggggtc atggctggta tctggttcct cccctgtgat tccttcttgg   1380

ggactccaag acaggacaag gaagactgga gccctccaga aacagatggg cccaggtccg   1440

taagctgagg attcagtccc ccctggattc aagcccagca tgtgcctacc cagccagatg   1500

ctccatgaac acagttcagg gggcccgaag acagcactgt tacctggagc ccacatacag   1560
```

-continued

```
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcctgtgga actgagtgag cagcagcagc aatgtcccac   3000
ctttcctgct ctcctcaagc tctcctcaag ctctgtctct tctggcaggc acaggagagt   3060
ggcctgaagg ctggcaggag gttgccgccc ctccaacctg gaattcctgg cagcagcagc   3120
ggctaggcct tcctcggagg cccgaccccc tcctccttct tggttcagct caggactctg   3180
agggttgctg cgtggaggca gtgcatgccc tgggcacagt gcccagttcc tgccca       3236
```

```
<210> SEQ ID NO 18
<211> LENGTH: 3532
<212> TYPE: DNA
<213> ORGANISM: Homo sapiens

<400> SEQUENCE: 18
```

```
tgcaagaaat gtagttctat ttattctctg ttctaatggg tataaacatt ttgttatcta     60
acttgaacat cataccaact caaaggcagg tcttactagc aatgactggg gctcagagag    120
gtttggcgac ttcacgaagg tcacacagct gtcaggggga aaagtcagaa cttggatcca    180
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
```

```
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
```

```
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctgctg gctcagaaac cacagcgtcc tgtgtccaag gtggaggggg tggcgtgagt   3120
cagacagtct ctgggagagt accacttagc tggccctctg ctctcactgc agaatcctta   3180
gtggctgttc cactggtagc aagatctacc atttactgag tcaccccaaa atgcctgatg   3240
ctgaagactt actgccgccc tgtggaactg agtgagcagc agcagcaatg tcccaccttt   3300
cctgctctcc tcaagctctc ctcaagctct gtctcttctg gcaggcacag gagagtggcc   3360
tgaaggctgg caggaggttg ccgcccctcc aacctggaat tcctggcagc agcagcggct   3420
aggccttcct cggaggcccg accccctcct ccttcttggt tcagctcagg actctgaggg   3480
ttgctgcgtg gaggcagtgc atgccctggg cacagtgccc agttcctgcc ca           3532
```

<210> SEQ ID NO 19
<211> LENGTH: 3340
<212> TYPE: DNA
<213> ORGANISM: Homo sapiens

<400> SEQUENCE: 19

```
tgcaagaaat gtagttctat ttattctctg ttctaatggg tataaacatt ttgttatcta     60
acttgaacat cataccaact caaaggcagg tcttactagc aatgactggg gctcagagag    120
gtttggcgac ttcacgaagg tcacacagct gtcaggggga aaagtcagaa cttggatcca    180
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
```

taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800 cggggggat agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcgattcac tgtcccaggt cagtggtggt gcctgaagct 3000
gaggagacag ggccctgtcc tcgtccgtat ttaagcagtg gatccagagg ggcaacgggg 3060
gaggctgctg tggaactgag tgagcagcag cagcaatgtc ccacctttcc tgctctcctc 3120
aagctctcct caagctctgt ctcttctggc aggcacagga gagtggcctg aaggctggca 3180
ggaggttgcc gcccctccaa cctggaattc ctggcagcag cagcggctag gccttcctcg 3240
gaggcccgac cccctcctcc ttcttggttc agctcaggac tctgagggtt gctgcgtgga 3300
ggcagtgcat gccctgggca cagtgcccag ttcctgccca 3340

<210> SEQ ID NO 20
<211> LENGTH: 3495
<212> TYPE: DNA
<213> ORGANISM: Homo sapiens

<400> SEQUENCE: 20
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcaggggga aaagtcagaa cttggatcca 180

-continued

```
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
```

-continued

```
gggtacggag gagttcctgg aagccttcat ggatctgagc ctccggaatc tccgtgaggt   2640

tgaaattcag gccctccagg atttcatcgt gagtgtcagc cttggtcccc agggagagca   2700

ttgcaaaggc tgtagcgatg ctcactgggg agaagaagat attggtgctg ttggactggt   2760

gtgccagctg gcggtatagg ctgaaggcga actcagccag gttgggggtg atcttgttga   2820

aggttgggtg atcctgatca tggtgggatg tatctgtctt ctgggcagca tctccctggg   2880

gatcctcagc cagggagaca gggaccaggc agcacaggcc tgccagcagg aggatgcccc   2940

acgagacaga agacggcatt gtcgattcac tgtcccaggt cagtggtggt gcctgaagct   3000

gaggagacag ggccctgtcc tcgtccgtat ttaagcagtg gatccagagg ggcaacgggg   3060

gaggctgctg gctcagaaac cacagcgtcc tgtgtccaag gtggaggggg tggcgtgagt   3120

cagacagtct ctgggagagt accacttagc tggccctctg ctctcactgc agaatcctta   3180

gtggctgttc cactggtagc aagatctacc atttactgag tcaccccaaa atgcctgatg   3240

ctgaagactt actgccgccc tttcctgctc tcctcaagct ctcctcaagc tctgtctctt   3300

ctggcaggca caggagagtg gcctgaaggc tggcaggagg ttgccgcccc tccaacctgg   3360

aattcctggc agcagcagcg gctaggcctt cctcggaggc ccgaccccct cctccttctt   3420

ggttcagctc aggactctga gggttgctgc gtggaggcag tgcatgccct gggcacagtg   3480

cccagttcct gccca                                                     3495
```

<210> SEQ ID NO 21
<211> LENGTH: 3492
<212> TYPE: DNA
<213> ORGANISM: Homo sapiens

<400> SEQUENCE: 21

```
tgcaagaaat gtagttctat ttattctctg ttctaatggg tataaacatt ttgttatcta     60

acttgaacat cataccaact caaaggcagg tcttactagc aatgactggg gctcagagag    120

gtttggcgac ttcacgaagg tcacacagct gtcaggggga aaagtcagaa cttggatcca    180

ggtcttcaga ctctcaggtc tggtgtcatc ctagggggct tggtgatggc catatcttta    240

atgtatttgt ggagagtgaa aggctgtcag tgagtaagct taagagaaca ggagacttgt    300

gtgggaaaca gtcggtatcc attgattaga ctgaatcatg tagaattgct aatttcacca    360

ttttgaacta tcgaaatcac tatttggtat gactcaacct catcctttaa gtacacattc    420

atgacagtga gtggttagac agtgattcct agattagttt gggatggggc agtgccttcc    480

ataggacaag gccattcctg gtagagacgg agggagcagg ctgtccttca gctaggggcc    540

caggggactt cctggctgct gtgtccttta gcagggcctt ggaggatgga aggactctcc    600

tggcccttac cacaggggct attcaggaac agcctcctgc cgtggcactg gagctgcggt    660

ggccctctga agactgcagg gacagcaaca ggcacaaaga agtcaggctg catgtggccc    720

cagtcgggac tcagaggagg aaagggaggg gttgcggggg tcaatgggtg atgtgcttcc    780

tctcccatag ctgaggagtc cttgcaatgg ccttcctgag ccatcagcag gcctatggcc    840

atgtgactag ggaggagaag ggatataggg taatggtctt ctggggcctg ctgggcctgg    900

tcaagtctga ggaggagata gagaaaacaa agcagagacc ctcctcttca tctggggaga    960

agggacctga ttctaaacgg agatatgtga ggctttctgg ggcagcgatg gaaggacaag   1020

gacagaatag gtgtccttgt tgccccatgg agaatgggct tcaggaagaa tctgcctcag   1080

tcattttcca gaagtgcctg agaggtgcag ggcccgagtc tggttaggtg acagcgggtc   1140
```

-continued

```
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctggct cagaaaccac agcgtcctgt gtccaaggtg gagggggtgg cgtgagtcag   3120
acagtctctg ggagagtacc acttagctgg ccctctgctc tcactgcaga atccttagtg   3180
gctgttccac tggtagcaag atctaccatt tactgagtca ccccaaaatg cctgatgctg   3240
aagacttact gccgcccttt cctgctctcc tcaagctctc ctcaagctct gtctcttctg   3300
gcaggcacag gagagtggcc tgaaggctgg caggaggttg ccgcccctcc aacctggaat   3360
tcctggcagc agcagcggct aggccttcct cggaggcccg acccccctcct ccttcttggt   3420
tcagctcagg actctgaggg ttgctgcgtg gaggcagtgc atgccctggg cacagtgccc   3480
agttcctgcc ca                                                         3492
```

<210> SEQ ID NO 22
<211> LENGTH: 3510
<212> TYPE: DNA
<213> ORGANISM: Homo sapiens

<400> SEQUENCE: 22
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcaggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840
atgtgactag ggaggagaag ggatataggg taatggtctt ctggggcctg ctgggcctgg 900
tcaagtctga ggaggagata gagaaaacaa agcagagacc ctcctcttca tctggggaga 960
agggacctga ttctaaacgg agatatgtga ggctttctgg ggcagcgatg gaaggacaag 1020
gacagaatag gtgtccttgt tgccccatgg agaatgggct tcaggaagaa tctgcctcag 1080
tcattttcca gaagtgcctg agaggtgcag ggcccgagtc tggttaggtg acagcgggtc 1140
aagaggagga cattgtcctc tctcttgtgt tgctgcagat gccacaaaac tgggccacgg 1200
cacgatcagg cagttctggg gcccccagga gggcagcctt ggggtgggca cagccagccc 1260
tggcaggatg agcaactctg ggtggggggg agtgggggat gagcaggggg acatgaagat 1320
gcttggtgga gcctggggtc atggctggta tctggttcct cccctgtgat tccttcttgg 1380
ggactccaag acaggacaag gaagactgga gccctccaga aacagatggg cccaggtccg 1440
taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800 cggggggat agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcgattcac tgtcccaggt cagtggtggt gcctgaagct 3000
gaggagacag ggccctgtcc tcgtccgtat ttaagcagtg gatccagagg ggcaacgggg 3060
gaggcgaaag gagtcattgt acctggctca gaaaccacag cgtcctgtgt ccaaggtgga 3120
gggggtggcg tgagtcagac agtctctggg agagtaccac ttagctggcc ctctgctctc 3180
actgcagaat ccttagtggc tgttccactg gtagcaagat ctaccattta ctgagtcacc 3240
ccaaaatgcc tgatgctgaa gacttactgc cgccctttcc tgctctcctc aagctctcct 3300
caagctctgt ctcttctggc aggcacagga gagtggcctg aaggctggca ggaggttgcc 3360
gcccctccaa cctggaattc ctggcagcag cagcggctag gccttcctcg gaggcccgac 3420
cccctcctcc ttcttggttc agctcaggac tctgagggtt gctgcgtgga ggcagtgcat 3480
gccctgggca cagtgcccag ttcctgccca 3510

<210> SEQ ID NO 23
<211> LENGTH: 3303
<212> TYPE: DNA
<213> ORGANISM: Homo sapiens

<400> SEQUENCE: 23
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcaggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720

```
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
```

```
gaggctgctt tcctgctctc ctcaagctct cctcaagctc tgtctcttct ggcaggcaca   3120
ggagagtggc ctgaaggctg gcaggaggtt gccgcccctc caacctggaa ttcctggcag   3180
cagcagcggc taggccttcc tcggaggccc gaccccctcc tccttcttgg ttcagctcag   3240
gactctgagg gttgctgcgt ggaggcagtg catgccctgg gcacagtgcc cagttcctgc   3300
cca                                                                 3303

<210> SEQ ID NO 24
<211> LENGTH: 3300
<212> TYPE: DNA
<213> ORGANISM: Homo sapiens

<400> SEQUENCE: 24

tgcaagaaat gtagttctat ttattctctg ttctaatggg tataaacatt ttgttatcta     60
acttgaacat cataccaact caaaggcagg tcttactagc aatgactggg gctcagagag    120
gtttggcgac ttcacgaagg tcacacagct gtcaggggga aaagtcagaa cttggatcca    180
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggaggga    1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggat agacatgggt atggcctcta aaaacatggc cccagcagct tcagtccctt    1860
```

```
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctttcc tgctctcctc aagctctcct caagctctgt ctcttctggc aggcacagga   3120
gagtggcctg aaggctggca ggaggttgcc gcccctccaa cctggaattc ctggcagcag   3180
cagcggctag gccttcctcg gaggcccgac cccctcctcc ttcttggttc agctcaggac   3240
tctgagggtt gctgcgtgga ggcagtgcat gccctgggca cagtgcccag ttcctgccca   3300
```

<210> SEQ ID NO 25
<211> LENGTH: 16
<212> TYPE: PRT
<213> ORGANISM: Unknown
<220> FEATURE:
<223> OTHER INFORMATION: Description of Unknown: Exemplary hydrophobic membrane translocation peptide

<400> SEQUENCE: 25

```
Ala Ala Val Ala Leu Leu Pro Ala Val Leu Leu Ala Leu Leu Ala Pro
1               5                   10                  15
```

<210> SEQ ID NO 26
<211> LENGTH: 11
<212> TYPE: PRT
<213> ORGANISM: Unknown
<220> FEATURE:
<223> OTHER INFORMATION: Description of Unknown: Exemplary hydrophobic membrane translocation analogue peptide

<400> SEQUENCE: 26

```
Ala Ala Leu Leu Pro Val Leu Leu Ala Ala Pro
1               5                   10
```

<210> SEQ ID NO 27

<211> LENGTH: 13
<212> TYPE: PRT
<213> ORGANISM: Human immunodeficiency virus

<400> SEQUENCE: 27

Gly Arg Lys Lys Arg Arg Gln Arg Arg Arg Pro Pro Gln
1 5 10

<210> SEQ ID NO 28
<211> LENGTH: 16
<212> TYPE: PRT
<213> ORGANISM: Drosophila sp.

<400> SEQUENCE: 28

Arg Gln Ile Lys Ile Trp Phe Gln Asn Arg Arg Met Lys Trp Lys Lys
1 5 10 15

<210> SEQ ID NO 29
<211> LENGTH: 19
<212> TYPE: RNA
<213> ORGANISM: Homo sapiens

<400> SEQUENCE: 29
cuggcacacc aguccaaca 19

<210> SEQ ID NO 30
<211> LENGTH: 19
<212> TYPE: RNA
<213> ORGANISM: Homo sapiens

<400> SEQUENCE: 30
aguccaacag caccaauau 19

<210> SEQ ID NO 31
<211> LENGTH: 19
<212> TYPE: RNA
<213> ORGANISM: Homo sapiens

<400> SEQUENCE: 31
uccaacagca ccaauaucu 19

<210> SEQ ID NO 32
<211> LENGTH: 19
<212> TYPE: RNA
<213> ORGANISM: Homo sapiens

<400> SEQUENCE: 32
ccaacagcac caauaucuu 19

<210> SEQ ID NO 33
<211> LENGTH: 19
<212> TYPE: RNA
<213> ORGANISM: Homo sapiens

<400> SEQUENCE: 33
aacagcacca auaucuucu 19

<210> SEQ ID NO 34
<211> LENGTH: 19
<212> TYPE: RNA
<213> ORGANISM: Homo sapiens

<400> SEQUENCE: 34
cuccccagug agcaucgcu 19

<210> SEQ ID NO 35
<211> LENGTH: 19
<212> TYPE: RNA
<213> ORGANISM: Homo sapiens

<400> SEQUENCE: 35
cccagugagc aucgcuaca 19

<210> SEQ ID NO 36
<211> LENGTH: 19
<212> TYPE: RNA
<213> ORGANISM: Homo sapiens

<400> SEQUENCE: 36
gugagcaucg cuacagccu 19

<210> SEQ ID NO 37
<211> LENGTH: 19
<212> TYPE: RNA
<213> ORGANISM: Homo sapiens

<400> SEQUENCE: 37
ugagcaucgc uacagccuu 19

<210> SEQ ID NO 38
<211> LENGTH: 19
<212> TYPE: RNA
<213> ORGANISM: Homo sapiens

<400> SEQUENCE: 38
gagcaucgcu acagccuuu 19

<210> SEQ ID NO 39
<211> LENGTH: 19
<212> TYPE: RNA
<213> ORGANISM: Homo sapiens

<400> SEQUENCE: 39
caucgcuaca gccuuugca 19

<210> SEQ ID NO 40
<211> LENGTH: 19
<212> TYPE: RNA
<213> ORGANISM: Homo sapiens

<400> SEQUENCE: 40
cuacagccuu ugcaaugcu 19

<210> SEQ ID NO 41
<211> LENGTH: 19
<212> TYPE: RNA
<213> ORGANISM: Homo sapiens

<400> SEQUENCE: 41
ggaccaaggc ugacacuca 19

<210> SEQ ID NO 42
<211> LENGTH: 19
<212> TYPE: RNA
<213> ORGANISM: Homo sapiens

<400> SEQUENCE: 42
auccuggagg gccugaauu 19

<210> SEQ ID NO 43
<211> LENGTH: 19
<212> TYPE: RNA
<213> ORGANISM: Homo sapiens

<400> SEQUENCE: 43
uccuggaggg ccugaauuu 19

<210> SEQ ID NO 44
<211> LENGTH: 19
<212> TYPE: RNA
<213> ORGANISM: Homo sapiens

<400> SEQUENCE: 44
uggauaaguu uuuggagga 19

<210> SEQ ID NO 45
<211> LENGTH: 19
<212> TYPE: RNA
<213> ORGANISM: Homo sapiens

<400> SEQUENCE: 45
ggauaaguuu uuggaggau 19

<210> SEQ ID NO 46
<211> LENGTH: 19
<212> TYPE: RNA
<213> ORGANISM: Homo sapiens

<400> SEQUENCE: 46
gacaccgaag aggccaaga 19

<210> SEQ ID NO 47
<211> LENGTH: 19
<212> TYPE: RNA
<213> ORGANISM: Homo sapiens

<400> SEQUENCE: 47
acaccgaaga ggccaagaa 19

<210> SEQ ID NO 48
<211> LENGTH: 19
<212> TYPE: RNA
<213> ORGANISM: Homo sapiens

<400> SEQUENCE: 48
caccgaagag gccaagaaa 19

<210> SEQ ID NO 49
<211> LENGTH: 19
<212> TYPE: RNA
<213> ORGANISM: Homo sapiens

<400> SEQUENCE: 49
aagaggccaa gaaacagau 19

<210> SEQ ID NO 50
<211> LENGTH: 19
<212> TYPE: RNA
<213> ORGANISM: Homo sapiens

<400> SEQUENCE: 50
gaggccaaga aacagauca 19

<210> SEQ ID NO 51
<211> LENGTH: 19
<212> TYPE: RNA
<213> ORGANISM: Homo sapiens

<400> SEQUENCE: 51
auuuggucaa ggagcuuga 19

<210> SEQ ID NO 52
<211> LENGTH: 19
<212> TYPE: RNA
<213> ORGANISM: Homo sapiens

<400> SEQUENCE: 52
ggucaaggag cuugacaga 19

<210> SEQ ID NO 53
<211> LENGTH: 19
<212> TYPE: RNA
<213> ORGANISM: Homo sapiens

<400> SEQUENCE: 53
ggagcuugac agagacaca 19

<210> SEQ ID NO 54
<211> LENGTH: 19
<212> TYPE: RNA
<213> ORGANISM: Homo sapiens

<400> SEQUENCE: 54
agcuugacag agacacagu 19

<210> SEQ ID NO 55
<211> LENGTH: 19
<212> TYPE: RNA
<213> ORGANISM: Homo sapiens

<400> SEQUENCE: 55
acaguuuuug cucuggguga 19

<210> SEQ ID NO 56
<211> LENGTH: 19
<212> TYPE: RNA
<213> ORGANISM: Homo sapiens

<400> SEQUENCE: 56
caguuuuugc ucuggugaa 19

<210> SEQ ID NO 57
<211> LENGTH: 19
<212> TYPE: RNA
<213> ORGANISM: Homo sapiens

<400> SEQUENCE: 57
uuugcucugg ugaauuaca 19

<210> SEQ ID NO 58
<211> LENGTH: 19
<212> TYPE: RNA
<213> ORGANISM: Homo sapiens

<400> SEQUENCE: 58
uugcucuggu gaauuacau 19

<210> SEQ ID NO 59
<211> LENGTH: 19
<212> TYPE: RNA
<213> ORGANISM: Homo sapiens

<400> SEQUENCE: 59
uacaucuucu uuaaaggca 19

<210> SEQ ID NO 60
<211> LENGTH: 19
<212> TYPE: RNA
<213> ORGANISM: Homo sapiens

<400> SEQUENCE: 60
aaugggagag acccuuuga 19

<210> SEQ ID NO 61
<211> LENGTH: 19
<212> TYPE: RNA
<213> ORGANISM: Homo sapiens

<400> SEQUENCE: 61
aggaagagga cuuccacgu 19

<210> SEQ ID NO 62
<211> LENGTH: 19
<212> TYPE: RNA
<213> ORGANISM: Homo sapiens

<400> SEQUENCE: 62
cguuuaggca uguuuaaca 19

<210> SEQ ID NO 63
<211> LENGTH: 19
<212> TYPE: RNA
<213> ORGANISM: Homo sapiens

<400> SEQUENCE: 63
guuuaggcau guuuaacau 19

<210> SEQ ID NO 64
<211> LENGTH: 19
<212> TYPE: RNA
<213> ORGANISM: Homo sapiens

<400> SEQUENCE: 64
ugggugcugc ugaugaaau 19

<210> SEQ ID NO 65
<211> LENGTH: 19
<212> TYPE: RNA
<213> ORGANISM: Homo sapiens

<400> SEQUENCE: 65
uuccugccug augagggga 19

<210> SEQ ID NO 66
<211> LENGTH: 19
<212> TYPE: RNA
<213> ORGANISM: Homo sapiens

<400> SEQUENCE: 66
ccugccugau gaggggaaa 19

<210> SEQ ID NO 67
<211> LENGTH: 19
<212> TYPE: RNA
<213> ORGANISM: Homo sapiens

<400> SEQUENCE: 67
agcaccugga aaaugaacu 19

<210> SEQ ID NO 68
<211> LENGTH: 19
<212> TYPE: RNA
<213> ORGANISM: Homo sapiens

<400> SEQUENCE: 68
uggaaaauga acucaccca 19

<210> SEQ ID NO 69
<211> LENGTH: 19
<212> TYPE: RNA
<213> ORGANISM: Homo sapiens

<400> SEQUENCE: 69
ccauuacugg aaccuauga 19

<210> SEQ ID NO 70
<211> LENGTH: 19
<212> TYPE: RNA
<213> ORGANISM: Homo sapiens

<400> SEQUENCE: 70
cauuacugga accuaugau 19

<210> SEQ ID NO 71
<211> LENGTH: 19
<212> TYPE: RNA
<213> ORGANISM: Homo sapiens

<400> SEQUENCE: 71
uuacuggaac cuaugaucu 19

<210> SEQ ID NO 72
<211> LENGTH: 19
<212> TYPE: RNA
<213> ORGANISM: Homo sapiens

<400> SEQUENCE: 72
acuggaaccu augaucuga 19

<210> SEQ ID NO 73
<211> LENGTH: 19
<212> TYPE: RNA
<213> ORGANISM: Homo sapiens

<400> SEQUENCE: 73
uguuggacug gugugccag 19

<210> SEQ ID NO 74
<211> LENGTH: 19
<212> TYPE: RNA

<213> ORGANISM: Homo sapiens

<400> SEQUENCE: 74
auauuggugc uguuggacu 19

<210> SEQ ID NO 75
<211> LENGTH: 19
<212> TYPE: RNA
<213> ORGANISM: Homo sapiens

<400> SEQUENCE: 75
agauauuggu gcuguugga 19

<210> SEQ ID NO 76
<211> LENGTH: 19
<212> TYPE: RNA
<213> ORGANISM: Homo sapiens

<400> SEQUENCE: 76
aagauauugg ugcuguugg 19

<210> SEQ ID NO 77
<211> LENGTH: 19
<212> TYPE: RNA
<213> ORGANISM: Homo sapiens

<400> SEQUENCE: 77
agaagauauu ggugcuguu 19

<210> SEQ ID NO 78
<211> LENGTH: 19
<212> TYPE: RNA
<213> ORGANISM: Homo sapiens

<400> SEQUENCE: 78
agcgaugcuc acuggggag 19

<210> SEQ ID NO 79
<211> LENGTH: 19
<212> TYPE: RNA
<213> ORGANISM: Homo sapiens

<400> SEQUENCE: 79
uguagcgaug cucacuggg 19

<210> SEQ ID NO 80
<211> LENGTH: 19
<212> TYPE: RNA
<213> ORGANISM: Homo sapiens

<400> SEQUENCE: 80
aggcuguagc gaugcucac 19

<210> SEQ ID NO 81
<211> LENGTH: 19
<212> TYPE: RNA
<213> ORGANISM: Homo sapiens

<400> SEQUENCE: 81
aaggcuguag cgaugcuca 19

<210> SEQ ID NO 82
<211> LENGTH: 19

<212> TYPE: RNA
<213> ORGANISM: Homo sapiens

<400> SEQUENCE: 82
aaaggcugua gcgaugcuc 19

<210> SEQ ID NO 83
<211> LENGTH: 19
<212> TYPE: RNA
<213> ORGANISM: Homo sapiens

<400> SEQUENCE: 83
ugcaaaggcu guagcgaug 19

<210> SEQ ID NO 84
<211> LENGTH: 19
<212> TYPE: RNA
<213> ORGANISM: Homo sapiens

<400> SEQUENCE: 84
agcauugcaa aggcuguag 19

<210> SEQ ID NO 85
<211> LENGTH: 19
<212> TYPE: RNA
<213> ORGANISM: Homo sapiens

<400> SEQUENCE: 85
ugagugucag ccuuggucc 19

<210> SEQ ID NO 86
<211> LENGTH: 19
<212> TYPE: RNA
<213> ORGANISM: Homo sapiens

<400> SEQUENCE: 86
aauucaggcc cuccaggau 19

<210> SEQ ID NO 87
<211> LENGTH: 19
<212> TYPE: RNA
<213> ORGANISM: Homo sapiens

<400> SEQUENCE: 87
aaauucaggc ccuccagga 19

<210> SEQ ID NO 88
<211> LENGTH: 19
<212> TYPE: RNA
<213> ORGANISM: Homo sapiens

<400> SEQUENCE: 88
uccuccaaaa acuuaucca 19

<210> SEQ ID NO 89
<211> LENGTH: 19
<212> TYPE: RNA
<213> ORGANISM: Homo sapiens

<400> SEQUENCE: 89
auccuccaaa aacuuaucc 19

<210> SEQ ID NO 90

<211> LENGTH: 19
<212> TYPE: RNA
<213> ORGANISM: Homo sapiens

<400> SEQUENCE: 90
ucuuggccuc uucgguguc 19

<210> SEQ ID NO 91
<211> LENGTH: 19
<212> TYPE: RNA
<213> ORGANISM: Homo sapiens

<400> SEQUENCE: 91
uucuuggccu cuucggugu 19

<210> SEQ ID NO 92
<211> LENGTH: 19
<212> TYPE: RNA
<213> ORGANISM: Homo sapiens

<400> SEQUENCE: 92
uuucuuggcc ucuucggug 19

<210> SEQ ID NO 93
<211> LENGTH: 19
<212> TYPE: RNA
<213> ORGANISM: Homo sapiens

<400> SEQUENCE: 93
aucuguuucu uggccucuu 19

<210> SEQ ID NO 94
<211> LENGTH: 19
<212> TYPE: RNA
<213> ORGANISM: Homo sapiens

<400> SEQUENCE: 94
ugaucuguuu cuuggccuc 19

<210> SEQ ID NO 95
<211> LENGTH: 19
<212> TYPE: RNA
<213> ORGANISM: Homo sapiens

<400> SEQUENCE: 95
ucaagcuccu ugaccaaau 19

<210> SEQ ID NO 96
<211> LENGTH: 19
<212> TYPE: RNA
<213> ORGANISM: Homo sapiens

<400> SEQUENCE: 96
ucugucaagc uccuugacc 19

<210> SEQ ID NO 97
<211> LENGTH: 19
<212> TYPE: RNA
<213> ORGANISM: Homo sapiens

<400> SEQUENCE: 97
ugugucucug ucaagcucc 19

<210> SEQ ID NO 98
<211> LENGTH: 19
<212> TYPE: RNA
<213> ORGANISM: Homo sapiens

<400> SEQUENCE: 98
acugugucuc ugucaagcu 19

<210> SEQ ID NO 99
<211> LENGTH: 19
<212> TYPE: RNA
<213> ORGANISM: Homo sapiens

<400> SEQUENCE: 99
ucaccagagc aaaaacugu 19

<210> SEQ ID NO 100
<211> LENGTH: 19
<212> TYPE: RNA
<213> ORGANISM: Homo sapiens

<400> SEQUENCE: 100
uucaccagag caaaaacug 19

<210> SEQ ID NO 101
<211> LENGTH: 19
<212> TYPE: RNA
<213> ORGANISM: Homo sapiens

<400> SEQUENCE: 101
uguaauucac cagagcaaa 19

<210> SEQ ID NO 102
<211> LENGTH: 19
<212> TYPE: RNA
<213> ORGANISM: Homo sapiens

<400> SEQUENCE: 102
auguaauuca ccagagcaa 19

<210> SEQ ID NO 103
<211> LENGTH: 19
<212> TYPE: RNA
<213> ORGANISM: Homo sapiens

<400> SEQUENCE: 103
ugccuuuaaa gaagaugua 19

<210> SEQ ID NO 104
<211> LENGTH: 19
<212> TYPE: RNA
<213> ORGANISM: Homo sapiens

<400> SEQUENCE: 104
ucaaaggguc ucucccauu 19

<210> SEQ ID NO 105
<211> LENGTH: 19
<212> TYPE: RNA
<213> ORGANISM: Homo sapiens

<400> SEQUENCE: 105
acguggaagu ccucuuccu 19

<210> SEQ ID NO 106
<211> LENGTH: 19
<212> TYPE: RNA
<213> ORGANISM: Homo sapiens

<400> SEQUENCE: 106
uguuaaacau gccuaaacg 19

<210> SEQ ID NO 107
<211> LENGTH: 19
<212> TYPE: RNA
<213> ORGANISM: Homo sapiens

<400> SEQUENCE: 107
auguuaaaca ugccuaaac 19

<210> SEQ ID NO 108
<211> LENGTH: 19
<212> TYPE: RNA
<213> ORGANISM: Homo sapiens

<400> SEQUENCE: 108
auuucaucag cagcaccca 19

<210> SEQ ID NO 109
<211> LENGTH: 19
<212> TYPE: RNA
<213> ORGANISM: Homo sapiens

<400> SEQUENCE: 109
uccccucauc aggcaggaa 19

<210> SEQ ID NO 110
<211> LENGTH: 19
<212> TYPE: RNA
<213> ORGANISM: Homo sapiens

<400> SEQUENCE: 110
uuuccccuca ucaggcagg 19

<210> SEQ ID NO 111
<211> LENGTH: 19
<212> TYPE: RNA
<213> ORGANISM: Homo sapiens

<400> SEQUENCE: 111
aguucauuuu ccaggugcu 19

<210> SEQ ID NO 112
<211> LENGTH: 19
<212> TYPE: RNA
<213> ORGANISM: Homo sapiens

<400> SEQUENCE: 112
ugggugaguu cauuuucca 19

<210> SEQ ID NO 113
<211> LENGTH: 19
<212> TYPE: RNA
<213> ORGANISM: Homo sapiens

<400> SEQUENCE: 113
ucauagguuc caguaaugg 19

<210> SEQ ID NO 114
<211> LENGTH: 19
<212> TYPE: RNA
<213> ORGANISM: Homo sapiens

<400> SEQUENCE: 114
aucauagguu ccaguaaug 19

<210> SEQ ID NO 115
<211> LENGTH: 19
<212> TYPE: RNA
<213> ORGANISM: Homo sapiens

<400> SEQUENCE: 115
agaucauagg uuccaguaa 19

<210> SEQ ID NO 116
<211> LENGTH: 19
<212> TYPE: RNA
<213> ORGANISM: Homo sapiens

<400> SEQUENCE: 116
ucagaucaua gguuccagu 19

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 117
cuggcacacc aguccaacat t 21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 118
aguccaacag caccaauaut t 21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 119
uccaacagca ccaauaucut t 21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 120
ccaacagcac caauaucuut t 21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 121
aacagcacca auaucuucut t 21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 122
cuccccagug agcaucgcut t 21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 123
cccagugagc aucgcuacat t 21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 124
gugagcaucg cuacagccut t 21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 125
ugagcaucgc uacagccuut t 21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 126
gagcaucgcu acagccuuut t 21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 127
caucgcuaca gccuuugcat t 21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 128
cuacagccuu ugcaaugcut t 21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 129
ggaccaaggc ugacacucat t 21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 130
auccuggagg gccugaauut t 21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 131
uccuggaggg ccugaauuut t 21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 132
uggauaaguu uuuggaggat t 21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 133
ggauaaguuu uuggaggaut t 21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 134
gacaccgaag aggccaagat t 21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 135
acaccgaaga ggccaagaat t 21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 136
caccgaagag gccaagaaat t 21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 137
aagaggccaa gaaacagaut t 21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 138
gaggccaaga aacagaucat t 21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 139
auuuggucaa ggagcuugat t 21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 140
ggucaaggag cuugacagat t 21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 141
ggagcuugac agagacacat t 21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 142
agcuugacag agacacagut t 21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 143
acaguuuuug cucuggugat t 21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 144
caguuuuugc ucuggugaat t 21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 145
uuugcucugg ugaauuacat t 21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 146
uugcucuggu gaauuacaut t 21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 147
uacaucuucu uuaaaggcat t 21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 148
aaugggagag acccuuugat t 21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 149
aggaagagga cuuccacgut t 21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 150
cguuuaggca uguuuaacat t 21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 151
guuuaggcau guuuaacaut t 21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 152
ugggugcugc ugaugaaaut t 21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 153
uuccugccug augaggggat t 21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 154
ccugccugau gaggggaaat t 21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence:
Synthetic oligonucleotide
<220> FEATURE:
<223> OTHER INFORMATION: Description of Combined DNA/RNA Molecule:
Synthetic oligonucleotide

<400> SEQUENCE: 155
agcaccugga aaaugaacut t 21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 156
uggaaaauga acucacccat t 21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 157
ccauuacugg aaccuaugat t 21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 158
cauuacugga accuaugaut t 21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 159
uuacuggaac cuaugaucut t 21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 160
acuggaaccu augaucugat t 21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 161
uguuggacug gugugccagt t 21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 162
auauuggugc uguuggacut t 21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 163
agauauuggu gcuguuggat t 21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 164
aagauauugg ugcuguuggt t 21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 165
agaagauauu ggugcuguut t 21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 166
agcgaugcuc acuggggagt t 21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 167
uguagcgaug cucacugggt t 21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 168
aggcuguagc gaugcucact t 21

<210> SEQ ID NO 169
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 169
aaggcuguag cgaugcucat t 21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 170
aaaggcugua gcgaugcuct t 21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 171
ugcaaaggcu guagcgaugt t 21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 172
agcauugcaa aggcuguagt t 21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 173
ugagugucag ccuuggucct t 21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 174
aauucaggcc cuccaggaut t 21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 175
aaauucaggc ccuccaggat t 21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 176
uccuccaaaa acuuauccat t 21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 177
auccuccaaa aacuuaucct t 21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 178
ucuuggccuc uucgguguct t 21

<210> SEQ ID NO 179
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
uucuuggccu cuucggugut t 21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
uuucuuggcc ucuucggugt t 21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
aucuguuucu uggccucuut t 21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
ugaucuguuu cuuggccuct t 21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
ucaagcuccu ugaccaaaut t 21

<210> SEQ ID NO 184
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184

ucugucaagc uccuugacct t                                              21


<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic
      oligonucleotide

<400> SEQUENCE: 185

ugugucucug ucaagcucct t                                              21


<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186

acugugucuc ugucaagcut t                                              21


<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187

ucaccagagc aaaaacugut t                                              21


<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188

uucaccagag caaaaacugt t                                              21
```

```
<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189

uguaauucac cagagcaaat t                                              21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190

auguaauuca ccagagcaat t                                              21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: Description of Combined DNA/RNA Molecule:
      Synthetic oligonucleotide

<400> SEQUENCE: 191

ugccuuuaaa gaagauguat t                                              21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 192

ucaaaggguc ucucccauut t                                              21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193

acguggaagu ccucuuccut t                                              21
```

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 194
uguuaaacau gccuaaacgt t 21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 195
auguuaaaca ugccuaaact t 21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 196
auuucaucag cagcacccat t 21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 197
uccccucauc aggcaggaat t 21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 198
uuuccccuca ucaggcaggt t 21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 199
aguucauuuu ccaggugcut t 21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 200
ugggugaguu cauuuuccat t 21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 201
ucauagguuc caguaauggt t 21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 202
aucauagguu ccaguaaugt t 21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 203

-continued

```
agaucauagg uuccaguaat t                                          21


<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204

ucagaucaua gguuccagut t                                          21
```